US008895272B2

(12) United States Patent
Hawkins et al.

(10) Patent No.: US 8,895,272 B2
(45) Date of Patent: Nov. 25, 2014

(54) METHODS FOR THE ECONOMICAL PRODUCTION OF BIOFUEL FROM BIOMASS

(71) Applicant: Gevo, Inc., Englewood, CO (US)

(72) Inventors: Andrew C. Hawkins, Parker, CO (US); David A. Glassner, Littleton, CO (US); Thomas Buelter, Denver, CO (US); James L. Wade, San Diego, CA (US); Peter Meinhold, Denver, CO (US); Matthew W. Peters, Highlands Ranch, CO (US); Patrick R. Gruber, Longmont, CO (US); William A. Evanko, Golden, CO (US); Aristos A. Aristidou, Highlands Ranch, CO (US); Marco Landwehr, Magdeburg (DE)

(73) Assignee: GEVO, Inc., Englewood, CO (US)

( * ) Notice: Subject to any disclaimer, the term of this patent is extended or adjusted under 35 U.S.C. 154(b) by 0 days.

(21) Appl. No.: 13/859,903

(22) Filed: Apr. 10, 2013

(65) Prior Publication Data
US 2013/0273622 A1  Oct. 17, 2013

Related U.S. Application Data

(63) Continuation of application No. 12/263,436, filed on Oct. 31, 2008, now Pat. No. 8,431,374.

(60) Provisional application No. 60/984,235, filed on Oct. 31, 2007, provisional application No. 60/984,521, filed on Nov. 1, 2007, provisional application No. 60/984,793, filed on Nov. 2, 2007, provisional application No. 60/985,155, filed on Nov. 2, 2007, provisional application No. 60/985,209, filed on Nov. 3, 2007, provisional application No. 60/985,460, filed on Nov. 5, 2007, provisional application No. 60/985,607, filed on Nov. 5, 2007, provisional application No. 60/986,151, filed on Nov. 7, 2007, provisional application No. 60/986,235, filed on Nov. 7, 2007, provisional application No. 60/987,984, filed on Nov. 14, 2007, provisional application No. 60/988,588, filed on Nov. 16, 2007, provisional application No. 60/989,032, filed on Nov. 19, 2007, provisional application No. 60/989,785, filed on Nov. 21, 2007, provisional application No. 61/014,297, filed on Dec. 17, 2007, provisional application No. 61/029,222, filed on Feb. 15, 2008.

(51) Int. Cl.
| C12P 7/16 | (2006.01) |
| C12P 7/24 | (2006.01) |
| C12P 7/62 | (2006.01) |
| C07K 14/245 | (2006.01) |
| C10G 1/04 | (2006.01) |
| C10L 1/02 | (2006.01) |
| C12N 9/04 | (2006.01) |
| C12N 9/02 | (2006.01) |
| C12N 9/28 | (2006.01) |
| C12N 9/34 | (2006.01) |
| C12N 9/42 | (2006.01) |
| C12N 9/26 | (2006.01) |

(52) U.S. Cl.
CPC ............ *C12P 7/16* (2013.01); *C07K 14/245* (2013.01); *C10G 1/04* (2013.01); *C10L 1/02* (2013.01); *C12N 9/0006* (2013.01); *C12N 9/0036* (2013.01); *C12N 9/2417* (2013.01); *C12N 9/2428* (2013.01); *C12N 9/2434* (2013.01); *C12Y 106/01002* (2013.01); *C12Y 302/01001* (2013.01); *C12Y 302/01003* (2013.01); *C12N 9/2414* (2013.01); *C12P 7/24* (2013.01); *C12P 7/62* (2013.01); *Y02E 50/16* (2013.01); *Y02E 50/10* (2013.01); *C10G 2300/4025* (2013.01); *C10G 2300/1014* (2013.01)
USPC ... 435/135; 435/160; 435/252.3; 435/252.33; 536/23.2

(58) Field of Classification Search
CPC ........ C07K 14/245; C07K 14/24; C12P 7/16; C12P 7/06; C12P 7/24; C12P 7/62; C12N 15/80; C12N 15/81
USPC .......... 435/135, 160, 252.3, 252.33; 536/23.2
See application file for complete search history.

(56) References Cited

U.S. PATENT DOCUMENTS

| 4,552,775 A | 11/1985 | Baeling et al. |
| 5,830,716 A | 11/1998 | Kojima et al. |
| 7,309,602 B2 | 12/2007 | David |
| 7,851,188 B2 | 12/2010 | Donaldson et al. |
| 8,101,808 B2 | 1/2012 | Evanko et al. |
| 8,133,715 B2 | 3/2012 | Buelter et al. |

(Continued)

FOREIGN PATENT DOCUMENTS

| WO | WO 00/03020 A1 | 1/2000 |
| WO | WO 2007/041269 A2 | 4/2007 |

(Continued)

OTHER PUBLICATIONS

Anderlund et al., "Expression of the *Escherichia coli* pntA and pntB genes, encoding nicotinamide nucleotide transhydrogenase, in *Saccharomyces cerevisiae* and its effect on product formation during anaerobic glucose fermentation," 1999, Appl. Env. Microbiology, vol. 65, p. 2333-2340.

(Continued)

*Primary Examiner* — Chih-Min Kam
(74) *Attorney, Agent, or Firm* — Cooley LLP

(57) ABSTRACT

Methods for producing a biofuel are provided. Also provided are biocatalysts that convert a feedstock to a biofuel.

18 Claims, 36 Drawing Sheets

(56) References Cited

U.S. PATENT DOCUMENTS

| | | |
|---|---|---|
| 8,153,415 B2 | 4/2012 | Buelter et al. |
| 8,158,404 B2 | 4/2012 | Lies et al. |
| 8,193,402 B2 | 6/2012 | Gruber et al. |
| 8,273,565 B2 | 9/2012 | Dundon et al. |
| 8,431,374 B2 | 4/2013 | Hawkins et al. |
| 2005/0089979 A1 | 4/2005 | Ezeji et al. |
| 2007/0087403 A1 | 4/2007 | Bestel-Corre et al. |
| 2007/0092957 A1 | 4/2007 | Donaldson et al. |
| 2007/0243235 A1 | 10/2007 | David |
| 2007/0243592 A1 | 10/2007 | David |
| 2007/0244719 A1 | 10/2007 | David |
| 2007/0275438 A1 | 11/2007 | David |
| 2008/0293101 A1 | 11/2008 | Peters et al. |
| 2008/0293125 A1 | 11/2008 | Subbian et al. |
| 2009/0006280 A1 | 1/2009 | David |
| 2009/0081746 A1 | 3/2009 | Liao et al. |
| 2009/0111154 A1 | 4/2009 | Liao et al. |
| 2009/0155869 A1 | 6/2009 | Buelter et al. |
| 2009/0171129 A1 | 7/2009 | Evanko et al. |
| 2009/0215137 A1 | 8/2009 | Hawkins et al. |
| 2009/0226990 A1 | 9/2009 | Hawkins et al. |
| 2009/0239270 A1 | 9/2009 | David |
| 2009/0274659 A1 | 11/2009 | David |
| 2009/0291469 A1 | 11/2009 | David |
| 2009/0299109 A1 | 12/2009 | Gruber et al. |
| 2010/0062505 A1 | 3/2010 | Gunawardena et al. |
| 2011/0223284 A1 | 9/2011 | David |
| 2011/0269185 A1 | 11/2011 | David |
| 2012/0040080 A1 | 2/2012 | Hawkins et al. |

FOREIGN PATENT DOCUMENTS

| | | |
|---|---|---|
| WO | WO 2007/050671 A2 | 5/2007 |
| WO | WO 2007/130518 A2 | 11/2007 |
| WO | WO 2007/130521 A2 | 11/2007 |
| WO | WO 2008/013996 A2 | 1/2008 |
| WO | WO 2008/098227 A2 | 8/2008 |

OTHER PUBLICATIONS

Atsumi, S et al., "Metabolic engineering of *Escherichia coli* for 1-butanol production," Metabolic Engineering 10(6):305-311 (2008).

Atsumi, S et al., "Non-fermentative pathways for synthesis of branched-chain higher alcohols as biofuels," Nature 451(7174):86-90 (2008).

Atsumi, S et al., "Metabolic engineering for advanced biofuels production from *Escherichia coli*," Current Opinion in Biotechnology 19(5):414-419 (2008).

Bacterial *E. coli* Growth Media (Jun. 8, 2012), http://www.exptec.com/Expression%20Technology/Bacteria%20growth%20media.htm.

Bahl H et al., "Chapter 5: Applied Acetone-Butanol Fermentation," Clostridia Biotechnology and Medical Applications (2001).

Chen CK and Blascheck HP, "Acetate enhances solvent production and prevents degeneration in *Clostridium beijerinckii* BA101," Applied Microbiology and Biotechnology 52:170-173 (1999).

Chen et al., "Increased isobutanol production in *Saccharomyces cerevisiae* by overexpression of genes in valin metabolism," Biotechnol. Biofuels 4:21 (2011).

Clarke et al., "Cloning and expression of the tranhydrogenase gene of *Escherichia coli*," 1985, J. of Bacteriology, vol. 162, p. 367-373.

dos Santos et al., "Manipulation of malic enzyme in *Saccharomyces cerevisiae* for increasing NADPH production capacity aerobically in different cellular compartments," 2004, Metabolic Engineering, vol. 6, p. 352-363.

Ezeji et al., "Bioproduction of butanol from biomass: from genes to bioreactors," Curr. Opin. Biotechnol. 18:220-227 (2007).

Ezeji, TC et al., "Butanol Fermentation Research: Upstream and Downstream Manipulations," The Chemical Record 4:305-314 (2004).

Gatesoupe, "Live yeasts in the gut: Natural occurrence, dietary introduction, and their effects on fish health and development," Aquaculture 267:20-30 (2007).

"Guide to Wine Yeast," 3 pages, http://www.brewerylane.com/wine/wineyeast.html (2011).

International Search Report and Written Opinion mailed Apr. 27, 2009 in the International (PCT) Application No. PCT/US08/82159, 11 pages.

International Search Report and Written Opinion mailed Apr. 27, 2009 in the International (PCT) Application No. PCT/US08/82160, 11 pages.

Jones, DT and Woods, DR, "Acetone-Butanol Fermentation Revisited," Microbiological Reviews 50(4):484-524 (1986).

Nevoigt et al., "Cells of the yeast *Saccharomyces cerevisiae* are transformable by DNA under non-artificial conditions," Yeast 16:1107-1110 (2000).

Qureshi et al., "Production of Acetone Butanol Ethanol (ABE) by a Hyper-Producing Mutant Strain of *Clostridium beijerinckii* BA101 and Recovery by Pervaporation," Biotechnol. Prog. 15(4):594-602 (1999).

Rouhollah, H et al., "Mixed sugar fermentation by *Pichia stipitis*, *Saccharomyces cerevisiae*, and an isolated xylose-fermenting *Kluyveromyces marxianus* and their cocultures," African J of Biotechnology 6(9):1110-1114 (2007).

The Alcohol Textbook, Fourth Edition, 2003. Nottingham University Press, Nottingham, United Kingdom. Jacques, K.A., W.M., Lyons, T.P., and Kelsall, D.R., eds.

Thorngate, III, "Yeast Strain and Wine Flavor: Nature or Nuture?" in Chemistry of Wine Flavor; Waterhouse et al., ACS Symposium Series 714:66-80; American Chemical Society: Washington, DC, 1988.

Verho et al., "Identification of the first fungal NADP-GAPDH from *Kluyveromyces lactis*," 2002, Biochemistry, vol. 41, p. 13833-13838.

Verho et al., "Engineering redox cofactor regeneration for improved pentose fermentation in *Saccharomyces cerevisiae*," 2003, Appl. Env. Microbiology, vol. 69, p. 5892-5897.

Weckbecker et al., "Improved synthesis of chiral alcohols with *Escherichia coli* cells co-expressing pyridine nucleotide transhydrogenase, NADP+-dependent alcohol dehydrogenase and NAD+-dependent formate dehydrogenase," 2004, Biotechnology Letters, vol. 26, p. 1739-1744.

Zaldivar, J et al., "Fuel ethanol production from lignocellulose: a challenge for metabolic engineering and process integration," Applied Microbiology and Biotechnology 56:17-34 (2001).

(pGV1698; SEQ ID NO: 28)

Taagaaaaccattattatcatgacattaacctataaaaataggcgtatcacgaggcccttcgtcttcacctcgagaattgtgagcggata
acaattgacattgtgagcggataacaagatactgagcacatcagcaggacgcactgaccgaattcattaaagaggagaaaggtac
aatgttgacaaaagcaacaaaagaacaaaaatcccttgtgaaaaacagaggggcggagcttgttgttgattgcttagtggagcaag
gtgtcacacatgtatttggcattccaggtgcaaaaattgatgcggtatttgacgctttacaagataaaggacctgaaattatcgttgcccg
gcacgaacaaaacgcagcattcatggcccaagcagtcggccgtttaactggaaaaaccgggagtcgtgttagtcacatcaggaccg
ggtgcctctaacttggcaacaggcctgctgacagcgaacactgaaggagaccctgtcgttgcgcttgctggaaacgtgatccgtgca
gatcgtttaaaacggacacatcaatctttggataatgcggcgctattccagccgattacaaaatacagtgtagaagttcaagatgtaaa
aaatataccggaagctgttacaaatgcatttaggatagcgtcagcagggcaggctggggccgcttttgtgagctttccgcaagatgttgt
gaatgaagtcacaaatacgaaaaacgtgcgtgctgttgcagcgccaaaactcggtcctgcagcagatgatgcaatcagtgcggcca
tagcaaaaatccaaacagcaaaacttcctgtcgttttggtcggcatgaaaggcggaagaccggaagcaattaaagcggttcgcaag
cttttgaaaaaggttcagcttccatttgttgaaacatatcaagctgccggtacccttctagagatttagaggatcaatatttggccgtatcg
gtttgttccgcaaccagcctggcgatttactgctagagcaggcagatgttgttctgacgatcggctatgacccgattgaatatgatccgaa
attctggaatatcaatggagaccggacaattatccatttagacgagattatcgctgacattgatcatgcttaccagcctgatcttgaattga
tcggtgacattccgtccacgatcaatcatatcgaacacgatgctgtgaaagtggaatttgcagagcgtgagcagaaaatcctttctgatt
taaaacaatatatgcatgaaggtgagcaggtgcctgcagattggaaatcagacagagcgcaccctcttgaaatcgttaaagagttgc
gtaatgcagtcgatgatcatgttacagtaacttgcgatatcggttcgcacgccatttggatgtcacgttatttccgcagctacgagccgtta
acattaatgatcagtaacggtatgcaaacactcggcgttgcgcttccttgggcaatcggcgcttcattggtgaaaccgggagaaaaag
tggtttctgtctctggtgacggcggtttcttattctcagcaatggaattagagacagcagttcgactaaaagcaccaattgtacacattgtat
ggaacgacagcacatatgacatggttgcattccagcaattgaaaaaatataaccgtacatctgcggtcgatttcggaaatatcgatatc
gtgaaatatgcggaaagcttcggagcaactggcttgcgcgtagaatcaccagaccagctggcagatgttctgcgtcaaggcatgaac
gctgaaggtcctgtcatcatcgatgtcccggttgactacagtgataacattaatttagcaagtgacaagcttccgaaagaattcgggga
actcatgaaaacgaaagctctctaggtcgacgaggagacaacattatggcgaattatttcaacactctgaacctgcgtcaacaactgg
cgcaactgggtaagtgccgtttcatgggtcgtgac

FIGURE 16A gagtttgcggacggtgcttcttatctgcaaggcaagaaggttgttattgttggttgcggtgcgcaaggcctgaatcaaggtctgaatatgc
gcgacagcggcctggacattagctatgcgctgcgcaaggaggctatcgcggaaaaacgtgctagctggcgcaaggctactgagaa
cggcttcaaggttggcacctatgaggagctgattccgcaagctgacctggttatcaatctgaccccagataaacaacatagcgacgtt
gttcgtactgttcaaccgctgatgaaggatggtgctgctctgggttatagccacggctttaacattgttgaggtaggtgaacaaattcgca
aggacattactgttgttatggtggctccaaagtgtccgggtactgaggttcgcgaggaatataagcgcggttttggtgttccaaccctgat
cgcggtgcatccagagaatgacccaaagggtgagggtatggctatcgcgaaggcgtgggctgcggcgactggcggccatcgcgct
ggcgttctggagagcagctttgtggctgaggttaagagcgatctgatgggtgaacagactattctgtgtggtatgctgcaagcgggtag
cctgctgtgttttgataaactggttgaggagggcactgacccggcgtatgcggagaagctgatccaatttggctgggagactattactga
ggcgctgaagcaaggtggtattactctgatgatggatcgcctgagcaatccagctaagctgcgcgcgtacgctctgagcgagcaact
gaaggaaattatggcaccgctgtttcaaaagcacatggatgatatcattagcggtgagtttagcagcggcatgatggctgattgggcg
aatgacgacaaaaagctgctgacttggcgcgaggaaactggtaagactgctttcgagactgctccacaatacgagggtaagattggt
gaacaagaatattttgacaagggtgttctgatgatcgctatggttaaggctggtgtggagctggcttttgagactatggttgacagcggtat
tatcgaggaaagcgcgtactacgagagcctgcatgaactgccactgatcgcgaatactattgcgcgcaaacgcctgtatgagatgaa
tgttgtgattagcgacactgcggaatatggcaattacctgtttagctatgcgtgcgttccactgctgaagccattcatggcggaactgcag
ccaggtgatctgggcaaggcgatcccagagggtgctgttgacaatggtcagctgcgcgacgttaatgaggctatccgttctcacgctat
cgaacaagttggcaaaaagctgcgtggttacatgaccgacatgaagcgcatcgcggtggctggctaacctagggcgttcggctgcg
gcgagcggtatcagctcactcaaaggcggtaatacggttatccacagaatcaggggataacgcaggaaagaacatgtgagcaaa
aggccagcaaaaggccaggaaccgtaaaaaggccgcgttgctggcgttttttccataggctccgccccccctgacgagcatcacaaa
aatcgacgctcaagtcagaggtggcgaaacccgacaggactataaagataccaggcgtttccccctggaagctccctcgtgcgctct
cctgttccgaccctgccgcttaccggatacctgtccgcctttctcccttcgggaagcgtggcgctttctcatagctcacgctgtaggtatctc
agttcggtgtaggtcgttcgctccaagctgggctgtgtgcacgaaccccccgttcagcccgaccgctgcgccttatccggtaactatcgt
cttgagtccaacccggtaagacacgacttatcgccactggcagcagccactggtaacaggattagcagagcgaggtatgtaggcgg
tgctacagagttcttgaagtggtggcctaactacg

FIGURE 16B gctacactagaaggacagtatttggtatctgcgctctgctgaagccagttaccttcggaaaaagagttggtagctcttgatccggcaaac
aaaccaccgctggtagcggtggttttttgtttgcaagcagcagattacgcgcagaaaaaaaggatctcaagaagatcctttgatcttttc
tacggggtctgacgctcagtggaacgaaaactcacgttaagggattttggtcatgactagtgcttggattctcaccaataaaaaacgcc
cggcggcaaccgagcgttctgaacaaatccagatggagttctgaggtcattactggatctatcaacaggagtccaagcgagctcgta
aacttggtctgacagttaccaatgcttaatcagtgaggcacctatctcagcgatctgtctatttcgttcatccatagttgcctgactccccgtc
gtgtagataactacgatacgggagggcttaccatctggccccagtgctgcaatgataccgcgagacccacgctcaccggctccagat
ttatcagcaataaaccagccagccggaagggccgagcgcagaagtggtcctgcaactttatccgcctccatccagtctattaattgttg
ccgggaagctagagtaagtagttcgccagttaatagtttgcgcaacgttgttgccattgctacaggcatcgtggtgtcacgctcgtcgtttg
gtatggcttcattcagctccggttcccaacgatcaaggcgagttacatgatcccccatgttgtgcaaaaaagcggttagctccttcggtcc
tccgatcgttgtcagaagtaagttggccgcagtgttatcactcatggttatggcagcactgcataattctcttactgtcatgccatccgtaag
atgcttttctgtgactggtgagtactcaaccaagtcattctgagaatagtgtatgcggcgaccgagttgctcttgcccggcgtcaatacgg
gataataccgcgccacatagcagaactttaaaagtgctcatcattggaaaacgttcttcggggcgaaaactctcaaggatcttaccgct
gttgagatccagttcgatgtaacccactcgtgcacccaactgatcttcagcatctttactttcaccagcgtttctgggtgagcaaaaacag
gaaggcaaaatgccgcaaaaaagggaataagggcgacacggaaatgttaatactcatactcttcctttttcaatattattgaagcattt
atcaggttattgtctcatgagcggatacatatttgaatgtatttagaaaaataaacaaataggggttccgcgcacatttccccgaaaagt
gccacctgacgtc

FIGURE 16C (pGV1720; SEQ ID NO: 29)

taagaaaccattattatcatgacattaacctataaaaataggcgtatcacgaggcccttcgtcttcacctcgagaattgtgagcggata
acaattgacattgtgagcggataacaagatactgagcacatcagcaggacgcactgaccgaattcattagtcgacattatgcggccg
cggatccataaggaggattaattaagacttcccgggtgatcccatggtacgcgtgctagaggcatcaaataaaacgaaaggctcagt
cgaaagactgggcctttcgttttatctgttgtttgtcggtgaacgctctcctgagtaggacaaatccgccgccctagacctagctagggta
cgggttttgctgcccgcaaacgggctgttctggtgttgctagtttgttatcagaatcgcagatccggcttcagccggtttgccggctgaaag
cgctatttcttccagaattgccatgattttttccccacgggaggcgtcactggctccgtgttgtcggcagctttgattcgataagcagcatc
gcctgtttcaggctgtctatgtgtgactgttgagctgtaacaagttgtctcaggtgttcaatttcatgttctagttgctttgttttactggtttcacct
gttctattaggtgttacatgctgttcatctgttacattgtcgatctgttcatggtgaacagctttaaatgcaccaaaaactcgtaaaagctctg
atgtatctatcttttttacaccgttttcatctgtgcatatggacagttttcccttttgatatctaacggtgaacagttgttctacttttgtttgttagtcttg
atgcttcactgatagatacaagagccataagaacctcagatccttccgtatttagccagtatgttctctagtgtggttcgttgttttttgcgtga
gccatgagaacgaaccattgagatcatgcttactttgcatgtcactcaaaaattttgcctcaaaactggtgagctgaattttttgcagttaaa
gcatcgtgtagtgtttttcttagtccgttacgtaggtaggaatctgatgtaatggttgttggtattttgtcaccattcatttttatctggttgttctcaa
gttcggttacgagatccatttgtctatctagttcaacttggaaaatcaacgtatcagtcgggcggcctcgcttatcaaccaccaatttcatat
tgctgtaagtgtttaaatctttacttattggtttcaaaacccattggttaagccttttaaactcatggtagttattttcaagcattaacatgaactta
aattcatcaaggctaatctctatatttgccttgtgagttttcttttgtgttagttcttttaataaccactcataaatcctcatagagtatttgttttcaa
aagacttaacatgttccagattatattttatgaattttttaactggaaaagataaggcaatatctcttcactaaaaactaattctaattttttcgc
ttgagaacttggcatagtttgtccactggaaaatctcaaagcctttaaccaaaggattcctgatttccacagttctcgtcatcagctctctgg
ttgctttagctaatacaccataagcattttccctactgatgttcatcatctgagcgtattggttataagtgaacgataccgtccgttctttccttgt
aggggttttcaatcgtggggttgagtagtgccacacagcataaaattagcttggtttcatgctccgttaagtcatagcgactaatcgctagtt
catttgctttgaaaacaactaattcagacatacatctcaattggtctaggtgattttaatcactataccaattgagatgggctagtcaatgat
aattactagtcctttcccgggagatctgggtatctgtaaattctgctagacctttgctggaaaacttgtaaattctgctagaccctctgtaaat
tccgctagacctttgtgtgttttttttgtttatattcaagtggttataatttatagaataaagaaagaataaaaaaagataaaaagaatagatc
ccagccctgtgtataactcactactttagtcagttccgc

FIGURE 17A agtattacaaaaggatgtcgcaaacgctgtttgctcctctacaaaacagaccttaaaaccctaaaggcttaagtagcaccctcgcaag
ctcgggcaaatcgctgaatattccttttgtctccgaccatcaggcacctgagtcgctgtcttttcgtgacattcagttcgctgcgctcacgg
ctctggcagtgaatgggggtaaatggcactacaggcgccttttatggattcatgcaaggaaactacccataatacaagaaaagcccg
tcacgggcttctcagggcgtttatggcgggtctgctatgtggtgctatctgacttttgctgttcagcagttcctgccctctgattttccagtctg
accacttcggattatcccgtgacaggtcattcagactggctaatgcacccagtaaggcagcggtatcatcaacaggcttacccgtctta
ctgtccctagtgcttggattctcaccaataaaaaaacgcccggcggcaaccgagcgttctgaacaaatccagatggagttctgaggtca
ttactggatctatcaacaggagtccaagcgagctctcgaacccagagtcccgctcagaagaactcgtcaagaaggcgatagaag
gcgatgcgctgcgaatcgggagcggcgataccgtaaagcacgaggaagcggtcagcccattcgccgccaagctcttcagcaatat
cacgggtagccaacgctatgtcctgatagcggtccgccacacccagccggccacagtcgatgaatccagaaaagcggccattttcc
accatgatattcggcaagcaggcatcgccatgggtcacgacgagatcctcgccgtcgggcatgcgcgccttgagcctggcgaacag
ttcggctggcgcgagcccctgatgctcttcgtccagatcatcctgatcgacaagaccggcttccatccgagtacgtgctcgctcgatgcg
atgtttcgcttggtggtcgaatgggcaggtagccggatcaagcgtatgcagccgccgcattgcatcagccatgatggatactttctcggc
aggagcaaggtgagatgacaggagatcctgccccggcacttcgcccaatagcagccagtcccttcccgcttcagtgacaacgtcga
gcacagctgcgcaaggaacgcccgtcgtggccagccacgatagccgcgctgcctcgtcctgcagttcattcagggcaccggacag
gtcggtcttgacaaaaagaaccgggcgcccctgcgctgacagccggaacacggcggcatcagagcagccgattgtctgttgtgccc
agtcatagccgaatagcctctccacccaagcggccggagaacctgcgtgcaatccatcttgttcaatcatgcgaaacgatcctcatcct
gtctcttgatcagatcttgatccctgcgccatcagatccttggcggcaagaaagccatccagtttactttgcagggcttcccaaccttacc
agagggcgccccagctggcaattccgacgtc

FIGURE 17B (pGV1745; SEQ ID NO: 30)

Taagaaaccattattatcatgacattaacctataaaaataggcgtatcacgaggcccttcgtcttcacctcgagaattgtgagcggata
acaattgacattgtgagcggataacaagatactgagcacatcagcaggacgcactgaccgaattcattagtcgacaggagaaaggt
actatgcgaattggcataccaagagaacggttaaccaatgaaacccgtgttgcagcaacgccaaaaacagtggaacagctgctga
aactgggttttaccgtcgcggtagagagcggcgcgggtcaactggcaagttttgacgataaagcgtttgtgcaagcgggcgctgaaat
tgtagaagggaatagcgtctggcagtcagagatcattctgaaggtcaatgcgccgttagatgatgaaattgcgttactgaatcctggga
caacgctggtgagttttatctggcctgcgcagaatccggaattaatgcaaaaacttgcggaacgtaacgtgaccgtgatggcgatgga
ctctgtgccgcgtatctcacgcgcacaatcgctggacgcactaagctcgatggcgaacatcgccggttatcgcgccattgttgaagcg
gcacatgaatttgggcgcttcttaccgggcaaattactgcggccgggaaagtgccaccggcaaaagtgatggtgattggtgcgggtg
ttgcaggtctggccgccattggcgcagcaaacagtctcggcgcgattgtgcgtgcattcgacacccgcccggaagtgaaagaacaa
gttcaaagtatgggcgcggaattcctcgagctggattttaaagaggaagctggcagcggcgatggctatgccaaagtgatgtcggac
gcgttcatcaaagcggaaatggaactctttgccgcccaggcaaaagaggtcgatatcattgtcaccaccgcgcttattccaggcaaac
cagcgccgaagctaattacccgtgaaatggttgactccatgaaggcgggcagtgtgattgttgacctggcagcccaaaacggcggc
aactgtgaatacaccgtgccgggtgaaatcttcactacggaaaatggtgtcaaagtgattggttataccgatcttccgggccgtctgccg
acgcaatcctcacagctttacggcacaaacctcgttaatctgctgaaactgttgtgcaaagagaaagacggcaatatcactgttgatttt
gatgatgtggtgattcgcggcgtgaccgtgatccgtgcgggcgaaattacctggccggcaccgccgattcaggtatcagctcagccgc
aggcggcacaaaaagcggcaccggaagtgaaaactgaggaaaaatgtacctgctcaccgtggcgtaaatacgcgttgatggcgc
tggcaatcattcttttggctggatggcaagcgttgcgccgaaagaattccttgggcacttcaccgttttcgcgctggcctgcgttgtcggtt
attacgtggtgtggaatgtatcgcacgcgctgcatacaccgttgatgtcggtcaccaacgcgatttcagggattattgttgtcggagcact
gttgcagattggccagggcggctgggttagcttccttagttttatcgcggtgcttatagccagcattaatattttcggtggcttcaccgtgact
cagcgcatgctgaaaatgttccgcaaaaattaaggggtaacatatgtctggaggattagttacagctgcatacattgttgccgcgatcct
gtttatcttcagtctggccggtctttcgaaacatgaaacgtctcgccagggtaacaacttcggtatcgccgggatggcgattgcgttaatc
gcaaccatttttggaccggatacgggtaatgttggctggatcttgctggcgatggtcattggtggggcaattggtatccgtctggcgaaga
aagttgaaatgaccgaaatgccagaactggtggc

FIGURE 18A gatcctgcatagcttcgtgggtctggcggcagtgctggttggctttaacagctatctgcatcatgacgcgggaatggcaccgattctggtc
aatattcacctgacggaagtgttcctcggtatcttcatcggggcggtaacgttcacgggttcggtggtggcgttcggcaaactgtgtggca
agatttcgtctaaaccattgatgctgccaaaccgtcacaaaatgaacctggcggctctggtcgtttccttcctgctgctgattgtatttgttcg
cacggacagcgtcggcctgcaagtgctggcattgctgataatgaccgcaattgcgctggtattcggctggcatttagtcgcctccatcgg
tggtgcagatatgccagtggtggtgtcgatgctgaactcgtactccggctgggcggctgcggctgcgggctttatgctcagcaacgacc
tgctgattgtgaccggtgcgctggtcggttcttcgggggctatcctttcttacattatgtgtaaggcgatgaaccgttcctttatcagcgttattg
cgggtggtttcggcaccgacggctcttctactggcgatgatcaggaagtgggtgagcaccgcgaaatcaccgcagaagagacagc
ggaactgctgaaaaactcccattcagtgatcattactccggggtacggcatggcagtcgcgcaggcgcaatatcctgtcgctgaaatt
actgagaaattgcgcgctcgtggtattaatgtgcgtttcggtatccacccggtcgcggggcgtttgcctggacatatgaacgtattgctgg
ctgaagcaaaagtaccgtatgacatcgtgctggaaatggacgagatcaatgatgactttgctgataccgataccgtactggtgattggt
gctaacgatacggttaacccggcggcgcaggatgatccgaagagtccgattgctggtatgcctgtgctggaagtgtggaaagcgca
gaacgtgattgtctttaaacgttcgatgaacactggctatgctggtgtgcaaaacccgctgttcttcaaggaaaacacccacatgctgttt
ggtgacgccaaagccagcgtggatgcaatcctgaaagctctgtaacgtcgacattatgcggccgcggatccataaggaggattaatt
aagacttcccgggtgatcccatggtacgcgtgctagaggcatcaaataaaacgaaaggctcagtcgaaagactgggcctttcgttttat
ctgttgtttgtcggtgaacgctctcctgagtaggacaaatccgccgccctagacctagctagggtacgggttttgctgcccgcaaacggg
ctgttctggtgttgctagtttgttatcagaatcgcagatccggcttcagccggtttgccggctgaaagcgctatttcttccagaattgccatga
ttttttcccacgggaggcgtcactggctcccgtgttgtcggcagctttgattcgataagcagcatcgcctgtttcaggctgtctatgtgtgac
tgttgagctgtaacaagttgtctcaggtgttcaatttcatgttctagttgctttgttttactggtttcacctgttctattaggtgttacatgctgttcatc
tgttacattgtcgatctgttcatggtgaacagctttaaatgcaccaaaaactcgtaaaagctctgatgtatctatcttttttacaccgttttcatct
gtgcatatggacagttttcccttgatatctaacggtgaacagttgttctacttttgtttgttagtcttgatgcttcactgatagatacaagagcc
ataagaacctcagatccttccgtatttagccagtatgttctctagtgtggttcgttgttttttgcgtgagccatgagaacgaaccattgagatc
atgcttactttgcatgtcactcaaaaattttgcctcaaaactggtgagctgaattttgcagttaaagcatcgtgtagtgttttcttagtccgtta
cgtaggtaggaatctgatgtaatggttgttggtat

FIGURE 18B tttgtcaccattcatttttatctggttgttctcaagttcggttacgagatccatttgtctatctagttcaacttggaaaatcaacgtatcagtcggg
cggcctcgcttatcaaccaccaatttcatattgctgtaagtgtttaaatctttacttattggtttcaaaacccattggttaagccttttaaactcat
ggtagttattttcaagcattaacatgaacttaaattcatcaaggctaatctctatatttgccttgtgagttttcttttgtgttagttcttttaataacca
ctcataaatcctcatagagtatttgttttcaaaagacttaacatgttccagattatattttatgaatttttttaactggaaaagataaggcaatat
ctcttcactaaaaactaattctaattttttcgcttgagaacttggcatagtttgtccactggaaaatctcaaagcctttaaccaaaggattcctg
atttccacagttctcgtcatcagctctctggttgctttagctaatacaccataagcattttccctactgatgttcatcatctgagcgtattggttat
aagtgaacgataccgtccgttctttccttgtagggttttcaatcgtggggttgagtagtgccacacagcataaaattagcttggtttcatgct
ccgttaagtcatagcgactaatcgctagttcatttgctttgaaaacaactaattcagacatacatctcaattggtctaggtgatttaatcact
ataccaattgagatgggctagtcaatgataattactagtcctttccgggagatctgggtatctgtaaattctgctagacctttgctggaaa
acttgtaaattctgctagaccctctgtaaattccgctagacctttgtgtgttttttttgtttatattcaagtggttataatttatagaataaagaaag
aataaaaaagataaaagaatagatcccagccctgtgtataactcactactttagtcagttccgcagtattacaaaaggatgtcgca
aacgctgtttgctcctctacaaaacagaccttaaaaccctaaaggcttaagtagcaccctcgcaagctcgggcaaatcgctgaatattc
cttttgtctccgaccatcaggcacctgagtcgctgtcttttcgtgacattcagttcgctgcgctcacggctctggcagtgaatgggggtaaa
tggcactacaggcgccttttatggattcatgcaaggaaactacccataatacaagaaaagcccgtcacgggcttctcagggcgtttat
ggcgggtctgctatgtggtgctatctgacttttgctgttcagcagttcctgccctctgattttccagtctgaccacttcggattatcccgtgaca
ggtcattcagactggctaatgcacccagtaaggcagcggtatcatcaacaggcttacccgtcttactgtccctagtgcttggattctcacc
aataaaaaacgcccggcggcaaccgagcgttctgaacaaatccagatggagttctgaggtcattactggatctatcaacaggagtcc
aagcgagctctcgaaccccagagtcccgctcagaagaactcgtcaagaaggcgatagaaggcgatgcgctgcgaatcgggagc
ggcgataccgtaaagcacgaggaagcggtcagcccattcgccgccaagctcttcagcaatatcacgggtagccaacgctatgtcct
gatagcggtccgccacacccagccggccacagtcgatgaatccagaaaagcggccattttccaccatgatattcggcaagcaggc
atcgccatgggtcacgacgagatcctcgccgtcgggcatgcgcgccttgagcctggcgaacagttcggctggcgcgagcccctgat
gctcttcgtccagatcatcctgatcgacaagaccggcttccatccgagtacgtgctcgctcgatgcgatgtttcgcttggtggtcgaatgg
gcaggtagccggatcaagcgtatgcagccgccgc

FIGURE 18C attgcatcagccatgatggatactttctcggcaggagcaaggtgagatgacaggagatcctgccccggcacttcgcccaatagcagc
cagtcccttcccgcttcagtgacaacgtcgagcacagctgcgcaaggaacgcccgtcgtggccagccacgatagccgcgctgcctc
gtcctgcagttcattcagggcaccggacaggtcggtcttgacaaaaagaaccgggcgccctgcgctgacagccggaacacggcg
gcatcagagcagccgattgtctgttgtgcccagtcatagccgaatagcctctccacccaagcggccggagaacctgcgtgcaatcca
tcttgttcaatcatgcgaaacgatcctcatcctgtctcttgatcagatcttgatccctgcgccatcagatccttggcggcaagaaagccat
ccagtttactttgcagggcttcccaaccttaccagagggcgc

FIGURE 18D (pGV1655; SEQ ID NO: 31)

Taagaaaccattattatcatgacattaacctataaaaataggcgtatcacgaggcccttcgtcttcacctcgagaattgtgagcggata
acaattgacattgtgagcggataacaagatactgagcacatcagcaggacgcactgaccgaattcattaaagaggagaaaggtac
catgtatacagtaggagattacctattagaccgattacacgagttaggaattgaagaaattttggagtccctggagactataacttaca
atttttagatcaaattatttcccgcaaggatatgaaatgggtcggaaatgctaatgaattaaatgcttcatatatggctgatggctatgctcg
tactaaaaaagctgccgcattcttacaacctttggagtaggtgaattgagtgcagttaatggattagcaggaagttacgccgaaaattt
accagtagtagaaatagtgggatcacctacatcaaaagttcaaaatgaaggaaaatttgttcatcatacgctggctgacggtgatttta
aacactttatgaaaatgcacgaacctgttacagcagctcgaactttactgacagcagaaaatgcaaccgttgaaattgaccgagtactt
tctgcactattaaaagaaagaaaacctgtctatatcaacttaccagttgatgttgctgctgcaaaagcagagaaaccctcactccctttg
aaaaaagaaaactcaacttcaaatacaagtgaccaagagatcttgaacaaaattcaagaaagcttgaaaaatgccaaaaaacca
atcgtgattacaggacatgaaataattagttttggcttagaaaaaaacagtctctcaatttatttcaaagacaaaactacctattacgacatt
aaactttggaaaaagttcagttgatgaagctctcccttcattttaggaatctataatggtaaactctcagagcctaatcttaaagaattcgt
ggaatcagccgacttcatcctgatgcttggagttaaactcacagactcttcaacaggagccttcactcatcatttaaatgaaaataaaat
gatttcactgaatatagatgaaggaaaaaatatttaacgaaagcatccaaaattttgattttgaatccctcatctcctctctcttagacctaag
cgaaatagaatacaaaggaaaatatatcgataaaaagcaagaagactttgttccatcaaatgcgctttatcacaagaccgcctatgg
caagcagttgaaaacctaactcaaagcaatgaaacaatcgttgctgaacaagggacatcattctttggcgcttcatcaatttcttaaaa
ccaaagagtcattttattggtcaacccttatggggatcaattggatatacattcccagcagcattaggaagccaaattgcagataaaga
aagcagacacctttatttattggtgatggttcacttcaacttacggtgcaagaattaggattagcaatcagagaaaaaattaatccaattt
gctttattatcaataatgatggttatacagtcgaaagagaaattcatggaccaaatcaaagctacaatgatattccaatgtggaattactc
aaaattaccagaatcatttggagcaacagaagaacgagtagtctcgaaaatcgttagaactgaaaatgaatttgtgtctgtcatgaaa
gaagctcaagcagatccaaatagaatgtactggattgagttaattttggcaaaagaagatgcaccaaaagtactgaaaaaaatggg
caaactatttgctgaacaaaatcataaggtcgacaggagatatactatgcctaaatatcgcagcgcaactactacccacggcc
gcaacatggcaggcgcgcgtgctctgtggcgtgcgactggtatgactgatgcggactttggcaaaccaatcattgctgtggttaatagct
ttactcagttcgttccaggccatgttcacctgcgtgacctgggcaagctggttgcggagcagatcgaggctgcgggtggtgtggcgaag
gaatttaacaccatcgctgttgacgacggtatcgcgatgggtcatggtggtatgctgtacagcctgccgagccgtgagctgattgcgga
cagcgtggaatacatggttaatgcgcattgtgcggatgcgatggtttgtattagcaactgtgataagattactccaggtatgctgatggcg
agcctgcgtctgaacatcccagttattttcgtgagcggtggtccaatggaagcgggtaagactaagctgagcgaccagattatcaaact
ggacctggtggacgctatgattcaaggtgctgatccaaaggttagcgatagccaatctgaccaagtggagcgcagcgcttgcccaac
ttgtggcagctgtagcggtatgttcactgcgaatagcatgaattgtctgactgaggctctgggtctgagccaaccaggtaatggtagcct
gctggcgactcatgcggatcgcaaacaactgtttctgaacgcgggcaagcgtatcgtggagctgactaagcgctactatgaacagaa
tgatgagtccgcgctgccacgcaacattgcgtccaaagctgctttcgagaatgcgatgaccctggacattgctatgggcggtagcacc
aatactgttctgcatctgctggctgctgctcaagaggctgagattgatttactatgtccgacattgacaaactgagccgtaaagtgccgc
aactgtgcaaggtggctccatctactcaaaagtatcacatggaggacgtgcatcgcgcgggtggcgtgattggcatcctgggtgagct
ggaccgtgctggtctgctgaatcgcgacgttaagaatgttctgggtctgaccctgccacagaccctggagcagtatgatgtgatgctga
ctcaagacgatgctgttaagaacatgtttcgtgctggtccggcgggtatccgcactacccaagcgtttagccaggactgtcgctgggac
accctggatgatgaccgtgcgaacggttgcattcgtagcctggaacatgcgtattctaaggatggtggtctggctgttctgtatggcaattt
cgctgagaatggttgtattgttaagaccgcgggtgttgacgattctattctgaagtttactggtccagctaaggtttatgagtctcaagatga
cgctgttgaggctatcctgggtggcaaggtggttgcgggtgacgttgttgttatccgttacgagggtccaaagggtggcccaggtatgca
agagatgctgtatccgacttctttctgaagagcatgggcctgggtaaggcgtgcgctctgattactgatggccgctttagcggcggtact
agcggcctgagcattggtcatgttagcccagaggctgcgtctggtggttctatcggtctgatcgaggacggcgatctgattgcgattgat
attccaaatcgcgggtatccaactgcaagtttctgacgcggagctggctgctcgccgcgaggctcaagatgcgcgtggcgataaggcg
tggaccccaaagaaccgcgagcgccaagttagcttcgcgctgcgcgcgtacgcctctctggcgacttctgcggataagggtgctgttc
gtgacaagagcaagctgggtggctaaacgcgtgctagaggcatcaaataaaacgaaaggctcagtcgaaagactgggcctttcgtt
ttatctgttgtttgtcggtgaacgctctcctgagtaggacaaatccgccgccctagacctagtagggtacggttttgctgcccgcaaac
gggctgttctggtgttgctagttgttatcagaatcgcagatccggcttcagccggtttgccggctgaaagcgctatttcttccagaattgcc
atgattttttccccacgggaggcgtcactggctcccgtgttgtcggcagctttgattcgataagcagcatcgcct

FIGURE 20A gtttcaggctgtctatgtgtgactgttgagctgtaacaagttgtctcaggtgttcaatttcatgttctagttgctttgttttactggtttcacctgttct
attaggtgttacatgctgttcatctgttacattgtcgatctgttcatggtgaacagctttaaatgcaccaaaaactcgtaaaagctctgatgta
tctatcttttttacaccgttttcatctgtgcatatggacagttttcccttttgatatctaacggtgaacagttgttctacttttgtttgttagtcttgatgct
tcactgatagatacaagagccataagaacctcgatccttccgtatttagccagtatgttctctagtgtggttcgttgttttgcgtgagccat
gagaacgaaccattgagatcatgcttactttgcatgtcactcaaaaattttgcctcaaaactggtgagctgaattttgcagttaaagcatc
gtgtagtgttttcttagtccgttacgtaggtaggaatctgatgtaatggttgttggtattttgtcaccattcattttatctggttgttctcaagttcg
gttacgagatccatttgtctatctagttcaacttggaaaatcaacgtatcagtcgggcggcctcgcttatcaaccaccaatttcatattgctg
taagtgtttaaatctttacttattggtttcaaaacccattggttaagccttttaaactcatggtagttattttcaagcattaacatgaacttaaattc
atcaaggctaatctctatatttgccttgtgagttttcttttgtgttagttcttttaataaccactcataaatcctcatagagtatttgttttcaaaaga
cttaacatgttccagattatattttatgaatttttttaactggaaaagataaggcaatatctcttcactaaaaactaattctaattttcgcttgag
aacttggcatagtttgtccactggaaaatctcaaagcctttaaccaaaggattcctgatttccacagttctcgtcatcagctctctggttgctt
tagctaatacaccataagcattttccctactgatgttcatcatctgagcgtattggtataagtgaacgataccgtccgttcttccttgtaggg
ttttcaatcgtggggttgagtagtgccacacagcataaaattagcttggtttcatgctccgttaagtcatagcgactaatcgctagttcatttg
ctttgaaaacaactaattcagacatacatctcaattggtctaggtgattttaatcactataccaattgagatgggctagtcaatgataattac
tagtccttttcccgggagatctgggtatctgtaaattctgctagacctttgctggaaaacttgtaaattctgctagaccctctgtaaattccgct
agacctttgtgtgtttttttgtttatattcaagtggttataatttatagaataaagaaagaataaaaaaagataaaaagaatagatcccagc
cctgtgtataactcactactttagtcagttccgcagtattacaaaaggatgtcgcaaacgctgtttgctcctctacaaaacagaccttaaa
accctaaaggcttaagtagcaccctcgcaagctcgggcaaatcgctgaatattccttttgtctccgaccatcaggcacctgagtcgctgt
cttttcgtgacattcagttcgctgcgctcacggctctggcagtgaatgggggtaaatggcactacaggcgccttttatggattcatgcaag
gaaactacccataatacaagaaaagcccgtcacgggcttctcagggcgtttatggcgggtctgctatgtggtgctatctgactttttgctg
ttcagcagttcctgccctctgatttccagtctgaccacttcggattatcccgtgacaggtcattcagactggctaatgcacccagtaaggc
agcggtatcatcaacaggcttacccgtcttactgtccctagtgcttggattctcaccaataaaaaacgcccggcggcaaccgagcgttc
tgaacaaatccagatggagttctgaggtcattactggatctatcaacaggagtccaagcgagctctcgaaccccagagtcccgctca
gaagaactcgtcaagaaggcgatagaaggcgatgcgctgcgaatcgggagcggcgataccgtaaagcacgaggaagcggtca
gcccattcgccgccaagctcttcagcaatatcacgggtagccaacgctatgtcctgatagcggtccgccacacccagccggccaca
gtcgatgaatccagaaaagcggccattttccaccatgatattcggcaagcaggcatcgccatgggtcacgacgagatcctcgccgtc
gggcatgcgcgccttgagcctggcgaacagttcggctggcgcgagccctgatgctcttcgtccagatcatcctgatcgacaagacc
ggcttccatccgagtacgtgctcgctcgatgcgatgtttcgcttggtggtcgaatgggcaggtagccggatcaagcgtatgcagccgcc
gcattgcatcagccatgatggatactttctcggcaggagcaaggtgagatgacaggagatcctgccccggcacttcgcccaatagca
gccagtcccttcccgcttcagtgacaacgtcgagcacagctgcgcaaggaacgcccgtcgtggccagccacgatagccgcgctgc
ctcgtcctgcagttcattcagggcaccggacaggtcggtcttgacaaaaagaaccgggcgcccctgcgctgacagccggaacacg
gcggcatcagagcagccgattgtctgttgtgcccagtcatagccgaatagcctctccacccaagcggccggagaacctgcgtgcaat
ccatcttgttcaatcatgcgaaacgatcctcatcctgtctcttgatcagatcttgatccctgcgccatcagatccttggcggcaagaaag
ccatccagtttactttgcagggcttcccaaccttaccagagggcgccccagctggcaattccgacgtc

FIGURE 20B (pGV1609; SEQ ID NO: 32)

Cgatatcaaattacgccccgccctgccactcatcgcagtactgttgtaattcattaagcattctgccgacatggaagccatcacagacg
gcatgatgaacctgaatcgccagcggcatcagcaccttgtcgccttgcgtataatatttgcccatggtgaaaacggggcgaagaagt
tgtccatattggccacgtttaaatcaaaactggtgaaactcacccagggattggctgagacgaaaaacatattctcaataaaccctttag
ggaaataggccaggttttcaccgtaacacgccacatcttgcgaatatatgtgtagaaactgccggaaatcgtcgtggtattcactccag
agcgatgaaaacgtttcagtttgctcatggaaaacggtgtaacaagggtgaacactatcccatatcaccagctcaccgtctttcattgcc
atacgaaactccggatgagcattcatcaggcgggcaagaatgtgaataaaggccggataaaacttgtgcttatttttctttacggtcttta
aaaaggccgtaatatccagctgaacggtctggttataggtacattgagcaactgactgaaatgcctcaaaatgttctttacgatgccatt
gggatatatcaacggtggtatatccagtgatttttttctccattttagcttccttagctcctgaaaatctcgataactcaaaaaatacgcccgg
tagtgatcttatttcattatggtgaaagttggaacctcttacgtgccgatcaacgtctcattttcgccagatatcgacgtctaagaaaccatta
ttatcatgacattaacctataaaaataggcgtatcacgaggccctttcgtcttcacctcgagaattgtgagcggataacaattgacattgt
gagcggataacaagatactgagcacatcagcaggacgcactgaccgaattcattaaagaggagaaaggtacaatgttgacaaaa
gcaacaaaagaacaaaaatcccttgtgaaaaacagaggggcggagcttgttgttgattgcttagtggagcaaggtgtcacacatgta
tttggcattccaggtgcaaaaattgatgcggtatttgacgctttacaagataaaggacctgaaattatcgttgcccggcacgaacaaaa
cgcagcattcatggcccaagcagtcggccgtttaactggaaaaaccgggagtcgtgttagtcacatcaggaccgggtgcctctaacttg
gcaacaggcctgctgacagcgaacactgaaggagaccctgtcgttgcgcttgctggaaacgtgatccgtgcagatcgttaaaacgg
acacatcaatctttggataatgcggcgctattccagccgattacaaaatacagtgtagaagttcaagatgtaaaaaatataccggaag
ctgttacaaatgcatttaggatagcgtcagcagggcaggctggggccgcttttgtgagctttccgcaagatgttgtgaatgaagtcacaa
atacgaaaaacgtgcgtgctgttgcagcgccaaaactcggtcctgcagcagatgatgcaatcagtgcggccatagcaaaaatccaa
acagcaaaacttcctgtcgtttggtcggcatgaaaggcggaagaccggaagcaattaaagcggttcgcaagcttttgaaaaaggttc
agcttccatttgttgaaacatatcaagctgccggtaccttctagagatttagaggatcaatatttttggccgtatcggtttgttccgcaacca
gcctggcgatttactgctagagcaggcagatgttgttctgacgatcggctatgacccgattgaatatgatccgaaattctggaatatcaat
ggagaccggacaattatccatttagacgagattatcgctgacattgatcatgcttaccagcctgatcttgaattgatcggtgacattccgtc
cacgatcaatcatatcgaacacgatgctgtgaaagtggaatttgcagagcgtgagcagaaaatcctttctgatttaaaacaatatatgc
atgaaggtgagcaggtgcctgcagattggaaatcagacagagcgcaccctcttgaaatcgttaaagagttgcgtaatgcagtcgatg
atcatgttacagtaacttgcgatatcggttcgcacgccatttggatgtcacgttatttccgcagctacgagccgttaacattaatgatcagta
acggtatgcaaacactcggcgttgcgcttcctgggcaatcggcgcttcattggtgaaaccgggagaaaaagtggtttctgtctctggtg
acggcggtttcttattctcagcaatggaattagagacagcagttcgactaaaagcaccaattgtacacattgtatggaacgacagcac
atatgacatggttgcattccagcaattgaaaaaatataaccgtacatctgcggtcgatttcggaaatatcgatatcgtgaaatatgcgga
aagcttcggagcaactggcttgcgcgtagaatcaccagaccagctggcagatgttctgcgtcaaggcatgaacgctgaaggtcctgt
catcatcgatgtcccggttgactacagtgataacattaatttagcaagtgacaagcttccgaaagaattcggggaactcatgaaaacg
aaagctctctaggtcgacgaggaatcaccatggctaactacttaatacactgaatctgcgccagcagctggcacagctgggcaaat
gtcgctttatgggccgcgatgaattcgccgatggcgcgagctaccttcagggtaaaaaagtagtcatcgtcggctgtggcgcacaggg
tctgaaccagggcctgaacatgcgtgattctggtctcgatatctcctacgctctgcgtaaagaagcgattgccgagaagcgcgcgtcct
ggcgtaaagcgaccgaaaatggttttaaagtgggtacttacgaagaactgatcccacaggcggatcggtgattaacctgacgccgg
acaagcagcactctgatgtagtgcgcaccgtacagccactgatgaaagacggcgcggcgctgggctactcgcacggtttcaacatc
gtcgaagtgggcgagcagatccgtaaagatatcaccgtagtgatggttgcgccgaaatgcccaggcaccgaagtgcgtgaagagt
acaaacgtgggttcggcgtaccgacgctgattgccgttcacccggaaaacgatccgaaaggcgaaggcatggcgattgccaaagc
ctgggcggctgcaaccggtggtcaccgtgcgggtgtgctggaatcgtccttcgttgcggaagtgaaatctgacctgatgggcgagcaa
accatcctgtgcggtatgttgcaggctggctctctgctgtgcttcgacaagctggtggaagaaggtaccgatccagcatacgcagaaa
aactgattcagttcggttgggaaaaccatcaccgaagcactgaaacagggcggcatcaccctgatgatggaccgtctctctaacccgg
cgaaactgcgtgcttatgcgcttctgaacagctgaaagagatcatggcaccctgttccagaaacatatggacgacatcatctccggc
gaattctcttccgtatgatggcggactgggccaacgatgataagaaactgctgacctggcgtgaagagaccggcaaaaccgcgttt
gaaaccgcgccgcagtatgaaggcaaatcggcgagcaggagtacttcgataaaggcgtactgatgattgcgatggtgaaagcgg
gcgttgaactggcgttcgaaaccatggtcgattccggcatcattgaagagtctgcatattatgaatcactgcacgagctgccgctgattg
ccaacaccatcgcccgtaagcgtctgtacgaaatgaacgtggttatctctgataccgctgagtacggta

Figure 22A actatctgttctcttacgcttgtgtgccgttgctgaaaccgtttatggcagagctgcaaccgggcgacctgggtaaagctattccggaagg
cgcggtagataacgggcaactgcgtgatgtgaacgaagcgattcgcagccatgcgattgagcaggtaggtaagaaactgcgcggc
tatatgacagatatgaaacgtattgctgttgcgggttaacccggaaggagatataccatgcctaagtaccgttccgccaccaccactca
tggtcgtaatatggcgggtgctcgtgcgctgtggcgcgccaccggaatgaccgacgccgatttcggtaagccgattatcgcggttgtga
actcgttcacccaatttgtaccgggtcacgtccatctgcgcgatctcggtaaactggtcgccgaacaaattgaagcggctggcggcgtt
gccaaagagttcaacaccattgcggtggatgatgggattgccatgggccacgggggatgctttattcactgccatctcgcgaactgat
cgctgattccgttgagtatatggtcaacgcccactgcgccgacgccatggtctgcatctctaactgcgacaaaatcaccccggggatg
ctgatggcttccctgcgcctgaatattccggtgatctttgtttccggcggcccgatggaggccgggaaaaccaaactttccgatcagatc
atcaagctcgatctggttgatgcgatgatccagggcgcagacccgaaagtatctgactcccagagcgatcaggttgaacgttccgcgt
gtccgacctgcggttcctgctccgggatgtttaccgctaactcaatgaactgcctgaccgaagcgctgggcctgtcgcagccgggcaa
cggctcgctgctggcaacccacgccgaccgtaagcagctgttccttaatgctggtaaacgcattgttgaattgaccaaacgttattacga
gcaaaacgacgaaagtgcactgccgcgtaatatcgccagtaaggcggcgtttgaaaacgccatgacgctggatatcgcgatgggtg
gatcgactaacaccgtacttcacctgctggcggcggcgcaggaagcggaaatcgacttcaccatgagtgatatcgataagctttcccg
caaggttccacagctgtgtaaagttgcgccgagcacccagaaataccatatggaagatgttcaccgtgctggtggtgttatcggtattct
cggcgaactggatcgcgcggggttactgaaccgtgatgtgaaaaacgtacttggcctgacgttgccgcaaacgctggaacaatacg
acgttatgctgacccaggatgacgcggtaaaaaatatgttccgcgcaggtcctgcaggcattcgtaccacacaggcattctcgcaag
attgccgttgggatacgctggacgacgatcgcgccaatggctgtatccgctcgctggaacacgcctacagcaaagacggcggcctg
gcggtgctctacggtaactttgcggaaaacggctgcatcgtgaaaacggcaggcgtcgatgacagcatcctcaaattcaccggcccg
gcgaaagtgtacgaaagccaggacgatgcggtagaagcgattctcggcggtaaagttgtcgccggagatgtggtagtaattcgctat
gaaggcccgaaaggcggtccggggatgcaggaaatgctctacccaaccagcttcctgaaatcaatgggtctcggcaaagcctgtg
cgctgatcaccgacggtcgtttctctggtggcacctctggtctttccatcggccacgtctcaccggaagcggcaagcggcggcagcatt
ggcctgattgaagatggtgacctgatcgctatcgacatcccgaaccgtggcattcagttacaggtaagcgatgccgaactggcggcg
cgtcgtgaagcgcaggacgctcgaggtgacaaagcctggacgccgaaaaatcgtaacgtcaggtctcctttgccctgcgtgcttat
gccagcctggcaaccagcgccgacaaaggcgcggtgcgcgataaatcgaaactgggggttaaacgcgtgctagaggcatcaa
ataaaacgaaaggctcagtcgaaagactgggccttctgttttatctgttgtttgtcggtgaacgctctcctgagtaggacaaatccgccgc
cctagacctaggggatatattccgcttcctcgctcactgactcgctacgctcggtcgttcgactgcggcgagcggaaatggcttacgaa
cggggcggagattcctggaagatgccaggaagatacttaacagggaagtgagagggccgcggcaaagccgttttccataggctc
cgccccctgacaagcatcacgaaatcgacgctcaaatcagtggtggcgaaacccgacaggactataaagataccaggcgtttcc
ccctggcggctccctcgtgcgctctcctgttcctgcctttcggtttaccggtgtcattccgctgttatggccgcgtttgtctcattccacgcctga
cactcagttccgggtaggcagttcgctccaagctggactgtatgcacgaaccccccgttcagtccgaccgctgcgccttatccggtaac
tatcgtcttgagtccaacccggaaagacatgcaaaagcaccactggcagcagccactggtaattgatttagaggagttagtcttgaag
tcatgcgccggttaaggctaaactgaaaggacaagttttggtgactgcgctcctccaagccagttacctcggttcaaagagttggtagct
cagagaaccttcgaaaaaccgccctgcaaggcggtttttttcgttttcagagcaagagattacgcgcagaccaaaacgatctcaagaa
gatcatcttattaatcagataaaatatttctagatttcagtgcaatttatctcttcaaatgtagcacctgaagtcagccccatacgatataagt
tgttactagtgcttggattctcaccaataaaaaacgcccggcggcaaccgagcgttctgaacaaatccagatggagttctgaggtcatt
actggatctatcaacaggagtccaagcgagct (pSA55; SEQ ID NO: 33)

Ctcgagaattgtgagcggataacaattgacattgtgagcggataacaagatactgagcacatcagcaggacgcactgaccgaattc
attaaagaggagaaaggtaccatgtatacagtaggagattacctattagaccgattacacgagttaggaattgaagaaattttggagt
ccctggagactataacttacaattttagatcaaattatttcccacaaggatatgaaatgggtcggaaatgctaatgaattaaatgcttcat
atatggctgatggctatgctcgtactaaaaaagctgccgcatttcttacaacctttggagtaggtgaattgagtgcagttaatggattagca
ggaagttacgccgaaaatttaccagtagtagaaatagtgggatcacctacatcaaaagttcaaaatgaaggaaaatttgttcatcata
cgctggctgacggtgattttaaacactttatgaaaatgcacgaacctgttacagcagctcgaactttactgacagcagaaaatgcaacc
gttgaaattgaccgagtacttctgcactattaaaagaaagaaaacctgtctatatcaacttaccagttgatgttgctgctgcaaaagcag
agaaaccctcactcccttgaaaaaggaaaactcaacttcaaatacaagtgaccaagaaattttgaacaaaattcaagaaagcttga
aaaatgccaaaaaaccaatcgtgattacaggacatgaaataattagttttggcttagaaaaaaacagtcactcaatttatttcaaagaca
aaactacctattacgacattaaactttggtaaaagttcagttgatgaagccctcccttcatttttaggaatctataatggtacactctcagag
cctaatcttaaagaattcgtggaatcagccgacttcatcttgatgcttggagttaaactcacagactcttcaacaggagccttcactcatc
atttaaatgaaaataaaatgatttcactgaatatagatgaaggaaaaatatttaacgaaagaatccaaaattttgattttgaatccctcatc
tcctctctcttagacctaagcgaaatagaatacaaaggaaaatatatcgataaaaagcaagaagactttgttccatcaaatgcgcttta
tcacaagaccgcctatggcaagcagttgaaaacctaactcaaagcaatgaaacaatcgttgctgaacaagggacatcattctttggc
gcttcatcaatttcttaaaaatcaaagagtcatttttattggtcaacccttatggggatcaattggatatacattcccagcagcattaggaagc
caaattgcagataaagaaagcagacaccttttatttattggtgatggttcacttcaacttacagtgcaagaattaggattagcaatcaga
gaaaaaattaatccaatttgctttattatcaataatgatggttatacagtcgaaagagaaattcatggaccaaatcaaagctacaatgat
attccaatgtggaattactcaaaattaccagaatcgtttggagcaacagaagatcgagtagtctcaaaaatcgttagaactgaaaatg
aatttgtgtctgtcatgaaagaagctcaagcagatccaaatagaatgtactggattgagttaattttggcaaaagaaggtgcaccaaaa
gtactgaaaaaaatgggcaaactatttgctgaacaaaatataatcataagcatgcaggagatataccatgtctattccagaaactcaaa
aagccattatcttctacgaatccaacggcaagttggagcataaggatatcccagttccaaagccaaagcccaacgaattgttaatcaa
cgtcaagtactctggtgtctgccacaccgatttgcacgcttggcatggtgactggccattgccaactaagttaccattagttggtggtcac
gaaggtgccggtgtcgttgtcggcatgggtgaaaacgttaagggctggaagatcggtgactacgccggtatcaaatggttgaacggtt
cttgtatggcctgtgaatactgtgaattgggtaacgaatccaactgtcctcacgctgacttgtctggttacacccacgacggttctttccaa
gaatacgctaccgctgacgctgttcaagccgctcacattcctcaaggtactgacttggctgaagtcgcgccaatcttgtgtgctggtatca
ccgtatacaaggctttgaagtctgccaacttgagagcaggccactgggcggccatttctggtgctgctggtggtctaggttcttggctgtt
caatatgctaaggcgatgggttacagagtcttaggtattgatggtggtccaggaaaggaagaattgttacctcgctcggtggtgaagta
ttcatcgacttcaccaaagagaaggacattgttagcgcagtcgttaaggctaccaacggcggtgcccacggtatcatcaatgtttccgtt
tccgaagccgctatcgaagcttctaccagatactgtagggcgaacggtactgttgtcttggttggtttgccagccggtgcaaagtgctcct
ctgatgtcttcaaccacgttgtcaagtctatctccattgtcggctcttacgtggggaacagagctgataccagagaagccttagatttctttg
ccagaggtctagtcaagtctccaataaaggtagttggcttatccagtttaccagaaatttacgaaaagatggagaagggccaaattgct
ggtagatacgttgttgacacttctaaataatctagaggcatcaaataaaacgaaaggctcagtcgaaagactgggcctttcgttttatctg
ttgtttgtcggtgaacgctctcctgagtaggacaaatccgccgccctagacctaggcgttcggctgcggcgagcggtatcagctcactc
aaaggcggtaatacggttatccacagaatcaggggataacgcaggaaagaacatgtgagcaaaaggccagcaaaaggccagg
aaccgtaaaaaggccgcgttgctggcgtttttccataggctccgcccccctgacgagcatcacaaaaatcgacgctcaagtcagagg
tggcgaaacccgacaggactataaagataccaggcgtttccccctggaagctccctcgtgcgctctcctgttccgaccctgccgcttac
cggatacctgtccgcctttctcccttcgggaagcgtggcgctttctcaatgctcacgctgtaggtatctcagttcggtgtaggtcgttcgctc
caagctgggctgtgtgcacgaaccccccgttcagcccgaccgctgcgccttatccggtaactatcgtcttgagtccaacccggtaaga
cacgacttatcgccactggcagcagccactggtaacaggattagcagagcgaggtatgtaggcggtgctacagagttcttgaagtgg
tggcctaactacggctacactagaaggacagtatttggtatctgcgctctgctgaagccagttaccttcggaaaaagagttggtagctctt
gatccggcaaacaaaccaccgctggtagcggtggtttttttgtttgcaagcagcagattacgcgcagaaaaaaggatctcaagaag
atcctttgatcttttctacggggtctgacgctcagtggaacgaaaactcacgttaagggattttggtcatgactagtgcttggattctcacca
ataaaaaacgcccggcggcaaccgagcgttctgaacaaatccagatggagttctgaggtcattactggatctatcaacaggagtcca
agcgagctcgtaaacttggtctgacagttaccaatgcttaatcagtgaggcacctatctcagcgatctgtctatttcgttcatccatagttgc
ctgactccccgtcgtgtagataactacgatacgggagggcttaccatctggccccagtgctgcaatgatac

FIGURE 24A cgcgagacccacgctcaccggctccagatttatcagcaataaaccagccagccggaagggccgagcgcagaagtggtcctgcaa
ctttatccgcctccatccagtctattaattgttgccgggaagctagagtaagtagttcgccagttaatagtttgcgcaacgttgttgccattgc
tacaggcatcgtggtgtcacgctcgtcgtttggtatggcttcattcagctccggttcccaacgatcaaggcgagttacatgatcccccatgt
tgtgcaaaaaagcggttagctccttcggtcctccgatcgttgtcagaagtaagttggccgcagtgttatcactcatggttatggcagcact
gcataattctcttactgtcatgccatccgtaagatgctttctgtgactggtgagtactcaaccaagtcattctgagaatagtgtatgcggcg
accgagttgctcttgcccggcgtcaatacgggataataccgcgccacatagcagaactttaaaagtgctcatcattggaaaacgttctt
cggggcgaaaactctcaaggatcttaccgctgttgagatccagttcgatgtaacccactcgtgcacccaactgatcttcagcatcttttac
tttcaccagcgtttctgggtgagcaaaaacaggaaggcaaaatgccgcaaaaaagggaataagggcgacacggaaatgttgaat
actcatactcttccttttcaatattattgaagcatttatcagggttattgtctcatgagcggatacatatttgaatgtatttagaaaaataaaca
aataggggttccgcgcacatttccccgaaaagtgccacctgacgtctaagaaaccattattatcatgacattaacctataaaaataggc
gtatcacgaggccctttcgtcttcac

FIGURE 24B (pSA69; SEQ ID NO: 34)

Taagaaaccattattatcatgacattaacctataaaaataggcgtatcacgaggcccttcgtcttcacctcgagaattgtgagcggata
acaattgacattgtgagcggataacaagatactgagcacatcagcaggacgcactgaccgaattcattaaagaggagaaaggtac
aatgttgacaaaagcaacaaaagaacaaaaatcccttgtgaaaaacagaggggcggagcttgttgttgattgcttagtggagcaag
gtgtcacacatgtatttggcattccaggtgcaaaaattgatgcggtatttgacgctttacaagataaaggacctgaaattatcgttgcccg
gcacgaacaaaacgcagcattcatggcccaagcagtcggccgtttaactggaaaaccgggagtcgtgttagtcacatcaggaccg
ggtgcctctaacttggcaacaggcctgctgacagcgaacactgaaggagaccctgtcgttgcgcttgctggaaacgtgatccgtgca
gatcgtttaaaacggacacatcaatctttggataatgcggcgctattccagccgattacaaaatacagtgtagaagttcaagatgtaaa
aaatataccggaagctgttacaaatgcatttaggatagcgtcagcagggcaggctggggccgcttttgtgagctttccgcaagatgttgt
gaatgaagtcacaaatacgaaaaacgtgcgtgctgttgcagcgccaaaactcggtcctgcagcagatgatgcaatcagtgcggcca
tagcaaaaatccaaacagcaaaacttcctgtcgttttggtcggcatgaaaggcggaagaccggaagcaattaaagcggttcgcaag
cttttgaaaaaggttcagcttccatttgttgaaacatatcaagctgccggtacccttctagagatttagaggatcaatattttggccgtatcg
gtttgttccgcaaccagcctggcgatttactgctagagcaggcagatgttgttctgacgatcggctatgacccgattgaatatgatccgaa
attctggaatatcaatggagaccggacaattatccatttagacagagattatcgctgacattgatcatgcttaccagcctgatcttgaattga
tcggtgacattccgtccacgatcaatcatatcgaacacgatgctgtgaaagtggaatttgcagagcgtgagcagaaaatcctttctgatt
taaaacaatatatgcatgaaggtgagcaggtgcctgcagattggaaatcagacagagcgcaccctcttgaaatcgttaaagagttgc
gtaatgcagtcgatgatcatgttacagtaacttgcgatatcggttcgcacgccatttggatgtcacgttatttccgcagctacgagccgtta
acattaatgatcagtaacggtatgcaaacactcggcgttgcgcttccttgggcaatcggcgcttcattggtgaaaccgggagaaaaag
tggttttctgtctctggtgacggcggtttcttattctcagcaatggaattagagacagcagttcgactaaaagcaccaattgtacacattgtat
ggaacgacagcacatatgacatggttgcattccagcaattgaaaaaatataaccgtacatctgcggtcgatttcggaaatatcgatatc
gtgaaatatgcggaaagcttcggagcaactggcttgcgcgtagaatcaccagaccagctggcagatgttctgcgtcaaggcatgaac
gctgaaggtcctgtcatcatcgatgtcccggttgactacagtgataacattaatttagcaagtgacaagcttccgaaagaattcgggga
actcatgaaaacgaaagctctctaggtcgacgaggaatcaccatggctaactacttcaatacactgaatctgcgccagcagctggca
cagctgggcaaatgtcgctttatgggccgcgatgaattcgccgatggcgcgagctaccttcagggtaaaaaagtagtcatcgtcggct
gtggcgcacagggtctgaaccagggcctgaacatgcgtgattctggtctcgatatctcctacgctctgcgtaaagaagcgattgccga
gaagcgcgcgtcctggcgtaaagcgaccgaaaatggttttaaagtgggtacttacgaagaactgatcccacaggcggatctggtgat
taacctgacgccggacaagcagcactctgatgtagtgcgcaccgtacagccactgatgaaagacggcgcggcgctgggctactcg
cacggtttcaacatcgtcgaagtgggcgagcagatccgtaaagatatcaccgtagtgatggttgcgccgaaatgcccaggcaccga
agtgcgtgaagagtacaaacgtgggttcggcgtaccgacgctgattgccgttcacccggaaaacgatccgaaaggcgaaggcatg
gcgattgccaaagcctgggcggctgcaaccggtggtcaccgtgcgggtgtgctggaatcgtccttcgttgcggaagtgaaatctgacc
tgatgggcgagcaaaccatcctgtgcggtatgttgcaggctggctctctgctgtgcttcgacaagctggtggaagaaggtaccgatcca
gcatacgcagaaaaactgattcagttcggttgggaaaccatcaccgaagcactgaaacagggcggcatcaccctgatgatggacc
gtctctctaacccggcgaaactgcgtgcttatgcgctttctgaacagctgaaagagatcatggcaccctgttccagaaacatatggac
gacatcatctccggcgaattctcttccggtatgatggcggactgggccaacgatgataagaaactgctgacctggcgtgaagagacc
ggcaaaaccgcgtttgaaaccgcgccgcagtatgaaggcaaaatcggcgagcaggagtacttcgataaaggcgtactgatgattg
cgatggtgaaagcgggcgttgaactggcgttcgaaaccatggtcgattccggcatcattgaagagtctgcatattatgaatcactgcac
gagctgccgctgattgccaacaccatcgcccgtaagcgtctgtacgaaatgaacgtggttatctctgataccgctgagtacggtaacta
tctgttctcttacgcttgtgtgccgttgctgaaaccgttatggcagagctgcaaccgggcgacctgggtaaagctattccggaaggcgc
ggtagataacgggcaactgcgtgatgtgaacgaagcgattcgcagccatgcgattgagcaggtaggtaagaaactgcgcggctata
tgacagatatgaaacgtattgctgttgcgggttaacccggaaggagatataccatgcctaagtaccgttccgccaccaccactcatggt
cgtaatatggcggtgctcgtgcgctgtggcgcgccaccggaatgaccgacgccgattcggtaagccgattatcgcggttgtgaact
cgttcacccaatttgtaccgggtcacgtccatctgcgcgatctcggtaaactggtcgccgaacaaattgaagcggctggcggcgttgcc
aaagagttcaacaccattgcggtggatgatgggattgccatgggccacggggggatgctttattcactgccatctcgcgaactgatcgc
tgattccgttgagtatatggtcaacgcccactgcgccgacgccatggtctgcatctctaactgcgacaaaatcaccccggggatgctga
tggcttccctgcgcctgaatattccggtgatctttgtttccggcggcccgatggaggcccgggaaaaccaaacttcccgatcagatcatca
agctcgatctggttgatgcgatgatccagggcgcagacccgaaagtatctgactccagagcgatc

FIGURE 26A aggttgaacgttccgcgtgtccgacctgcggttcctgctccgggatgtttaccgctaactcaatgaactgcctgaccgaagcgctgggc
ctgtcgcagccgggcaacggctcgctgctggcaacccacgccgaccgtaagcagctgttccttaatgctggtaaacgcattgttgaatt
gaccaaacgttattacgagcaaaacgacgaaagtgcactgccgcgtaatatcgccagtaaggcggcgtttgaaaacgccatgacg
ctggatatcgcgatgggtggatcgactaacaccgtacttcacctgctggcggcggcgcaggaagcggaaatcgacttcaccatgagt
gatatcgataagctttcccgcaaggttccacagctgtgtaaagttgcgccgagcacccagaaataccatatggaagatgttcaccgtg
ctggtggtgttatcggtattctcggcgaactggatcgcgcggggttactgaaccgtgatgtgaaaaacgtacttggcctgacgttgccgc
aaacgctggaacaatacgacgttatgctgacccaggatgacgcggtaaaaaatatgttccgcgcaggtcctgcaggcattcgtacca
cacaggcattctcgcaagattgccgttgggatacgctggacgacgatcgcgccaatggctgtatccgctcgctggaacacgcctaca
gcaaagacggcggcctggcggtgctctacggtaactttgcggaaaacggctgcatcgtgaaaacggcaggcgtcgatgacagcat
cctcaaattcaccggcccggcgaaagtgtacgaaagccaggacgatgcggtagaagcgattctcggcggtaaagttgtcgccgga
gatgtggtagtaattcgctatgaaggcccgaaaggcggtccggggatgcaggaaatgctctacccaaccagcttcctgaaatcaatg
ggtctcggcaaagcctgtgcgctgatcaccgacggtcgtttctctggtggcacctctggtctttccatcggccacgtctcaccggaagcg
gcaagcggcggcagcattggcctgattgaagatggtgacctgatcgctatcgacatcccgaaccgtggcattcagttacaggtaagc
gatgccgaactggcggcgcgtcgtgaagcgcaggacgctcgaggtgacaaagcctggacgccgaaaaatcgtgaacgtcaggtc
tcctttgccctgcgtgcttatgccagcctggcaaccagcgccgacaaaggcgcggtgcgcgataaatcgaaactggggggttaaacg
cgtgctagaggcatcaaataaaacgaaaggctcagtcgaaagactgggcctttcgttttatctgttgtttgtcggtgaacgctctcctgag
taggacaaatccgccgccctagacctaggggatatattccgcttcctcgctcactgactcgctacgctcggtcgttcgactgcggcgag
cggaaatggcttacgaacggggcggagatttcctggaagatgccaggaagatacttaacagggaagtgagagggccgcggcaaa
gccgttttccataggctccgccccctgacaagcatcacgaaatctgacgctcaaatcagtggtggcgaaaccgacaggactata
aagataccaggcgtttccccctggcggctccctcgtgcgctctcctgttcctgcctttcggtttaccggtgtcattccgctgttatgccgcgt
ttgtctcattccacgcctgacactcagtccgggtaggcagttcgctccaagctggactgtatgcacgaaccccccgttcagtccgaccg
ctgcgccttatccggtaactatcgtcttgagtccaacccggaaagacatgcaaaagcaccactggcagcagccactggtaattgatta
gaggagttagtcttgaagtcatgcgccggttaaggctaaactgaaaggacaagttttggtgactgcgctcctccaagccagttacctcg
gttcaaagagttggtagctcagagaaccttcgaaaaaccgccctgcaaggcggttttttcgttttcagagcaagagagattacgcgcagac
caaaacgatctcaagaagatcatcttattaatcagataaaatatttctagatttcagtgcaatttatctcttcaaatgtagcacctgaagtca
gccccatacgatataagttgttactagtgcttggattctcaccaataaaaaacgcccgcggcaaccgagcgttctgaacaaatccag
atggagttctgaggtcattactggatctatcaacaggagtccaagcgagctctcgaaccccagagtcccgctcagaagaactcgtca
agaaggcgatagaaggcgatgcgctgcgaatcgggagcggcgataccgtaaagcacgaggaagcggtcagcccattcgccgcc
aagctcttcagcaatatcacgggtagccaacgctatgtcctgatagcggtccgccacacccagccggccacagtcgatgaatccag
aaaagcggccattttccaccatgatattcggcaagcaggcatcgccatgggtcacgacgagatcctcgccgtcgggcatgcgcgcct
tgagcctggcgaacagttcggctggcgcgagcccctgatgctcttcgtccagatcatcctgatcgacaagaccggcttccatccgagt
acgtgctcgctcgatgcgatgtttcgcttggtggtcgaatgggcaggtagccggatcaagcgta
tgcagccgccgcattgcatcagccatgatggatactttctcggcaggagcaaggtgagatgacaggagatcctgccccggcacttcg
cccaatagcagccagtcccttcccgcttcagtgacaacgtcgagcacagctgcgcaaggaacgcccgtcgtggccagccacgata
gccgcgctgcctcgtcctgcagttcattcagggcaccggacaggtcggtcttgacaaaaagaaccgggcgcccctgcgctgacagc
cggaacacggcggcatcagagcagccgattgtcgttgtgcccagtcatagccgaatagcctctccacccaagcggccggagaac
ctgcgtgcaatccatcttgttcaatcatgcgaaacgatcctcatcctgtctcttgatcagatcttgatccctgcgccatcagatccttggcg
gcaagaaagccatccagtttactttgcagggcttcccaaccttaccagagggcgccccagctggcaattccgacgtc

FIGURE 26B

SEQUENCE LISTING

```
<160> NUMBER OF SEQ ID NOS: 35

<210> SEQ ID NO 1
<211> LENGTH: 62
<212> TYPE: DNA
<213> ORGANISM: Artificial Sequence
<220> FEATURE:
<223> OTHER INFORMATION: Synthetic primer

<400> SEQUENCE: 1
gttatctagt tgtgcaaaac atgctaatgt agccaccaaa tcgtgtaggc tggagctgct    60
tc                                                                  62

<210> SEQ ID NO 2
<211> LENGTH: 61
<212> TYPE: DNA
<213> ORGANISM: Artificial Sequence
<220> FEATURE:
<223> OTHER INFORMATION: Synthetic primer

<400> SEQUENCE: 2
gcagtttcac cttctacata atcacgaccg tagtaggtat cattccgggg atccgtcgac    60
c                                                                   61

<210> SEQ ID NO 3
<211> LENGTH: 65
<212> TYPE: DNA
<213> ORGANISM: Artificial Sequence
<220> FEATURE:
<223> OTHER INFORMATION: Synthetic primer

<400> SEQUENCE: 3
ttggctgaac ggtagggtat attgtcacca cctgttggaa tgttggtgta ggctggagct    60
gcttc                                                               65

<210> SEQ ID NO 4
<211> LENGTH: 65
<212> TYPE: DNA
<213> ORGANISM: Artificial Sequence
<220> FEATURE:
<223> OTHER INFORMATION: Synthetic primer

<400> SEQUENCE: 4
```

```
gtatccagca taccttccag cgcgttctgt tcaaatgcgc tcaggattcc ggggatccgt    60
cgacc                                                                65

<210> SEQ ID NO 5
<211> LENGTH: 65
<212> TYPE: DNA
<213> ORGANISM: Artificial Sequence
<220> FEATURE:
<223> OTHER INFORMATION: Synthetic primer

<400> SEQUENCE: 5
cttaacccgc aacagcaata cgtttcatat ctgtcatata gccgcattcc ggggatccgt    60
cgacc                                                                65

<210> SEQ ID NO 6
<211> LENGTH: 60
<212> TYPE: DNA
<213> ORGANISM: Artificial Sequence
<220> FEATURE:
<223> OTHER INFORMATION: Synthetic primer

<400> SEQUENCE: 6
caccgagatc ctggtcaaag tgggcgacaa agttgaagcc gtgtaggctg gagctgcttc    60

<210> SEQ ID NO 7
<211> LENGTH: 60
<212> TYPE: DNA
<213> ORGANISM: Artificial Sequence
<220> FEATURE:
<223> OTHER INFORMATION: Synthetic primer

<400> SEQUENCE: 7
gcggtggtcg aaggagagag aaatcggcag catcagacgc attccgggga tccgtcgacc    60

<210> SEQ ID NO 8
<211> LENGTH: 45
<212> TYPE: DNA
<213> ORGANISM: Artificial Sequence
<220> FEATURE:
<223> OTHER INFORMATION: Synthetic primer

<400> SEQUENCE: 8
gtcggtgaac gctctcctga gtagggtgta ggctggagct gcttc                    45

<210> SEQ ID NO 9
<211> LENGTH: 69
<212> TYPE: DNA
<213> ORGANISM: Artificial Sequence
<220> FEATURE:
<223> OTHER INFORMATION: Synthetic primer

<400> SEQUENCE: 9
cacaacatca cgaggaatca ccatggctaa ctacttcaat acaccacgag gccctttcgt    60
cttcacctc                                                            69

<210> SEQ ID NO 10
<211> LENGTH: 67
<212> TYPE: DNA
<213> ORGANISM: Artificial Sequence
<220> FEATURE:
<223> OTHER INFORMATION: Synthetic primer

<400> SEQUENCE: 10
```

```
gttatctagt tgtgcaaaac atgctaatgt agccaccaaa tccacgaggc cctttcgtct    60
tcacctc                                                              67
```

<210> SEQ ID NO 11
<211> LENGTH: 30
<212> TYPE: DNA
<213> ORGANISM: Artificial Sequence
<220> FEATURE:
<223> OTHER INFORMATION: Synthetic primer

<400> SEQUENCE: 11

```
ttaaggtacc atgcgaattg gcataccaag                                     30
```

<210> SEQ ID NO 12
<211> LENGTH: 31
<212> TYPE: DNA
<213> ORGANISM: Artificial Sequence
<220> FEATURE:
<223> OTHER INFORMATION: Synthetic primer

<400> SEQUENCE: 12

```
taatgtcgac gcaatcctga aagctctgta a                                   31
```

<210> SEQ ID NO 13
<211> LENGTH: 42
<212> TYPE: DNA
<213> ORGANISM: Artificial Sequence
<220> FEATURE:
<223> OTHER INFORMATION: Synthetic primer

<400> SEQUENCE: 13

```
gctcactcaa aggcggtaat acgtgtaggc tggagctgct tc                       42
```

<210> SEQ ID NO 14
<211> LENGTH: 42
<212> TYPE: DNA
<213> ORGANISM: Artificial Sequence
<220> FEATURE:
<223> OTHER INFORMATION: Synthetic primer

<400> SEQUENCE: 14

```
gaagcagctc cagcctacac gtattaccgc ctttgagtga gc                       42
```

<210> SEQ ID NO 15
<211> LENGTH: 65
<212> TYPE: DNA
<213> ORGANISM: Artificial Sequence
<220> FEATURE:
<223> OTHER INFORMATION: Synthetic primer

<400> SEQUENCE: 15

```
ccattctgtt gcttttatgt ataagaacag gtaagcccta ccatgattcc ggggatccgt    60
cgacc                                                                65
```

<210> SEQ ID NO 16
<211> LENGTH: 64
<212> TYPE: DNA
<213> ORGANISM: Artificial Sequence
<220> FEATURE:
<223> OTHER INFORMATION: Synthetic primer

<400> SEQUENCE: 16

```
ccgataggct tccgccatcg tcgggtagtt aaaggtggtg ttgagtgtag gctggagctg    60
cttc                                                                 64
```

<210> SEQ ID NO 17
<211> LENGTH: 70
<212> TYPE: DNA
<213> ORGANISM: Artificial Sequence
<220> FEATURE:
<223> OTHER INFORMATION: Synthetic primer

<400> SEQUENCE: 17
gcctttattg tacgcttttt actgtacgat ttcagtcaaa tctaacacga ggccctttcg    60
tcttcacctc                                                          70

<210> SEQ ID NO 18
<211> LENGTH: 65
<212> TYPE: DNA
<213> ORGANISM: Artificial Sequence
<220> FEATURE:
<223> OTHER INFORMATION: Synthetic primer

<400> SEQUENCE: 18
aagtacgcag taaataaaaa atccacttaa gaaggtaggt gttacattcc ggggatccgt    60
cgacc                                                               65

<210> SEQ ID NO 19
<211> LENGTH: 65
<212> TYPE: DNA
<213> ORGANISM: Artificial Sequence
<220> FEATURE:
<223> OTHER INFORMATION: Synthetic primer

<400> SEQUENCE: 19
ccattctgtt gcttttatgt ataagaacag gtaagcccta ccatggagaa ttgtgagcgg    60
ataac                                                               65

<210> SEQ ID NO 20
<211> LENGTH: 42
<212> TYPE: DNA
<213> ORGANISM: Artificial Sequence
<220> FEATURE:
<223> OTHER INFORMATION: Synthetic primer

<400> SEQUENCE: 20
gcaatcctga aagctctgta acattccggg gatccgtcga cc                      42

<210> SEQ ID NO 21
<211> LENGTH: 42
<212> TYPE: DNA
<213> ORGANISM: Artificial Sequence
<220> FEATURE:
<223> OTHER INFORMATION: Synthetic primer

<400> SEQUENCE: 21
ggtcgacgga tccccggaat gttacagagc tttcaggatt gc                      42

<210> SEQ ID NO 22
<211> LENGTH: 28
<212> TYPE: DNA
<213> ORGANISM: Artificial Sequence
<220> FEATURE:
<223> OTHER INFORMATION: Synthetic primer

<400> SEQUENCE: 22
gtgaaaacgc aggttaagct ggcttagc                                      28

<210> SEQ ID NO 23
<211> LENGTH: 27
<212> TYPE: DNA
<213> ORGANISM: Artificial Sequence
<220> FEATURE:
<223> OTHER INFORMATION: Synthetic primer

<400> SEQUENCE: 23
atactgttat ctggctttta gtaagcc                                27

<210> SEQ ID NO 24
<211> LENGTH: 26
<212> TYPE: DNA
<213> ORGANISM: Artificial Sequence
<220> FEATURE:
<223> OTHER INFORMATION: Synthetic primer

<400> SEQUENCE: 24
gacataacat aagctggagc aggtag                                 26

<210> SEQ ID NO 25
<211> LENGTH: 24
<212> TYPE: DNA
<213> ORGANISM: Artificial Sequence
<220> FEATURE:
<223> OTHER INFORMATION: Synthetic primer

<400> SEQUENCE: 25
tacaacctgt ggcgctgatg cgtc                                   24

<210> SEQ ID NO 26
<211> LENGTH: 25
<212> TYPE: DNA
<213> ORGANISM: Artificial Sequence
<220> FEATURE:
<223> OTHER INFORMATION: Synthetic primer

<400> SEQUENCE: 26
caggagcctg tgtagcgttt atagg                                  25

<210> SEQ ID NO 27
<211> LENGTH: 25
<212> TYPE: DNA
<213> ORGANISM: Artificial Sequence
<220> FEATURE:
<223> OTHER INFORMATION: Synthetic primer

<400> SEQUENCE: 27
tcatgttcct gtagggtgcc atcag                                  25

<210> SEQ ID NO 28
<211> LENGTH: 5336
<212> TYPE: DNA
<213> ORGANISM: Artificial Sequence
<220> FEATURE:
<223> OTHER INFORMATION: Synthetic polynucleotide

<400> SEQUENCE: 28
taagaaacca ttattatcat gacattaacc tataaaaata ggcgtatcac gaggcccttt      60
cgtcttcacc tcgagaattg tgagcggata acaattgaca ttgtgagcgg ataacaagat    120
actgagcaca tcagcaggac gcactgaccg aattcattaa agaggagaaa ggtacaatgt    180
tgacaaaagc aacaaaagaa caaaaatccc ttgtgaaaaa cagaggggcg agcttgttg     240 ttgattgctt agtggagcaa ggtgtcacac atgtatttgg cattccaggt gcaaaaattg    300

```
atgcggtatt tgacgcttta caagataaag gacctgaaat tatcgttgcc cggcacgaac    360
aaaacgcagc attcatggcc caagcagtcg gccgtttaac tggaaaaccg ggagtcgtgt    420
tagtcacatc aggaccgggt gcctctaact tggcaacagg cctgctgaca gcgaacactg    480
aaggagaccc tgtcgttgcg cttgctggaa acgtgatccg tgcagatcgt ttaaaacgga    540
cacatcaatc tttggataat gcggcgctat ccagccgat tacaaaatac agtgtagaag     600
ttcaagatgt aaaaaatata ccggaagctg ttacaaatgc atttaggata gcgtcagcag    660
ggcaggctgg ggccgctttt gtgagctttc gcaagatgt tgtgaatgaa gtcacaaata     720
cgaaaaacgt gcgtgctgtt gcagcgccaa aactcggtcc tgcagcagat gatgcaatca    780
gtgcggccat agcaaaaatc caaacagcaa aacttcctgt cgttttggtc ggcatgaaag    840
gcggaagacc ggaagcaatt aaagcggttc gcaagctttt gaaaaaggtt cagcttccat    900
ttgttgaaac atatcaagct gccggtaccc tttctagaga tttagaggat caatattttg    960
gccgtatcgg tttgttccgc aaccagcctg gcgatttact gctagagcag gcagatgttg    1020
ttctgacgat cggctatgac ccgattgaat atgatccgaa attctggaat atcaatggag    1080
accggacaat tatccattta gacgagatta tcgctgacat tgatcatgct taccagcctg    1140
atcttgaatt gatcggtgac attccgtcca cgatcaatca tatcgaacac gatgctgtga    1200
aagtggaatt tgcagagcgt gagcagaaaa tcctttctga tttaaaacaa tatatgcatg    1260
aaggtgagca ggtgcctgca gattggaaat cagacagagc gcaccctctt gaaatcgtta    1320
aagagttgcg taatgcagtc gatgatcatg ttacagtaac ttgcgatatc ggttcgcacg    1380
ccatttggat gtcacgttat ttccgcagct acgagccgtt aacattaatg atcagtaacg    1440
gtatgcaaac actcggcgtt gcgcttcctt gggcaatcgg cgcttcattg gtgaaaccgg    1500
gagaaaaagt ggtttctgtc tctggtgacg gcggtttctt attctcagca atggaattag    1560
agacagcagt tcgactaaaa gcaccaattg tacacattgt atggaacgac agcacatatg    1620
acatggttgc attccagcaa ttgaaaaaat ataaccgtac atctgcggtc gatttcggaa    1680
atatcgatat cgtgaaatat gcggaaagct tcggagcaac tggcttgcgc gtagaatcac    1740
cagaccagct ggcagatgtt ctgcgtcaag gcatgaacgc tgaaggtcct gtcatcatcg    1800
atgtcccggt tgactacagt gataacatta atttagcaag tgacaagctt ccgaaagaat    1860
tcggggaact catgaaaacg aaagctctct aggtcgacga ggagacaaca ttatggcgaa    1920
ttatttcaac actctgaacc tgcgtcaaca actggcgcaa ctgggtaagt gccgtttcat    1980
gggtcgtgac gagtttgcgg acggtgcttc ttatctgcaa gcaagaaagg ttgttattgt    2040
tggttgcggt gcgcaaggcc tgaatcaagg tctgaatatg cgcgacagcg gcctggacat    2100
tagctatgcg ctgcgcaagg aggctatcgc ggaaaaacgt gctagctggc gcaaggctac    2160
tgagaacggc ttcaaggttg gcacctatga ggagctgatt ccgcaagctg acctggttat    2220
caatctgacc ccagataaac aacatagcga cgttgttcgt actgttcaac cgctgatgaa    2280
ggatggtgct gctctgggtt atagccacgg ctttaacatt gttgaggtag gtgaacaaat    2340
tcgcaaggac attactgttg ttatggtggc tccaaagtgt ccgggtactg aggttcgcga    2400
ggaatataag cgcggttttg tgttccaac cctgatcgcg gtgcatccag agaatgaccc    2460
aaagggtgag ggtatggcta tcgcgaaggc gtgggctgcg gcgactggcg gccatcgcgc    2520
tggcgttctg gagagcagct tgtggctga ggttaagagc gatctgatgg gtgaacagac    2580
tattctgtgt ggtatgctgc aagcgggtag cctgctgtgt tttgataaac tggttgagga    2640
```

```
gggcactgac ccggcgtatg cggagaagct gatccaattt ggctgggaga ctattactga    2700
ggcgctgaag caaggtggta ttactctgat gatggatcgc ctgagcaatc cagctaagct    2760
gcgcgcgtac gctctgagcg agcaactgaa ggaaattatg gcaccgctgt tcaaaagca    2820
catggatgat atcattagcg gtgagtttag cagcggcatg atggctgatt gggcgaatga    2880
cgacaaaaag ctgctgactt ggcgcgagga actggtaag actgctttcg agactgctcc     2940
acaatacgag ggtaagattg gtgaacaaga atattttgac aagggtgttc tgatgatcgc    3000
tatggttaag gctggtgtgg agctggcttt tgagactatg gttgacagcg gtattatcga    3060
ggaaagcgcg tactacgaga gcctgcatga actgccactg atcgcgaata ctattgcgcg    3120
caaacgcctg tatgagatga atgttgtgat tagcgacact gcggaatatg gcaattacct    3180
gtttagctat gcgtgcgttc cactgctgaa gccattcatg gcggaactgc agccaggtga    3240
tctgggcaag gcgatcccag agggtgctgt tgacaatggt cagctgcgcg acgttaatga    3300
ggctatccgt tctcacgcta tcgaacaagt tggcaaaaag ctgcgtggtt acatgaccga    3360
catgaagcgc atcgcggtgg ctggctaacc tagggcgttc ggctgcggcg agcggtatca    3420
gctcactcaa aggcggtaat acggttatcc acagaatcag gggataacgc aggaaagaac    3480
atgtgagcaa aaggccagca aaaggccagg aaccgtaaaa aggccgcgtt gctggcgttt    3540
ttccataggc tccgcccccc tgacgagcat cacaaaaatc gacgctcaag tcagaggtgg    3600
cgaaacccga caggactata agataccag gcgtttcccc ctggaagctc cctcgtgcgc     3660
tctcctgttc cgaccctgcc gcttaccgga tacctgtccg cctttctccc ttcgggaagc    3720
gtggcgcttt ctcatagctc acgctgtagg tatctcagtt cggtgtaggt cgttcgctcc    3780
aagctgggct gtgtgcacga acccccgtt cagcccgacc gctgcgcctt atccggtaac     3840
tatcgtcttg agtccaaccc ggtaagacac gacttatcgc cactggcagc agccactggt    3900
aacaggatta gcagagcgag gtatgtaggc ggtgctacag agttcttgaa gtggtggcct    3960
aactacggct acactagaag gacagtattt ggtatctgcg ctctgctgaa gccagttacc    4020
ttcggaaaaa gagttggtag ctcttgatcc ggcaaacaaa ccaccgctgg tagcggtggt    4080
ttttttgttt gcaagcagca gattacgcgc agaaaaaaag gatctcaaga agatcctttg    4140
atcttttcta cggggtctga cgctcagtgg aacgaaaact cacgttaagg gattttggtc    4200
atgactagtg cttggattct caccaataaa aaacgcccgg cggcaaccga gcgttctgaa    4260
caaatccaga tggagttctg aggtcattac tggatctatc aacaggagtc caagcgagct    4320
cgtaaacttg gtctgacagt taccaatgct taatcagtga ggcacctatc tcagcgatct    4380
gtctatttcg ttcatccata gttgcctgac tccccgtcgt gtagataact acgatacggg    4440
agggcttacc atctggcccc agtgctgcaa tgataccgcg agacccacgc tcaccggctc    4500
cagatttatc agcaataaac cagccagccg gaagggccga gcgcagaagt ggtcctgcaa    4560
ctttatccgc ctccatccag tctattaatt gttgccggga agctagagta agtagttcgc    4620
cagttaatag tttgcgcaac gttgttgcca ttgctacagg catcgtggtg tcacgctcgt    4680
cgtttggtat ggcttcattc agctccggtt cccaacgatc aaggcgagtt acatgatccc    4740
ccatgttgtg caaaaaagcg gttagctcct tcggtcctcc gatcgttgtc agaagtaagt    4800
tggccgcagt gttatcactc atggttatgg cagcactgca taattctctt actgtcatgc    4860
catccgtaag atgcttttct gtgactggtg agtactcaac caagtcattc tgagaatagt    4920
gtatgcggcg accgagttgc tcttgcccgg cgtcaatacg gataatacc gccacata      4980
gcagaacttt aaaagtgctc atcattggaa aacgttcttc ggggcgaaaa ctctcaagga    5040
```

```
tcttaccgct gttgagatcc agttcgatgt aacccactcg tgcacccaac tgatcttcag    5100
catcttttac tttcaccagc gtttctgggt gagcaaaaac aggaaggcaa aatgccgcaa    5160
aaaagggaat aagggcgaca cggaaatgtt gaatactcat actcttcctt tttcaatatt    5220
attgaagcat ttatcagggt tattgtctca tgagcggata catatttgaa tgtatttaga    5280
aaaataaaca aatagggggt ccgcgcacat ttccccgaaa agtgccacct gacgtc        5336
```

<210> SEQ ID NO 29
<211> LENGTH: 3644
<212> TYPE: DNA
<213> ORGANISM: Artificial Sequence
<220> FEATURE:
<223> OTHER INFORMATION: Synthetic polynucleotide

<400> SEQUENCE: 29

```
taagaaacca ttattatcat gacattaacc tataaaaata ggcgtatcac gaggcccttt      60
cgtcttcacc tcgagaattg tgagcggata acaattgaca ttgtgagcgg ataacaagat     120
actgagcaca tcagcaggac gcactgaccg aattcattag tcgacattat gcggccgcgg     180
atccataagg aggattaatt aagacttccc gggtgatccc atggtacgcg tgctagaggc     240
atcaaataaa acgaaaggct cagtcgaaag actgggcctt tcgttttatc tgttgtttgt     300
cggtgaacgc tctcctgagt aggacaaatc cgccgcccta gacctagcta gggtacgggt     360
tttgctgccc gcaaacgggc tgttctggtg ttgctagttt gttatcagaa tcgcagatcc     420
ggcttcagcc ggtttgccgg ctgaaagcgc tatttcttcc agaattgcca tgatttttc      480 cccacgggag gcgtcactgg ctcccgtgtt gtcggcagct tgattcgat aagcagcatc      540 gcctgtttca ggctgtctat gtgtgactgt tgagctgtaa caagttgtct caggtgttca    600
atttcatgtt ctagttgctt tgttttactg gtttcacctg ttctattagg tgttacatgc    660
tgttcatctg ttacattgtc gatcgtcca tggtgaacag ctttaaatgc accaaaaact     720
cgtaaaagct ctgatgtatc tatctttttt acaccgtttt catctgtgca tatggacagt    780 ttccctttg atatctaacg tgaacagtt gttctacttt tgtttgttag tcttgatgct       840
tcactgatag atacaagagc cataagaacc tcagatcctt ccgtatttag ccagtatgtt    900
ctctagtgtg gttcgttgtt tttgcgtgag ccatgagaac gaaccattga gatcatgctt    960
actttgcatg tcactcaaaa attttgcctc aaaactggtg agctgaattt ttgcagttaa   1020
agcatcgtgt agtgtttttc ttagtccgtt acgtaggtag aatctgatg taatggttgt    1080 tggtatttg tcaccattca ttttttatctg gttgttctca agttcggtta cgagatccat   1140
ttgtctatct agttcaactt ggaaaatcaa cgtatcagtc gggcggcctc gcttatcaac   1200
caccaatttc atattgctgt aagtgtttaa atctttactt attggtttca aaacccattg   1260
gttaagcctt ttaaactcat ggtagttatt ttcaagcatt aacatgaact taaattcatc   1320
aaggctaatc tctatatttg ccttgtgagt tttcttttgt gttagttctt ttaataacca   1380
ctcataaatc ctcatagagt atttgttttc aaaagactta acatgttcca gattatattt   1440
tatgaatttt tttaactgga aaagataagg caatatctct tcactaaaaa ctaattctaa   1500 ttttcgctt gagaacttgg catagtttgt ccactggaaa atctcaaagc ctttaaccaa    1560
aggattcctg atttccacag ttctcgtcat cagctctctg gttgctttag ctaatacacc   1620
ataagcattt tccctactga tgttcatcat ctgagcgtat tggttataag tgaacgatac   1680
cgtccgttct ttccttgtag ggttttcaat cgtgggggttg agtagtgcca cacagcataa   1740
```

| | |
|---|---|
| aattagcttg gtttcatgct ccgttaagtc atagcgacta atcgctagtt catttgcttt | 1800 |
| gaaaacaact aattcagaca tacatctcaa ttggtctagg tgattttaat cactatacca | 1860 |
| attgagatgg gctagtcaat gataattact agtccttttc ccgggagatc tgggtatctg | 1920 |
| taaattctgc tagacctttg ctggaaaact tgtaaattct gctagaccct ctgtaaattc | 1980 |
| cgctagacct ttgtgtgttt ttttttgttta tattcaagtg gttataattt atagaataaa | 2040 |
| gaaagaataa aaaagataa aagaataga tcccagccct gtgtataact cactacttta | 2100 |
| gtcagttccg cagtattaca aaaggatgtc gcaaacgctg tttgctcctc tacaaaacag | 2160 |
| accttaaaac cctaaaggct taagtagcac cctcgcaagc tcgggcaaat cgctgaatat | 2220 |
| tccttttgtc tccgaccatc aggcacctga gtcgctgtct ttttcgtgac attcagttcg | 2280 |
| ctgcgctcac ggctctggca gtgaatgggg gtaaatggca ctacaggcgc cttttatgga | 2340 |
| ttcatgcaag gaaactaccc ataatacaag aaaagcccgt cacgggcttc tcagggcgtt | 2400 |
| ttatggcggg tctgctatgt ggtgctatct gacttttttgc tgttcagcag ttcctgccct | 2460 |
| ctgattttcc agtctgacca cttcggatta tcccgtgaca ggtcattcag actggctaat | 2520 |
| gcacccagta aggcagcggt atcatcaaca ggcttacccg tcttactgtc cctagtgctt | 2580 |
| ggattctcac caataaaaaa cgcccggcgg caaccgagcg ttctgaacaa atccagatgg | 2640 |
| agttctgagg tcattactgg atctatcaac aggagtccaa gcgagctctc gaacccccaga | 2700 |
| gtcccgctca gaagaactcg tcaagaaggc gatagaaggc gatgcgctgc gaatcggag | 2760 |
| cggcgatacc gtaaagcacg aggaagcggt cagcccattc gccgccaagc tcttcagcaa | 2820 |
| tatcacgggt agccaacgct atgtcctgat agcggtccgc cacacccagc cggccacagt | 2880 |
| cgatgaatcc agaaaagcgg ccatttttcca ccatgatatt cggcaagcag gcatcgccat | 2940 |
| gggtcacgac gagatcctcg ccgtcgggca tgcgcgcctt gagcctggcg aacagttcgg | 3000 |
| ctggcgcgag cccctgatgc tcttcgtcca gatcatcctg atcgacaaga ccggcttcca | 3060 |
| tccgagtacg tgctcgctcg atgcgatgtt tcgcttggtg gtcgaatggg caggtagccg | 3120 |
| gatcaagcgt atgcagccgc cgcattgcat cagccatgat ggatactttc tcggcaggag | 3180 |
| caaggtgaga tgacaggaga tcctgccccg gcacttcgcc caatagcagc cagtcccttc | 3240 |
| ccgcttcagt gacaacgtcg agcacagctg cgcaaggaac gcccgtcgtg gccagccacg | 3300 |
| atagccgcgc tgcctcgtcc tgcagttcat tcagggcacc ggacaggtcg gtcttgacaa | 3360 |
| aaagaaccgg gcgcccctgc gctgacagcc ggaacacggc ggcatcagag cagccgattg | 3420 |
| tctgttgtgc ccagtcatag ccgaatagcc tctccaccca agcggccgga gaacctgcgt | 3480 |
| gcaatccatc ttgttcaatc atgcgaaacg atcctcatcc tgtctcttga tcagatcttg | 3540 |
| atcccctgcg ccatcagatc cttggcggca agaaagccat ccagtttact ttgcagggct | 3600 |
| tcccaacctt accagagggc gccccagctg gcaattccga cgtc | 3644 |

<210> SEQ ID NO 30
<211> LENGTH: 6575
<212> TYPE: DNA
<213> ORGANISM: Artificial Sequence
<220> FEATURE:
<223> OTHER INFORMATION: Synthetic polynucleotide

<400> SEQUENCE: 30

| | |
|---|---|
| taagaaacca ttattatcat gacattaacc tataaaaata ggcgtatcac gaggcccttt | 60 |
| cgtcttcacc tcgagaattg tgagcggata acaattgaca ttgtgagcgg ataacaagat | 120 |
| actgagcaca tcagcaggac gcactgaccg aattcattag tcgacaggag aaaggtacta | 180 |

```
tgcgaattgg cataccaaga gaacggttaa ccaatgaaac ccgtgttgca gcaacgccaa    240
aaacagtgga acagctgctg aaactgggtt ttaccgtcgc ggtagagagc ggcgcgggtc    300
aactggcaag ttttgacgat aaagcgtttg tgcaagcggg cgctgaaatt gtagaaggga    360
atagcgtctg gcagtcagag atcattctga aggtcaatgc gccgttagat gatgaaattg    420
cgttactgaa tcctgggaca acgctggtga gttttatctg gcctgcgcag aatccggaat    480
taatgcaaaa acttgcggaa cgtaacgtga ccgtgatggc gatggactct gtgccgcgta    540
tctcacgcgc acaatcgctg gacgcactaa gctcgatggc gaacatcgcc ggttatcgcg    600
ccattgttga agcggcacat gaatttgggc gcttctttac cgggcaaatt actgcggccg    660
ggaaagtgcc accggcaaaa gtgatggtga ttggtgcggg tgttgcaggt ctggccgcca    720
ttggcgcagc aaacagtctc ggcgcgattg tgcgtgcatt cgacacccgc ccggaagtga    780
aagaacaagt tcaaagtatg ggcgcggaat cctcgagctg gattttaaa gaggaagctg     840
gcagcggcga tggctatgcc aaagtgatgt cggacgcgtt catcaaagcg gaaatggaac    900
tctttgccgc ccaggcaaaa gaggtcgata tcattgtcac caccgcgctt attccaggca    960
aaccagcgcc gaagctaatt acccgtgaaa tggttgactc catgaaggcg ggcagtgtga   1020
ttgttgacct ggcagcccaa aacggcggca actgtgaata caccgtgccg ggtgaaatct   1080
tcactacgga aaatggtgtc aaagtgattg gttataccga tcttccgggc cgtctgccga   1140
cgcaatcctc acagctttac ggcacaaacc tcgttaatct gctgaaactg ttgtgcaaag   1200
agaaagacgg caatatcact gttgattttg atgatgtggt gattcgcggc gtgaccgtga   1260
tccgtgcggg cgaaattacc tggccggcac cgccgattca ggtatcagct cagccgcagg   1320
cggcacaaaa agcggcaccg gaagtgaaaa ctgaggaaaa atgtacctgc tcaccgtggc   1380
gtaaatacgc gttgatggcg ctggcaatca ttcttttggg ctggatggca agcgttgcgc   1440
cgaaagaatt ccttgggcac ttcaccgttt tcgcgctggc ctgcgttgtc ggttattacg   1500
tggtgtggaa tgtatcgcac gcgctgcata caccgttgat gtcggtcacc aacgcgattt   1560
cagggattat tgttgtcgga gcactgttgc agattggcca gggcggctgg gttagcttcc   1620
ttagttttat cgcggtgctt atagccagca ttaatatttt cggtggcttc accgtgactc   1680
agcgcatgct gaaaatgttc cgcaaaaatt aagggggtaac atatgtctgg aggattagtt   1740
acagctgcat acattgttgc cgcgatcctg tttatcttca gtctggccgg tctttcgaaa   1800
catgaaacgt ctcgccaggg taacaacttc ggtatcgccg ggatggcgat tgcgttaatc   1860
gcaaccattt ttggaccgga tacgggtaat gttggctgga tcttgctggc gatggtcatt   1920
ggtgggcaa ttggtatccg tctggcgaag aaagttgaaa tgaccgaaat gccagaactg   1980
gtggcgatcc tgcatagctt cgtgggtctg gcggcagtgc tggttggctt taacagctat   2040
ctgcatcatg acgcgggaat ggcaccgatt ctggtcaata ttcacctgac ggaagtgttc   2100
ctcggtatct tcatcgggc ggtaacgttc acgggttcgg tggtggcgtt cggcaaactg   2160
tgtggcaaga tttcgtctaa accattgatg ctgccaaacc gtcacaaaat gaacctggcg   2220
gctctggtcg tttccttcct gctgctgatt gtatttgttc gcacggacag cgtcggcctg   2280
caagtgctgg cattgctgat aatgaccgca attgcgctgg tattcggctg gcatttagtc   2340
gcctccatcg gtggtgcaga tatgccagtg gtggtgtcga tgctgaactc gtactccggc   2400
tgggcggctg cggctgcggg ctttatgctc agcaacgacc tgctgattgt gaccggtgcg   2460
ctggtcggtt cttcggggc tatcctttct tacattatgt gtaaggcgat gaaccgttcc   2520
```

```
tttatcagcg ttattgcggg tggtttcggc accgacggct cttctactgg cgatgatcag   2580
gaagtgggtg agcaccgcga aataccgcca gaagagacag cggaactgct gaaaaactcc   2640
cattcagtga tcattactcc ggggtacggc atggcagtcg cgcaggcgca atatcctgtc   2700
gctgaaatta ctgagaaatt gcgcgctcgt ggtattaatg tgcgtttcgg tatccacccg   2760 gtcgcgggc gtttgcctgg acatatgaac gtattgctgg ctgaagcaaa agtaccgtat    2820
gacatcgtgc tggaaatgga cgagatcaat gatgactttg ctgataccga taccgtactg   2880
gtgattggtg ctaacgatac ggttaacccg gcggcgcagg atgatccgaa gagtccgatt   2940
gctggtatgc ctgtgctgga agtgtggaaa gcgcagaacg tgattgtctt taaacgttcg   3000
atgaacactg gctatgctgg tgtgcaaaac ccgctgttct tcaaggaaaa cacccacatg   3060
ctgtttggtg acgccaaagc cagcgtggat gcaatcctga agctctgta acgtcgacat     3120 tatgcggccg cggatccata aggaggatta attaagactt cccgggtgat cccatggtac   3180
gcgtgctaga ggcatcaaat aaaacgaaag gctcagtcga agactgggc ctttcgtttt    3240 atctgttgtt tgtcggtgaa cgctctcctg agtaggacaa atccgccgcc ctagacctag   3300
ctagggtacg ggttttgctg cccgcaaacg ggctgttctg gtgttgctag tttgttatca   3360
gaatcgcaga tccggcttca gccggtttgc cggctgaaag cgctatttct tccagaattg   3420
ccatgatttt ttccccacgg gaggcgtcac tggctcccgt gttgtcggca gctttgattc   3480
gataagcagc atcgcctgtt tcaggctgtc tatgtgtgac tgttgagctg taacaagttg   3540
tctcaggtgt tcaatttcat gttctagttg ctttgtttta ctggtttcac ctgttctatt   3600
aggtgttaca tgctgttcat ctgttacatt gtcgatctgt tcatggtgaa cagctttaaa   3660
tgcaccaaaa actcgtaaaa gctctgatgt atctatcttt tttacaccgt tttcatctgt   3720
gcatatggac agttttccct ttgatatcta acggtgaaca gttgttctac ttttgtttgt   3780
tagtcttgat gcttcactga tagatacaag agccataaga acctcagatc cttccgtatt   3840
tagccagtat gttctctagt gtggttcgtt gttttttgcgt gagccatgag aacgaaccat   3900
tgagatcatg cttactttgc atgtcactca aaaattttgc ctcaaaactg gtgagctgaa   3960
tttttgcagt taaagcatcg tgtagtgttt ttcttagtcc gttacgtagg taggaatctg   4020
atgtaatggt tgttggtatt ttgtcaccat tcattttat ctggttgttc tcaagttcgg    4080
ttacgagatc catttgtcta tctagttcaa cttggaaaat caacgtatca gtcgggcggc   4140
ctcgcttatc aaccaccaat ttcatattgc tgtaagtgtt taaatcttta cttattggtt   4200
tcaaaaccca ttggttaagc cttttaaact catggtagtt attttcaagc attaacatga   4260
acttaaattc atcaaggcta atctctatat ttgccttgtg agttttcttt tgtgttagtt   4320
cttttaataa ccactcataa atcctcatag agtatttgtt ttcaaaagac ttaacatgtt   4380
ccagattata ttttatgaat tttttttaact ggaaaagata aggcaatatc tcttcactaa   4440
aaactaattc taattttttcg cttgagaact tggcatagtt tgtccactgg aaaatctcaa   4500
agcctttaac caaaggattc ctgatttcca cagttctcgt catcagctct ctggttgctt   4560
tagctaatac accataagca ttttccctac tgatgttcat catctgagcg tattggttat   4620
aagtgaacga taccgtccgt tctttccttg tagggttttc aatcgtgggg ttgagtagtg   4680
ccacacagca taaaattagc ttggtttcat gctccgttaa gtcatagcga ctaatcgcta   4740
gttcatttgc tttgaaaaca actaattcag acatacatct caattggtct aggtgatttt   4800
aatcactata ccaattgaga tgggctagtc aatgataatt actagtcctt ttcccgggag   4860
atctgggtat ctgtaaattc tgctagacct ttgctggaaa acttgtaaat tctgctagac   4920
```

```
cctctgtaaa ttccgctaga cctttgtgtg ttttttttgt ttatattcaa gtggttataa    4980
tttatagaat aaagaaagaa taaaaaaaga taaaaagaat agatcccagc cctgtgtata    5040
actcactact ttagtcagtt ccgcagtatt acaaaaggat gtcgcaaacg ctgtttgctc    5100
ctctacaaaa cagaccttaa aaccctaaag gcttaagtag caccctcgca agctcgggca    5160
aatcgctgaa tattcctttt gtctccgacc atcaggcacc tgagtcgctg tcttttcgt     5220 gacattcagt tcgctgcgct cacggctctg gcagtgaatg ggggtaaatg gcactacagg    5280
cgccttttat ggattcatgc aaggaaacta cccataatac aagaaaagcc cgtcacgggc    5340
ttctcagggc gttttatggc gggtctgcta tgtggtgcta tctgactttt tgctgttcag    5400
cagttcctgc cctctgattt tccagtctga ccacttcgga ttatcccgtg acaggtcatt    5460
cagactggct aatgcaccca gtaaggcagc ggtatcatca acaggcttac ccgtcttact    5520
gtccctagtg cttggattct caccaataaa aaacgcccgg cggcaaccga gcgttctgaa    5580
caaatccaga tggagttctg aggtcattac tggatctatc aacaggagtc caagcgagct    5640
ctcgaacccc agagtcccgc tcagaagaac tcgtcaagaa ggcgatagaa ggcgatgcgc    5700
tgcgaatcgg gagcggcgat accgtaaagc acgaggaagc ggtcagccca ttcgccgcca    5760
agctcttcag caatatcacg ggtagccaac gctatgtcct gatagcggtc gccacaccc     5820 agccggccac agtcgatgaa tccagaaaag cggccatttt ccaccatgat attcggcaag    5880
caggcatcgc catgggtcac gacgagatcc tcgccgtcgg gcatgcgcgc cttgagcctg    5940
gcgaacagtt cggctggcgc gagccccctga tgctcttcgt ccagatcatc ctgatcgaca    6000
agaccggctt ccatccgagt acgtgctcgc tcgatgcgat gtttcgcttg gtggtcgaat    6060
gggcaggtag ccggatcaag cgtatgcagc cgccgcattg catcagccat gatggatact    6120
ttctcggcag gagcaaggtg agatgacagg agatcctgcc ccggcacttc gcccaatagc    6180
agccagtccc ttcccgcttc agtgacaacg tcgagcacag ctgcgcaagg aacgcccgtc    6240
gtggccagcc acgatagccg cgctgcctcg tcctgcagtt cattcagggc accggacagg    6300
tcggtcttga caaaaagaac cgggcgcccc tgcgctgaca gccggaacac ggcggcatca    6360
gagcagccga ttgtctgttg tgcccagtca tagccgaata gcctctccac ccaagcggcc    6420
ggagaacctg cgtgcaatcc atcttgttca atcatgcgaa acgatcctca tcctgtctct    6480
tgatcagatc ttgatcccct gcgccatcag atccttggcg gcaagaaagc catccagttt    6540
actttgcagg gcttcccaac cttaccagag ggcgc                              6575
```

<210> SEQ ID NO 31
<211> LENGTH: 7112
<212> TYPE: DNA
<213> ORGANISM: Artificial Sequence
<220> FEATURE:
<223> OTHER INFORMATION: Synthetic polynucleotide

<400> SEQUENCE: 31

```
taagaaacca ttattatcat gacattaacc tataaaaata ggcgtatcac gaggcccttt     60
cgtcttcacc tcgagaattg tgagcggata acaattgaca ttgtgagcgg ataacaagat    120
actgagcaca tcagcaggac gcactgaccg aattcattaa agaggagaaa ggtaccatgt    180
atacagtagg agattaccta ttagaccgat tacacgagtt aggaattgaa gaaattttg     240 gagtccctgg agactataac ttacaatttt tagatcaaat tatttcccgc aaggatatga    300
aatgggtcgg aaatgctaat gaattaaatg cttcatatat ggctgatggc tatgctcgta    360
```

```
ctaaaaaagc tgccgcattt cttacaacct ttggagtagg tgaattgagt gcagttaatg      420
gattagcagg aagttacgcc gaaaatttac cagtagtaga aatagtggga tcacctacat      480
caaaagttca aaatgaagga aaatttgttc atcatacgct ggctgacggt gattttaaac      540
actttatgaa aatgcacgaa cctgttacag cagctcgaac tttactgaca gcagaaaatg      600
caaccgttga aattgaccga gtactttctg cactattaaa agaaagaaaa cctgtctata      660
tcaacttacc agttgatgtt gctgctgcaa aagcagagaa accctcactc cctttgaaaa      720
aagaaaactc aacttcaaat acaagtgacc aagagatctt gaacaaaatt caagaaagct      780
tgaaaaatgc caaaaaacca atcgtgatta caggacatga ataattagt tttggcttag       840 aaaaaacagt ctctcaattt atttcaaaga caaaactacc tattacgaca ttaaactttg      900 gaaaagttc agttgatgaa gctctcccctt cattttaagg aatctataat ggtaaactct       960
cagagcctaa tcttaaagaa ttcgtggaat cagccgactt catcctgatg cttggagtta     1020
aactcacaga ctcttcaaca ggagccttca ctcatcattt aaatgaaat aaaatgattt     1080 cactgaatat agatgaagga aaatatttta acgaaagcat ccaaaatttt gattttgaat     1140
ccctcatctc ctctctctta gacctaagcg aaatagaata caaggaaaa tatatcgata     1200 aaaagcaaga agactttgtt ccatcaaatg cgcttttatc acaagaccgc ctatggcaag     1260
cagttgaaaa cctaactcaa agcaatgaaa caatcgttgc tgaacaaggg acatcattct     1320
ttggcgcttc atcaatttc ttaaaaccaa agagtcattt tattggtcaa cccttatggg      1380
gatcaattgg atatacattc ccagcagcat taggaagcca aattgcagat aaagaaagca     1440
gacacctttt atttattggt gatggttcac ttcaacttac ggtgcaagaa ttaggattag     1500
caatcagaga aaaaattaat ccaatttgct ttattatcaa taatgatggt tatacagtcg     1560
aaagagaaat tcatggacca aatcaaagct acaatgatat tccaatgtgg aattactcaa     1620
aattaccaga atcatttgga gcaacagaag aacgagtagt ctcgaaaatc gttagaactg     1680
aaaatgaatt tgtgtctgtc atgaaagaag ctcaagcaga tccaaataga atgtactgga     1740
ttgagttaat tttggcaaaa aagatgcac caaaagtact gaaaaaatg gcaaactat       1800 ttgctgaaca aaataaatca taaggtcgac aggagatata ctatgcctaa atatcgcagc     1860
gcaactacta cccacggccg caacatggca ggcgcgcgtg ctctgtggcg tgcgactggt     1920
atgactgatg cggactttgg caaaccaatc attgctgtgg ttaatagctt tactcagttc     1980
gttccaggcc atgttcacct gcgtgacctg ggcaagctgg ttgcggagca gatcgaggct     2040
gcgggtggtg tggcgaagga atttaacacc atcgctgttg acgacggtat cgcgatgggt     2100
catggtggta tgctgtacag cctgccgagc cgtgagctga ttgcggacag cgtggaatac     2160
atggttaatg cgcattgtgc ggatgcgatg gtttgtatta gcaactgtga taagattact     2220
ccaggtatgc tgatggcgag cctgcgtctg aacatcccag ttattttcgt gagcggtggt     2280
ccaatggaag cgggtaagac taagctgagc gaccagatta tcaaactgga cctggtggac     2340
gctatgattc aaggtgctga tccaaaggtt agcgatagcc aatctgacca agtggagcgc     2400
agcgcttgcc caacttgtgg cagctgtagc ggtatgttca ctgcgaatag catgaattgt     2460
ctgactgagg ctctgggtct gagccaacca ggtaatggta gcctgctggc gactcatgcg     2520
gatcgcaaac aactgtttct gaacgcgggc aagcgtatcg tggagctgac taagcgctac     2580
tatgaacaga tgatgagtc cgcgctgcca cgcaacattg cgtccaaagc tgctttcgag     2640
aatgcgatga cctggacat tgctatgggc ggtagcacca atactgttct gcatctgctg     2700
gctgctgctc aagaggctga gattgatttt actatgtccg acattgacaa actgagccgt     2760
```

-continued

```
aaagtgccgc aactgtgcaa ggtggctcca tctactcaaa agtatcacat ggaggacgtg      2820
catcgcgcgg gtggcgtgat tggcatcctg ggtgagctgg accgtgctgg tctgctgaat      2880
cgcgacgtta agaatgttct gggtctgacc ctgccacaga ccctggagca gtatgatgtg      2940
atgctgactc aagacgatgc tgttaagaac atgtttcgtg ctggtccggc gggtatccgc      3000
actacccaag cgtttagcca ggactgtcgc tgggacaccc tggatgatga ccgtgcgaac      3060
ggttgcattc gtagcctgga acatgcgtat tctaaggatg gtggtctggc tgttctgtat      3120
ggcaatttcg ctgagaatgg ttgtattgtt aagaccgcgg tgttgacga ttctattctg       3180 aagtttactg gtccagctaa ggtttatgag tctcaagatg acgctgttga ggctatcctg      3240
ggtggcaagg tggttgcggg tgacgttgtt gttatccgtt acgagggtcc aaagggtggc      3300
ccaggtatgc aagagatgct gtatccgact tcttttctga agagcatggg cctgggtaag      3360
gcgtgcgctc tgattactga tggccgcttt agcggcggta ctagcggcct gagcattggt      3420
catgttagcc cagaggctgc gtctggtggt tctatcggtc tgatcgagga cggcgatctg      3480
attgcgattg atattccaaa tcgcggtatc caactgcaag tttctgacgc ggagctggct      3540
gctcgccgcg aggctcaaga tgcgcgtggc gataaggcgt ggaccccaaa gaaccgcgag      3600
cgccaagtta gcttcgcgct gcgcgcgtac gcctctctgg cgacttctgc ggataagggt      3660
gctgttcgtg acaagagcaa gctgggtggc taaacgcgtg ctagaggcat caaataaaac      3720
gaaaggctca gtcgaaagac tgggcctttc gttttatctg ttgtttgtcg gtgaacgctc      3780
tcctgagtag gacaaatccg ccgcctaga cctagctagg gtacgggttt tgctgcccgc       3840
aaacgggctg ttctggtgtt gctagtttgt tatcagaatc gcagatccgg cttcagccgg      3900
tttgccggct gaaagcgcta tttcttccag aattgccatg attttttccc cacgggaggc      3960
gtcactggct cccgtgttgt cggcagcttt gattcgataa gcagcatcgc ctgtttcagg      4020
ctgtctatgt gtgactgttg agctgtaaca agttgtctca ggtgttcaat ttcatgttct      4080
agttgctttg ttttactggt ttcacctgtt ctattaggtg ttacatgctg ttcatctgtt      4140
acattgtcga tctgttcatg gtgaacagct ttaaatgcac caaaaactcg taaaagctct      4200
gatgtatcta tcttttttac accgttttca tctgtgcata tggacagttt tcccttttgat      4260 atctaacggt gaacagttgt tctactttg tttgttagtc ttgatgcttc actgatagat       4320
acaagagcca taagaacctc agatccttcc gtatttagcc agtatgttct ctagtgtggt      4380
tcgttgtttt tgcgtgagcc atgagaacga accattgaga tcatgcttac tttgcatgtc      4440
actcaaaaat tttgcctcaa aactggtgag ctgaattttt gcagttaaag catcgtgtag      4500
tgtttttctt agtccgttac gtaggtagga atctgatgta atggttgttg gtattttgtc      4560
accattcatt tttatctggt tgttctcaag ttcggttacg agatccattt gtctatctag      4620
ttcaacttgg aaaatcaacg tatcagtcgg gcggcctcgc ttatcaacca ccaatttcat      4680
attgctgtaa gtgtttaaat cttttactttat tggtttcaaa acccattggt taagcctttt   4740
aaactcatgg tagttatttt caagcattaa catgaactta aattcatcaa ggctaatctc      4800
tatatttgcc ttgtgagttt tcttttgtgt tagttctttt aataaccact cataaatcct      4860
catagagtat ttgttttcaa aagacttaac atgttccaga ttatatttta tgaattttt      4920 taactggaaa agataaggca atatctcttc actaaaaact aattctaatt tttcgcttga      4980
gaacttggca tagtttgtcc actggaaaat ctcaaagcct ttaaccaaag gattcctgat      5040
ttccacagtt ctcgtcatca gctctctggt tgctttagct aatacaccat aagcattttc      5100
```

```
cctactgatg ttcatcatct gagcgtattg gttataagtg aacgataccg tccgttcttt      5160
ccttgtaggg ttttcaatcg tggggttgag tagtgccaca cagcataaaa ttagcttggt      5220
ttcatgctcc gttaagtcat agcgactaat cgctagttca tttgctttga aaacaactaa      5280
ttcagacata catctcaatt ggtctaggtg attttaatca ctataccaat tgagatgggc      5340
tagtcaatga taattactag tccttttccc gggagatctg gtatctgta aattctgcta       5400 gacctttgct ggaaaacttg taaattctgc tagaccctct gtaaattccg ctagaccttt      5460
gtgtgttttt tttgtttata ttcaagtggt tataatttat agaataaaga aagaataaaa      5520
aaagataaaa agaatagatc ccagccctgt gtataactca ctactttagt cagttccgca      5580
gtattacaaa aggatgtcgc aaacgctgtt tgctcctcta caaacagac cttaaaaccc       5640 taaaggctta agtagcaccc tcgcaagctc gggcaaatcg ctgaatattc cttttgtctc      5700
cgaccatcag gcacctgagt cgctgtcttt ttcgtgacat tcagttcgct gcgctcacgg      5760
ctctggcagt gaatgggggt aaatggcact acaggcgcct tttatggatt catgcaagga      5820
aactacccat aatacaagaa aagcccgtca cgggcttctc agggcgtttt atggcgggtc      5880
tgctatgtgg tgctatctga ctttttgctg ttcagcagtt cctgccctct gattttccag      5940
tctgaccact tcggattatc ccgtgacagg tcattcagac tggctaatgc acccagtaag      6000
gcagcggtat catcaacagg cttacccgtc ttactgtccc tagtgcttgg attctcacca      6060
ataaaaaacg cccggcggca accgagcgtt ctgaacaaat ccagatggag ttctgaggtc      6120
attactggat ctatcaacag gagtccaagc gagctctcga accccagagt cccgctcaga      6180
agaactcgtc aagaaggcga tagaaggcga tgcgctgcga atcgggagcg gcgataccgt      6240
aaagcacgag gaagcggtca gcccattcgc cgccaagctc ttcagcaata tcacgggtag      6300
ccaacgctat gtcctgatag cggtccgcca cacccagccg ccacagtcg atgaatccag       6360 aaaagcggcc attttccacc atgatattcg gcaagcaggc atcgccatgg gtcacgacga      6420
gatcctcgcc gtcgggcatg cgcgccttga gcctggcgaa cagttcggct ggcgcgagcc      6480
cctgatgctc ttcgtccaga tcatcctgat cgacaagacc ggcttccatc cgagtacgtg      6540
ctcgctcgat gcgatgtttc gcttggtggt cgaatgggca ggtagccgga tcaagcgtat      6600
gcagccgccg cattgcatca gccatgatgg atactttctc ggcaggagca aggtgagatg      6660
acaggagatc ctgccccggc acttcgccca atagcagcca gtcccttccc gcttcagtga      6720
caacgtcgag cacagctgcg caaggaacgc ccgtcgtggc cagccacgat agccgcgctg      6780
cctcgtcctg cagttcattc agggcaccgg acaggtcggt cttgacaaaa gaaccgggc      6840 gcccctgcgc tgacagccgg aacacggcgg catcagagca gccgattgtc tgttgtgccc      6900
agtcatagcc gaatagcctc tccacccaag cggccggaga acctgcgtgc aatccatctt      6960
gttcaatcat gcgaaacgat cctcatcctg tctcttgatc agatcttgat ccctgcgcc      7020 atcagatcct ggcggcaag aaagccatcc agtttacttt gcagggcttc ccaaccttac       7080
cagagggcgc cccagctggc aattccgacg tc                                    7112

<210> SEQ ID NO 32
<211> LENGTH: 7093
<212> TYPE: DNA
<213> ORGANISM: Artificial Sequence
<220> FEATURE:
<223> OTHER INFORMATION: Synthetic polynucleotide

<400> SEQUENCE: 32
cgatatcaaa ttacgccccg ccctgccact catcgcagta ctgttgtaat tcattaagca       60
```

-continued

```
ttctgccgac atggaagcca tcacagacgg catgatgaac ctgaatcgcc agcggcatca      120
gcaccttgtc gccttgcgta taatatttgc ccatggtgaa acggggggcg aagaagttgt      180
ccatattggc cacgtttaaa tcaaaactgg tgaaactcac ccagggattg gctgagacga      240
aaaacatatt ctcaataaac cctttaggga ataggccag gttttcaccg taacacgcca       300
catcttgcga atatatgtgt agaaactgcc ggaaatcgtc gtggtattca ctccagagcg      360
atgaaaacgt ttcagtttgc tcatggaaaa cggtgtaaca agggtgaaca ctatcccata     420
tcaccagctc accgtctttc attgccatac gaaactccgg atgagcattc atcaggcggg      480
caagaatgtg aataaaggcc ggataaaact tgtgcttatt tttctttacg gtctttaaaa      540
aggccgtaat atccagctga acggtctggt tataggtaca ttgagcaact gactgaaatg      600
cctcaaaatg ttctttacga tgccattggg atatatcaac ggtggtatat ccagtgattt      660
ttttctccat tttagcttcc ttagctcctg aaaatctcga taactcaaaa aatacgcccg      720
gtagtgatct tatttcatta tggtgaaagt tggaacctct tacgtgccga tcaacgtctc      780
attttcgcca gatatcgacg tctaagaaac cattattatc atgacattaa cctataaaaa      840
taggcgtatc acgaggccct ttcgtcttca cctcgagaat tgtgagcgga taacaattga      900
cattgtgagc ggataacaag atactgagca catcagcagg acgcactgac cgaattcatt      960
aaagaggaga aagtacaat gttgacaaaa gcaacaaaag aacaaaaatc ccttgtgaaa       1020
aacagagggg cggagcttgt tgttgattgc ttagtggagc aaggtgtcac acatgtattt     1080
ggcattccag gtgcaaaaat tgatgcggta tttgacgctt tacaagataa aggacctgaa     1140
attatcgttg cccggcacga acaaaacgca gcattcatgg cccaagcagt cggccgttta     1200
actggaaaac cggagtcgt gttagtcaca tcaggaccgg gtgcctctaa cttggcaaca      1260
ggcctgctga cagcgaacac tgaaggagac cctgtcgttg cgcttgctgg aaacgtgatc      1320
cgtgcagatc gtttaaaacg gacacatcaa tctttggata tgcggcgct attccagccg       1380 attacaaaat acagtgtaga agttcaagat gtaaaaaata taccggaagc tgttacaaat     1440
gcatttagga tagcgtcagc agggcaggct ggggccgctt ttgtgagctt ccgcaagat      1500 gttgtgaatg aagtcacaaa tacgaaaaac gtgcgtgctg ttgcagcgcc aaaactcggt     1560
cctgcagcag atgatgcaat cagtgcggcc atagcaaaaa tccaaacagc aaaacttcct     1620
gtcgttttgg tcggcatgaa aggcggaaga ccggaagcaa ttaaagcggt tcgcaagctt     1680
ttgaaaaagg ttcagcttcc atttgttgaa acatatcaag ctgccggtac cctttctaga     1740
gatttagagg atcaatattt tggccgtatc ggtttgttcc gcaaccagcc tggcgattta     1800
ctgctagagc aggcagatgt tgttctgacg atcggctatg acccgattga atatgatccg     1860
aaattctgga atatcaatgg agaccggaca attatccatt tagacgagat tatcgctgac     1920
attgatcatg cttaccagcc tgatcttgaa ttgatcggtg acattccgtc cacgatcaat     1980
catatcgaac acgatgctgt gaaagtggaa tttgcagagc gtgagcagaa atcctttct     2040 gatttaaaac aatatatgca tgaaggtgag caggtgcctg cagattggaa atcagacaga     2100
gcgcaccctc ttgaaatcgt taaagagttg cgtaatgcag tcgatgatca tgttacagta     2160
acttgcgata tcggttcgca cgccatttgg atgtcacgtt atttccgcag ctacgagccg     2220
ttaacattaa tgatcagtaa cggtatgcaa acactcggcg ttgcgcttcc ttgggcaatc     2280
ggcgcttcat tggtgaaacc gggagaaaaa gtggtttctg tctctggtga cggcggtttc     2340
ttattctcag caatggaatt agagacagca gttcgactaa aagcaccaat tgtacacatt     2400
```

```
gtatggaacg acagcacata tgacatggtt gcattccagc aattgaaaaa atataaccgt   2460
acatctgcgg tcgatttcgg aaatatcgat atcgtgaaat atgcggaaag cttcggagca   2520
actggcttgc gcgtagaatc accagaccag ctggcagatg ttctgcgtca aggcatgaac   2580
gctgaaggtc ctgtcatcat cgatgtcccg gttgactaca gtgataacat taatttagca   2640
agtgacaagc ttccgaaaga attcggggaa ctcatgaaaa cgaaagctct ctaggtcgac   2700
gaggaatcac catggctaac tacttcaata cactgaatct gcgccagcag ctggcacagc   2760
tgggcaaatg tcgctttatg ggccgcgatg aattcgccga tggcgcgagc taccttcagg   2820
gtaaaaaagt agtcatcgtc ggctgtggcg cacagggtct gaaccagggc ctgaacatgc   2880
gtgattctgg tctcgatatc tcctacgctc tgcgtaaaga agcgattgcc gagaagcgcg   2940
cgtcctggcg taaagcgacc gaaaatggtt ttaaagtggg tacttacgaa gaactgatcc   3000
cacaggcgga tctggtgatt aacctgacgc cggacaagca gcactctgat gtagtgcgca   3060
ccgtacagcc actgatgaaa gacgcgcgcg cgctgggcta ctcgcacggt ttcaacatcg   3120
tcgaagtggg cgagcagatc cgtaaagata tcaccgtagt gatggttgcg ccgaaatgcc   3180
caggcaccga agtgcgtgaa gagtacaaac gtgggttcgg cgtaccgacg ctgattgccg   3240
ttcacccgga aaacgatccg aaaggcgaag gcatggcgat tgccaaagcc tgggcggctg   3300
caaccggtgg tcaccgtgcg ggtgtgctgg aatcgtcctt cgttgcggaa gtgaaatctg   3360
acctgatggg cgagcaaacc atcctgtgcg gtatgttgca ggctggctct ctgctgtgct   3420
tcgacaagct ggtggaagaa ggtaccgatc cagcatacgc agaaaaactg attcagttcg   3480
gttgggaaac catcaccgaa gcactgaaac agggcggcat caccctgatg atggaccgtc   3540
tctctaaccc ggcgaaactg cgtgcttatg cgctttctga acagctgaaa gagatcatgg   3600 caccctgtt ccagaaacat atggacgaca tcatctccgg cgaattctct tccggtatga   3660
tggcggactg ggccaacgat gataagaaac tgctgacctg gcgtgaagag accggcaaaa   3720
ccgcgtttga aaccgcgccg cagtatgaag gcaaaatcgg cgagcaggag tacttcgata   3780
aaggcgtact gatgattgcg atggtgaaag cgggcgttga actggcgttc gaaaccatgg   3840
tcgattccgg catcattgaa gagtctgcat attatgaatc actgcacgag ctgccgctga   3900
ttgccaacac catcgcccgt aagcgtctgt acgaaatgaa cgtggttatc tctgataccg   3960
ctgagtacgc taactatctg ttctcttacg cttgtgtgcc gttgctgaaa ccgtttatgg   4020
cagagctgca accgggcgac ctgggtaaag ctattccgga aggcgcggta gataacgggc   4080
aactgcgtga tgtgaacgaa gcgattcgca gccatgcgat tgagcaggta ggtaagaaac   4140
tgcgcggcta tatgacagat atgaaacgta ttgctgttgc gggttaaccc ggaaggagat   4200
ataccatgcc taagtaccgt tccgccacca ccactcatgg tcgtaatatg gcgggtgctc   4260
gtgcgctgtg gcgcgccacc ggaatgaccg acgccgattt cggtaagccg attatcgcgg   4320
ttgtgaactc gttcacccaa tttgtaccgg gtcacgtcca tctgcgcgat ctcgtaaac    4380 tggtcgccga acaaattgaa gcggctggcg gcgttgccaa agagttcaac accattgcgg   4440
tggatgatgg gattgccatg ggccacgggg gatgctttta ttcactgcca tctcgcgaac   4500
tgatcgctga ttccgttgag tatatggtca acgcccactg cgccgacgcc atggtctgca   4560
tctctaactg cgacaaaatc accccgggga tgctgatggc ttccctgcgc ctgaatattc   4620
cggtgatctt tgtttccggc ggcccgatgg aggccgggaa aaccaaactt ccgatcaga   4680 tcatcaagct cgatctggtt gatgcgatga tccaggcgc agacccgaaa gtatctgact   4740
cccagagcga tcaggttgaa cgttccgcgt gtccgacctg cggttcctgc tccgggatgt   4800
```

```
ttaccgctaa ctcaatgaac tgcctgaccg aagcgctggg cctgtcgcag ccgggcaacg    4860
gctcgctgct ggcaacccac gccgaccgta agcagctgtt ccttaatgct ggtaaacgca    4920
ttgttgaatt gaccaaacgt tattacgagc aaaacgacga aagtgcactg ccgcgtaata    4980
tcgccagtaa ggcggcgttt gaaaacgcca tgacgctgga tatcgcgatg ggtggatcga    5040
ctaacaccgt acttcacctg ctggcggcgg cgcaggaagc ggaaatcgac ttcaccatga    5100
gtgatatcga taagctttcc cgcaaggttc cacagctgtg taaagttgcg ccgagcaccc    5160
agaaatacca tatggaagat gttcaccgtg ctggtggtgt tatcggtatt ctcggcgaac    5220
tggatcgcgc ggggttactg aaccgtgatg tgaaaaacgt acttggcctg acgttgccgc    5280
aaacgctgga acaatacgac gttatgctga cccaggatga cgcggtaaaa aatatgttcc    5340
gcgcaggtcc tgcaggcatt cgtaccacac aggcattctc gcaagattgc cgttgggata    5400
cgctggacga cgatcgcgcc aatggctgta tccgctcgct ggaacacgcc tacagcaaag    5460
acggcggcct ggcggtgctc tacggtaact ttgcggaaaa cggctgcatc gtgaaaacgg    5520
caggcgtcga tgacagcatc ctcaaattca ccggcccggc gaaagtgtac gaaagccagg    5580
acgatgcggt agaagcgatt ctcggcgta aagttgtcgc cggagatgtg gtagtaattc    5640
gctatgaagg cccgaaaggc ggtccgggga tgcaggaaat gctctaccca accagcttcc    5700
tgaaatcaat gggtctcggc aaagcctgtg cgctgatcac cgacggtcgt ttctctggtg    5760
gcacctctgg tctttccatc ggccacgtct caccggaagc ggcaagcggc ggcagcattg    5820
gcctgattga agatggtgac ctgatcgcta tcgacatccc gaaccgtggc attcagttac    5880
aggtaagcga tgccgaactg gcggcgcgtc gtgaagcgca ggacgctcga ggtgacaaag    5940
cctggacgcc gaaaaatcgt gaacgtcagg tctcctttgc cctgcgtgct tatgccagcc    6000
tggcaaccag cgccgacaaa ggcgcggtgc gcgataaatc gaaactgggg ggttaaacgc    6060
gtgctagagg catcaaataa aacgaaaggc tcagtcgaaa gactgggcct ttcgttttat    6120
ctgttgtttg tcggtgaacg ctctcctgag taggacaaat ccgccgccct agacctaggg    6180
gatatattcc gcttcctcgc tcactgactc gctacgctcg gtcgttcgac tgcggcgagc    6240
ggaaatggct tacgaacggg gcggagattt cctggaagat gccaggaaga tacttaacag    6300
ggaagtgaga gggccgcggc aaagccgttt ttccataggc tccgcccccc tgacaagcat    6360
cacgaaatct gacgctcaaa tcagtggtgg cgaaacccga caggactata agataccag    6420 gcgtttcccc ctggcggctc cctcgtgcgc tctcctgttc ctgcctttcg gtttaccggt    6480
gtcattccgc tgttatggcc gcgtttgtct cattccacgc ctgacactca gttccgggta    6540
ggcagttcgc tccaagctgg actgtatgca cgaaccccc gttcagtccg accgctgcgc    6600
cttatccggt aactatcgtc ttgagtccaa cccggaaaga catgcaaaag caccactggc    6660
agcagccact ggtaattgat ttagaggagt tagtcttgaa gtcatgcgcc ggttaaggct    6720
aaactgaaag acaagttttt ggtgactgcg ctcctccaag ccagttacct cggttcaaag    6780
agttggtagc tcagagaacc ttcgaaaaac cgccctgcaa ggcggttttt tcgttttcag    6840
agcaagagat tacgcgcaga ccaaaacgat ctcaagaaga tcatcttatt aatcagataa    6900
aatatttcta gatttcagtg caatttatct cttcaaatgt agcacctgaa gtcagcccca    6960
tacgatataa gttgttacta gtgcttggat tctcaccaat aaaaaacgcc cggcggcaac    7020
cgagcgttct gaacaaatcc agatggagtt ctgaggtcat tactggatct atcaacagga    7080
gtccaagcga gct                                                      7093
```

<210> SEQ ID NO 33
<211> LENGTH: 4946
<212> TYPE: DNA
<213> ORGANISM: Artificial Sequence
<220> FEATURE:
<223> OTHER INFORMATION: Synthetic polynucleotide

<400> SEQUENCE: 33

| | | | | | |
|---|---|---|---|---|---|
| ctcgagaatt | gtgagcggat | aacaattgac | attgtgagcg | gataacaaga | tactgagcac | 60 |
| atcagcagga | cgcactgacc | gaattcatta | aagaggagaa | aggtaccatg | tatacagtag | 120 |
| gagattacct | attagaccga | ttacacgagt | taggaattga | agaaattttt | ggagtccctg | 180 |
| gagactataa | cttacaattt | ttagatcaaa | ttatttccca | caaggatatg | aaatgggtcg | 240 |
| gaaatgctaa | tgaattaaat | gcttcatata | tggctgatgg | ctatgctcgt | actaaaaaag | 300 |
| ctgccgcatt | tcttacaacc | tttggagtag | gtgaattgag | tgcagttaat | ggattagcag | 360 |
| gaagttacgc | cgaaaattta | ccagtagtag | aaatagtggg | atcacctaca | tcaaaagttc | 420 |
| aaaatgaagg | aaaatttgtt | catcatacgc | tggctgacgg | tgattttaaa | cactttatga | 480 |
| aaatgcacga | acctgttaca | gcagctcgaa | ctttactgac | agcagaaaat | gcaaccgttg | 540 |
| aaattgaccg | agtactttct | gcactattaa | agaaagaaa | acctgtctat | atcaacttac | 600 |
| cagttgatgt | tgctgctgca | aaagcagaga | accctcact | cccttttgaaa | aaggaaaact | 660 |
| caacttcaaa | tacaagtgac | caagaaattt | tgaacaaaat | tcaagaaagc | ttgaaaaatg | 720 |
| ccaaaaaacc | aatcgtgatt | acaggacatg | aaataattag | ttttggctta | gaaaaaacag | 780 |
| tcactcaatt | tatttcaaag | acaaaactac | ctattcgac | attaaacttt | ggtaaaagtt | 840 |
| cagttgatga | agccctccct | tcatttttag | gaatctataa | tggtacactc | tcagagccta | 900 |
| atcttaaaga | attcgtggaa | tcagccgact | tcatcttgat | gcttggagtt | aaactcacag | 960 |
| actcttcaac | aggagccttc | actcatcatt | taaatgaaaa | taaatgatt | tcactgaata | 1020 |
| tagatgaagg | aaaaatattt | aacgaaagaa | tccaaaattt | tgattttgaa | tccctcatct | 1080 |
| cctctctctt | agacctaagc | gaaatagaat | acaaggaaa | atatatcgat | aaaaagcaag | 1140 |
| aagactttgt | tccatcaaat | gcgcttttat | cacaagaccg | cctatggcaa | gcagttgaaa | 1200 |
| acctaactca | aagcaatgaa | acaatcgttg | ctgaacaagg | gacatcattc | tttggcgctt | 1260 |
| catcaatttt | cttaaaatca | aagagtcatt | ttattggtca | acccttatgg | ggatcaattg | 1320 |
| gatatacatt | cccagcagca | ttaggaagcc | aaattgcaga | taaagaaagc | agacacctttt | 1380 |
| tatttattgg | tgatggttca | cttcaactta | cagtgcaaga | attaggatta | gcaatcagag | 1440 |
| aaaaaattaa | tccaatttgc | tttattatca | ataatgatgg | ttatacagtc | gaaagagaaa | 1500 |
| ttcatggacc | aaatcaaagc | tacaatgata | ttccaatgtg | gaattactca | aaattaccag | 1560 |
| aatcgtttgg | agcaacagaa | gatcgagtag | tctcaaaaat | cgttagaact | gaaaatgaat | 1620 |
| ttgtgtctgt | catgaaagaa | gctcaagcag | atccaaatag | aatgtactgg | attgagttaa | 1680 |
| ttttggcaaa | agaaggtgca | ccaaaagtac | tgaaaaaaat | gggcaaacta | tttgctgaac | 1740 |
| aaaataaatc | ataagcatgc | aggagatata | ccatgtctat | tccagaaact | caaaaagcca | 1800 |
| ttatcttcta | cgaatccaac | ggcaagttgg | agcataagga | tatcccagtt | ccaaagccaa | 1860 |
| agcccaacga | attgttaatc | aacgtcaagt | actctggtgt | ctgccacacc | gatttgcacg | 1920 |
| cttggcatgg | tgactggcca | ttgccaacta | agttaccatt | agttggtggt | cacgaaggtg | 1980 |
| ccggtgtcgt | tgtcggcatg | ggtgaaaacg | ttaagggctg | gaagatcggt | gactacgccg | 2040 |
| gtatcaaatg | gttgaacggt | tcttgtatgg | cctgtgaata | ctgtgaattg | ggtaacgaat | 2100 |

```
ccaactgtcc tcacgctgac ttgtctggtt acacccacga cggttctttc caagaatacg    2160
ctaccgctga cgctgttcaa gccgctcaca ttcctcaagg tactgacttg gctgaagtcg    2220
cgccaatctt gtgtgctggt atcaccgtat acaaggcttt gaagtctgcc aacttgagag    2280
caggccactg ggcggccatt tctggtgctg ctggtggtct aggttctttg gctgttcaat    2340
atgctaaggc gatgggttac agagtcttag gtattgatgg tggtccagga aaggaagaat    2400
tgtttacctc gctcggtggt gaagtattca tcgacttcac caaagagaag gacattgtta    2460
gcgcagtcgt taaggctacc aacggcggtg cccacggtat catcaatgtt ccgtttccg     2520 aagccgctat cgaagcttct accagatact gtagggcgaa cggtactgtt gtcttggttg    2580
gtttgccagc cggtgcaaag tgctcctctg atgtcttcaa ccacgttgtc aagtctatct    2640
ccattgtcgg ctcttacgtg gggaacagag ctgataccag agaagcctta gatttctttg    2700
ccagaggtct agtcaagtct ccaataaagg tagttggctt atccagttta ccagaaattt    2760
acgaaaagat ggagaagggc caaattgctg gtagatacgt tgttgacact tctaaataat    2820
ctagaggcat caaataaaac gaaaggctca gtcgaaagac tgggcctttc gttttatctg    2880
ttgtttgtcg gtgaacgctc tcctgagtag gacaaatccg ccgccctaga cctaggcgtt    2940
cggctgcggc gagcggtatc agctcactca aaggcggtaa tacggttatc cacagaatca    3000
ggggataacg caggaaagaa catgtgagca aaaggccagc aaaaggccag gaaccgtaaa    3060
aaggccgcgt tgctggcgtt tttccatagg ctccgccccc ctgacgagca tcacaaaaat    3120
cgacgctcaa gtcagaggtg gcgaaacccg acaggactat aaagatacca ggcgtttccc    3180
cctggaagct ccctcgtgcg ctctcctgtt ccgaccctgc cgcttaccgg atacctgtcc    3240
gcctttctcc cttcgggaag cgtggcgctt tctcaatgct cacgctgtag gtatctcagt    3300
tcggtgtagg tcgttcgctc caagctgggc tgtgtgcacg aaccccccgt tcagcccgac    3360
cgctgcgcct tatccggtaa ctatcgtctt gagtccaacc cggtaagaca cgacttatcg    3420
ccactggcag cagccactgg taacaggatt agcagagcga ggtatgtagg cggtgctaca    3480
gagttcttga agtggtggcc taactacggc tacactagaa ggacagtatt tggtatctgc    3540
gctctgctga agccagttac cttcggaaaa agagttggta gctcttgatc cggcaaacaa    3600
accaccgctg gtagcggtgg tttttttgtt tgcaagcagc agattacgcg cagaaaaaaa    3660
ggatctcaag aagatccttt gatcttttct acggggtctg acgctcagtg gaacgaaaac    3720
tcacgttaag ggattttggt catgactagt gcttggattc tcaccaataa aaaacgcccg    3780
gcggcaaccg agcgttctga acaaatccag atggagttct gaggtcatta ctggatctat    3840
caacaggagt ccaagcgagc tcgtaaactt ggtctgacag ttaccaatgc ttaatcagtg    3900 aggcaccctat ctcagcgatc tgtctatttc gttcatccat agttgcctga ctccccgtcg    3960
tgtagataac tacgatacgg gagggcttac catctggccc cagtgctgca atgataccgc    4020
gagacccacg ctcaccggct ccagatttat cagcaataaa ccagccagcc ggaagggccg    4080
agcgcagaag tggtcctgca actttatccg cctccatcca gtctattaat tgttgccggg    4140
aagctagagt aagtagttcg ccagttaata gtttgcgcaa cgttgttgcc attgctacag    4200
gcatcgtggt gtcacgctcg tcgtttggta tggcttcatt cagctccggt tcccaacgat    4260
caaggcgagt tacatgatcc cccatgttgt gcaaaaaagc ggttagctcc ttcggtcctc    4320
cgatcgttgt cagaagtaag ttggccgcag tgttatcact catggttatg gcagcactgc    4380
ataattctct tactgtcatg ccatccgtaa gatgcttttc tgtgactggt gagtactcaa    4440
```

```
ccaagtcatt ctgagaatag tgtatgcggc gaccgagttg ctcttgcccg gcgtcaatac    4500
gggataatac cgcgccacat agcagaactt taaaagtgct catcattgga aaacgttctt    4560
cggggcgaaa actctcaagg atcttaccgc tgttgagatc cagttcgatg taacccactc    4620
gtgcacccaa ctgatcttca gcatctttta ctttcaccag cgtttctggg tgagcaaaaa    4680
caggaaggca aaatgccgca aaaagggaa taagggcgac acggaaatgt tgaatactca    4740
tactcttcct ttttcaatat tattgaagca tttatcaggg ttattgtctc atgagcggat    4800
acatatttga atgtatttag aaaaataaac aatagggggt tccgcgcaca tttccccgaa    4860
aagtgccacc tgacgtctaa gaaaccatta ttatcatgac attaacctat aaaaataggc    4920
gtatcacgag gccctttcgt cttcac                                         4946
```

<210> SEQ ID NO 34
<211> LENGTH: 7248
<212> TYPE: DNA
<213> ORGANISM: Artificial Sequence
<220> FEATURE:
<223> OTHER INFORMATION: Synthetic polynucleotide

<400> SEQUENCE: 34

```
taagaaacca ttattatcat gacattaacc tataaaaata ggcgtatcac gaggcccttt     60
cgtcttcacc tcgagaattg tgagcggata caattgaca ttgtgagcgg ataacaagat     120
actgagcaca tcagcaggac gcactgaccg aattcattaa agaggagaaa ggtacaatgt    180
tgacaaaagc aacaaaagaa caaaaatccc ttgtgaaaaa cagaggggcg agcttgttg    240 ttgattgctt agtggagcaa ggtgtcacac atgtatttgg cattccaggt gcaaaaattg    300
atgcggtatt tgacgcttta caagataaag gacctgaaat tatcgttgcc cggcacgaac    360
aaaacgcagc attcatggcc caagcagtcg gccgtttaac tggaaaaccg ggagtcgtgt    420
tagtcacatc aggaccgggt gcctctaact tggcaacagg cctgctgaca gcgaacactg    480
aaggagaccc tgtcgttgcg cttgctgaaa acgtgatccg tgcagatcgt ttaaaacgga    540
cacatcaatc tttggataat gcggcgctat tccagccgat tacaaaatac agtgtagaag    600
ttcaagatgt aaaaaatata ccggaagctg ttacaaatgc atttaggata gcgtcagcag    660
ggcaggctgg ggccgctttt gtgagctttc gcaagatgt tgtgaatgaa gtcacaaata    720
cgaaaaacgt gcgtgctgtt gcagcgccaa aactcggtcc tgcagcagat gatgcaatca    780
gtgcggccat agcaaaaatc caaacagcaa aacttcctgt cgttttggtc ggcatgaaag    840
gcggaagacc ggaagcaatt aaagcggttc gcaagctttt gaaaaaggtt cagcttccat    900
ttgttgaaac atatcaagct gccggtaccc tttctagaga tttagaggat caatattttg    960
gccgtatcgg tttgttccgc aaccagcctg gcgattact gctagagcag gcagatgttg    1020
ttctgacgat cggctatgac ccgattgaat atgatccgaa attctggaat atcaatggag    1080 accgggacaat tatccattta gacgagatta tcgctgacat tgatcatgct taccagcctg    1140
atcttgaatt gatcggtgac attccgtcca cgatcaatca tatcgaacac gatgctgtga    1200
aagtggaatt tgcagagcgt gagcagaaaa tcctttctga tttaaaacaa tatatgcatg    1260
aaggtgagca ggtgcctgca gattggaaat cagacagagc gcaccctctt gaaatcgtta    1320
aagagttgcg taatgcagtc gatgatcatg ttacagtaac ttgcgatatc ggttcgcacg    1380
ccatttggat gtcacgttat ttccgcagct acgagccgtt aacattaatg atcagtaacg    1440
gtatgcaaac actcggcgtt gcgcttcctt gggcaatcgg cgcttcattg gtgaaaccgg    1500
gagaaaaagt ggtttctgtc tctggtgacg gcggtttctt attctcagca atggaattag    1560
```

```
agacagcagt tcgactaaaa gcaccaattg tacacattgt atggaacgac agcacatatg   1620
acatggttgc attccagcaa ttgaaaaaat ataaccgtac atctgcggtc gatttcggaa   1680
atatcgatat cgtgaaatat gcggaaagct tcggagcaac tggcttgcgc gtagaatcac   1740
cagaccagct ggcagatgtt ctgcgtcaag gcatgaacgc tgaaggtcct gtcatcatcg   1800
atgtcccggt tgactacagt gataacatta atttagcaag tgacaagctt ccgaaagaat   1860
tcggggaact catgaaaacg aaagctctct aggtcgacga ggaatcacca tggctaacta   1920
cttcaataca ctgaatctgc cgcagcagct ggcacagctg gcaaatgtc gctttatggg    1980 ccgcgatgaa ttcgccgatg gcgcgagcta ccttcagggt aaaaaagtag tcatcgtcgg   2040
ctgtggcgca cagggtctga accagggcct gaacatgcgt gattctggtc tcgatatctc   2100
ctacgctctg cgtaaagaag cgattgccga gaagcgcgcg tcctggcgta aagcgaccga   2160
aaatggtttt aaagtgggta cttacgaaga actgatccca caggcggatc tggtgattaa   2220
cctgacgccg gacaagcagc actctgatgt agtgcgcacc gtacagccac tgatgaaaga   2280
cggcgcggcg ctgggctact cgcacggttt caacatcgtc gaagtgggcg agcagatccg   2340
taaagatatc accgtagtga tggttgcgcc gaaatgccca ggcaccgaag tgcgtgaaga   2400
gtacaaacgt gggttcggcg taccgacgct gattgccgtt cacccggaaa acgatccgaa   2460
aggcgaaggc atggcgattg ccaaagcctg gcggctgca accggtggtc accgtgcggg    2520
tgtgctggaa tcgtccttcg ttgcggaagt gaaatctgac ctgatgggcg agcaaaccat   2580
cctgtgcggt atgttgcagg ctggctctct gctgtgcttc gacaagctgg tggaagaagg   2640
taccgatcca gcatacgcag aaaaactgat tcagttcggt tgggaaacca tcaccgaagc   2700
actgaaacag ggcggcatca ccctgatgat ggaccgtctc tctaacccgg cgaaactgcg   2760
tgcttatgcg ctttctgaac agctgaaaga gatcatggca cccctgttcc agaaacatat   2820
ggacgacatc atctccggcg aattctcttc cggtatgatg gcggactggg ccaacgatga   2880
taagaaactg ctgacctggc gtgaagagac cggcaaaacc gcgtttgaaa ccgcgccgca   2940
gtatgaaggc aaaatcggcg agcaggagta cttcgataaa ggcgtactga tgattgcgat   3000
ggtgaaagcg ggcgttgaac tggcgttcga accatggtc gattccggca tcattgaaga    3060
gtctgcatat tatgaatcac tgcacgagct gccgctgatt gccaacacca tcgcccgtaa   3120
gcgtctgtac gaaatgaacg tggttatctc tgataccgct gagtacggta actatctgtt   3180
ctcttacgct tgtgtgccgt tgctgaaacc gtttatggca gagctgcaac cgggcgacct   3240
gggtaaagct attccggaag cgcggtaga taacgggcaa ctgcgtgatg tgaacgaagc    3300
gattcgcagc catgcgattg agcaggtagg taagaaactg cgcggctata tgacagatat   3360
gaaacgtatt gctgttgcgg gttaacccgg aaggagatat accatgccta agtaccgttc   3420
cgccaccacc actcatggtc gtaatatggc gggtgctcgt gcgctgtggc gcgccaccgg   3480
aatgaccgac gccgatttcg gtaagccgat tatcgcggtt gtgaactcgt tcacccaatt   3540
tgtaccgggt cacgtccatc tgcgcgatct cggtaaactg gtcgccgaac aaattgaagc   3600
ggctggcggc gttgccaaag agttcaacac cattgcggtg gatgatggga ttgccatggg   3660
ccacgggggg atgctttatt cactgccatc tcgcgaacta tcgctgatt ccgttgagta    3720 tatggtcaac gcccactgcg ccgacgccat ggtctgcatc tctaactgcg acaaaatcac   3780 cccgggggatg ctgatggctt ccctgcgcct gaatattccg gtgatctttg tttccgcgg   3840 cccgatggag gccgggaaaa ccaaactttc cgatcagatc atcaagctcg atctggttga   3900
```

```
tgcgatgatc cagggcgcag acccgaaagt atctgactcc cagagcgatc aggttgaacg   3960
ttccgcgtgt ccgacctgcg gttcctgctc cgggatgttt accgctaact caatgaactg   4020
cctgaccgaa gcgctgggcc tgtcgcagcc gggcaacggc tcgctgctgg caacccacgc   4080
cgaccgtaag cagctgttcc ttaatgctgg taaacgcatt gttgaattga ccaaacgtta   4140
ttacgagcaa aacgacgaaa gtgcactgcc gcgtaatatc gccagtaagg cggcgtttga   4200
aaacgccatg acgctggata tcgcgatggg tggatcgact aacaccgtac ttcacctgct   4260
ggcggcggcg caggaagcgg aaatcgactt caccatgagt gatatcgata agctttcccg   4320
caaggttcca cagctgtgta agttgcgcc gagcacccag aaataccata tggaagatgt   4380
tcaccgtgct ggtggtgtta tcggtattct cggcgaactg gatcgcgcgg ggttactgaa   4440
ccgtgatgtg aaaaacgtac ttggcctgac gttgccgcaa acgctggaac aatacgacgt   4500
tatgctgacc caggatgacg cggtaaaaaa tatgttccgc gcaggtcctg caggcattcg   4560
taccacacag gcattctcgc aagattgccg ttgggatacg ctggacgacg atcgcgccaa   4620
tggctgtatc cgctcgctgg aacacgccta cagcaaagac ggcggcctgg cggtgctcta   4680
cggtaacttt gcggaaaacg gctgcatcgt gaaaacggca ggcgtcgatg acagcatcct   4740
caaattcacc ggcccggcga agtgtacga agccaggac gatgcggtag aagcgattct   4800
cggcggtaaa gttgtcgccg agatgtggt agtaattcgc tatgaaggcc gaaaggcgg   4860
tccggggatg caggaaatgc tctacccaac cagcttcctg aaatcaatgg gtctcggcaa   4920
agcctgtgcg ctgatcaccg acggtcgttt ctctggtggc acctctggtc tttccatcgg   4980
ccacgtctca ccggaagcgg caagcggcgg cagcattggc ctgattgaag atggtgacct   5040
gatcgctatc gacatcccga accgtggcat tcagttacag gtaagcgatg ccgaactggc   5100
ggcgcgtcgt gaagcgcagg acgctcgagg tgacaaagcc tggacgccga aaaatcgtga   5160
acgtcaggtc tcctttgccc tgcgtgctta tgccagcctg gcaaccagcg ccgacaaagg   5220
cgcggtgcgc gataaatcga aactgggggg ttaaacgcgt gctagaggca tcaaataaaa   5280
cgaaaggctc agtcgaaaga ctgggccttt cgttttatct gttgtttgtc ggtgaacgct   5340
ctcctgagta ggacaaatcc gccgccctag acctaggga tatattccgc ttcctcgctc   5400
actgactcgc tacgctcggt cgttcgactg cggcgagcgg aaatggctta cgaacggggc   5460
ggagatttcc tggaagatgc caggaagata cttaacaggg aagtgagagg ccgcggcaa   5520
agccgttttt ccataggctc cgcccccctg acaagcatca cgaaatctga cgctcaaatc   5580
agtggtggcg aaacccgaca ggactataaa gataccaggc gtttccccct ggcggctccc   5640
tcgtgcgctc tcctgttcct gcctttcggt ttaccggtgt cattccgctg ttatggccgc   5700
gtttgtctca ttccacgcct gacactcagt tccgggtagg cagttcgctc caagctggac   5760
tgtatgcacg aaccccccgt tcagtccgac cgctgcgcct tatccggtaa ctatcgtctt   5820
gagtccaacc cggaaagaca tgcaaaagca ccactggcag cagccactgg taattgattt   5880
agaggagtta gtcttgaagt catgcgccgg ttaaggctaa actgaaagga caagttttgg   5940
tgactgcgct cctccaagcc agttacctcg gttcaaagag ttggtagctc agagaaccctt   6000
cgaaaaccg ccctgcaagg cggttttttc gttttcagag caagagatta cgcgcagacc   6060
aaaacgatct caagaagatc atcttattaa tcagataaaa tatttctaga tttcagtgca   6120
atttatctct tcaaatgtag cacctgaagt cagccccata cgatataagt tgttactagt   6180
gcttggattc tcaccaataa aaaacgcccg gcggcaaccg agcgttctga acaaatccag   6240
atggagttct gaggtcatta ctggatctat caacaggagt ccaagcgagc tctcgaaccc   6300
```

```
cagagtcccg ctcagaagaa ctcgtcaaga aggcgataga aggcgatgcg ctgcgaatcg    6360
ggagcggcga taccgtaaag cacgaggaag cggtcagccc attcgccgcc aagctcttca    6420
gcaatatcac gggtagccaa cgctatgtcc tgatagcggt ccgccacacc cagccggcca    6480
cagtcgatga atccagaaaa gcggccattt tccaccatga tattcggcaa gcaggcatcg    6540
ccatgggtca cgacgagatc ctcgccgtcg ggcatgcgcg ccttgagcct ggcgaacagt    6600
tcggctggcg cgagccsctg atgctcttcg tccagatcat cctgatcgac aagaccggct    6660
tccatccgag tacgtgctcg ctcgatgcga tgtttcgctt ggtggtcgaa tgggcaggta    6720
gccggatcaa gcgtatgcag ccgccgcatt gcatcagcca tgatggatac tttctcggca    6780
ggagcaaggt gagatgacag gagatcctgc cccggcactt cgcccaatag cagccagtcc    6840
cttcccgctt cagtgacaac gtcgagcaca gctgcgcaag gaacgcccgt cgtggccagc    6900
cacgatagcc gcgctgcctc gtcctgcagt tcattcaggg caccggacag gtcggtcttg    6960
acaaaaagaa ccgggcgccc ctgcgctgac agccggaaca cggcggcatc agagcagccg    7020
attgtctgtt gtgcccagtc atagccgaat agcctctcca cccaagcggc cggagaacct    7080
gcgtgcaatc catcttgttc aatcatgcga aacgatcctc atcctgtctc ttgatcagat    7140
cttgatcccc tgcgccatca gatccttggc ggcaagaaag ccatccagtt tactttgcag    7200
ggcttcccaa ccttaccaga gggcgcccca gctggcaatt ccgacgtc                 7248
```

<210> SEQ ID NO 35
<211> LENGTH: 45
<212> TYPE: DNA
<213> ORGANISM: Artificial Sequence
<220> FEATURE:
<223> OTHER INFORMATION: Synthetic primer

<400> SEQUENCE: 35

```
gaagcagctc cagcctacac cctactcagg agagcgttca ccgac              45
```

METHODS FOR THE ECONOMICAL PRODUCTION OF BIOFUEL FROM BIOMASS

CROSS REFERENCE TO RELATED APPLICATIONS

This application is a continuation of U.S. Utility application Ser. No. 12/263,436 filed Oct. 31, 2008, now U.S. Pat. No. 8,431,374, which claims the benefit of U.S. Provisional Application Ser. No. 60/984,235 filed Oct. 31, 2007; U.S. Provisional Application Ser. No. 60/984,521 filed Nov. 1, 2007; U.S. Provisional Application Ser. No. 60/984,793 filed Nov. 2, 2007; U.S. Provisional Application Ser. No. 60/985, 155 filed Nov. 2, 2007; U.S. Provisional Application Ser. No. 60/985,209 filed Nov. 3, 2007; U.S. Provisional Application Ser. No. 60/985,460 filed Nov. 5, 2007; U.S. Provisional Application Ser. No. 60/985,607 filed Nov. 5, 2007; U.S. Provisional Application Ser. No. 60/986,151 filed Nov. 7, 2007; U.S. Provisional Application Ser. No. 60/986,235 filed Nov. 7, 2007; U.S. Provisional Application Ser. No. 60/987, 984 filed Nov. 14, 2007; U.S. Provisional Application Ser. No. 60/988,588 filed Nov. 16, 2007; U.S. Provisional Application Ser. No. 60/989,032, filed Nov. 19, 2007; U.S. Provisional Application Ser. No. 60/989,785 filed Nov. 21, 2007; U.S. Provisional Application Ser. No. 61/014,297 filed Dec. 17, 2007; and U.S. Provisional Application Ser. No. 61/029, 222 filed Feb. 15, 2008. This application is also related to the U.S. patent application entitled "Methods for the Economical Production of Biofuel Precursors that is also a Biofuel from Biomass" with U.S. Utility application Ser. No. 12/263,442 filed Oct. 31, 2008. Accordingly, this application incorporates by reference in its entirety all subject matter of the above-referenced applications to the extent such subject matter is not inconsistent herewith.

TECHNICAL FIELD

The disclosure relates generally to methods and compositions for producing biofuels.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: GEVO_017_28US_SeqList.txt, date recorded: Apr. 5, 2013, file size 62 kilobytes).

BACKGROUND

Biofuels have a long history ranging back to the beginning on the 20th century. As early as 1900, Rudolf Diesel demonstrated at the World Exhibition in Paris, France, an engine running on peanut oil. Soon thereafter, Henry Ford demonstrated his Model T running on ethanol derived from corn. Petroleum-derived fuels displaced biofuels in the 1930s and 1940s due to increased supply and efficiency at a lower cost.

Market fluctuations in the 1970s, due the Arab oil embargo and the Iranian revolution, coupled to the decrease in U.S. oil production led to an increase in crude oil prices and a renewed interest in biofuels. Today, many interest groups, including policy makers, industry planners, aware citizens, and the financial community, are interested in substituting petroleum-derived fuels with biomass-derived biofuels. The leading motivation for developing biofuels is of economical nature, namely, the threat of 'peak oil', the point at which the consumption rate of crude oil exceeds the supply rate, thus leading to significantly increased fuel cost, and resulting in an increased demand for alternative fuels.

Biofuels tend to be produced with local agricultural resources in many, relatively small facilities, and are seen as a stable and secure supply of fuels independent of geopolitical problems associated with petroleum. At the same time, biofuels enhance the agricultural sector of national economies. In addition, environmental concerns relating to the possibility of carbon dioxide related climate change is an important social and ethical driving force which is starting to result in government regulations and policies such as caps on carbon dioxide emissions from automobiles, taxes on carbon dioxide emissions, and tax incentives for the use of biofuels.

The acceptance of biofuels depends primarily on economical competitiveness of biofuels when compared to petroleum-derived fuels. As long as biofuels cannot compete in cost with petroleum-derived fuels, use of biofuels will be limited to specialty applications and niche markets. Today, the use of biofuels is limited to ethanol and biodiesel. Currently, ethanol is made by fermentation from corn in the US and from sugar cane in Brazil and is competitive with petroleum-derived gasoline, exclusive of subsidies or tax benefits, if crude oil costs above $50 USD per barrel and $40 USD per barrel, respectively. Biodiesel has a breakeven price of crude oil of over $60 USD/barrel to be competitive with petroleum-based diesel (Nexant Chem. Systems. 2006. Final Report, Liquid Biofuels: Substituting for Petroleum, White Plains, N.Y.).

SUMMARY

In an embodiment, there is provided a method of making a biofuel, comprising providing a biocatalyst selected to convert a feedstock into the biofuel at a yield of at least 80 percent theoretical yield, a productivity of at least 0.75 grams biofuel per liter per hour, and a titer equivalent to a lower one of (i) a solubility limit of the biofuel in water under the process conditions and (ii) 2% (w/w) of the biofuel in water; providing the biocatalyst selected to have at least two properties from a. to l. as follows: a. the biocatalyst selected to convert at least two sugars, including each of (i) at least one of a six-carbon sugar and a six-carbon sugar oligomer, and (ii) at least one five-carbon sugar, derived from at least one of starch, cellulose, hemicellulose, and pectin into the biofuel; b. the biocatalyst exhibiting a level of endotoxin toxicity or exotoxin toxicity, wherein the level of endotoxin or exotoxin toxicity in the biocatalyst has a median lethal dose (LD50) of at least 1000-fold more than the amount present in 1 kilogram of at least one of a DDG and a DDGS product; c. the biocatalyst containing no DNA markers; d. the biocatalyst operable to produce the biofuel free of byproducts that would require additional processing steps for removal from the biofuel; e. the biocatalyst operable at a pH value between about 2 to about 7 to produce the biofuel; f. the biocatalyst selected to have a recoverable productivity from a sudden change of about 1 pH unit from the first pH, the fermentation having a second pH that lasts for up to three hours before returning to the first pH; g. the biocatalyst operable within a temperature range of about 30° C. to about 60° C. to produce the biofuel; h. the biocatalyst selected to have a recoverable productivity from a sudden change of about 10° C. from the first temperature, the fermentation having a second temperature that lasts for up to three hours before returning to the first temperature; i. the biocatalyst operable in a medium where mineral salts composed of major and minor bioelements and vitamins are provided in addition to the feedstock; j. the biocatalyst selected to have a growth rate of at least 0.2 per hour; k. one attribute chosen from (1) providing an anaerobic biocatalyst operable at dissolved oxygen concentrations across a range of about 0% to about 0.01% to produce the biofuel, and (2) providing a facultative anaerobic biocatalyst modified to inhibit aerobic respiration with dissolved oxygen present, the biocatalyst operable with the dissolved oxygen present; and l. providing an anaerobic biocatalyst selected to have a productivity that fully recovers from an exposure to more than 1% air saturation that lasts for up to three hours; and cultivating the biocatalyst in a culture medium until a recoverable quantity of the biofuel is produced; and recovering the biofuel.

In another embodiment, there is provided a method of making a biofuel, comprising providing a biocatalyst selected to convert a feedstock into the biofuel at a yield of at least 80 percent theoretical yield, a productivity of at least 0.75 grams biofuel per gram cell dry weight, and a titer equivalent to a lower one of (i) a solubility limit of the biofuel in water under the process conditions and (ii) 2% (w/w) of the biofuel in water; providing the biocatalyst selected to convert at least two sugars, including each of (i) at least one of a six-carbon sugar and a six-carbon sugar oligomer, and (ii) at least one five-carbon sugar, derived from at least one of starch, cellulose, hemicellulose, and pectin into the biofuel; providing the biocatalyst exhibiting a level of endotoxin toxicity or exotoxin toxicity, wherein the level of endotoxin or exotoxin toxicity in the biocatalyst has a median lethal dose (LD50) of at least 1000-fold more than the amount present in 1 kilogram of at least one of a DDG and a DDGS product; providing the biocatalyst that contains no DNA markers; and providing the biocatalyst operable to produce the biofuel free of byproducts that would require additional processing steps for removal from the biofuel; providing the biocatalyst operable at a pH value between about 2 to about 7 to produce the biofuel; providing the biocatalyst selected to have a recoverable productivity from a sudden change of about 1 pH unit from the first pH, the fermentation having a second pH that lasts for up to three hours before returning to the first pH; providing the biocatalyst operable within a temperature range of about 30° C. to about 60° C. to produce the biofuel; providing the biocatalyst selected to have a recoverable productivity from a sudden change of about 10° C. from the first temperature, the fermentation having a second temperature that lasts for up to three hours before returning to the first temperature; providing the biocatalyst operable in a medium where mineral salts composed of major and minor bioelements and vitamins are provided in addition to the feedstock; providing the biocatalyst selected to have a growth rate of at least 0.2 per hour; providing the biocatalyst selected to have one attribute chosen from: a. providing an anaerobic biocatalyst operable at dissolved oxygen concentrations across a range of about 0% to about 0.01% to produce the biofuel, and wherein the anaerobic biocatalyst has a productivity that fully recovers from an exposure to more than 1% air saturation that lasts for up to three hours; and b. providing a facultative anaerobic biocatalyst modified to inhibit aerobic respiration with dissolved oxygen present, the biocatalyst operable with the dissolved oxygen present; cultivating the biocatalyst in a culture medium until a recoverable quantity of the biofuel is produced; and recovering the biofuel.

In still another embodiment, there is provided a method of making a biofuel, comprising providing a biocatalyst selected to convert a feedstock into the biofuel at a yield of at least 80 percent theoretical yield, a productivity of at least 0.75 grams biofuel per liter per hour, and a titer equivalent to a lower one of (i) a solubility limit of the biofuel in water under the process conditions and (ii) 2% (w/w) of the biofuel in water; providing the biocatalyst operable to produce the biofuel free of byproducts that would require additional processing steps for removal from the biofuel; providing the biocatalyst operable at a pH value between about 2 to about 7 to produce the biofuel; providing the biocatalyst that has a growth rate of at least 0.2 per hour; and providing the biocatalyst operable within a temperature range of about 30° C. to about 60° C. to produce the biofuel; providing the biocatalyst operable in a medium where mineral salts composed of major and minor bioelements and vitamins are provided in addition to the feedstock; cultivating the biocatalyst in a culture medium until a recoverable quantity of the biofuel is produced; and recovering the biofuel.

In yet another embodiment, there is provided a method of making a biofuel, comprising providing a biocatalyst selected to convert a feedstock into the biofuel at a yield of at least 80 percent theoretical yield, a productivity of at least 0.75 grams biofuel per liter per hour, and a titer equivalent to a lower one of (i) a solubility limit of the biofuel in water under the process conditions and (ii) 2% (w/w) of the biofuel in water; and cultivating the biocatalyst in a culture medium until a recoverable quantity of the biofuel is produced; and recovering the biofuel.

In another embodiment, methods of making a biofuel are provided that include providing a biocatalyst selected to convert a feedstock into the biofuel at a yield of at least 80 percent of theoretical, a productivity of at least 0.75 grams biofuel per liter per hour, and a titer equivalent to a lower one of (i) a solubility limit of the biofuel in water under the process conditions and (ii) 2% (w/w) of the biofuel in water. The methods further include providing the biocatalyst selected to have at least two properties from: a) the biocatalyst selected to convert at least two sugars, including each of (i) at least one of a six-carbon sugar and a six-carbon sugar oligomer, and (ii) at least one five-carbon sugar, derived from at least one of starch, cellulose, hemicellulose, and pectin into the biofuel; b) the biocatalyst exhibiting a level of endotoxin toxicity or exotoxin toxicity, wherein the level of endotoxin or exotoxin toxicity in the biocatalyst has a median lethal dose (LD50) of at least 1000-fold more than the amount present in 1 kilogram of at least one of a DDG and a DDGS product; c) the biocatalyst containing no DNA markers; d) the biocatalyst operable to produce the biofuel free of byproducts that would require additional processing steps for removal from the biofuel; e) the biocatalyst operable at a pH value between about 2 to about 7 to produce the biofuel; f) the biocatalyst selected to have a recoverable productivity from a sudden change of about 1 pH unit from the first pH; g) the biocatalyst operable within a temperature range of about 30° C. to about 60° C. to produce the biofuel; h) the biocatalyst selected to have a recoverable productivity from a sudden change of about 5° C. from the first temperature; i) the biocatalyst operable in a medium where mineral salts composed of major and minor bioelements are provided in addition to the feedstock; j) the biocatalyst selected to have a growth rate of at least 0.2 per hour; k) one attribute chosen from (1) providing a facultative anaerobic biocatalyst operable at dissolved oxygen concentrations across a range of about 0% to about 0.01% to produce the biofuel; and l) providing an anaerobic biocatalyst selected to have a productivity that fully recovers from an exposure to more than 1% air saturation that lasts for up to three hours. The methods further include cultivating the biocatalyst in a culture medium until a recoverable quantity of the biofuel is produced. The methods optionally include recovering the biofuel.

In another embodiment, methods of making a biofuel are provided that include providing a biocatalyst selected to convert a feedstock into the biofuel at a yield of at least 80 percent theoretical yield, a productivity of at least 0.75 grams biofuel per gram cell dry weight, and a titer equivalent to a lower one of (i) a solubility limit of the biofuel in water under the process conditions and (ii) 2% (w/w) of the biofuel in water. The biocatalyst is further selected to convert at least two sugars, including each of (i) at least one of a six-carbon sugar and a six-carbon sugar oligomer, and (ii) at least one five-carbon sugar, derived from at least one of starch, cellulose, hemicellulose, and pectin into the biofuel. The biocatalyst exhibits a level of endotoxin toxicity or exotoxin toxicity having a median lethal dose (LD50) of at least 1000-fold more than the amount present in 1 kilogram of at least one of a DDG and a DDGS product. The biocatalyst contains no DNA markers and is operable to produce the biofuel free of byproducts that require additional processing steps for removal from the biofuel. The biocatalyst is operable at a pH value between about 2 to about 7 and is selected to have a recoverable productivity from a change of about 1 pH unit from the first pH. The biocatalyst is operable within a temperature range of about 30° C. to about 60° C. and is selected to have a recoverable productivity from a change of about 5° C. from the first temperature. The biocatalyst is operable in a medium where only mineral salts composed of major and minor bioelements are provided in addition to the feedstock and has a growth rate of at least 0.2 per hour. The biocatalyst is further selected to have one attribute chosen from: a) operable at dissolved oxygen concentrations across a range of about 0% to about 0.01% to produce the biofuel, or b) a productivity that fully recovers from an exposure to more than 1% air saturation that lasts for up to three hours. The methods further include cultivating the biocatalyst in a culture medium until a recoverable quantity of the biofuel is produced. The methods optionally include recovering the biofuel.

In another embodiment, a method of making a biofuel is provided. The method includes: providing a biocatalyst selected to convert a feedstock into the biofuel at a yield of at least 80 percent of theoretical, a productivity of at least 0.75 grams biofuel per liter per hour, and a titer equivalent to a lower one of (i) a solubility limit of the biofuel in water under the process conditions and (ii) 2% (w/w) of the biofuel in water; providing the biocatalyst selected to have at least two properties from a. to l. as follows: a. the biocatalyst selected to convert at least two sugars, including each of (i) at least one of a six-carbon sugar and a six-carbon sugar oligomer, and (ii) at least one five-carbon sugar, derived from at least one of starch, cellulose, hemicellulose, and pectin into the biofuel; b. the biocatalyst exhibiting a level of endotoxin toxicity or exotoxin toxicity, wherein the level of endotoxin or exotoxin toxicity in the biocatalyst has a median lethal dose (LD50) of at least 1000-fold more than the amount present in 1 kilogram of at least one of a DDG and a DDGS product; c. the biocatalyst containing no DNA markers; d. the biocatalyst operable to produce the biofuel free of byproducts that would require additional processing steps for removal from the biofuel; e. the biocatalyst operable at a pH value between about 2 to 10 to produce the biofuel; f. the biocatalyst selected to have a recoverable productivity from a sudden change of about 1 pH unit from the first pH; g. the biocatalyst operable within a temperature range of about 20° C. to 60° C. to produce the biofuel; h. the biocatalyst selected to have a recoverable productivity from a sudden change of about 5° C. from the first temperature; i. the biocatalyst operable in a medium comprising feedstock; j. the biocatalyst selected to have a growth rate of at least 0.2 per hour; k. providing a facultative anaerobic biocatalyst operable at dissolved oxygen concentrations across a range of about 0% to about 0.01% air saturation to produce the biofuel; and l. providing an anaerobic biocatalyst selected to have a productivity that recovers from an exposure to more than 1% air saturation that lasts for up to three hours; and cultivating the biocatalyst in a culture medium until a recoverable quantity of the biofuel is produced; and optionally recovering the biofuel.

In another embodiment, a method of making a biofuel is provided. The method includes: providing a biocatalyst selected to convert a feedstock into the biofuel at a yield of at least 80 percent theoretical yield, a productivity of at least 0.75 grams biofuel per liter per hour, and a titer equivalent to a lower one of (i) a solubility limit of the biofuel in water under the process conditions and (ii) 2% (w/w) of the biofuel in water; and cultivating the biocatalyst in a culture medium until a recoverable quantity of the biofuel is produced; and optionally recovering the biofuel.

In another embodiment, a biofuel produced by any method set forth in the present application is provided. In general, the biofuel includes a 14C/12C ratio of 1:0 to about 0:11.

In another embodiment, a method of making a biofuel is provided. The method includes: a) providing a feedstock comprising a sugar selected from the group consisting of: i) a six-carbon sugar; ii) a six-carbon sugar oligomer; iii) a five-carbon sugar; and iv) any combination of i) through iii), wherein the sugar is obtained from starch, cellulose, hemicellulose, or pectin; and b) contacting the feedstock of a) with a biocatalyst that converts the feedstock into a biofuel at: i) a yield of at least 68 percent theoretical yield; ii) a productivity of at least 0.75 grams biofuel per liter per hour change claims; and iii) a lower one of (A) a solubility limit of the biofuel in water under the process conditions and (B) 1.6% (w/v) of the biofuel in water; and c) optionally recovering the biofuel.

In another embodiment, a method of making a biofuel is provided. The method includes: a) providing a feedstock comprising galactose obtained from starch, cellulose, hemicellulose, or pectin; and b) contacting the feedstock of a) with a biocatalyst that converts the feedstock into a biofuel at: i) a yield of at least about 90 percent of the yield of the biocatalyst wherein the feedstock comprises glucose; ii) a productivity of at least about 90 percent of the productivity of the biocatalyst wherein the feedstock comprises glucose; and iii) a titer of at least about 90 percent of the titer of the biocatalyst wherein the feedstock comprises glucose; and c) optionally recovering the biofuel.

In another embodiment, a method of making a biofuel is provided, The method includes: a) providing a feedstock comprising mannose obtained from starch, cellulose, hemicellulose, or pectin; and b) contacting the feedstock of a) with a biocatalyst that converts the feedstock into a biofuel at: i) a yield of at least about 90 percent of the yield of the biocatalyst wherein the feedstock comprises glucose; ii) a productivity of at least about 90 percent of the productivity of the biocatalyst wherein the feedstock comprises glucose; and iii) a titer of at least about 90 percent of the titer of the biocatalyst wherein the feedstock comprises glucose; and c) optionally recovering the biofuel.

In another embodiment, a method of making a biofuel is provided. The method includes: a) providing a feedstock comprising xylose obtained from starch, cellulose, hemicellulose, or pectin; and b) contacting the feedstock of a) with a biocatalyst that converts the feedstock into a biofuel at: i) a yield of at least about 69 percent of the yield of the biocatalyst wherein the feedstock comprises glucose; ii) a productivity of at least about 56 percent of the productivity of the biocatalyst wherein the feedstock comprises glucose; and iii) a titer of at least about 59 percent of the titer of the biocatalyst wherein the feedstock comprises glucose; and c) optionally recovering the biofuel.

In another embodiment, a method of making a biofuel is provided. The method includes: a) providing a feedstock comprising arabinose obtained from starch, cellulose, hemicellulose, or pectin; and b) contacting the feedstock of a) with a biocatalyst that converts the feedstock into a biofuel at: i) a yield of at least about 56 percent of the yield of the biocatalyst wherein the feedstock comprises glucose; ii) a productivity of at least about 70 percent of the productivity of the biocatalyst wherein the feedstock comprises glucose; and iii) a titer of at least about 54 percent of the titer of the biocatalyst wherein the feedstock comprises glucose; and c) optionally recovering the biofuel.

In another embodiment, a method of making a biofuel is provided. The method includes: a) providing a feedstock comprising lactose; and b) contacting the feedstock of a) with a biocatalyst that converts the feedstock into a biofuel at: i) a productivity of at least about 90 percent of the productivity of the biocatalyst wherein the feedstock comprises glucose; and ii) a titer of at least about 90 percent of the titer of the biocatalyst wherein the feedstock comprises glucose; and c) optionally recovering the biofuel.

In another embodiment, a method of making a biofuel is provided. The method includes: a) providing a feedstock comprising sucrose; and b) contacting the feedstock of a) with a biocatalyst that converts the feedstock into a biofuel at: i) a productivity of at least about 50 percent of the productivity of the biocatalyst wherein the feedstock comprises glucose; and ii) a titer of at least about 50 percent of the titer of the biocatalyst wherein the feedstock comprises glucose; and c) optionally recovering the biofuel.

In another embodiment, a method of making a biofuel provided. The method includes: a) providing a feedstock comprising a six carbon sugar obtained from starch, cellulose, hemicellulose, or pectin; and b) contacting the feedstock of a) with a biocatalyst that converts the feedstock into a biofuel at: i) a yield of at least about 90 percent of the yield of the biocatalyst wherein the feedstock comprises glucose; ii) a productivity of at least about 90 percent of the productivity of the biocatalyst wherein the feedstock comprises glucose; and iii) a titer of at least about 90 percent of the titer of the biocatalyst wherein the feedstock comprises glucose; and c) optionally recovering the biofuel.

In another embodiment, a method of making a biofuel is provided. The method includes: a) providing a feedstock comprising a five carbon sugar obtained from starch, cellulose, hemicellulose, or pectin; and b) contacting the feedstock of a) with a biocatalyst that converts the feedstock into a biofuel at: i) a yield of at least about 55 percent of the yield of the biocatalyst wherein the feedstock comprises glucose; ii) a productivity of at least about 55 percent of the productivity of the biocatalyst wherein the feedstock comprises glucose; and iii) a titer of at least about 55 percent of the titer of the biocatalyst wherein the feedstock comprises glucose; and c) optionally recovering the biofuel.

In another embodiment, a method of producing a biofuel is provided. The method includes contacting a feedstock with a biocatalyst, wherein the method produces a biofuel at a total titer of greater than about 22 g/L.

In another embodiment, a method of producing a biofuel is provided. The method includes contacting a feedstock with a biocatalyst, wherein the method produces a biofuel at a yield of greater than about 80 percent theoretical.

In another embodiment, a method of producing a biofuel is provided. the method includes contacting a feedstock with a biocatalyst, wherein the method produces a biofuel at a productivity of greater than about 2 g biofuel per L per hour.

In another embodiment, an isolated or recombinant biocatalyst is provided. The biocatalyst includes a recombinant biochemical pathway to produce isobutanol from fermentation of a suitable bio-mass, wherein the recombinant biochemical pathway comprises elevated activity of: a) a KARI as compared to a parental microorganism; and b) a ALS as compared to a parental microorganism, wherein the biocatalyst produces recoverable amounts of isobutanol.

In some implementations, the parental microorganism is SA237.

In another embodiment, an isolated or recombinant biocatalyst is provided. The biocatalyst includes a recombinant biochemical pathway to produce isobutanol from fermentation of a suitable bio-mass, wherein the recombinant biochemical pathway comprises decreased activity of: a) a DHAD as compared to a parental microorganism; and b) a kivd as compared to a parental microorganism, wherein the biocatalyst produces recoverable amounts of isobutanol.

In another embodiment, an isolated or recombinant biocatalyst is provided. The biocatalyst includes a recombinant biochemical pathway to produce isobutanol from fermentation of a suitable bio-mass, wherein the recombinant biochemical pathway comprises decreased activity of: a) DHAD as compared to a parental microorganism; and increased activity of: b) ALS is broader as compared to a parental microorganism; and c) KAR1 as compared to a parental microorganism.

In another embodiment, an isolated or recombinant biocatalyst including a genotype of E. coli BW25113, and further comprising a genotype of: ΔldhA-fnr::FRT, ΔadhE::FRT, Δfrd::FRT, Δpta::FRT, pflB::FRT, Δmdh::FRT, ΔaceF::FRT (laclq+), pSA55, pSA69, wherein the isolated or recombinant biocatalyst produces isobutanol from a carbon source, is provided. In some implementations the biocatalyst is GEVO1530, pSA55, or pSA69.

In another embodiment, an isolated or recombinant biocatalyst including a genotype of E. coli B, and further comprising a genotype of: ΔadhE::FRT-kan-FRT, attB::(Sp+ laclq+tetR+), pSA55, pGV1609), wherein the isolated or recombinant biocatalyst produces a metabolite comprising isobutanol from a carbon source, is provided. In some implementations the biocatalyst is GEVO 1821.

In another embodiment, an isolated or recombinant biocatalyst including a genotype of (E. coli BW25113, and further comprising a genotype of: ΔldhA-fnr::FRT, ΔadhE::FRT, Δfrd::FRT, Δpta::FRT, pflB::FRT, F' (laclq+), pGV1655, pGV1698, wherein the isolated or recombinant biocatalyst produces isobutanol from a carbon source, is provided. In some implementations the biocatalyst is GEVO1780.

In another embodiment, an isolated or recombinant biocatalyst including a genotype of E. coli BW25113, and further comprising a genotype of: ΔldhA-fnr::FRT, Δfrd::FRT, Δpta::FRT, F' (laclq+), ΔadhE::[pLlacO1::kivd::ilvDco:: FRT], ΔpflB::[pLlacO1::alsS::ilvCco::FRT] ΔsthA:: [pLlacO1::pntA::pntB::FRT]), wherein the isolated or recombinant biocatalyst produces isobutanol from a carbon source, is provided. In some implementations the biocatalyst is GEVO1886.

In another embodiment, an isolated or recombinant biocatalyst including a genotype of E. coli BW25113, and further comprising a genotype of: ΔldhA-fnr::FRT, ΔadhE::FRT, Δfrd::FRT, Δpta::FRT, pflB::FRT, F' (laclq+), ΔilvC: [PLlacO1::kivd::ilvDco::FRT], pGV1698, wherein the isolated or recombinant biocatalyst produces isobutanol from a carbon source, is provided. In some implementations the biocatalyst is GEVO 1748, pGV1698.

In another embodiment, an isolated or recombinant biocatalyst including a genotype of *E. coli* BW25113, and further comprising a genotype of: ΔldhA-fnr::FRT, Δfrd::FRT, Δpta::FRT, pflB::FRT, F' (laclq+), ΔadhE::[PLlacO1::kivd::ilvDco::FRT], pGV1698, wherein the isolated or recombinant biocatalyst produces isobutanol from a carbon source, is provided. In some implementations the biocatalyst is GEVO1749, pGV1698.

In another embodiment, an isolated or recombinant biocatalyst including a genotype of *E. coli* BW25113, and further comprising a genotype of: ΔldhA-fnr::FRT, ΔadhE::FRT, Δfrd::FRT, ΔpflB::FRT, Δpta::FRT, F' (laclq+), ΔilvC::[PLlacO1::kivd::ilvDco::FRT], ΔsthA::FRT, pGV1698, wherein the isolated or recombinant biocatalyst produces isobutanol from a carbon source, is provided. In some implementations the biocatalyst is GEVO1844, pGV1698.

In another embodiment, an isolated or recombinant biocatalyst including a genotype of GEVO1748, and further comprising a genotype of: pGV1745, pGV1698, wherein the isolated or recombinant biocatalyst produces isobutanol from a carbon source, is provided.

In some implementations, an isolated or recombinant biocatalyst is GEVO1846.

In another embodiment, an isolated or recombinant biocatalyst including a genotype of *E. coli* BW25113, and further comprising a genotype of: ΔldhA-fnr::FRT, Δfrd::FRT, Δpta::FRT, F' (laclq+), ΔadhE::[pLlacO1::kivd::ilvDco::FRT], pflB::[pLlacO1::alsS::ilvCco::FRT], wherein the isolated or recombinant biocatalyst produces isobutanol from a carbon source, is provided. In some implementations the biocatalyst is GEVO1859.

In another embodiment, an isolated or recombinant biocatalyst including a genotype of *E. coli* BW25113, and further comprising a genotype of: ΔldhA-fnr::FRT, Δfrd::FRT, Δpta::FRT, ΔadhE::[pLlacO1::kivd::ilvDco::FRT], ΔpflB::[pLlacO1::alsS::ilvCco::FRT] ΔsthA::[pLlacO1::pntA::pntB::FRT], wherein the isolated or recombinant biocatalyst produces isobutanol from a carbon source, is provided. In some implementations the biocatalyst is GEVO1948.

In various embodiments, a biofuel may be produced by any biocatalyst provided herein. In general, the biocatalyst contacts a feedstock under fermentation conditions suitable for producing a biofuel. In some implementations, the biofuel is isobutanol.

In another embodiment, an isolated or recombinant nucleic acid including pLlacO1::alsS::ilvC::ilvD, p15A, and Cm, is provided. In some implementations, the nucleic acid is pGV1609.

In another embodiment, an isolated or recombinant nucleic acid including pLlacO1::kivd::ilvDco, pSC101, and Kan, is provided. In some implementations, the nucleic acid is pGV1655.

In another embodiment, an isolated or recombinant nucleic acid including PLlacO1::alsS::ilvCco, ColE1, and Amp, is provided. In some implementations the nucleic acid is pGV1698.

In another embodiment, an isolated or recombinant nucleic acid including pLlacO1::pntAB, pSC101, and Kan, is provided. In some implementations the nucleic acid is pGV1745.

In another embodiment, a biocatalyst selected to convert a feedstock into the biofuel at a yield of at least 80 percent theoretical yield, a productivity of at least 0.75 grams biofuel per liter per hour, and a titer equivalent to a lower one of (i) a solubility limit of the biofuel in water under the process conditions and (ii) 2% (w/w) of the biofuel in water, is provided. The biocatalyst selected to have the following properties: a. the biocatalyst operable to produce the biofuel free of byproducts that would require additional processing steps for removal from the biofuel; and b. the biocatalyst selected to have a growth rate of at least 0.2 per hour.

BRIEF DESCRIPTION OF THE DRAWINGS

The above and other features of the disclosure including various details of construction and combinations of parts will now be more particularly described with reference to the accompanying drawings and pointed out in the claims. It will be understood that the particular method and system embodying the disclosure is shown by way of illustration only and not as a limitation of the disclosure. The principles and features of this disclosure may be employed in varied and numerous embodiments without departing from the scope of the disclosure. Illustrative embodiments of the invention are illustrated in the drawings, in which:

FIGS. 16A through 16C illustrate a nucleic acid sequence of pGV1698 (SEQ ID NO: 28).

FIGS. 17A through 17B illustrate a nucleic acid sequence of pGV1720 (SEQ ID NO: 29).

FIGS. 18A through 18D illustrate a nucleic acid sequence pGV1745 (SEQ ID NO: 30).

FIGS. 20A through 20B illustrate a nucleic acid sequence pGV1655 (SEQ ID NO: 31).

FIGS. 22A through 22B illustrate a nucleic acid sequence pGV1609 (SEQ ID NO: 32).

FIGS. 24A through 24B illustrate a nucleic acid sequence pSA55 (SEQ ID NO: 33).

FIGS. 26A through 26B illustrate a nucleic acid sequence pSA69 (SEQ ID NO: 34).

DETAILED DESCRIPTION

Figure 1:
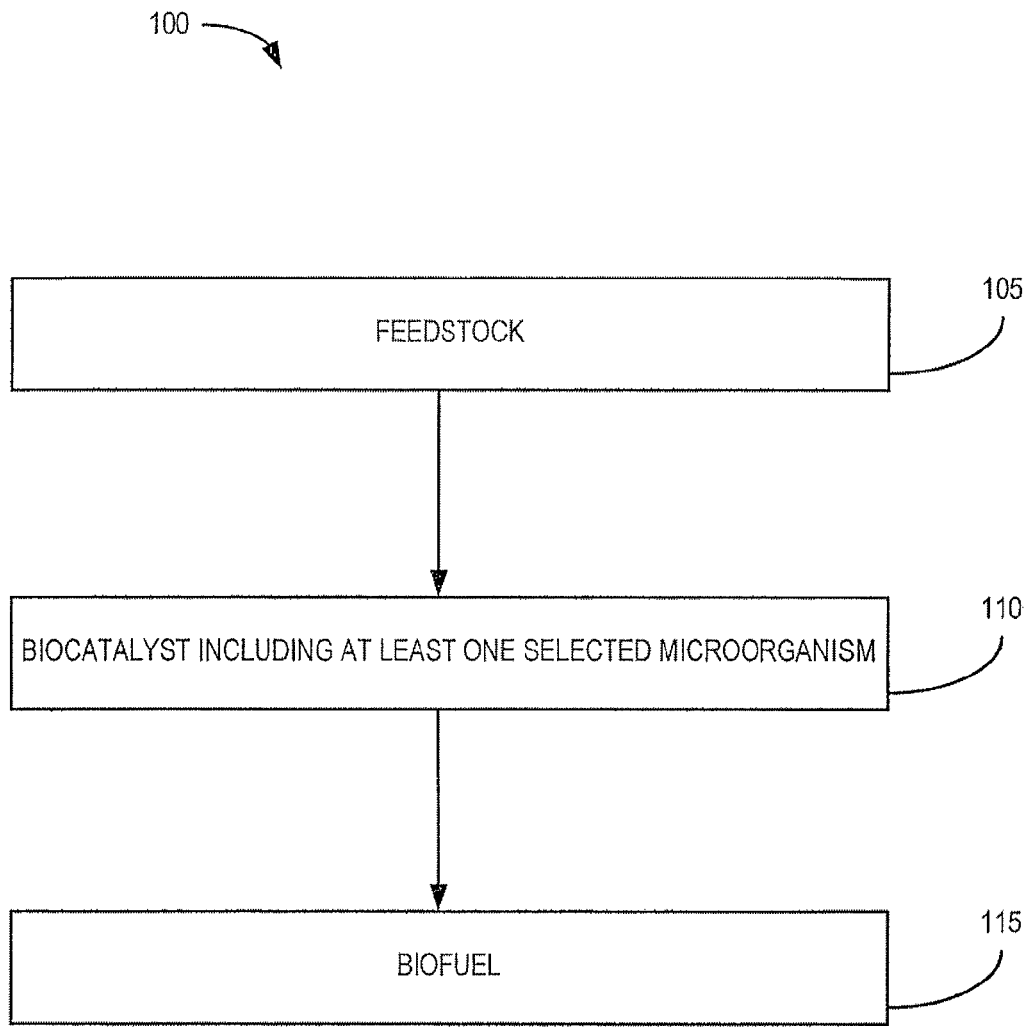
FIG. 1 illustrates a process of making a biofuel.

As used herein and in the appended claims, the singular forms "a," "and," and "the" include plural referents unless the context clearly dictates otherwise. Thus, for example, reference to "a polynucleotide" includes a plurality of such polynucleotides and reference to "the microorganism" includes reference to one or more microorganisms, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Any publications discussed above and throughout the text are provided solely for their disclosure prior to the filing date of the present application. Nothing herein is to be construed as an admission that the inventors are not entitled to antedate such disclosure by virtue of prior disclosure.

The term "biocatalyst" means a living system or cell of any type that speeds up chemical reactions by lowering the activation energy of the reaction and is neither consumed nor altered in the process. Biocatalysts may include, but are not limited to, microorganisms such as yeasts, fungi, bacteria, and archaea.

The biocatalyst herein disclosed can convert various carbon sources into biofuels. The term "carbon source" generally refers to a substance suitable to be used as a source of carbon for prokaryotic or eukaryotic cell growth. Carbon sources include, but are not limited to, biomass hydrolysates, starch, sucrose, cellulose, hemicellulose, xylose, and lignin, as well as monomeric components of these substrates. Carbon sources can comprise various organic compounds in various forms, including, but not limited to polymers, carbohydrates, acids, alcohols, aldehydes, ketones, amino acids, peptides, etc. These include, for example, various monosaccharides such as glucose, dextrose (D-glucose), maltose, oligosaccharides, polysaccharides, saturated or unsaturated fatty acids, succinate, lactate, acetate, ethanol, etc., or mixtures thereof. Photosynthetic organisms can additionally produce a carbon source as a product of photosynthesis. In some embodiments, carbon sources may be selected from biomass hydrolysates and glucose.

The term "feedstock" is defined as a raw material or mixture of raw materials supplied to a biocatalyst or fermentation process from which other products can be made. For example, a carbon source, such as biomass or the carbon compounds derived from biomass, are a feedstock for a biocatalyst that produces a biofuel in a fermentation process. However, a feedstock may contain nutrients other than a carbon source.

The term "medium" refers to an aqueous solution that minimally includes water and feedstock, but may include additional components, such as mineral salts comprised of major and minor bioelements, vitamins, and other components.

The term "fermentation" or "fermentation process" is defined as a process in which a biocatalyst is cultivated in a culture medium containing raw materials, such as feedstock and nutrients, wherein the biocatalyst converts raw materials, such as a feedstock, into products.

The term "major bioelements" refers to carbon, nitrogen, phosphorus, sulfur, oxygen, hydrogen, sodium, potassium, magnesium, calcium, iron, and chlorine.

The term "minor bioelements" refers to zinc, manganese, selenium, cobalt, copper, nickel, vanadium, molybdenum, chromium, and tungsten.

The term "traditional carbohydrates" refers to sugars and starches generated from specialized plants, such as sugar cane, corn, and wheat. Frequently, these specialized plants concentrate sugars and starches in portions of the plant, such as grains, that are harvested and processed to extract the sugars and starches. Traditional carbohydrates may be used as food and also to a lesser extent as renewable feedstocks for fermentation processes to generate biofuels and chemicals.

The term "biomass" as used herein refers primarily to the stems, leaves, and starch-containing portions of green plants, and is mainly comprised of starch, lignin, cellulose, hemicellulose, and/or pectin. Biomass can be decomposed by either chemical or enzymatic treatment to the monomeric sugars and phenols of which it is composed (Wyman, C. E. 2003 Biotechnological Progress 19:254-62). This resulting material, called biomass hydrolysate, is neutralized and treated to remove trace amounts of organic material that may adversely affect the biocatalyst, and is then used as a feedstock for fermentations using a biocatalyst.

The term "starch" as used herein refers to a polymer of glucose readily hydrolyzed by digestive enzymes. Starch is usually concentrated in specialized portions of plants, such as potatoes, corn kernels, rice grains, wheat grains, and sugar cane stems.

The term "lignin" as used herein refers to a polymer material, mainly composed of linked phenolic monomeric compounds, such as p-coumaryl alcohol, coniferyl alcohol, and sinapyl alcohol, which forms the basis of structural rigidity in plants and is frequently referred to as the woody portion of plants. Lignin is also considered to be the non-carbohydrate portion of the cell wall of plants.

The term "cellulose" as used herein refers is a long-chain polymer polysaccharide carbohydrate of beta-glucose of formula $(C_6H_{10}O_5)_n$, usually found in plant cell walls in combination with lignin and any hemicellulose.

The term "hemicellulose" refers to a class of plant cell-wall polysaccharides that can be any of several heteropolymers. These include xylan, xyloglucan, arabinoxylan, arabinogalactan, glucuronoxylan, glucomannan and galactomannan. Monomeric components of hemicellulose include, but are not limited to: D-galactose, L-galactose, D-mannose, L-rhamnose, L-fucose, D-xylose, L-arabinose, and D-glucuronic acid. This class of polysaccharides is found in almost all cell walls along with cellulose. Hemicellulose is lower in weight than cellulose and cannot be extracted by hot water or chelating agents, but can be extracted by aqueous alkali. Polymeric chains of hemicellulose bind pectin and cellulose in a network of cross-linked fibers forming the cell walls of most plant cells.

The term "pectin" as used herein refers to a class of plant cell-wall heterogeneous polysaccharides that can be extracted by treatment with acids and chelating agents. Typically, 70-80% of pectin is found as a linear chain of α-(1-4)-linked D-galacturonic acid monomers. The smaller RG-I fraction of pectin is comprised of alternating (1-4)-linked galacturonic acid and (1-2)-linked L-rhamnose, with substantial arabinogalactan branching emanating from the rhamnose residue. Other monosaccharides, such as D-fucose, D-xylose, apiose, aceric acid, Kdo, Dha, 2-O-methyl-D-fucose, and 2-O-methyl-D-xylose, are found either in the RG-II pectin fraction (<2%), or as minor constituents in the RG-I fraction.

Proportions of each of the monosaccharides in relation to D-galacturonic acid vary depending on the individual plant and its micro-environment, the species, and time during the growth cycle. For the same reasons, the homogalacturonan and RG-I fractions can differ widely in their content of methyl esters on GalA residues, and the content of acetyl residue esters on the C-2 and C-3 positions of GalA and neutral sugars.

The term "cell dry weight" or "CDW" refers to the weight of the biocatalyst after the water contained in the biocatalyst has been removed using methods known to one skilled in the art. CDW is reported in g/L. CDW may be calculated from optical density, when a conversion factor is known. For example, a conversion factor of 0.25 g CDW/L per $OD_{600}$ is used to calculate g CDW/L from optical density for E. coli.

The term "biomass-derived inhibitor" refers to organic or inorganic compounds derived from biomass during the pretreatment process that impair a biocatalyst during a fermentation process. Examples of biomass-derived inhibitors include, but are not limited to: furfural, 5-hydroxymethylfurfural, 4-hydroxybenzaldehyde, syringaldehyde, vanillin, catechol, coniferyl alcohol, furfuryl alcohol, guaiacol, hydroquinone, methylcatechol, acetic acid, and vanillyl alcohol.

The term "biofuel" refers to a fuel in which all carbon contained within the fuel is derived from biomass and is biochemically converted, at least in part, into a fuel by a biocatalyst. A biofuel is further defined as a non-ethanol compound which contains less than 0.5 oxygen atoms per carbon atom. A biofuel is a fuel in its own right, but may be blended with petroleum-derived fuels to generate a fuel. A biofuel may be used as a replacement for petrochemically-derived gasoline, diesel fuel, or jet fuel.

The term "biofuel precursor" refers to an organic molecule in which all of the carbon contained within the molecule is derived from biomass, and is biochemically converted from a feedstock into the precursor. A biofuel precursor is not a biofuel in its own right, e.g., it not configured for engine combustion, but may be configured for conversion, either chemically or biochemically, into a biofuel.

The term "log P" is defined as the logarithm of the octanol: water partition coefficient, "P", of a compound.

The term "volumetric productivity" is defined as the amount of product per volume of medium in a fermenter per unit of time. In other words, the rate is the amount of product per unit of time, e.g., g/hr, inasmuch as the volume of the fermenter may be fixed at a chosen volume. Units used can be reported as grams biofuel per liter per hour.

The term "specific productivity" is defined as the rate of formation of the product. To describe productivity as an inherent parameter of the microorganism or biocatalyst and not of the fermentation process, productivity is herein further defined as the specific productivity in g product per g of cell dry weight (CDW) per hour (g product g $CDW^{-1}$ $h^{-1}$).

The term "yield" is defined as the amount of product obtained per unit weight of raw material and may be expressed as g product/g substrate. Yield may be expressed as a percentage of the theoretical yield. "Theoretical yield" is defined as the maximum amount of product that can be generated per a given amount of substrate as dictated by the stoichiometry of the metabolic pathway used to make the product. For example, theoretical yield for one typical conversion of glucose to butanol is 0.41 g/g. As such, a yield of butanol from glucose of 0.39 g/g would be expressed as 95% of theoretical or 95% theoretical yield.

The term "titer" is defined as the strength of a solution or the concentration of a substance in solution. For example, the titer of a biofuel in a fermentation broth is described as g of biofuel in solution per liter of fermentation broth. The term "titre" is used interchangeably throughout with the term "titer".

The term "tolerance" is defined as the ability of the biocatalyst to maintain its specific productivity at a given concentration of an inhibitor. The term "tolerant" describes a biocatalyst that maintains its specific productivity at a given concentration of an inhibitor. For example, if in the presence of 2% of an inhibitor a biocatalyst maintains the specific productivity that it had at 0 to 2%, the biocatalyst is tolerant to 2% of the inhibitor or has a tolerance to 2% of the inhibitor.

The term "rate of inhibition" is defined as the rate of decrease of the specific productivity of a biocatalyst relative to the increased concentration of an inhibitor, at inhibitor levels above the inhibitory concentration.

The term "resistance" is defined as the property of a biocatalyst to have a low rate of inhibition in the presence of increasing concentrations of an inhibitor in the fermentation broth. The term "more resistant" describes a biocatalyst that has a lower rate of inhibition towards an inhibitor than another biocatalyst with a higher rate of inhibition towards the same inhibitor. For example, two biocatalysts A and B, both with a tolerance of 2% to an inhibitor biofuel and a specific productivity of 1 g product g $CDW^{-1}$ $h^{-1}$, exhibit at 3% biofuel a specific productivity of 0.5 g product g $CDW^{-1}$ $h^{-1}$ and 0.75 g product g $CDW^{-1}$ $h^{-1}$ for A and B, respectively. The biocatalyst B is more resistant than A.

A "facultative anaerobic organism" or a "facultative anaerobic microorganism" or a "facultative anaerobic biocatalyst" is defined as an organism that can grow in either the presence or in the absence of oxygen.

A "strictly anaerobic organism" or a "strictly anaerobic microorganism" or a "strictly anaerobic biocatalyst" is defined as an organism that cannot grow in the presence of oxygen and which does not survive exposure to any concentration of oxygen.

An "anaerobic organism" or an "anaerobic microorganism" or an "anaerobic biocatalyst" is defined as an organism that cannot grow in the presence of oxygen. "Aerobic conditions" are defined as conditions under which the oxygen concentration in the fermentation medium is sufficiently high for a aerobic or facultative anaerobic microorganism to use as a terminal electron acceptor.

In contrast, "Anaerobic conditions" are defined as conditions under which the oxygen concentration in the fermentation medium is too low for the microorganism to use as a terminal electron acceptor. Anaerobic conditions may be achieved by sparging a fermentation medium with an inert gas such as nitrogen until oxygen is no longer available to the microorganism as a terminal electron acceptor. Alternatively, anaerobic conditions may be achieved by the microorganism respiring the available oxygen of the fermentation until oxygen is unavailable to the microorganism as a terminal electron acceptor.

The term "byproduct" means an undesired product related to the production of biofuel. Byproducts are generally disposed as waste, adding cost to a process.

The term "co-product" means a secondary or incidental product related to the production of biofuel. Co-products have potential commercial value that increases the overall value of biofuel production, and may be the deciding factor as to the viability of a particular biofuel production process.

The term "distillers dried grains", abbreviated herein as DDG, refers to the solids remaining after a fermentation, usually consisting of unconsumed feedstock solids, remaining nutrients, protein, fiber, and oil, as well as biocatalyst cell debris. The term may also include soluble residual material from the fermentation and is then referred to as "distillers dried grains and solubles" (DDGS). DDG or DDGS are an example of a co-product from a biofuel production process.

The term "nutrient" is defined as a chemical compound that is used by a biocatalyst to grow and survive. Nutrients can be organic compounds such as carbohydrates and amino acids or inorganic compound such as metal salts.

The term "complex nutrient" is defined as a nutrient source containing mostly monomeric organic compounds used by a biocatalyst for the production of proteins, DNA, lipids, and carbohydrates. The term "rich nutrient" is used interchangeably throughout with the term complex nutrient. Typically, complex nutrients or rich nutrients are derived from biological materials, such as slaughterhouse waste, dairy wastes, or agricultural residues. Complex nutrients or rich nutrients include, but are not limited to: yeast extract, tryptone, peptone, soy extract, corn steep liquor, soy protein, and casein.

The term "natural DNA" is defined as DNA (deoxyribonucleic acid) that is greater than 99.9% derived from the organism in which it is contained. For example, a biocatalyst that contains 4,635,035 native DNA base pairs out of 4,639,675 base pairs is said to contain only natural DNA.

The term "native DNA" is defined as a DNA sequence that is 100% derived from the organism in which it is contained.

The term "foreign DNA" is defined as a DNA sequence that is 100% derived from an organism other than the organism in which it is contained.

The term "genus" is defined as a taxonomic group of related species according to the Taxonomic Outline of Bacteria and Archaea (Garrity, G. M., Lilburn, T. G., Cole, J. R., Harrison, S. H., Euzeby, J., and Tindall, B. J. (2007) The Taxonomic Outline of Bacteria and Archaea. TOBA Release 7.7, March 2007. Michigan State University Board of Trustees.

The term "species" is defined as a collection of closely related organisms with greater than 97% 16S ribosomal RNA sequence homology and greater than 70% genomic hybridization and sufficiently different from all other organisms so as to be recognized as a distinct unit.

The abbreviation "GMO" is used herein to refer to a genetically modified organism.

The term "feed grade" as used herein, means material that may be ingested by animals without harming the animal. Examples of feed grade materials may be found in the annual publication of the Association of American Feed Control Officials. Ingestible materials may or may not be a nutrient source for the animal.

The term "endotoxin" as used herein refers to the lipopolysaccharide (LPS) portion of the cell wall of certain gram negative bacteria, which acts as a toxin when solubilized.

The term "exotoxin" as used herein refers to a protein released extracellularly by a microorganism as it grows and produces immediate damage to animals and animal cells. Most exotoxins fall into one of three categories, which include, for example, cytolytic toxins, A-B toxins, and superantigen toxins. Cytolytic toxins enzymatically attack cell components and cause lysis. The A-B toxins are two-component toxins that permit transfer of one component into the target cell through the membrane and cause damage to the target cell. Superantigen toxins stimulate large numbers of immune response cells and cause damage to the target organism.

The term "sudden change" is defined as an increase or decrease that occurs within three hours or less.

"Aerobic metabolism" refers to a biochemical process in which oxygen is used to make energy, typically in the form of ATP, from carbohydrates. Typical aerobic metabolism occurs via glycolysis and the TCA cycle, wherein a single glucose molecule is metabolized completely into carbon dioxide in the presence of oxygen.

In contrast, "anaerobic metabolism" refers to a biochemical process in which oxygen is not the final acceptor of electrons contained in NADH. Anaerobic metabolism can be divided into anaerobic respiration, in which compounds other than oxygen serve as the terminal electron acceptor, and fermentation, in which the electrons from NADH are utilized to generate a reduced product via a "fermentative pathway."

In "fermentative pathways", NADH donates its electrons to a molecule produced by the same metabolic pathway that produced the electrons carried in NADH. For example, in one of the fermentative pathways of certain yeast strains, NADH generated through glycolysis transfers its electrons to pyruvate, yielding lactate. Fermentative pathways are usually active under anaerobic conditions but may also occur under aerobic conditions, under conditions where NADH is not fully oxidized via the respiratory chain. For example, above certain glucose concentrations, crabtree positive yeasts produce large amounts of ethanol under aerobic conditions.

The term "homologue," "homolog," or "homologous" refers to nucleic acid or protein sequences or protein structures that are related to each other by descent from a common ancestral sequence or structure. All members of a gene family are homologues or homologous, by definition.

The term "analogue" or "analogous" refers to nucleic acid or protein sequences or protein structures that are related to one another in function only and are not from common descent or do not share a common ancestral sequence. Analogues may differ in sequence but may share a similar structure, due to convergent evolution. For example, two enzymes are analogues or analogous if the enzymes catalyze the same reaction of conversion of a substrate to a product, are unrelated in sequence, and irrespective of whether the two enzymes are related in structure.

The term "recombinant microorganism" and "recombinant host cell" are used interchangeably herein and refer to microorganisms that have been genetically modified to express or over-express endogenous polynucleotides, or to express heterologous polynucleotides, such as those included in a vector, or which have a reduction in expression of an endogenous gene. The polynucleotide generally encodes a target enzyme involved in a metabolic pathway for producing a desired metabolite. It is understood that the terms "recombinant microorganism" and "recombinant host cell" refer not only to the particular recombinant microorganism but to the progeny or potential progeny of such a microorganism. Because certain modifications may occur in succeeding generations due to either mutation or environmental influences, such progeny may not, in fact, be identical to the parent cell, but are still included within the scope of the term as used herein.

Accordingly, a "parental microorganism" or a "parental strain" functions as a reference cell for successive genetic modification events. Each modification event can be accomplished by introducing a nucleic acid molecule in to the reference cell. The introduction facilitates the expression or over-expression of a target enzyme. It is understood that the term "facilitates" encompasses the activation of endogenous polynucleotides encoding a target enzyme through genetic modification of e.g., a promoter sequence in a parental microorganism. It is further understood that the term "facilitates" encompasses the introduction of heterologous polynucleotides encoding a target enzyme in to a parental microorganism.

As used herein, the term "metabolically engineered" or "metabolic engineering" involves rational pathway design and assembly of biosynthetic genes, genes associated with operons, and control elements of such polynucleotides, for the production of a desired metabolite. "Metabolically engineered" can further include optimization of metabolic flux by regulation and optimization of transcription, translation, protein stability and protein functionality using genetic engineering and appropriate culture condition including the reduction of, disruption, or knocking out of, a competing metabolic pathway that competes with an intermediate leading to a desired pathway.

The terms "metabolically engineered microorganism" and "modified microorganism" are used interchangeably herein and refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

Dissolved oxygen is expressed throughout as the percentage of saturating concentration of oxygen in water.

The term "DNA marker" is used herein to refer to any DNA sequence which encodes a protein that confers resistance to a chemical or physical condition that is applied to the organism in which the DNA marker sequence is contained. For example, a common DNA marker is an antibiotic resistance DNA marker, such as the kan gene APH(3')II. The kan gene encodes a protein that confers resistance to the antibiotic kanamycin. Thus, the organism in which the APH(3')II gene is present and expressed is resistant to kanamycin.

The term "scar DNA" is used herein to describe short pieces of foreign DNA of 100 nucleotide base pairs in length or less that is contained within the chromosome of the biocatalyst. Scar DNA is not translated into a protein. Scar DNA may not positively or negatively affect the performance of a biocatalyst on its own, but may be used as a replacement for a removed or deleted native gene from the biocatalyst.

"Carbon of atmospheric origin" as used herein refers to carbon atoms from carbon dioxide molecules that have recently, in the last few decades, been free in the earth's atmosphere. Such carbons in mass are identifiable by the ratio of particular radioisotopes as described herein. "Green carbon", "atmospheric carbon", "environmentally friendly carbon", "life-cycle carbon", "non-fossil fuel based carbon", "non-petroleum based carbon", "carbon of atmospheric origin", and "biobased carbon" are used synonymously herein.

"Carbon of fossil origin" as used herein refers to carbon of petrochemical origin. Carbon of fossil origin is identifiable by means described herein. "Fossil fuel carbon", "fossil carbon", "polluting carbon", "petrochemical carbon", "petrocarbon" and "carbon of fossil origin" are used synonymously herein.

"Renewably-based" denotes that the carbon content of the biomaterial and subsequent products made from the biomaterial is from a "new carbon" source as measured by ASTM test method D 6866-05 Determining the Biobased Content of Natural Range Materials Using Radiocarbon and Isotope Ratio Mass Spectrometry Analysis, incorporated herein by reference. This test method measures the 14C/12C isotope ratio in a sample and compares it to the 14C/12C isotope ratio in a standard 100% biobased material to give percent biobased content of the sample. "Biobased materials" are further defined as organic materials in which the carbon comes from recently (on a human time scale) fixated $CO_2$ present in the atmosphere using sunlight energy (photosynthesis). On land, this $CO_2$ is captured or fixated by plant life (e.g., agricultural crops or forestry materials). In the oceans, the $CO_2$ is captured or fixated by photosynthesizing bacteria or phytoplankton. A biobased material has a 14C/12C isotope ratio in range of from 1:0 to greater than 0:1. Contrarily, a fossil-based material, has a 14C/12C isotope ratio of 0:1.

A small amount of the carbon dioxide in the atmosphere is radioactive. This 14C carbon dioxide is created when nitrogen is struck by a cosmic ray generated neutron, causing the nitrogen to lose a proton and form carbon of atomic mass 14, which is immediately oxidized to carbon dioxide. This radioactive isotope represents a small, but measurable, fraction of atmospheric carbon. Atmospheric carbon dioxide is processed by green plants to make organic molecules during the process known as photosynthesis. Virtually all forms of life on Earth depend on this green plant production of organic molecule to produce the chemical energy that facilitates growth and reproduction. Therefore, the 14C that exists in the atmosphere becomes part of all life forms, and their biological products. These renewably based organic molecules that biodegrade to $CO_2$ do not contribute to global warming as there is no net increase of carbon emitted to the atmosphere. In contrast, fossil fuel based carbon does not have the signature 14C:12C ratio of atmospheric carbon dioxide.

Methods and strategies for converting biomass derived carbohydrates to commodity chemicals and biofuels are listed below. FIG. 1 illustrates a process 100 of making a biofuel. Generally, process 100 may include providing a feedstock 105 to a biocatalyst including at least one selected biocatalyst 110. In turn, the biocatalyst 110 may be selected to produce a biofuel 115. A business strategy that employs the use of an economical method for the production of biofuels is herein disclosed.

Specialized plants such as sugar cane, corn, and wheat provide much of the traditional carbohydrates used today for food and renewable fuels and chemicals production. The well established processes for extraction of traditional carbohydrates from plants include sucrose from sugar cane and dextrose syrup from corn grain. Sucrose and dextrose are the most widely used fermentative sugars. Sucrose and dextrose are also currently the lowest cost and the most widely available traditional carbohydrates, having large uses in the food industry and lower volume use as fermentation feedstocks. To eliminate potential competition with food, processes for the production of fuels and chemicals that avoid using traditional carbohydrates like sucrose and dextrose syrup derived from specialty plants are being developed.

Economical production of biofuels from biomass-derived organic compounds via fermentation processes depends upon biocatalysts that catalyze this conversion in very specific ways described herein. A method of producing biofuels makes use of biocatalysts that exhibit certain properties which decrease the cost of the fermentation part of the biofuel production process. A business strategy is disclosed that employs the use of an economical method for the production of biofuels.

TABLE 1

The contents of cellulose, hemicellulose, and lignin in common agricultural residues and wastes.[a]

| Lignocellulosic materials | Cellulose (%) | Hemicellulose (%) | Lignin (%) |
| --- | --- | --- | --- |
| Hardwood stems | 40-55 | 24-40 | 18-25 |
| Softwood stems | 45-50 | 25-35 | 25-35 |
| Nut shells | 25-30 | 25-30 | 30-40 |
| Corn cobs | 45 | 35 | 15 |
| Grasses | 25-40 | 35-50 | 10-30 |

TABLE 1-continued

The contents of cellulose, hemicellulose, and lignin in
common agricultural residues and wastes.[a]

| Lignocellulosic materials | Cellulose (%) | Hemicellulose (%) | Lignin (%) |
|---|---|---|---|
| Paper | 85-99 | 0 | 0-15 |
| Wheat straw | 30 | 50 | 15 |
| Sorted refuse | 60 | 20 | 20 |
| Leaves | 15-20 | 80-85 | 0 |
| Cotton seed hairs | 80-95 | 5-20 | 0 |
| Newspaper | 40-55 | 25-40 | 18-30 |
| Waste papers from chemical pulps | 60-70 | 10-20 | 5-10 |
| Primary wastewater solids | 8-15 | NA[b] | 24-29 |
| Swine waste | 6.0 | 28 | NA[b] |
| Solid cattle manure | 1.6-4.7 | 1.4-3.3 | 2.7-5.7 |
| Coastal Bermuda grass | 25 | 35.7 | 6.4 |
| Switch grass | 45 | 31.4 | 12.0 |

[a]Sources: Boopathy, R., 1998. Bioresour. Technol. 64, 1-6.; Cheung, S. W., Anderson, B. C., 1997. Bioresour.Technol. 59, 81-96.; Dewes, T., Hueunsche, E., 1998. Biol. Agric. Hortic. 16, 251-268.; Reshamwala, S., Shawky, B. T., Dale, B. E., 1995. Appl. Biochem. Biotechnol. 51/52, 43-55.; Sun, Y. and Cheng, J. 2002. Bioresour. Technol. 83: 1-11.
[b]NA—Not available.

Plant material or biomass of all types is typically composed of about 70% carbohydrates, typically cellulose and hemicellulose (Table 1). In addition, some waste materials also contain carbohydrate materials in the form of processed biomass (Table 1). Biomass is targeted as a low cost and renewable feedstock for future liquid transportation fuels, organic chemicals, and biomaterials. Biomass is renewable and captures carbon, in the form of carbon dioxide, from the air. Biomass is an excellent source of renewable feedstocks for the production of biofuels and chemicals through processes like fermentation using a biocatalyst. Additionally, technology for extracting carbon sources, including carbohydrates, from recalcitrant biomass consisting of cellulose, hemicellulose, and lignin, is in the final stages of development for commercial use.

Biomass may be treated mechanically, chemically, thermochemically, and/or enzymatically to generate soluble carbohydrates from the pectin, cellulose, and hemicellulose fractions of biomass (Wyman, C. E. et al. 2005 Bioresource Technology 96:1959-1966). The soluble carbohydrates, which consist mainly of six-carbon sugars (hexoses) such as glucose, and five-carbon sugars (pentoses) such as xylose, are used as substrates in fermentations with a biocatalyst to generate products like ethanol. Generally, the lignin fraction of biomass is used as fuel for combustion within the fermentation plant (Zaldivar, J. et al. 2001 Applied Microbiology and Biotechnology 56:17-34).

Methods and strategies for the production of commodity biofuels and chemicals from renewable feedstocks, like traditional carbohydrates and biomass, are known in the art. The vast majority of processes use only traditional carbohydrates and not carbohydrates derived from other sources of biomass. For example, in one strategy, the yeast *Saccharomyces cerevisiae* is used to generate ethanol from starch or sugar derived from corn or sugar cane. While this process is mature, it is not currently able to use pentoses or other parts of biomass as a feedstock at the industrial scale and is therefore not very efficient overall with respect to use of other sources biomass as a feedstock (Zaldivar, J. et al. 2001 Applied Microbiology and Biotechnology 56:17-34). In another example, the bacterium *Clostridium acetobutylicum* was used to produce acetone, butanol, and ethanol (the so-called 'ABE process') from a variety of substrates, most commonly molasses and corn starch (Jones, D. T. 1986 Microbiological Reviews 50:484-524). While the ABE process was a major industrial process for more than 60 years, this process suffered from low yields of desired compounds (e.g. butanol) and low productivity. Low yield and low productivity of the ABE process meant that this process could not compete economically with petrochemically-derived butanol or acetone and was generally abandoned by the end of the 20th century. In the US, the ABE process was abandoned in the 1960s, in South Africa ABE was abandoned in the 1980s, in England this happened in the 1950s, in China ABE was abandoned around 2004. In Russia the ABE process was abandoned in the late 1980s and in Egypt ABE process was abandoned in the 1970s. Recently, renewed interest in the ABE process has sparked a new era of research into the improvement of the process (Duerre, P. 2007 Biotechnology Journal 2:1-10).

In another example, a commodity chemical produced from a renewable feedstock is acetic acid. Acetic acid is produced fermentatively from glucose by *Acetobacter* species of bacteria. However, in the acetic acid process, the yields are only 75-80% of the theoretical yield of 0.67 g/g glucose (Danner, H. 1999 Chemical Society Reviews 28:395-405). Lactic acid is another commodity chemical produced from fermentation of a renewable feedstock. Lactic acid is produced from glucose or sucrose by bacterial species, such as *Lactobacillus* or fungal species, such as *Mucor*, fermentatively (John, R. et al. 2007 Applied Microbiology and Biotechnology 74:524-534). Neither acetic acid nor lactic acid is directly useful as a transportation fuel.

Ethanol may be produced from biomass or biomass derived carbohydrates. Currently, two organisms, *Escherichia coli* and *Zymomonas mobilis*, may be used to produce ethanol from biomass or biomass derived carbohydrates. This process involves several unit operations (e.g. biomass hydrolysis, separation of cellulose and hemicellulose hydrolysate streams, separate hemicellulose and cellulose hydrolysate fermentations) and pretreatment of the biomass is required (e.g., fractionation of biomass into cellulose and hemicellulose fractions, detoxification of some fractions before fermentation, a solid/liquid separation step) (Zaldivar, J. et al. 2001 Applied Microbiology and Biotechnology 56:17-34 and Ingram, L. O. et al. 1999 Biotechnol Prog 15:855-866.) In another example, *Clostridium* species was used in Russia to produce butanol through an ABE fermentation of a feedstock that contained not more than 5% biomass hydrolysate (mainly from hemicellulose), or carbohydrates derived from treated biomass. While the solvent yields for this ABE process were roughly equivalent to the process using only starch or sucrose, the majority of the feedstock still consisted of sucrose-containing molasses and thus competed with food supplies (Zverlov, V. V. et al. 2006 Appl. Microbiol. Biotechnol. 71: 587-597). Further, the Russian process would currently suffer from poor economics, as the large portion of traditional carbohydrate feedstock in that process would make it more expensive than a process that could use greater fractions of organic compounds derived from other sources of biomass.

Recently, an ABE fermentation using wheat straw hydrolysate was demonstrated (Qureshi N. et al. 2007 Bioprocess Biosyst. Eng. online DOI:10.1007/s00449-007-0137-9). Also, an ABE process that produces butanol from corn fiber xylan was demonstrated (Qureshi N. et al. 2006 Biotechnol. Prog. 22:673-680). Another example for ABE with cellulosics is the use of corn cob hydrolysates as a feed stock (Marchal, R. et al 1992 Bioresource Technology 42:205-217; Nativel F. et al 1992 Int. J. Solar Energy 11:219-229). Also wood hydrolysates were used in ABE (Maddox, I. S, and Murray, E., Production of n-butanol by fermentation of wood hydrolysate, Biotechnol. Lett., 5, 175, 1983; Yu, E. K. C., L.

Deschatelets, and J. N. Saddler. 1984). The bioconversion of wood hydrolyzates to butanol and butanediol. Biotechnol. Lett. 6:327-332). Aspen wood xylan mixed with powdered cellulose was used in a two stage fermentation set up using *Clostridium thermocellum* in a first stage and then metabolizing with *Clostridium acetobutylicum* in a second stage (Jones, D. T. and Woods, D. R. Acetone-Butanol Fermentation revisited. Microbiological Reviews, 1986, 50:484-524; Yu, E. K. C., Chan, M. K. H., and Saddler, J. N., Butanol production from cellulosic substrates by sequential co-culture of *Clostridium thermocellum* and *C. acetobutylicum*, Biotechnol. Lett., 7, 509, 1985).

To produce commodity biofuels and chemicals from renewable biomass substrates in an economically-viable process, improved biocatalysts must be generated. For example, research to generate biocatalysts that produce ethanol from biomass and use more of the carbon compounds present, such as pentoses and hexoses, has followed two strategies (1) improve the production of ethanol in biocatalysts that can use both pentoses and hexoses, and (2) engineer pentose utilization into ethanol producing biocatalysts that use only hexoses. However, neither strategy has produced a biocatalyst with industrially relevant properties yet (Gray, K. et al. 2006 Current Opinion in Chemical Biology 10). There is a need in the art to generate efficient and economical biocatalysts for the production of other commodity biofuels and chemicals. There is also a need to generate biocatalysts that not only use any feedstock or source of carbohydrates available, but also possess several other performance characteristics that favor an economical industrial process for the production of biofuels and chemicals.

Methods of converting biomass-derived organic compounds into biofuels use biocatalysts that have certain performance characteristics or combinations of performance characteristics to enable a more economical process for the production of biofuels. These performance characteristics include the following and are described in detail below: uses any feedstock, biomass-derived organic compound, or carbohydrate source as a substrate; resistant and tolerant to high levels of biofuel and/or product, reaching a high titer of biofuel or product; high productivity; low or no toxin levels; high product yields; low production of undesired metabolites or byproducts; uses natural DNA; no DNA markers; acceptable temperature tolerance; acceptable pH tolerance; uses simple nutrients; the ability of a biocatalyst to recover from brief periods of varying oxygen availability; the ability of a biocatalyst to recover from brief periods of the presence of oxygen; the ability of a biocatalyst to tolerate the presence of small amounts of oxygen throughout the fermentation process; the ability of a biocatalyst to produce a biofuel under anaerobic conditions; produces a biofuel. An ideal biocatalyst for the production of a biofuel in an economical process has several or all of the above performance characteristics and yields a process that is economically favorable for the production of a biofuel.

Biomass processed via thermo-chemical and enzymatic hydrolysis processes provide a variety of substrates for fermentation. Since raw materials account for the majority of the production cost for biologically produced commodity chemicals and biofuels, it is important to utilize most, if not all carbon-containing compounds from renewable substrates.

In some cases, especially for commodity chemicals, the substrate cost can represent up to 70% of the value of the product (Danner, H. 1999 Chemical Society Reviews 28:395-405). Corn for example is typically processed into starch and further processed to dextrose. However, when corn is processed to starch there are a variety of impurities present. Some of the impurities are corn gluten, gluten meal and germ. Others are a variety of starch, dextrin and soluble dextrins or other and/or all oligomers and dextrose. Here, dextrose (glucose) is currently the only feedstock for further fermentation.

Inhibitors, such as furfurals, metals, and other inorganics are sometimes generated during the biomass pre-treatment process. Biofuel production from biomass requires pretreatment of biomass to release carbohydrates from polymeric substances within the biomass (such as cellulose, hemicellulose, and pectin). One common pretreatment method is acid hydrolysis. During acid hydrolysis pretreatment, a number of toxic compounds are generated from biomass, such as soluble aromatic aldehydes from lignin, furfural from pentoses and 5-hydroxymethylfurfural from hexoses. Examples of aldehydes are: furfural, 5-hydroxymethylfurfural, 4-hydroxybenzaldehyde, syringaldehyde, and vanillin (du Preez, 1994 Enzyme Microb Technol 16; Hahn-Hagerdahl, 1996 Appl Biochem Biotechnol 57/58; Hahn-Hagerdahl et al., 1991 Appl Biochem Biotechnol 28/29). These toxins retard the fermentation of hemicellulose containing syrups by conventional biocatalysts (Zaldivar J Biotech Bioeng 1999, 65). The toxicity of these compounds is related to their hydrophobicity. The toxin levels can be reduced by ion-exchange resins (Frazer and McCaskey, 1989, Biomass 18; Frazer and McCaskey 1991 Enzyme Microb Technol 13), molecular exclusion chromatography (Buchert et al., 1990 Proc Biotech Int 25), laccase (Jonsson et al., 1998 Appl Microbiol Biotechnol 49), and treatment at high pH using lime (Perego et al., 1990 J Indust Microbiol 6), but all have limitations. The removal of these toxins from the feedstock is currently expensive and may not suitable for an economic biofuel process.

During hydrolysis, a variety of growth inhibitory alcohols are also produced which include aromatic alcohols from lignin and furfuryl alcohol from pentose destruction. For example, some of the inhibitory alcohols produced include catechol, coniferyl alcohol, furfuryl alcohol, guaiacol, hydroquinone, methylcatechol, and vanillyl alcohol. The toxicities of these compounds are directly related to their hydrophobicity. In binary combination, the extent of growth inhibition was roughly additive for most compounds tested. However, combinations with furfuryl alcohol and furfural appear synergistic in toxicity. When compared individually, alcohol components which are formed during hemicellulose hydrolysis are less toxic for growth than the aldehydes and organic acids either on a weight basis or a molar basis (Zaldivar J et al. Biotechnol. Bioeng. 1999 65:24-33 and 66:203-10).

Binary combinations of catechol with 4-hydroxybenzaldehyde, and vanillin with catechol, furfural, or 4-hydroxybenzaldehyde showed synergistic effect on toxicity on *Klyveromyces marxianus* and caused a 60-90% decrease in cell mass production. The presence of aldehydes in the fermentation medium strongly inhibited cell growth and ethanol production. *Kluyveromyces marxianus* reduces aldehydes to their corresponding alcohols to mitigate the toxicity of these compounds. The total reduction of aldehydes was needed to start ethanol production. Vanillin, in binary combination, was dramatically toxic and was the only compound for which inhibition could not be overcome by yeast strain assimilation, causing a 90% reduction in both cell growth and fermentation (Ballesteros 2004 Biotechnol Prog).

Furans and phenols generally inhibit growth and ethanol production rate but not the ethanol yields in *Saccharomyces cerevisiae*. Within the same phenol functional group (aldehyde, ketone, and acid) the inhibition of volumetric ethanol productivity was found to depend on the amount of methoxyl substituents and hence hydrophobicity (log P) (Klinke H B 2004 Appl Microbiol Biotechnol). *Thermoanaerobacter mathranii* A3M3 can grow on pentoses and produce ethanol in hydrolysate without any need for detoxification (Klinke 2001 Appl Microbiol Biotechnol).

Despite the generation of inhibitory substances from the pretreatment of biomass, the most economical of all renewable feedstocks is biomass and carbohydrates derived therefrom.

Process economics for products are enhanced by conversion of all carbohydrates in a feedstock to targeted products. Carbohydrates in plants are found in a variety of forms from monomeric sugars to crystalline polymers such as cellulose and hemicellulose. In fact, most carbohydrates in plants are found as hemicellulose, cellulose, and pectins prior to physico-chemical, thermal, and enzymatic conversions. The primary carbohydrates derived from hemicellulose are D-galactose, L-galactose, D-mannose, L-rhamnose, L-fucose, D-xylose, L-arabinose, and D-glucuronic acid. The primary carbohydrates derived from cellulose are D-glucose, cellobiose, cellotriose, and other dextrins. The primary carbohydrates derived from pectins are D-galacturonic acid, L-rhamnose, D-galactose, L-arabinose and D-xylose.

Acetate is present as a byproduct in biomass hydrolysates. For example, in corn fiber hydrolysates the acetate carry over from the biomass treatment amounted to 3 g/L in the ABE fermentation (Ezeji et al. 2007 Biotechnology and Bioengineering, 97:1460-1469). In other examples, biomass hydrolysate derived from corn stover may contain 7-12 g/L acetate (National Renewable Energy Laboratory publication NREL/TP-510-32438; McMillan, J. D., National Renewable Energy Laboratory, presentation at DOE/NASULGC Biomass & Solar Energy Workshops, Aug. 3-4, 2004).

The performance characteristics of the biocatalyst described herein include a high productivity of the conversion of a feedstock to a biofuel.

Productivity has an impact on capital costs for a biofuel plant and depends on the amount of biocatalyst used during the fermentation and the specific activity of the biocatalyst. High volumetric productivity of the biocatalyst shortens the process time and, therefore, for a given plant size, increases the output of the plant over the plant lifetime. This increases the return on the capital investment and decreases the cost of the biofuel. High cell density fermentation increases the volumetric productivity and reduces investment costs. However, it also increases the cost for producing the cell mass, which is a function of the price for added nutrients and decreases the product yield since substrate is converted to biomass. Therefore, a high specific activity which measures the efficiency of the biocatalyst, translates to a lower amount of cell mass required in the fermentation step. For example, ethanol production plants operate at volumetric productivities ranging from 1-3 g ethanol $L^{-1}$ $h^{-1}$ with the specific ethanol productivity, e.g., for *Saccharomyces cerevisiae* being about 2 g ethanol g cell dry weight $(CDW)^{-1}$ $h^{-1}$ (Appl. Microbiol. Biotechnol. 2007 74:937-953), and about 2.1 g ethanol g $CDW^{-1}$ $h^{-1}$ for an engineered *Escherichia coli* biocatalyst (U.S. Pat. No. 5,424,202).

Specific productivity of the biocatalyst depends on the capacity of the terminal pathway converting an intermediate of the carbon metabolism of the host organism into a biofuel. Another limiting factor for the specific productivity is the glycolytic flux of the biocatalyst. For the biocatalyst production of certain chemicals, typical glycolytic fluxes reported in the literature are summarized in Table 2. The economic production of a biofuel by fermentation requires cells that consume a carbohydrate feedstock at similar or higher rates.

TABLE 2

Glycolytic flux achieved in biocatalytic processes converting glucose into products.

| Reference | Strain or Biocatalyst | Substrate | Product | Glycolytic flux [g g $CDW^{-1}$ $h^{-1}$] |
|---|---|---|---|---|
| Elbing, K. et al. 2004. Appl. Environ. Micro. 70: 5323-5330 | *Saccharomyces cerevisiae* CEN.PK2-1C | glucose | ethanol | 3.24 |
| Papagianni, M. et al. Microbial Cell Factories. 2007. 6: 16. | *Lactococcus lactis* spp. *lactis* LM0230 | glucose | lactate | 4.59 |
| Fong, S. et al. 2005. Biotechnol. Bioengineering. 91: 643-648. | *E. coli* MG1655 (pta, adhE), evolved | glucose | lactate | 4.14 |
| Zhu, J. and Shimizu, K. 2004. Appl. Microbiol. Biotechnol. 64: 367-375 | *E. coli* BW25113 (pfl) | glucose | lactate | 1.47 |
| Van Hoek, P. et al. 2003. WO 03/102200 A2. | *Kluyveromyces marxianus* (PDC) | glucose | lactate | 2.66 |
| Das Neves, M. A. et al. 2007. J. Food Process Engineering. 30: 338-356 | *Zymomonas mobilis* NBRC 13758 | glucose | ethanol | 10.9 |
| Das Neves, M. A. et al. 2007. J. Food Process Engineering. 30: 338-356 | *Saccharomyces cerevisiae* | glucose | ethanol | 1.02 |
| Smits, H. P. et al. 2000. Yeast. 16: 1325-1334. | *Saccharomyces cerevisiae* CEN.PK.K45 | glucose | ethanol | 4.4 |
| Zhou, S. et al. 2006. Biotechnol. Lett. 28: 671-676. | *E. coli* (engineered) | glucose | lactate | 7.2 |
| Causey, T. B. et al. 2003. Proc. Nat. Acad. Sci. USA. 100: 825-832. | *E. coli* (engineered) | glucose | acetate | 3.24 |
| Roca, C. et al. 2003. Appl. Environ. Micro. 69: 4732-4736. | *Saccharomyces cerevisiae* TMB 3001 | glucose | ethanol | 4.5 |
| Zhou, S. et al. 2006. Biotechnol. Lett. 28: 663-670. | *E. coli* B (engineered) | glucose | lactate | 1.3 |

Economical production of biofuels from biomass-derived organic compounds via fermentation processes depends upon biocatalysts that catalyze this conversion in very specific ways described herein. A method of producing biofuels makes use of biocatalysts that exhibit certain properties which decrease the cost of the fermentation part of the biofuel production process. An important characteristic of the biocatalyst is that the biocatalyst contains DNA consisting of natural DNA. It is important that the biocatalyst functions in a low cost and efficient manner within the overall biofuels production process on the low cost nutrient. A business strategy is disclosed that employs the use of an economical method for the production of biofuels. Low cost biofuel production requires the biocatalyst to provide optimal productivity and yield on carbohydrate and biofuel concentration. Further, biocatalysts that contain DNA consisting of natural DNA allow the spent biocatalyst to be used as an animal feed supplement, as fertilizer, or disposed of as waste with minimal treatment. An ideal biocatalyst with these performance characteristics for the production of a biofuel yields a process that is economically favorable for the production of a commodity biofuel or chemical.

Natural organisms may be used in the production of fuels or chemicals by fermentation. Frequently, however, microorganisms must be modified to be useful industrial biocatalysts. For example, nucleic acids derived from a foreign organism may be inserted into a biocatalyst to alter the properties of the biocatalyst. Nucleic acids that encode pathways for the production of chemical compounds, like amino acids or biofuels, may be inserted into a biocatalyst. Sometimes, several genes must be transferred to a biocatalyst to generate a useful product. Other times, only one or two genes may be required. It is also possible to insert nucleic acids that impart other properties on a biocatalyst that are not directly involved with the conversion of a feedstock into a product, but nevertheless enhance the ability of a biocatalyst to convert feedstock into product at an industrial scale. For example, nucleic acid sequences that enhance the tolerance of biocatalysts to stressful conditions or compounds may be inserted into a biocatalyst (Papoutsakis, E. T. et al. U.S. Pat. No. 6,960,465 B1, 2005).

During development of a biocatalyst, it may be necessary to alter the natural state of the biocatalyst to remove unwanted features or products, prior to the use of the biocatalyst in industrial scale fermentation. Methods to impair or remove genes or parts of genes from a biocatalyst can be random or targeted. In a random approach, chemical or physical mutagens may be used to accelerate the natural mutation frequencies of a biocatalyst and paired with selection for improved performance or removal of unwanted products or features. In a directed approach, specific genes of known or unknown function may be removed or inhibited through genetic modification. For example, in order to redirect the carbon flow within a biocatalyst into an introduced metabolic pathway for the production of a biofuel, it may be necessary to remove or impair genes that encode native metabolic pathways in a biocatalyst. European Union (EU) regulations define genetically modified organisms (GMOs) which are modified using techniques that require in vitro genetic modifications (European Commission Regulation 1830/2003/EC, and Regulation1839/2003/EC). Organisms that are only modified by non targeted mutagenesis, mutations and alterations generated using viral infection, and introduction of DNA by sexual transmission of DNA between organisms are not considered GMOs by the EU, therefore their use in the EU is not restricted.

Common targeted methods used to remove DNA from the genome of biocatalysts may leave behind genetic markers, such as DNA markers or genes that encode antibiotic resistance, or short segments of DNA, such as scar DNA, used as enzyme recognition sequences to remove said genetic markers. Similarly, common methods are used to insert DNA into the genome of biocatalysts. Insertion methods may also leave behind DNA markers or scar DNA in the genome of a biocatalyst. Further, extra-chromosomal elements, such as plasmids, cosmids, bacterial artificial chromosomes or yeast artificial chromosomes, or phage, may be used to confer desirable properties to a biocatalyst. These extra-chromosomal elements are usually stabilized by the use of DNA markers contained within the extra-chromosomal elements. Extra-chromosomal elements may contain other foreign DNA as well, such as origins of replication, multiple cloning sites, repressor genes, terminators, and promoters. Origins of replication, multiple cloning sites, terminators, and promoters do not encode for proteins in the biocatalyst. Further, segments of enzyme recognition sequences, or scar DNA, used to remove genetic markers from the chromosome of a biocatalyst, do not encode for proteins within the biocatalyst. However, DNA markers and repressor genes usually encode proteins that provide antibiotic resistance and repress desired promoter regions, respectively.

The foreign DNA incorporated into the biocatalyst can originate from within the same species, within the same genus, from a different genus, or from a different taxa as the biocatalyst. The evolutionary distance of the organisms might have an influence on the limitations of use for the engineered organism. For example, The United States Environmental Protection Agency regulates organisms that contain DNA from organisms in different genera.

Biocatalysts that contain foreign DNA may pose several environmental and food safety concerns, depending on how the spent biocatalyst is used after industrial fermentation processes. One concern is the release of live biocatalysts into the environment. Biocatalysts that contain foreign DNA may be properly deactivated or killed prior to release into the environment. Another concern is the transfer of foreign DNA, such as DNA markers, from modified biocatalysts into other organisms in the environment. For example, transfer of a DNA marker that encodes a protein for antibiotic resistance to a pathogenic or opportunistic pathogenic microorganism in the environment may inhibit treatment of humans or animals infected with said organism. In some cases, biocatalysts that contain foreign genes may produce proteins that lead to allergic or undesired reactions in humans or animals. In this case, the spent biocatalyst must be not be used in applications that lead to human or animal contact with proteins contained within the spent biocatalyst. Here, spent biocatalysts may be incinerated for disposal or for energy generation. Alternatively, the spent biocatalyst may be used as a complex nutrient in another industrial fermentation or degraded through an anaerobic sludge digestion treatment process.

For an economic industrial fermentation process, the spent biocatalyst has the highest possible value. In this case, it is more economical to sell spent biocatalyst as a co-product, like DDG, than to incinerate the spent biocatalyst for energy or disposal. Spent biocatalyst that does not contain foreign DNA may be used directly as a fertilizer or may be incinerated to generate a potash-rich fertilizer. Depending on the treatment required to generate fertilizer from spent biocatalyst, it may or may not have economic value (Spivey, M. J. Process Biochemistry. November 1978. pp 2-4, 25). Generally, the energy generated from the incineration of spent biocatalyst is of less value than selling the spent biocatalyst as part of DDG. Engineered organisms generally require more elaborate equipment to ensure the containment of the biocatalyst within the fermentation process. Accidental release of an engineered biocatalyst through fermentation off-gas and spills should be avoided. Additional capital equipment can be installed to contain spills and prevent release of an engineered biocatalyst through fermentation off-gas. The additional capital cost necessary for the fermentation equipment adds to the overall process cost for biocatalysts containing foreign DNA relative to organisms that contains DNA consisting of natural DNA.

One paper describes the creation of an *E. coli* biocatalyst for fuel ethanol production. The *E. coli* biocatalyst does not contain any foreign genes (Kim, Y. 2007 Applied and Environmental Microbiology 73(6)). Another paper describes generation of a yeast strain with no foreign genes that can use a 5 carbon sugar as a substrate and may be suitable for further development as industrial biocatalysts (Attfield, P. V. 2006 FEMS Yeast Research 6). *Clostridia* sp. fermentations for the production of acetone, butanol, and ethanol used biocatalysts that were not genetically modified to contain foreign DNA (Jones, D. T. and Woods, D. R. Acetone-Butanol Fermentation revisited. Microbiological Reviews, 1986, 50:484-524; Spivey, M. J. Process Biochemistry. November 1978, 25:2-4). The ABE process was the only industrial scale biofuel process that used a biocatalyst that contained DNA consisting of natural DNA. The spent biocatalyst generated during ABE fermentations was commonly sold as an animal feed supplement (Jones, D. T. and Woods, D. R. Acetone-Butanol Fermentation revisited. Microbiological Reviews, 1986, 50:484-524).

There is a need in the art to generate efficient and economical biocatalysts for the production of biofuels and chemicals. There is also a need to generate biocatalysts that not only use any feedstock or source of carbohydrates available, but also possess several other performance characteristics that favor an economical industrial process for the production of biofuels and chemicals.

The pH of a fermentation is regulated primarily by adding acidic or basic solutions to the fermentation broth. Regulating the pH of a fermentation adds operating cost to the process in many ways. For example, the acid and base used to adjust the pH must be purchased. Further, the addition of solutions of acid or base to the fermentation dilutes the product, increasing the downstream recovery costs of the desired product. Additionally, the acid and base added to the fermentation generate salts that are of little or no value and must be treated as waste. The adjustment of pH by the addition of acid or base also generates heat that must be removed from the fermentation with additional expensive cooling equipment. For these reasons, it is desirable to use a biocatalyst that functions at a wide range of pH values to decrease or eliminate the need to control the pH of the fermentation.

Biocatalysts that function at low pH values, i.e. less than pH 4, are especially valuable because most microorganisms that commonly contaminate industrial fermentations do not grow at lower pH values. Additionally, when biomass hydrolysate is used as a fermentation substrate, the pH value of the hydrolysate is low and is usually raised by the addition of base prior to use as a fermentation feedstock. If a biocatalyst can function at the pH level of biomass hydrolysate that does not require addition of base prior to fermentation, it will greatly decrease the production cost of the fermentation.

In addition to functioning at low pH values, a biocatalyst that can withstand rapid pH changes in either direction is particularly valuable. Further, a biocatalyst that can withstand short durations of pH values one or more pH units above or below the optimum pH for the fermentation is particularly valuable. For example, costs associated with the dilution of the fermentation broth during pH adjustments can be reduced if stronger acids or bases are used for pH adjustment. If the biocatalyst can withstand the quick pH change in the immediate vicinity of the addition, which may include exposure to highly concentrated acids and bases, then stronger acids and bases can be used.

The pH value of the fermentation impacts the number of potential contaminants. In the pH range of 5.5 to 7.0, which is typical for bacterial fermentations, many organisms are viable. Therefore, this pH makes continuous operation unfeasible. For batch fermentations in the pH range of 5.5 to 7.0, sanitary equipment and careful aseptic procedures allow for largely contaminant-free operation, but adds expense. At lower pH values of 4 to 5.5, many bacteria do not grow or metabolize well. However, lactic acid producing bacteria are prevalent at this pH range and many fungal strains, including yeast, function very well in the pH range of 4 to 5.5. Continuous fermentation will likely be difficult, but batch fermentation will require sanitary equipment and aseptic procedures for contaminant-free operations. At pH values lower than 4, many fungal strains can be competitive and thus may contaminate a fermentation in this pH range. Bacterial strains that convert carbohydrates to products are rare at pH values below 4 and with any additional pressures, particularly from organic acids, the bacteria cannot grow.

Simultaneous saccharification and fermentation, where feedstock materials are treated to permit efficient fermentation and a biocatalyst simultaneously converts the treated feedstock material to desired products, is preferred over separate saccharification and fermentation processes. Simultaneous saccharification and fermentation is preferred over a separate saccharification and fermentation process because sugars generated in the separate process are vulnerable to non-productive consumption by contaminating organisms prior to use in fermentation (Lynd, Lee R et al., Consolidated bioprocessing of cellulosic biomass: an update. Current Opinion in Biotechnology. 2005. 16:577-583). For simultaneous saccharification and fermentation, the pH needs to permit optimal function of both the saccharification enzymes and biocatalyst in the hydrolysate solution or fermentation broth. For example, hydrolysis of cellulose by cellulase enzymes can be started in an independent saccharification process. However, since the concentration of sugars is low enough to support microbial activity, processing operations need to account for the microbial activity. Limited duration batches, followed by cleaning-in-place (CIP) of the vessels and associated piping, is required. Given the need to minimize sugar loss and tank volume for saccharification and fermentation, some portion of the saccharification must be done in concert with the fermentation.

The whole process is more effective if the needs of the saccharification enzymes, the biocatalyst, and the necessity to keep out competitive microorganisms can be accomplished at high rates, simultaneously with one another (Mojovic et al., Fuel 85 (2006) 1750-1755). This requires the pH of the simultaneous saccharification and fermentation (SSF) to be optimal for the enzyme, the biocatalyst, and the retardation of potential contaminants. Enzymes that are added for the degradation of both cellulose and starch have optimal activities in the pH 4-5 range. Biomass hydrolysates and dry mill fermentation processes typically suffer contaminations from bacteria, most often lactic acid producing bacteria. Lactic acid and other bacteria can be stopped by the presence of organic acids in the acid form. To accomplish this, the pH must be low enough relative to the organic acid pKa to provide organic acid in the acid form at concentrations above 5 g/L. Generally, this level of organic acid in the acid form retards bacterial activity in a sugar solution.

Finally, biomass hydrolysates, in particular, contain acetic acid derived from the hydrolysis of hemicellulose. The pKa of acetic acid is about 4.8. Therefore, it has a significant inhibitory impact on the biocatalyst if present in sufficient concentration. Many biomass feedstocks provide acetic acid concentrations of 5 to 15 g/l when pretreated at biomass solid concentrations of 10 to 30%. At a pH of 4.8, 5 to 15 g/l of acetic acid are present which retards bacterial contaminants and many fungal contaminants. The economic benefits of a biocatalyst that can operate at lower pH values include 1) improved yields by reducing contaminant competition for feedstock, 2) ability to use continuous fermentation, 3) enzymes used in saccharification are kept in the optimal pH range thus reducing enzyme load and cost, and 4) in a simultaneous saccharification and fermentation process, the biocatalyst is able to convert sugars at a higher rate to desired products.

Continuous fuel ethanol fermentations are run at pH values less than 4.0. The ethanol fermentations are conducted with yeast and the production of ethanol is anaerobic. Citric acid is produced aerobically at pH values much less than 4.0, as the citric acid is not neutralized. Air is required so the organism producing the citric acid can respire on glucose providing the metabolic energy to excrete the organic acids from the cell. This illustrates the additional challenge that microorganisms or biocatalysts face in an environment containing organic acids at pH values lower than the pKa for the organic acid. For biomass feedstocks, once the hemicellulose component is hydrolyzed, a significant quantity of acetic acid, often in the range of 1%, is present. Even *Saccharomyces cerevisiae* at pH values less than 5 is very ineffective in growth or fermentation in the presence of acetic acid (Verduyn, C 1991 *Antonie van Leeuwenhoek* 60: 325-353).

An ideal biocatalyst therefore will operate at low pH, pH values in the range of 2 to 4, without organic acid challenge. In the presence of organic acids, such as acetic, lactic, or other organic acids, the biocatalyst will need to perform in the pH range of 2 to 5, the higher pH reflecting the increased difficulty for the biocatalyst in the presence of free organic acids (organic acids below their pKa value). As an example, the ideal biocatalyst will need to perform significantly better than *Saccharomyces cerevisiae* typified as baker's yeast or used in fuel ethanol production in order to provide the lowest manufacturing cost.

Fermentation temperature impacts the cost of biofuel production in several ways. For example, in a case where cooling water is not recirculated, the quantity of water required to cool the fermentation increases when fermentation temperature increases if the biocatalyst used does not tolerate higher temperatures. In another example, where cooling water is recirculated and cooled by an energy-consuming chiller, energy costs to cool the fermentation increases when fermentation temperature increases if the biocatalyst used does not tolerate higher temperatures. In the case of simultaneous saccharification and fermentation, the fermentation temperature affects the functionality of the enzymes used to provide fermentable carbon sources to the biocatalysts. Generally, the higher the temperature, the more active the enzymes. Additionally, in normal industrial fermentation operating environments, contaminant organisms are more likely than not sensitive to high temperatures. Thus, fermentations using biocatalysts that have a higher temperature tolerance are less prone to contamination when the fermentation is operated at higher temperature.

For corn dry milling and biomass based production processes, the temperature of the fermentation affects the cost of using simultaneous saccharification and fermentation processes. Typically to reduce capital costs it is desired to do some or all of the enzymatic saccharification of starch, cellulose or hemicellulose or breakdown products of all three, in the fermentation vessel along with fermentative conversion to the desired biofuels. Frequently, raw materials for industrial fermentations require pretreatment, such as saccharification of corn starch or release of monomeric carbohydrates from biomass. These pretreatments are usually performed at elevated temperatures, sometimes 50° C. to greater than 60° C. In fermentations where the biocatalyst is not tolerant to these temperatures, the pretreated substrates must be cooled prior to subsequent fermentation. However, if a biocatalyst is tolerant to higher temperatures, the process can be either be simultaneous or will require less cooling of the substrate prior to fermentation, increasing the total productivity of the process and thus decreasing the overall cost. In addition to having decreased operating costs, fermentations operating at increased temperatures use less capital equipment for cooling the pretreated carbon sources prior to fermentation, resulting in a more economical process with respect to capital costs.

Without temperature control, the temperature of a fermentation will generally increase over time due to heat generated by biocatalyst metabolism and by mechanical agitation of the fermentation broth (Weir, E. Dale et al. Plant/Operations Progress. 1986. 5:142-7). The amount of heat produced by agitation depends upon the size of the fermentation vessel and the nature of the feedstock used. Specifically, the quantity of solids that the feedstock adds to the fermenter will affect the amount of heat generated due to friction. Raw cane sugar (unrefined sucrose recovered from sugar cane plant), which mostly dissolves into the fermentation broth, adds few solids into the fermentation. Dry milled corn adds a substantial quantity of solids into the fermentation that approaches 20-30% by weight in some of the high concentration fermentations run today (Bothast et al. 2005 Applied Microbiology and Biotechnology 67:19-25). Likewise the quantity of solids in a biomass fermentation, at the start, will also approach 20% depending on the character of the biomass material (The Phyllis Database for Biomass and Waste, Energy Research Centre of the Netherlands). A higher fermentation temperature for the production of biofuel precursors would permit the use of a lower quantity of cooling water, a smaller size of heat exchangers, a smaller size of cooling towers, and potentially eliminate any need for chilled water equipment and operation. As these items all contribute to both capital and operating costs of the fermentation, elimination of these items in higher temperature fermentations yields a more economical fermentation process. If the biocatalyst can operate at higher temperatures, e.g. 30-40° C. and higher, the need for chilled water is reduced or eliminated and thus decreasing operating and capital costs for heat exchange (Banat, I. M. et al. 1998. World Journal of Microbiology and Biotechnology. 14:809-821).

In addition to functioning at higher temperature values, a biocatalyst that can withstand rapid temperature changes in either direction is particularly valuable. Further, a biocatalyst is particularly valuable that can withstand short durations of temperature of ten or more degrees Celsius above or below the optimum temperature for the fermentation. For example, costs associated with the control of temperature of a fermentation can be reduced if the biocatalyst can withstand temperature fluctuations caused by changes in ambient environmental temperature when no temperature control is employed. If the biocatalyst can withstand brief temperature changes, then temperature changes due to operator error and equipment malfunction will not reduce the productivity of the biocatalyst below an economic threshold.

The temperature of the fermentation impacts the number of potential contaminants. In the temperature range of 25° C. to 40° C., which is typical for bacterial fermentations, many microorganisms are viable. Therefore, this temperature may make continuous operation unfeasible. For batch fermentations in the temperature range of 25° C. to 40° C., sanitary equipment and careful aseptic procedures allow for largely contaminant-free operation, but add expense. At higher temperature values of 40° C. to 60° C., many bacteria do not grow or metabolize well. Thus, in an industrial fermentation using a biocatalyst that functions at higher temperatures, competition from potential contaminating microorganisms is reduced. This results in a more economic fermentation because high yield and high productivity of the desired product is maintained.

There is a need in the art to generate efficient and economical biocatalysts for the production of biofuels and chemicals. There is also a need to generate biocatalysts that not only use any feedstock or source of carbohydrates available, but also possess several other performance characteristics that favor an economical industrial process for the production of biofuels and chemicals.

Given the fact that raw materials, primarily the carbon source such as dextrose or sucrose, represent a large fraction (30-60% in many cases) of the overall cost of producing biofuels and chemicals using industrial biological processes, maximizing conversion yields of sugars to product is of primary importance (Hermann B G, Patel M. Today's and tomorrow's bio-based bulk chemicals from white biotechnology: a techno-economic analysis. Appl. Biochem. Biotechnol. 2007 March; 136(3):361-88; Fan Z, Lynd L R. Conversion of paper sludge to ethanol, II: process design and economic analysis. Bioprocess Biosyst Eng. 2007 January; 30(1):35-45). Hence, production organisms as well as associated processes must be optimized such that conversion yields close to maximum theoretical are achieved. For instance, early engineered yeast strains for converting the biomass pentose sugar xylose to ethanol were based on expressing the oxidoreductases xylose reductase and xylitol dehydrogenase. As a result of the redox imbalances and other metabolic constraints, such strains excreted a large fraction of the utilized carbon source in the form of the undesirable by-product xylitol instead of the target product ethanol (Pitkanen et al. 2003. Metabolic Engineering 5:16-31; Hahn-Hägerdal B, Karhumaa K, Fonseca C, Spencer-Martins I, Gorwa-Grauslund M F. Appl Microbiol Biotechnol. 2007 April; 74:937-53). Pathway optimization that involved replacement of the oxidoreductases with a xylose isomerase from anaerobic fungal sources addressed this critical issue which in turn resulted in high conversion yields, as well as conversion rates, while minimizing or eliminating the accumulation or xylitol (Rajgarhia, Vineet at al. US 20060234364 A1 (2006); Kuyper, M. et al., 2005. FEMS Yeast Research 5:399-409). In other instances, byproducts may inhibit the production organism, compromising conversion yields and rates, as well as product titers. For example, the by-product acetate significantly inhibits fermentation performance when engineered E. coli strains are used for the production of ethanol (Zaldivar J, Ingram L O. Biotechnol. Bioeng. 1999. 66:203-10) or 1,3-propanediol (Cameron, D. C., Altaras, N. E., Hoffman M L, Shaw, A. J. Biotechnol. Prog. 1998. 14:116-25). In the case of the ABE process, substantial quantities of carbon are typically diverted to acetone instead of butanol thus limiting process yields and rates (Qureshi, N., Blaschek, H. P. J. Ind. Microbiol. Biotechnol. 2001. 27:292-7). Byproducts also pose significant downstream and separations issues, especially when additional unit operations to reduce impurity levels below product specifications must be installed to remove these byproducts. This results in a more capital intensive process. Additionally, processes with byproducts have higher operating costs and are potentially more difficult to operate than processes with little or no byproducts. This is especially true in cases where byproduct types and concentrations vary with time or from batch-to-batch. For instance, fermentations for the production of the biopolymer intermediates L-lactic acid or 1,3-propanediol must generate a product with very tight specifications with regards to byproduct types and levels, as this can impact the downstream polymerization process (Grabar T B, Zhou S, Shanmugam K T, Yomano L P, Ingram L O. Biotechnol Lett. 2006. 28:1527-35; Avraham M. Baniel, Robert P. Jansen, Asher Vitner, Anthony Baiada. 2006. U.S. Pat. No. 7,056,439).

For example, biocatalysts may economically convert biomass into biofuel, to produce fuels that meet at least one of the fuel specifications established by the American Society for Testing and Materials (ASTM) after the biofuel is recovered from the fermentation broth. Such production specification include, but are not limited to, ASTM D4814 for gasoline, ASTM D910 for aviation gasoline, ASTM D1655 for aviation turbine fuel, and ASTM D975 for diesel fuel. Specifications ASTM D4814 for gasoline, ASTM D910 for aviation gasoline, ASTM D1655 for aviation turbine fuel, and ASTM D975 for diesel fuel and are hereby incorporated herein by reference. In the case where an ASTM standard does not exist for a particular biofuel, for example isobutanol, then a more stringent standard for use of the compound as a solvent may be consulted, for example ASTM D1719-05. For example, ASTM standard method D3242 is referenced in the ASTM specifications to describe the maximum amount of organic acids that are acceptable in fuels, i.e. less than 0.10 mg potassium hydroxide/gram fuel is required to neutralize any acidic material present in the fuel. Biocatalysts that produce products that meet ASTM specifications without extensive purification are economically advantageous because additional processing is not required to remove organic acid impurities from the product.

In another example, undesirable byproducts such as aldehydes, ketones, and ethers, which give rise to oxidative degradation of the fuel or participate in the formation of unstable deposits in fuel systems, must be removed (Zrelov, V. N et al. USSR. Korroziya i Zashchita v Neftegazovoi Promyshlennosti. 1972. 5:12-15; Zrelov, V. N. USSR. Itogi Nauki, Tekhnologiya Organicheskikh Veshchestv. 1968. 1967:5-78). Undesirable byproducts such as aldehydes, ketones, and ethers are incompatible with aviation fuels, which must pass ASTM specifications for oxidative stability (ASTM D3241) and gum content (ASTM D381). Thus, biocatalysts used to produce biofuels that produce less aldehydes, ketones, and ethers are more economical than biocatalysts that produce higher quantities of these compounds. Similarly, biocatalysts must not produce any byproducts or impurities which may lead to metal corrosion. Biofuels produced by the biocatalysts should be capable of passing a 2-hour copper corrosion test at 100° C. (ASTM D130).

In an economical industrial fermentation process, a biocatalyst produces a high level, or titer, of the desired product. A high product titer reduces the cost of downstream processing and product separation and can reduce the operating costs associated with purification of the product. In a fermentation process to produce a biofuel, the higher the biofuel concentration, the less cost of recovering that biofuel from the fermentation broth during product recovery. High product titers also reduce the waste streams coming out of the fermentation and out of the downstream processing, which reduces the overall process cost. In order for a biocatalyst to produce high levels of biofuel during fermentation, the biocatalyst must be tolerant and resistant to high levels of the biofuel.

Biofuels, such as linear and branched alcohols, alkanes, and aromatics have different levels of hydrophobicity. Table 3 lists some properties of linear and branched chain alcohols, some of which are biofuels. Hydrophobicity is commonly measured by the octanol:water partition coefficient (P) or expressed as the logarithm of this value (log P) (Laane, C. 1987. Biotechnology and Bioengineering 30). The toxicity of a compound, like a biofuel, correlates with the log P of the compound when log P is between 1 and 4. Within the range of 0 to 1, a compound with a higher log P is generally more toxic to a cell than a compound with a lower log P (Heipieper, H. et al. 2007. Applied Microbial. Biotechnology 74:961-973). Compounds with a log P value of greater than 1 are generally less toxic to biocatalysts than compounds with a log P value of 0 to 1.

Little prior art exists relating to the resistance of biocatalysts to biofuels and related compounds during their production. Most biofuel resistance prior art is related to the resistance of cells to externally applied biofuels, solvents, or similar compounds. It has been found that resistance of a biofuel or related compound by cells that are producing the compound versus cells that are simply exposed to the compound externally may not be identical. Specifically, relevant resistance limits in the prior art that are levels produced by the organism, and not added externally, include ethanol at 97 g/L, produced in yeast (Lin, Y. et al. 2006 Appl. Microbiol. Biotechnol. 69:627-642); butanol at 21 g/L (Chen, C. K. 1999 Applied Microbiology and Biotechnology 52; Formanek, J 1998 WO 98/51813; Blascheck, H. 2002 U.S. Pat. No. 6,358, 717 BI), and isopropanol at 5.5 g/L (Groot, W. 1986. Biotechnology Letters 6(11)) produced in bacteria (*Clostridium*); octanol at 20 g/L; but the solubility limit is <1.1 g/L so remaining partitions out in two-phase system used (Chen, Q. 1995. Journal of Bacteriology 177(23)); decanol at 750 mg/L, and dodecanol at 310 mg/L, produced in bacteria (gram negative bacteria) (Elgaali, H. 2002 Journal of Basic Microbiology 42(6) and Hamilton-Kemp, T. 2005. Current Microbiology 51); isobutanol produced in yeasts at 1800 mg/L (Golubkov, I. WO 2005040392A1).

The biocatalyst of the invention produces high levels of biofuel during a fermentation process and is resistant to high levels of the biofuel product. The biocatalyst of this invention functions normally or with minimal impairment in the presence of high levels of biofuel product. Tert-butanol appears to be made only synthetically from petrochemical routes and no prior art describing the production of tert-buanol in a biocatalyst exists. Hexanol is reportedly produced in yeast fermentations of grape feedstocks during the production of wine in very small amounts. Concentrations in the range of 1-5 mg/L have been documented as a fermentation product during the production of wines (Garde-Cerdan, T. 2006 Eur. Food Res. Technol. 222: 15-25 and Malacrino, P 2005 Letters in Applied Microbiology, 40: 466-472).

TABLE 3

Properties of some biofuel compounds.

| Compound | Solubility in water (20° C., unless noted) | log P[1] |
|---|---|---|
| 2-propanol | miscible | 0.14 |
| 1-propanol | miscible | 0.34 |
| tert-butanol | Very good (>100 g/L) | 0.4 |
| 2-butanol | 125 g/L | 0.6 |
| isobutanol | 85 g/L @25° C. | 0.79 |
| 1-butanol | 77 g/L | 0.88 |
| 1-hexanol | 5.9 g/L | 2.03 |
| 1-octanol | 0.30 mg/L | 3 |
| 1-decanol | insoluble | 3.97 |

[1]Data from International Programme on Chemical Safety INCHEM; Kabelitz, N. 2003 FEMS Microbiology Letters 220

In an economic fermentation process, as many of the products of the fermentation as possible, including the co-products that contain biocatalyst cell material, should have value. Insoluble material produced during fermentations using grain feedstocks, like corn, is frequently sold as protein and vitamin rich animal feed called distiller's dried grains (DDG). The term may also include soluble residual material from the fermentation and is then referred to as "distillers dried grains and solubles" (DDGS). To be a valuable animal feed, the spent biocatalyst material that is part of the insoluble fraction produced during the fermentation process must not degrade the feed quality of the DDG or DDGS.

Corn dry milling can be used to provide a low cost substrate for biofuel production. Corn dry milling and fermentation result in a substantial volume of the co-product DDG or DDGS, which make up about 35% of the initial corn dry mass. DDG or DDGS are typically used as cattle feed.

One example of an element of toxicity in some biocatalysts is endotoxin. Endotoxin commonly refers to the component of the outer membrane of gram negative bacteria called lipopolysaccharide, or LPS, or a portion of the LPS molecule. LPS is a structural feature of gram negative bacteria and provides a barrier separating the cell from the external milieu, with particular protection from hydrophobic compounds. Endotoxin may be immunogenic and toxic to animals and is therefore not desirable or desirable in very low levels in biocatalysts that may be sold as a component of DDG or DDGS.

Some genera of bacteria, like the enteric bacteria *Shigella, Escherichia*, and *Salmonella*, contain endotoxin that can be especially immunogenic and toxic. One example is the toxicity of the LPS of a pathogenic *E. coli* 011:B4 that was measured to be LD50=18 mg/kg in rat toxicity testing (Fletcher, M. A., et al. Journal of Surgical Research 1993 55:147-154). There are reports on the different levels of toxicity of endotoxin among different strains of bacteria (Mayer, H. 1984. Reviews in Infectious Diseases 6(4); Barasoain, I. 1979. Revista Clinica Espanola 155(3)). For example, LPS was extracted from microorganisms present in the rumen of cattle and the toxicity of this LPS was compared to *E. coli* and *Salmonella* LPS (Nagaraja, T. G. et al. 1978. Journal of Animal Science 47:226-234). The toxicity of the *E. coli* and Salmonella LPS was at least four to six times more toxic than that extracted from rumen microorganisms, indicating variable toxicity of LPS among different bacteria. Additionally, endotoxin toxicity can vary among strains of the same species of gram negative bacteria and levels can even be completely non-toxic in some strains (Mayer, H. et al. 1984. Rev. Infect. Dis. 6:542-545). Therefore, naturally occurring gram negative strains can be identified that have low endotoxin levels or low endotoxin toxicity. Selection of a biocatalyst for the production of biofuels that has low endotoxin levels or low endotoxin toxicity increases the value of the fermentation process because the spent biocatalyst may be used in a DDG or DDGS co-product. Further, modification of a biocatalyst to reduce endotoxin levels or lower endotoxin toxicity increases the value of the fermentation process because the spent biocatalyst may be used in a DDG or DDGS co-product.

There are some reports regarding reducing the toxicity of endotoxin while retaining immunogenicity for the application of vaccine development (Steeghs L. et al. 2004. Journal of Endotoxin Research 10(2); Van der Ley, P. et al. 2001. Infection and Immunity 69(10); Van der Ley, P. et al. WO2000026384). Therefore, it is possible to reduce the toxicity of endotoxin in strains of gram negative bacteria. However, there are no reports of a biocatalyst for the production of biofuels through fermentation being modified to reduce the levels or toxicity of endotoxin.

Another type of toxin present in some microorganisms is an exotoxin. An exotoxin is a protein released extracellularly by a microorganism as it grows and produces immediate damage to animals and animal cells. Most exotoxins fall into one of three categories, which include cytolytic toxins, A-B toxins, and superantigen toxins. Cytolytic toxins enzymatically attack cell components and cause lysis. The A-B toxins are two-component toxins that permit transfer of one component into the target cell through the membrane and cause damage to the target cell. Superantigen toxins stimulate large numbers of immune response cells and cause damage to the target organism. Exotoxins can be produced by both gram positive and gram negative bacteria and higher organisms, like fungi and yeasts. The presence of exotoxins in DDG or DDGS renders the DDG or DDGS inedible (not feed grade) and invaluable. Therefore, a biocatalyst that produces biofuels by fermentation and becomes part of the DDG or DDGS product must not produce any exotoxins. Exclusion of exotoxins from a biocatalyst strain can be accomplished by selecting exotoxin-free strains or modifying exotoxin-producing strains such that they no longer produce exotoxins. Exotoxins are proteins and thus can be inactivated by being degraded. A common mechanism of protein inactivation or degradation is digestion of the protein by specialized enzymes called proteases. Another common mechanism of protein inactivation or degradation is digestion of the protein by specialized enzymes called peptidases. Another common mechanism of protein inactivation or degradation is digestion of the protein by specialized enzymes called amidases. Table 4 lists some common exotoxins.

TABLE 4

Common exotoxins produced by microorganisms.

| Organism | Disease | Toxin or factor* | Action |
| --- | --- | --- | --- |
| Bacillus anthracis | Anthrax | Lethal factor (LF) Edema factor (EF) Protective antigen (PA) (AB) | PA is the cell-binding B component, EF causes edema, LF causes cell death |
| Bacillus cereus | Food poisoning | Enterotoxin (?) | Induces fluid loss from intestinal cells |
| Bordetella pertussis | Whooping cough | Pertussis toxin (AB) | Blocks G protein signal transduction, kills cells |
| Clostridium botulinum | Botulism | Neurotoxin (AB) | Flaccid paralysis |
| Clostridium tetani | Tetanus | Neurotoxin (AB) | Spastic paralysis |
| Clostridium perfringens | Gas gangrene, food poisoning | α-Toxin (CT) β-Toxin (CT) γ-Toxin (CT) δ-Toxin (CT) χ-Toxin (E) λ-Toxin (E) Enterotoxin (CT) | Hemolysis (lecithinase) Hemolysis Hemolysis Hemolysis (cardiotoxin) Collagenase Protease Alters permeability of intestinal epithelium |
| Corynebacterium diphtheriae | Diphtheria | Diphtheria toxin (AB) | Inhibits protein synthesis in eukaryotes |
| Escherichia coli (enteropathogenic strains only) | Gastroenteritis | Enterotoxin (AB) | Induces fluid loss from intestinal cells |
| Pseudomonas aeruginosa. | P. aeruginosa infections | Exotoxin A (AB) | Inhibits protein synthesis |
| Salmonella spp | Salmonellosis, typhoid fever, paratyphoid fever | Enterotoxin (AB) Cytotoxin (CT) | Inhibits protein synthesis and lyses host cells Induces fluid loss from intestinal cells |
| Shigella dysenteriae | Bacterial dysentery | Enterotoxin (AB) | Inhibits protein synthesis |
| Staphylococcus aureus | Pyrogenic (pus-forming) infections (boils, and so on), respiratory infections, food | α-Toxin (CT) Toxic shock syndrome toxin (SA) Exfoliating toxin A and B (SA) Leukocidin (CT) β-Toxin (CT) γ-Toxin (CT) δ-Toxin (CT) | Hemolysis Systemic shock Peeling of skin, shock Destroys leukocytes Hemolysis Kills cells Hemolysis, leukolysis |

TABLE 4-continued

Common exotoxins produced by microorganisms.

| Organism | Disease | Toxin or factor* | Action |
|---|---|---|---|
| | poisoning, toxic shock syndrome, scalded skin syndrome | Enterotoxin A, B, C, D, and E (SA) Coagulase (E) | Induce vomiting, diarrhea, shock Induces fibrin clotting |
| *Streptococcus pyogenes* | Pyrogenic infections, tonsillitis, scarlet fever | Streptolysin O (CT) Streptolysin S (CT) Erythrogenic toxin (SA) Streptokinase (E) Hyaluronidase (E) | Hemolysin Hemolysin Causes scarlet fever rash Dissolves fibrin clots Dissolves hyaluronic acid in connective tissue |
| *Vibrio cholerae* | Cholera | Enterotoxin (AB) | Induces fluid loss from intestinal cells |

*(AB), A-B toxin; (CT), cytolytic toxin; (E), enzymatic virulence factor; (SA), superantigen toxin; (?), not classified.

Economic studies indicate that the predominant factor accounting for the production cost for commodity chemicals and biofuels from fermentation processes is attributed to the feedstock cost. An important measure of the process economics is therefore the product yield. Complete substrate utilization is one of the prerequisites to render biofuel processes economically competitive. Therefore, not only must the biocatalyst convert all carbon sources within a feedstock to the biofuel, it must also perform this conversion to near completion. The ABE process reaches a 80% theoretical yield of butanol, corresponding to 0.33 g butanol/g glucose (Jones, D. T. and Woods, D. R. Acetone-Butanol Fermentation revisited. Microbiological Review 1986, 50:484-524). As an example for a commodity chemical produced by fermentation, the ethanol fermentation process of sugar and starch generally reaches 90-95% of the theoretical yield, equivalent to 0.45-0.48 g/g sugar in the raw material. Typical yields for other processes are shown in Table 5, below.

TABLE 5

Typical yields of fermentation processes.

| Document Name | Strain | Substrate | Product | $g\,g^{-1}$ | % of theoretical | Yield Biomass $g\,g^{-1}$ |
|---|---|---|---|---|---|---|
| Liu Journal of Applied Microbiology 100 (2006) p. 1043-1053 | *Torulopsis glabrata* | glucose | pyruvate | 0.49 | 50 | |
| Liu Journal of Applied Microbiology 100 (2006) p. 1043-1053 | *Torulopsis glabrata* (engineered) | glucose | pyruvate | 0.52 | 53 | |
| Elbing Applied and Environmental Microbiology 70 (2004) p. 5323-5330 | *Saccharomyces cerevisiae* CEN.PK2-1C | glucose | ethanol | 0.33 | 63 | |
| Papagiann Microbial Cell Factories 6 (2007) | *Lactococcus lactis* spp. *lactis* LM0230 | glucose | lactate | | 96 | |
| Fong Biotechnology and Bioengineering 91 (2005) p. 643-648 | *E. coli* MG1655 (pta, adhE), evolved | glucose | lactate | 0.7 | | |
| Zhu Applied Microbiology and Biotechnology 64 (2004) p. 367-375 | *E. coli* BW25113 (pfl) | glucose | lactate | 0.73 | | |
| PCT Patent WO03102200A2 | *Kluyveromyces marxianus* (PDC) | glucose | lactate | 0.89 | 89 | |

TABLE 5-continued

Typical yields of fermentation processes.

| Document Name | Strain | Substrate | Product | g g$^{-1}$ | Yield % of theoretical | Biomass g g$^{-1}$ |
|---|---|---|---|---|---|---|
| Das Neves Journal of Food Process Engineering 30 (2007) p. 338-356 | *Zymomonas mobilis* NBRC 13758 | glucose | ethanol | 0.48 | 94 | 0.03 |
| Das Neves Journal of Food Process Engineering 30 (2007) p. 338-356 | *Saccharomyces cerevisiae* | glucose | ethanol | 0.43 | 84 | 0.08 |
| Smits Yeast 16 (2000) p. 1325-1334 | *Saccharomyces cerevisiae* CEN.PK.K45 | glucose | ethanol | 0.35 | | 0.08 |
| Huang Applied Biochemistry and Biotechnology 98-100 (2002) p. 909-920 | *Candida krusei* | glucose | glycerol | 0.51 | | |
| Qureshi Food and Bioproducts Processing 84 (2006) p. 114-122 | *E. coli* (engineered) | xylose | ethanol | 0.47 | | |
| Causey Proceedings of the National Academy of Sciences 100 (2003) p. 825-832 | *E. coli* (engineered) | glucose | acetate | | 86 | |
| Grabar Biotechnology Letters 28 (2006) p. 1527-1535 | *E. coli* B (engineered) | glucose | lactate | 0.98 | 98 | |
| Causey Proceedings of the National Academy of Sciences 101 (2004) p. 2235-2240 | *E. coli* W3110 (engineered) | glucose | pyruvate | 0.75 | 77.9 | |
| Danner Chemical Society Reviews 28 (1999) p. 395-405 | *Acetobacter* | | acetate | 0.55 | 80 | |
| Kwon Journal of Bioscience and Bioengineering 101 (2006) p. 13-18 | *Candida tropicalis* KCTC 10457 | xylose | xylitol | 0.9 | | |
| Roca Applied and Environmental Microbiology 69 (2003) p. 4732-4736 | *Saccharomyces cerevisiae* TMB 3001 | glucose | ethanol | 0.42 | 80 | |
| Zhou Biotechnology Letters 28 (2006) p. 663-670 | *E. coli* B (engineered) | glucose | lactate | 0.98 | 98 | 1.67 |
| Geertman Metabolic Engineering 8 (2006) p. 532-542 | *Saccharomyces cerevisiae* (engineered) | glucose | glycerol | 0.46 | | 0.073 |

TABLE 5-continued

Typical yields of fermentation processes.

| Document Name | Strain | Substrate | Product | Yield $g\,g^{-1}$ | % of theoretical | Biomass $g\,g^{-1}$ |
|---|---|---|---|---|---|---|
| U.S. Pat. No. 7,141,410 | Candida sonorensis (engineered) | glucose | lactate | 0.9 | 0.9 | 5.1 |

For a biocatalyst to produce a biofuel most economically, a single product is desired. Extra products reduce primary product yield increasing capital and operating costs, particularly if those extra, undesired products have little or no value. Extra products also require additional capital and operating costs to separate these products from the product or biofuel of interest.

Low cost biofuels production technology for converting a variety of plant based feedstocks to biofuels is required for an economic business system. Low cost feedstock, low cost carbohydrate hydrolysis technology, efficient biofuel recovery and purification technology, and a low cost and efficient biocatalyst for conversion of carbohydrates to the targeted biofuel or biofuel intermediate are required. A critical characteristic of the low cost and efficient biocatalyst is that maximum biocatalyst efficiency can be obtained with a low cost nutrient source. Biocatalysts require a nitrogen source, a carbon source, trace minerals, and, in some cases, amino acids or vitamins. Often, complex nutrient sources, such as yeast extract, tryptone and peptone, are utilized to provide nitrogen, amino acids, trace minerals, and vitamins required for biocatalyst growth and biofuels production. However, these complex nutrient sources, while effective, are costly at typical concentrations utilized. Lower cost complex nutrient sources include corn steep liquor, soy bean meal, and other protein containing streams, which, done inadvertently through typical processing or done intentionally, are hydrolyzed to yield amino acids, vitamins, as well as minerals. Nutrient sources of this type are typically low cost, but can impact the recovery process negatively. Many times, a significant quantity of nutrients needs to be added (1 or more percent by weight of the fermentation broth) which adds to the cost both of the nutrient and the recovery process. Defined nutrient packages containing a nitrogen source, vitamins, and amino acids, as well as trace minerals, can be used for many biocatalysts. This type of media is a low cost nutrient source for biofuels production, as well as for the recovery and purification of biofuels. In one embodiment, a nutrient package provides maximum efficiency function of the biocatalyst, e.g., volumetric productivity, yield and final biofuel concentration, and has the lowest combined cost for the nutrient itself and the cost impact on downstream biofuel processing. In an embodiment, a biocatalyst utilizes a low cost nutrient package that provides biocatalyst and process efficiency so as to yield the lowest cost biofuel production.

Economical production of biofuels from biomass-derived organic compounds via fermentation processes depends upon biocatalysts that catalyze this conversion as described herein. A method of producing biofuels makes use of biocatalysts that exhibit certain properties which decrease the cost of the fermentation component of the biofuel production process. An important characteristic of the biocatalyst is the use of a low cost nutrient package that provides efficient biocatalyst function and reduces product recovery costs. The low cost nutrient package may include one, or more of carbohydrates, organic compounds, minerals, amino acids, oils, vitamins, salts, and spent biocatalyst from fermentations. It is important that the biocatalyst functions in a low cost and efficient manner within the overall biofuels production process on the low cost nutrient package. A business strategy is disclosed that employs the use of an economical method for the production of biofuels. Low cost biofuel production requires the biocatalyst to provide optimal productivity and yield on carbohydrate and biofuel concentration. Low cost nutrients and biocatalyst performance should support low cost recovery and purification of the biofuel. A biocatalyst with these performance characteristics for the production of a biofuel yields a process that is economically favorable for the production of a commodity biofuel or chemical.

Fermentation biocatalysts require nutrients to grow and support cellular metabolism. However, nutrients have a cost and any unconsumed nutrient added must ultimately be removed from the product. Product recovery and purification typically accounts for substantially more than 50% of the capital cost of a fermentation process. For low cost products, such as biofuels, typically greater than 80% of the capital cost results from product recovery and purification. Product recovery costs, composed mainly of energy costs, often approach 50% of the variable cash operating costs and increase as the number and amount of byproducts or unconsumed nutrients present increase. The cost of a fermentation process may be decreased by minimizing the number and amount of nutrients added and by using low cost nutrients.

Feedstocks vary in their nutrient content. Therefore, the low cost nutrient package for a biocatalyst will vary depending on the specific feedstock used. For example, high dextrose corn syrup contains very little nutrients other than the dextrose, requiring the addition of several nutrients before use in a fermentation. In another example, a dry milled corn stream from a jet cooker contains many nutrients and functions as a stand-alone nutrient package and feedstock for biofuel fermentation. However, addition of very specific nutrients, such as a nitrogen source, at low cost, can improve the fermentation performance resulting in a lower biofuel production cost.

Some industrially useful biocatalysts synthesize all of the materials required to build and maintain a cell from very simple sources of major and minor bioelements. Simple sources of major and minor bioelements are monomeric sugars and salts containing cations such as ammonia, calcium, sodium, potassium, and anions such as sulfate, phosphate and nitrate (van Dijken J P, Weusthuis R A, Pronk J T, Kinetics of growth and sugar consumption in yeasts, Antonie Van Leeuwenhoek, 1993; 63(3-4):343-52; and Chemical Marketing Reporter). Generally, these simple sources of major and minor bioelements are the least expensive. Other industrially useful biocatalysts can grow using simple sources of major and minor bioelements only if they are supplemented with a small amount of one or two more expensive nutrients, such as vitamins or amino acids. The use of more expensive nutrients is not necessarily prohibitive, if used sparingly. For example, vitamins are costly on a unit mass basis but typically single digit part per million concentrations may be all that is required to supplement the nutrients of a biocatalyst to allow growth of the biocatalyst or increase performance of the biocatalyst in a biofuel production process. In general, for an economic process, materials that are relatively expensive per unit mass must be used sparingly, and lower cost nutrients may be used in larger quantities.

The addition of a more expensive nutrient can be economical if it results in an improved performance of the fermentation, resulting in higher productivities and product concentrations (Thomas K C, Ingledew W M, Fuel alcohol production: effects of free amino nitrogen on fermentation of very-high-gravity wheat mashes, Appl Environ Microbiol. 1990 July; 56(7):2046-50; Casey G P, Magnus C A, Ingledew W M, High-Gravity Brewing: Effects of Nutrition on Yeast Composition, Fermentative; Ability, and Alcohol Production, Appl Environ Microbiol. 1984 September; 48(3):639-646; Wood B E, Yomano L P, York S W, Ingram L O, Development of industrial-medium-required elimination of the 2,3-butanediol fermentation pathway to maintain ethanol yield in an ethanologenic strain of *Klebsiella oxytoca*, Biotechnol Prog. 2005 September-October; 21(5):1366-72; and Wang F Q, Gao C J, Yang C Y, Xu P, Optimization of an ethanol production medium in very high gravity fermentation, Biotechnol Lett. 2007 February; 29(2):233-6. Epub 2006 Nov. 8.) Higher productivities result in lower capital costs and lower operating costs. Higher product concentrations reduce the operating costs, particularly energy costs, and typically provide a higher product to impurity ratio with respect to the final product to the fermentation broth processed. However, in an embodiment, the biocatalyst performs at its highest productivity using only low cost major and minor bioelements as the low cost nutrient package in addition to the feedstock.

Fermentation vessels and downstream processing equipment of a biofuel manufacturing facility can be built from different materials, depending on the composition of the fermentation broth. Stainless steel is frequently used because it is more resistant to corrosion caused by chloride ions in the aqueous solutions. However, even stainless steel can be damaged by chloride ions that get incorporated into the steel and lead to stress corrosion cracking of the stainless steel. Carbon steel is a lower cost alternative to stainless steel. It is less resistant to corrosion caused by chloride ions and can therefore only be used as building material if the chloride content of the fermentation broth is minimized. Also, the lifetime of the equipment that is in contact with the fermentation broth is shorter when high concentrations of chloride ions are present. This is associated with higher operating costs due to higher maintenance costs and faster capital depreciation.

Chlorine is one of the major bioelements required for growth of microorganisms. The amounts of chloride necessary to support growth and metabolic activity of biocatalysts are strain specific. A biocatalyst that functions at low concentrations of chloride ions allows the use of lower cost material, such as carbon steel for the fermentation equipment. Such a biocatalyst reduces capital and operating costs of a biofuel production facility.

For an economical process, it is essential that the biocatalyst used performs as well in a medium composed of only inexpensive nutrients in addition to the feedstock as it does in more expensive medium. For the production of biofuels, a performance parameter is the yield of biofuels produced from feedstock. Typically, a yield of greater than 0.35 g/g of biofuel on six-carbon sugars is required for an economically viable process.

Biocatalysts for the fermentative production of biofuels require some nutrients in order to grow cells and produce the biofuel(s) of interest. Biocatalysts uptake some of the carbohydrate feedstock in order to grow and convert most of the feedstock into a targeted biofuel. In addition to the carbohydrate feedstock, microorganisms require mineral salts, amino acids, lipids and vitamins to grow and produce biofuels. In many cases, complex nutrient sources, such as yeast extract, peptone, corn steep liquor, soy protein meal, and other sources that include some or all of the microorganism requirements, are utilized to meet the microorganism needs. Sometimes, the complex nutrients are 'processed' with enzymes, acids, etc., in order to hydrolyze insoluble components into solution.

The objective of adding nutrients is to provide for biocatalyst growth and conversion of carbohydrates to biofuels. The cost of nutrients directly, and the cost of removing the unused nutrients downstream, is balanced by the productivity and final concentration that the biocatalyst can achieve with the nutrients added. The source of carbohydrate feedstock also impacts the type and quantity of fermentation nutrients required. A pure carbohydrate source with no impurities will require addition of a complete nutrient medium. For a low cost business system or method to produce a biofuel, some impurities in the carbohydrate feed may be acceptable. Carbohydrates produced by extraction of sugar from sugar cane, hydrolysis of cellulosic biomass, dry milling of corn and wet milling of corn all contain some impurities.

Microorganisms can be classified by their oxygen requirements. Aerobic microorganisms, or aerobes, require oxygen for metabolism and survival. The amount of oxygen required by different aerobes may vary. Anaerobic microorganisms, or anaerobes, do not require oxygen for metabolism or survival. Some anaerobes tolerate the presence of oxygen, while others do not. Still other microorganisms can grow and metabolize either with or without oxygen present in their environment. These microorganisms are referred to as facultative anaerobes (Gottschalk, G, "Bacterial Metabolism" 2nd Ed. Springer-Verlag New York, 1986).

The presence of oxygen may lead to the generation of highly-reactive oxygen species. For example, hydrogen peroxide, superoxide anion, and hydroxyl radicals, may damage the cell in a number of ways. The presence of reactive oxygen species can lead to protein, DNA, and membrane damage. Most organisms contain genes coding for defense mechanisms against toxic oxygen species like superoxide dismutase, and catalase. These enzymes degrade the reactive oxygen species (Storz, G, Hengge-Aronis, R, Bacterial Stress Response, 2000, ASM Press Washington D.C.). Many anaerobic microorganisms do not have these defense mechanisms and therefore are vulnerable to the presence of even small amounts of oxygen in their environment, which can lead to the generation of toxic oxygen species. Some anaerobes contain superoxide dismutase and can therefore tolerate exposure to oxygen for brief periods of time (McCord, J M, et al., 1971 PNAS, 68:1024-1027). During exposure to oxygen these strains survive in a state of suspended animation, meaning that they stop growth and metabolism. After oxygen is removed from the environment surrounding the microorganism, cells start growing and metabolizing again.

In an anaerobic fermentation process under anaerobic conditions, oxygen is excluded from the process. Usually, the fermentation broth is stripped of oxygen through application of heat or oxygen-free gasses, like nitrogen or carbon dioxide, at the beginning of the fermentation. During the fermentation, oxygen is prevented from entering the fermentation broth by a cushion of oxygen-free gas above the surface of the broth and maintenance of pressure inside the fermenter. If oxygen gets into a fermentation that uses a strictly anaerobic biocatalyst, growth and metabolism may cease and the cells may no longer function as a biocatalyst. Even if oxygen is removed from the fermentation after some time, the cells may be damaged and no longer function as a biocatalyst.

If oxygen gets into a fermentation that uses an anaerobic biocatalyst that can tolerate oxygen for brief periods of time, growth and metabolism cease and productivity of the process is reduced as long as oxygen is present. Once oxygen is then removed from the fermentation after some time, the cells are viable and the biocatalyst does regain its productivity.

If oxygen gets into a fermentation that uses a facultative anaerobic biocatalyst that can grow and metabolize in the presence as well as in the absence of oxygen, the biocatalyst metabolizes oxygen. Because aerobic metabolism is more energy efficient than anaerobic metabolism in these organisms, the organisms shift their metabolism to aerobic metabolism as long as oxygen is present, which may lead to undesired results in the fermentation. For example, oxygen used for respiration leads to undesired loss of carbon to carbon dioxide and reduced yield of the desired biofuel product. If the influx of oxygen into the fermenter is stopped, the oxygen present in the fermenter is consumed by the biocatalyst. Once oxygen is removed from the fermentation after some time, the cells are viable and the biocatalyst regains its productivity.

In some cases, it is economically advantageous to use a biocatalyst that can tolerate small amounts of oxygen without reducing process performance, such as productivity or yield, throughout a fermentation process. A fermentation that does not completely exclude oxygen is operated more economically. The operating costs are reduced because less oxygen-free gas is required for the fermentation and measures to remove oxygen from the fermentation broth, such as application of heat or steam, are reduced or not required. It is known in the art that the cryogenic production of oxygen-free inert gasses, such as nitrogen, helium, or carbon dioxide, is possible. However, at large scale, the use of oxygen-free inert gasses to maintain oxygen-free conditions would add cost to a fermentation process. An alternative strategy to produce low oxygen inert gasses is also known in the art. Pressure swing adsorption (PSA) is a method for the generation of inert gasses that contain about 0.5% oxygen or less. The use of PSA generates oxygen-limited inert gasses at about one-third the cost of cryogenically-produced gasses. However, PSA generates gasses that would be unsuitable for a completely oxygen-free process because of the trace amounts of oxygen present. A biocatalyst for the production of biofuels that can tolerate 0.5% oxygen would be unaffected and therefore quite valuable in the art. Further, fermentations that are operated on large scales require large fermentation vessels that may not be oxygen impermeable. This is because building large fermentation vessels that completely exclude oxygen require higher capital investment.

Productivity has an impact on capital costs for a biofuel plant and depends on the amount of biocatalyst used during the fermentation and the specific activity of the biocatalyst. Volumetric productivity of the biocatalyst shortens the process time and, therefore, for a given plant size, increases the output of the plant over the plant lifetime. This increases the return on the capital investment and decreases the cost of the biofuel.

Any one of the biocatalyst properties discussed herein may have a positive effect on the process economics of a biofuel production process. However, the biocatalyst should have a combination of several or all of these properties to permit an economic biofuel production process. For example a biocatalyst that produces a biofuel from biomass derived carbon sources with the addition of few or no nutrients in addition to the feedstock, at high productivity, titer and yield may produce biofuel more economically than a biocatalyst that only has one of these four properties. The combination of the different process biocatalyst properties discussed supra into one biocatalyst may result in a biocatalyst that allows a biofuel production process to be more economical than would be expected from the sum of the effects of the individual properties. For example if the biocatalyst does not contain DNA markers, nor produces toxins, then the economic effect of these properties is larger than the economic effect of either of these properties alone. The combination of these properties allows the DDGS of the biofuel production process to be used as animal feed, which is not possible if the biocatalyst has DNA markers or if the biocatalyst produces toxins. Use of DDGS as animal feed is the most economical use of spent biocatalyst available for a biofuel production process.

The biocatalyst properties discussed herein may not provide equal economic value to the biofuel production process. For example yield, titer and productivity may have a larger impact on process economics than oxygen tolerance or pH tolerance. The most preferred biocatalyst properties are yield, titer and productivity followed by operating temperature and pH ranges, lack of byproducts, high growth rate, and operation with only feedstock and mineral salts added. The other properties described herein also have economic value for the biofuel production process.

Accordingly, the engineered isobutanol pathway to convert pyruvate to isobutanol can be, but is not limited to, the following reactions:

1. 2 pyruvate→acetolactate+$CO_2$
2. acetolactate+NADPH→2,3-dihydroxyisovalerate+NADP+
3. 2,3-dihydroxyisovalerate→alpha-ketoisovalerate
4. alpha-ketoisovalerate→isobutyraldehyde+$CO_2$
5. isobutyraldehyde+NADPH→isobutanol+NADP+

These reactions are carried out by the enzymes 1) Acetolactate Synthase (ALS), 2) Ketol-acid Reducto-Isomerase (KAR1), 3) Dihydroxy-acid dehydratase (DHAD), 4) Ketoisovalerate decarboxylase (KIVD), and 5) an Isobutyraldehyde Dehydrogenase (IDH).

Plasmids disclosed herein were generally based upon parental plasmids described previously (Lutz, R. & Bujard, H. (1997) *Nucleic Acids* Research 25(6):1203-1210). pGV1698 and pGV1655 produce optimized levels of isobutanol pathway enzymes in a production host when compared to other expression systems in the art. Compared to the expression of the isobutanol pathway from pSA55 and pSA69 as described in (WO 2008/098227) BIOFUEL PRODUCTION BY RECOMBINANT MICROORGANISMS, pGV1698 and pGV1655 lead to higher expression of ilvC and alsS and lower expression levels for kivd and ilvD. These changes are the result of differences in plasmid copy numbers. Also the genes coding for ilvD and ilvC were codon optimized for *E. coli*. This leads to optimized expression of the genes and it also avoids recombination of these genes with their native copies on the *E. coli* chromosome, thus stabilizing the production strain. The combination of two plasmids with the pSC101 and the ColE1 origin of replication in one cell as realized in a production strain carrying pGV1698 and pGV1655 is known to be more stable than the combination of two plasmids with p15A and ColE1 origins respectively as was used in the prior art ((WO 2008/098227) BIOFUEL PRODUCTION BY RECOMBINANT MICROORGANISMS).

SA237 is a derivative of JCL260, both of which was described in the art ((WO 2008/098227) BIOFUEL PRODUCTION BY RECOMBINANT MICROORGANISMS). SA237 was shown to produce isobutanol.

It is understood that a range of microorganisms can be modified to include a recombinant metabolic pathway suitable for the production of isobutanol. It is also understood that various microorganisms can act as "sources" for genetic material encoding target enzymes suitable for use in a recombinant microorganism provided herein.

The exogenous nucleic acid molecule contained within a host cell of the disclosure can be maintained within that cell in any form. For example, exogenous nucleic acid molecules can be integrated into the genome of the cell or maintained in an episomal state that can stably be passed on ("inherited") to daughter cells. Such extra-chromosomal genetic elements (such as plasmids, etc.) can additionally contain selection markers that ensure the presence of such genetic elements in daughter cells. Moreover, the host cells can be stably or transiently transformed. In addition, the host cells described herein can contain a single copy, or multiple copies of a particular exogenous nucleic acid molecule as described above.

Host microorganisms within the scope of the invention may have reduced enzymatic activity such as reduced alcohol dehydrogenase activity. The term "reduced" as used herein with respect to a particular enzymatic activity refers to a lower level of enzymatic activity than that measured in a comparable host cell of the same species. Thus, host cells lacking alcohol dehydrogenase activity are considered to have reduced alcohol dehydrogenase activity since most, if not all, comparable host cells of the same species have at least some alcohol dehydrogenase activity. Such reduced enzymatic activities can be the result of lower enzyme expression level, lower specific activity of an enzyme, or a combination thereof. Many different methods can be used to make host cells having reduced enzymatic activity. For example, a host cell can be engineered to have a disrupted enzyme-encoding locus using common mutagenesis or knock-out technology.

Genes that are deleted or knocked-out to produce the microorganisms herein disclosed are exemplified for E. coli. One skilled in the art can easily identify corresponding, homologous genes or genes encoding for enzymes which compete with the isobutanol producing pathway for carbon and/or NAD(P)HNADH in other microorganisms by conventional molecular biology techniques (such as sequence homology search, cloning based on homologous sequences, and other techniques, etc.). Once identified, the target gene(s) can be deleted or knocked-out in these host organisms according to well-established molecular biology methods.

In an embodiment, the deletion of a gene of interest occurs according to the principle of homologous recombination. According to this embodiment, an integration cassette containing a module comprising at least one marker gene is flanked on either side by DNA fragments homologous to those of the ends of the targeted integration site. After transforming the host microorganism with the cassette by appropriate methods, homologous recombination between the flanking sequences may result in the marker replacing the chromosomal region in between the two sites of the genome corresponding to flanking sequences of the integration cassette. The homologous recombination event may be facilitated by a recombinase enzyme that may be native to the host microorganism or may be heterologous and transiently overexpressed.

In addition, certain point-mutation(s) can be introduced which results in an enzyme with reduced activity.

It is understood that integration of all the genes of a metabolic pathway that lead to a product into the genome of the production strain eliminates the need of a plasmid expression system, as the enzymes are produced from the E. coli chromosome. The integration of pathway genes avoids loss of productivity over time due to plasmid loss. This is important for long fermentation times and for fermentations in large scale where the seed train is long and the production strain has to go through many doublings from the first inoculation to the end of the large scale fermentation. The present methods and biocatalysts encompass integration of genetic elements into a host genome in order to produce a biofuel.

Integrated genes are maintained in the strain without selection. This allows the construction of production strains that are free of marker genes which are commonly used for maintenance of plasmids. Marker genes and especially antibiotic markers are problematic for regulatory approval of a production organism. Also, the use of the spent biocatalyst as DDGs may be more limited for biocatalysts that contain markers. Production strains with integrated pathway genes can contain minimal amounts of foreign DNA since there are no origins of replication and other non coding DNA necessary that have to be in plasmid based systems. The biocatalyst with integrated pathway genes improves the yield of a production process because it avoids energy and carbon requiring processes. These processes are the replication of many copies of plasmids and the production of non-pathway active proteins like marker proteins in the production strain.

The expression of pathway genes on multi copy plasmids can lead to over expression phenotypes for certain genes. These phenotypes can be growth retardation, inclusion bodies, and cell death. Therefore the expression levels of genes on multi copy plasmids has to be controlled effectively by using inducible expression systems, optimizing the time of induction of said expression system, and optimizing the amount of inducer provided. The use of an inducible promoter system leads to additional costs for the inducer which can be prohibitive for large scale production. The time of induction has to be correlated to the growth phase of the biocatalyst, which can be followed by measuring of optical density in the fermentation broth. Feedstocks that are commonly used in fermentation like corn liquefact interfere with the determination of cell density making the determination of the right time of induction difficult. This leads to additional costs on a more complex fermentation method and it causes inconsistencies between fermentation runs.

A biocatalyst that has all pathway genes integrated on its chromosome is far more likely to allow constitutive expression since the lower number of gene copies avoids over expression phenotypes. Thus integration of pathway genes makes the process more economical.

Alternatively, antisense technology can be used to reduce enzymatic activity. For example, host cells can be engineered to contain a cDNA that encodes an antisense molecule that prevents an enzyme from being made. The term "antisense molecule" as used herein encompasses any nucleic acid molecule that contains sequences that correspond to the coding strand of an endogenous polypeptide. An antisense molecule also can have flanking sequences (e.g., regulatory sequences). Thus antisense molecules can be ribozymes or antisense oligonucleotides. A ribozyme can have any general structure including, without limitation, hairpin, hammerhead, or axhead structures, provided the molecule cleaves RNA.

In certain embodiments, deletion of the genes encoding for these enzymes improves the isobutanol yield because more carbon and/or NADH is made available to one or more polypeptide(s) for producing isobutanol.

In certain embodiments, the DNA sequences deleted from the genome of the recombinant microorganism encode an enzyme selected from the group consisting of: D-lactate dehydrogenase, pyruvate formate lyase, acetaldehyde/alcohol dehydrogenase, phosphate acetyl transferase, fumarate reductase, malate dehydrogenase, transhydrogenase, and pyruvate dehydrogenase.

In particular when the microorganism is E. coli, the DNA sequences deleted from the genome can be selected from the group consisting of IdhA, pflB, pflDC, adhE, pta, ackA, frd, mdh, sthA, aceE and aceF.

The enzymes D-lactate dehydrogenase, pyruvate formate lyase, acetaldehyde/alcohol dehydrogenase, phosphate acetyl transferase, acetate kinase A, fumarate reductase, malate dehydrogenase and pyruvate dehydrogenase, may be required for certain competing endogenous pathways that produce succinate, lactate, acetate, ethanol, formate, carbon dioxide and/or hydrogen gas.

In particular, the enzyme D-lactate dehydrogenase (encoded in E. coli by IdhA), couples the oxidation of NADH to the reduction of pyruvate to D-lactate. Deletion of IdhA has previously been shown to eliminate the formation of D-lactate in a fermentation broth (Causey, T. B. et al, 2003, Proc. Natl. Acad. Sci., 100, 825-32).

The enzyme Pyruvate formate lyase (encoded in E. coli by pflB), oxidizes pyruvate to acetyl-CoA and formate. Deletion of pflB has proven important for the overproduction of acetate (Causey, T. B. et al, 2003, Proc. Natl. Acad. Sci., 100, 825-32), pyruvate (Causey, T. B. et al, 2004, Proc. Natl. Acad. Sci., 101, 2235-40) and lactate (Zhou, S., 2005, Biotechnol. Lett., 27, 1891-96). Formate can further be oxidized to $CO_2$ and hydrogen by a formate hydrogen lyase complex, but deletion of this complex should not be necessary in the absence of pflB. pflDC is a homolog of pflB and can be activated by mutation. As indicated above, the pyruvate formate lyase may not need to be deleted for anaerobic fermentation of isobutanol. A (heterologous) NADH-dependent formate dehydrogenase may be provided, if not already available in the host, to effect the conversion of pyruvate to acetyl-CoA coupled with NADH production.

The enzyme acetaldehyde/alcohol dehydrogenase (encoded in E. coli by adhE) is involved the conversion of acetyl-CoA to acetaldehyde dehydrogenase and alcohol dehydrogenase. In particular, under aerobic conditions, pyruvate is also converted to acetyl-CoA, acetaldehyde dehydrogenase and alcohol dehydrogenase, but this reaction is catalyzed by a multi-enzyme pyruvate dehydrogenase complex, yielding $CO_2$ and one equivalent of NADH. Acetyl-CoA fuels the TCA cycle but can also be oxidized to acetaldehyde and ethanol by acetaldehyde dehydrogenase and alcohol dehydrogenase, both encoded by the gene adhE. These reactions are each coupled to the reduction of one equivalents NADH.

The enzymes phosphate acetyl transferase (encoded in E. coli by pta) and acetate kinase A (encoded in E. coli by ackA), are involved in the pathway which converts acetyl-CoA to acetate via acetyl phosphate. Deletion of ackA has previously been used to direct the metabolic flux away from acetate production (Underwood, S. A. et al, 2002, Appl. Environ. Microbiol., 68, 6263-72; Zhou, S. D. et al, 2003, Appl. Environ. Microbiol., 69, 399-407), but deletion of pta should achieve the same result.

The enzyme fumarate reductase (encoded in E. coli by frd) is involved in the pathway which converts pyruvate to succinate. In particular, under anaerobic conditions, phosphoenolpyruvate can be reduced to succinate via oxaloacetate, malate and fumarate, resulting in the oxidation of two equivalents of NADH to NAD+. Each of the enzymes involved in those conversions could be inactivated to eliminate this pathway. For example, the final reaction catalyzed by fumarate reductase converts fumarate to succinate. The electron donor for this reaction is reduced menaquinone and each electron transferred results in the translocation of two protons. Deletion of frd has proven useful for the generation of reduced pyruvate products.

The expression of gene fnr is associated with a series of activities in E. coli. The pathways associated to the activity expressed by fnr are usually related to oxygen utilization that is down regulated as oxygen is depleted and in a reciprocal fashion, alternative anaerobic pathways for fermentation are upregulated by Fnr. An indication of those pathways can be found in Chrystala Constantinidou et al., "A Reassessment of the FNR Regulon and Transcriptomic Analysis of the Effects of Nitrate, Nitrite, NarXL, and NarQP as Escherichia coli K12 Adapts from Aerobic to Anaerobic Growth," J. Biol. Chem., 2006, 281:4802-4815 Kirsty Salmon et al., "Global Gene Expression Profiling in Escherichia coli K12—The Effects Of Oxygen Availability And FNR" J. Biol. Chem. 2003, 278(32):29837-55" and Kirsty A. Salmon et al. "Global Gene Expression Profiling in Escherichia coli K12—the Effects of Oxygen Availability and ArcA" J. Biol. Chem., 2005, 280(15):15084-15096, all incorporated by reference in their entirety in the present application.

The deletion of the soluble transhydrogenase coded by sthA from the E. coli genome avoids the conversion of NADPH to NADH which is the natively catalyzed reaction of this enzyme. In strains that are engineered to increase the supply of NADPH to the isobutanol pathway the deletion of sthA can avoid the creation of a futile cycle which would interconvert the redox cofactor while consuming ATP.

aceF codes for a subunit of the pyruvate dehydrogenase complex (pdh) which catalyzes the conversion of pyruvate to acetyl-CoA. The deletion of aceF eliminates a pathway that competes with the isobutanol pathway for the metabolite pyruvate. A production strain lacking pdh activity should have a higher isobutanol yield than the isogenic strain with active pdh.

mdh codes for the malate dehydrogenase (Mdh). This enzyme catalyzes one step of the TCA cycle. The TCA cycle converts acetyl-CoA to $CO_2$ and a disruption of the TCA or a reduction of the flux through the TCA will increase the yield of isobutanol by avoiding $CO_2$ production.

The F' episomal plasmid present in some biocatalyst strains, such as GEVO1886, contains several genes, including a copy of the lacI repressor as well as the Tn10 operon, which contains a DNA marker for resistance to the antibiotic tetracycline and simultaneously confers sensitivity to fusaric acid. Removal of the F' plasmid from certain biocatalyst strains, especially those strains that do not contain other DNA markers, leads to the creation of a strain with no DNA markers. For example, GEVO1886 contains no other DNA markers, neither on the chromosome nor on a plasmid and therefore, removal of the F' plasmid from this strain creates a strain with no DNA markers. Removal of the F' plasmid does not affect the production of isobutanol or other biofuels from certain strains, especially those biocatalyst strains that contain a metabolic pathway for the production of a biofuel, such as isobutanol. The sensitivity to fusaric acid will be exploited as a counter-selectable method to obtain a variant of GEVO1886 that is fusaric acid-resistant ($Fus^R$) and tetracycline-sensitive ($Tc^S$) and thus has lost the F' plasmid and has the tetracycline DNA marker removed. Loss of the plasmid is confirmed by PCR using F' plasmid-specific primer pairs.

Figure 2:
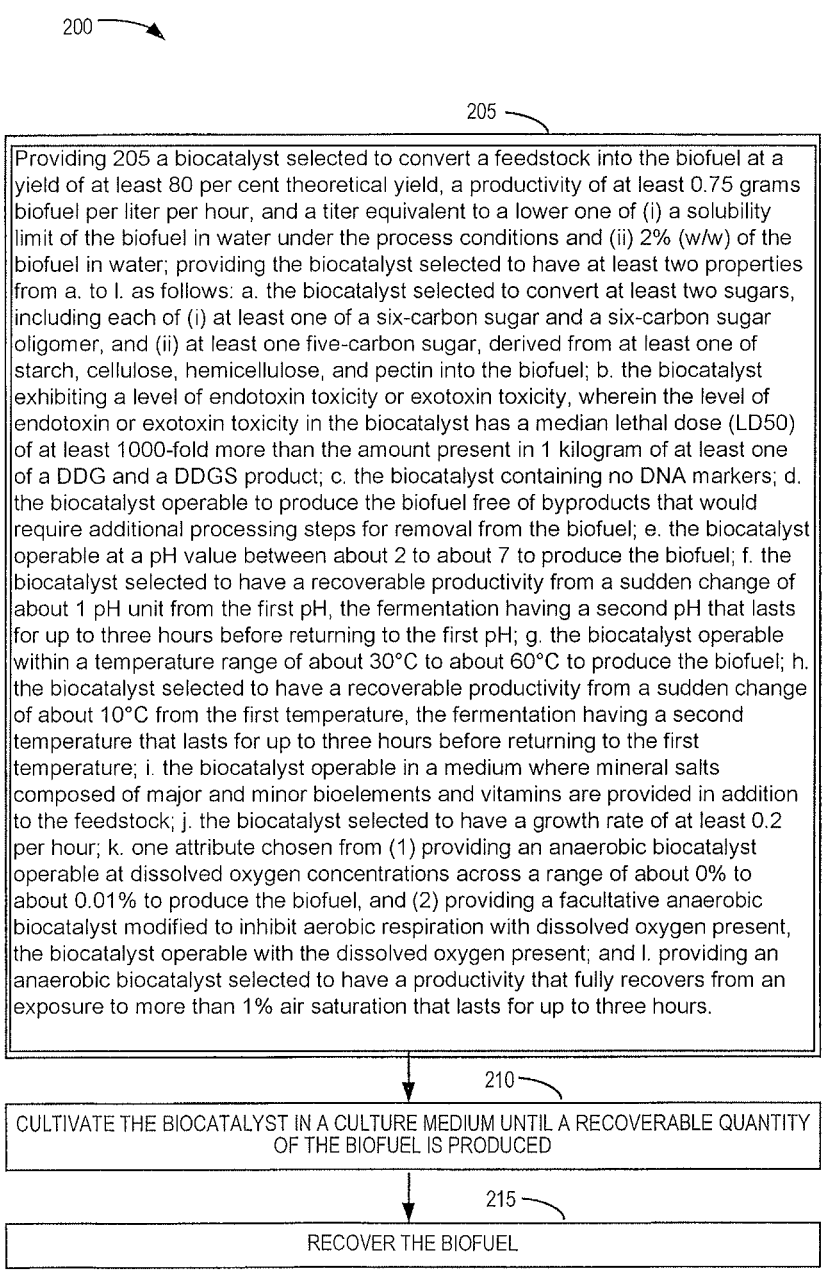
FIG. 2 illustrates an exemplary embodiment of making a biofuel.

Referring to FIG. 2, and in an exemplary embodiment, there is shown a method 200 of method of making a biofuel. Method 200 may include providing 205 a biocatalyst selected to convert a feedstock into the biofuel at a yield of at least 80 percent theoretical yield, a productivity of at least 0.75 grams biofuel per liter per hour, and a titer equivalent to a lower one of (i) a solubility limit of the biofuel in water under the process conditions and (ii) 2% (w/w) of the biofuel in water; providing the biocatalyst selected to have at least two properties from a. to l. as follows: a. the biocatalyst selected to convert at least two sugars, including each of (i) at least one of a six-carbon sugar and a six-carbon sugar oligomer, and (ii) at least one five-carbon sugar, derived from at least one of starch, cellulose, hemicellulose, and pectin into the biofuel; b. the biocatalyst exhibiting a level of endotoxin toxicity or exotoxin toxicity, wherein the level of endotoxin or exotoxin toxicity in the biocatalyst has a median lethal dose (LD50) of at least 1000-fold more than the amount present in 1 kilogram of at least one of a DDG and a DDGS product; c. the biocatalyst containing no DNA markers; d. the biocatalyst operable to produce the biofuel free of byproducts that would require additional processing steps for removal from the biofuel; e. the biocatalyst operable at a pH value between about 2 to about 7 to produce the biofuel; f. the biocatalyst selected to have a recoverable productivity from a sudden change of about 1 pH unit from the first pH, the fermentation having a second pH that lasts for up to three hours before returning to the first pH; g. the biocatalyst operable within a temperature range of about 30° C. to about 60° C. to produce the biofuel; h. the biocatalyst selected to have a recoverable productivity from a sudden change of about 10° C. from the first temperature, the fermentation having a second temperature that lasts for up to three hours before returning to the first temperature; i. the biocatalyst operable in a medium where mineral salts composed of major and minor bioelements and vitamins are provided in addition to the feedstock; j. the biocatalyst selected to have a growth rate of at least 0.2 per hour; k. one attribute chosen from (1) providing an anaerobic biocatalyst operable at dissolved oxygen concentrations across a range of about 0% to about 0.01% to produce the biofuel, and (2) providing a facultative anaerobic biocatalyst modified to inhibit aerobic respiration with dissolved oxygen present, the biocatalyst operable with the dissolved oxygen present; and l. providing an anaerobic biocatalyst selected to have a productivity that fully recovers from an exposure to more than 1% air saturation that lasts for up to three hours. Method 200 may further include cultivating 210 the biocatalyst in a culture medium until a recoverable quantity of the biofuel is produced. Method 200 may include recovering 215 the biofuel.

Figure 3:
FIG. 3 illustrates an exemplary embodiment of making a biofuel.

Referring to FIG. 3, and in an exemplary embodiment, there is shown a method 300 of making a biofuel. Method 300 may include providing 305 a biocatalyst selected to convert a feedstock into the biofuel at a yield of at least 80 percent theoretical yield, a productivity of at least 0.75 grams biofuel per gram cell dry weight, and a titer equivalent to a lower one of (i) a solubility limit of the biofuel in water under the process conditions and (ii) 2% (w/w) of the biofuel in water; providing the biocatalyst selected to convert at least two sugars, including each of (i) at least one of a six-carbon sugar and a six-carbon sugar oligomer, and (ii) at least one five-carbon sugar, derived from at least one of starch, cellulose, hemicellulose, and pectin into the biofuel; providing the biocatalyst exhibiting a level of endotoxin toxicity or exotoxin toxicity, wherein the level of endotoxin or exotoxin toxicity in the biocatalyst has a median lethal dose (LD50) of at least 1000-fold more than the amount present in 1 kilogram of at least one of a DDG and a DDGS product; providing the biocatalyst that contains no DNA markers; and providing the biocatalyst operable to produce the biofuel free of byproducts that would require additional processing steps for removal from the biofuel; providing the biocatalyst operable at a pH value between about 2 to about 7 to produce the biofuel; providing the biocatalyst selected to have a recoverable productivity from a sudden change of about 1 pH unit from the first pH, the fermentation having a second pH that lasts for up to three hours before returning to the first pH; providing the biocatalyst operable within a temperature range of about 30° C. to about 60° C. to produce the biofuel; providing the biocatalyst selected to have a recoverable productivity from a sudden change of about 10° C. from the first temperature, the fermentation having a second temperature that lasts for up to three hours before returning to the first temperature; providing the biocatalyst operable in a medium where mineral salts composed of major and minor bioelements and vitamins are provided in addition to the feedstock; providing the biocatalyst selected to have a growth rate of at least 0.2 per hour; providing the biocatalyst selected to have one attribute chosen from: a. providing an anaerobic biocatalyst operable at dissolved oxygen concentrations across a range of about 0% to about 0.01% to produce the biofuel, and wherein the anaerobic biocatalyst has a productivity that fully recovers from an exposure to more than 1% air saturation that lasts for up to three hours; and b. providing a facultative anaerobic biocatalyst modified to inhibit aerobic respiration with dissolved oxygen present, the biocatalyst operable with the dissolved oxygen present. Method 300 may further include cultivating 310 the biocatalyst in a culture medium until a recoverable quantity of the biofuel is produced. Method 300 may include recovering 315 the biofuel.

Figure 4:
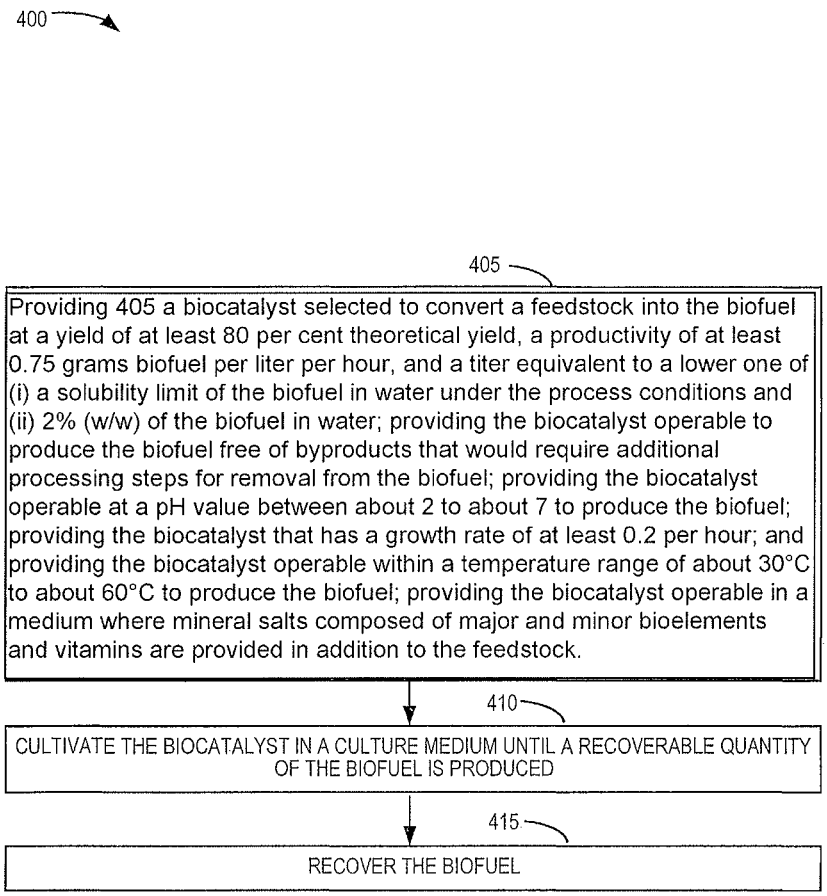
FIG. 4 illustrates an exemplary embodiment of making a biofuel.

Referring to FIG. 4, and in an exemplary embodiment, there is shown a method 400 of making a biofuel. Method 400 may include providing 405 a biocatalyst selected to convert a feedstock into the biofuel at a yield of at least 80 percent theoretical yield, a productivity of at least 0.75 grams biofuel per liter per hour, and a titer equivalent to a lower one of (i) a solubility limit of the biofuel in water under the process conditions and (ii) 2% (w/w) of the biofuel in water; providing the biocatalyst operable to produce the biofuel free of byproducts that would require additional processing steps for removal from the biofuel; providing the biocatalyst operable at a pH value between about 2 to about 7 to produce the biofuel; providing the biocatalyst that has a growth rate of at least 0.2 per hour; and providing the biocatalyst operable within a temperature range of about 30° C. to about 60° C. to produce the biofuel; providing the biocatalyst operable in a medium where mineral salts composed of major and minor bioelements and vitamins are provided in addition to the feedstock. Method 400 may further include cultivating 410 the biocatalyst in a culture medium until a recoverable quantity of the biofuel is produced. Method 400 may include recovering 415 the biofuel.

Figure 5:
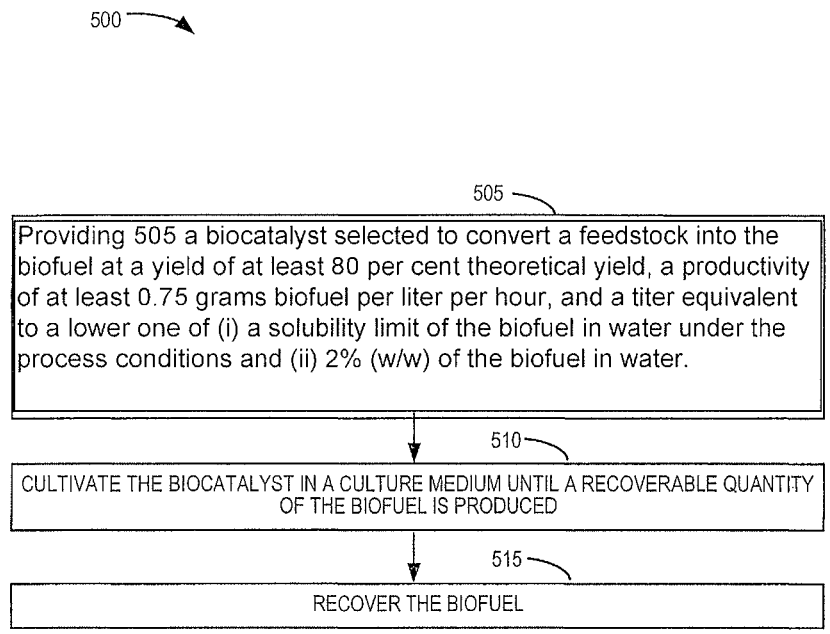
FIG. 5 illustrates an exemplary embodiment of making a biofuel.

Referring to FIG. 5, and in an exemplary embodiment, there is shown a method 500 of making a biofuel. Method 500 may include providing 505 a biocatalyst selected to convert a feedstock into the biofuel at a yield of at least 80 percent theoretical yield, a productivity of at least 0.75 grams biofuel per liter per hour, and a titer equivalent to a lower one of (i) a solubility limit of the biofuel in water under the process conditions and (ii) 2% (w/w) of the biofuel in water. Method 500 may further include cultivating 510 the biocatalyst in a culture medium until a recoverable quantity of the biofuel is produced. Method 500 may include recovering 515 the biofuel.

EXAMPLES

Example 1

A cellulosic material consisting of 45% cellulose, 25% hemicellulose, 22% lignin and 8% other materials is pretreated to yield slurry of 8% insoluble cellulose with about 4% insoluble lignin, 1% glucose, 40 g/L xylose, 2 g/L mannose, 2 g/L galactose, 1 g/L arabinose, 5 g/L acetic acid in solution. Three equal portions of the pretreated cellulosic material are put into agitated saccharification and fermentation vessels. All three are charged with cellulase enzyme sufficient to hydrolyze 80% of the cellulose in 72 hours. Three different biocatalysts are added to the vessels. One biocatalyst, added to vessel number A1, converts only glucose to butanol. A second biocatalyst, added to fermenter number A2, converts glucose and xylose to butanol. A third biocatalyst, added to fermenter number A3, converts glucose, xylose, mannose, galactose and arabinose to butanol.

The vessels are agitated for 72 hours. At the end of 72 hours the fermentation broth is analyzed for butanol content. Fermenter number A1 has 29.5 g/L butanol. Fermenter number A2 contains 44.3 g/L butanol. Fermenter number A3 contains 46.1 g/L butanol.

Economic analysis of the three fermenters shows that revenue from butanol recovered from fermenter A2 is 50.2% higher than the revenue from butanol recovered from fermenter A1. The revenue from butanol from fermenter A3 is 56.3% higher than the revenue from butanol recovered from fermenter number A1. The revenue from butanol from fermenter number A3 is 4.1% higher than the revenue from butanol from fermenter number A2. The biocatalyst with the broadest sugar consumption ability, biocatalyst A3, provides an economic advantage because more product is produced from the same quantity of feedstock and same feedstock processing capital. Therefore, this example demonstrates that a biocatalyst that consumes more than one sugar in the feedstock is preferred because overall costs related to the feedstock are reduced.

Example 2

Dry corn is milled into a fine powder. The dry milled corn is slurried and jet cooked at temperature of about 105° C. and then alpha-amylase enzyme is added to produce corn liquefact. The stream is cooled and gluco-amylase is added. After a short saccharification time of about 5-6 hours the slurry is cooled to about 32° C. The slurry solids concentration at this point is 361 g/kg (insoluble & soluble solids). Two equal aliquots of the corn slurry are placed in two identical batch fermenter tanks. Both tanks are inoculated with biocatalysts that can convert dextrose to isobutanol: Tank B1 is inoculated with biocatalyst B1 and Tank B2 is inoculated with biocatalyst B2. Both biocatalysts B1 & B2 are genetically engineered to convert dextrose to isobutanol: B1 is engineered in a way such that it contains DNA consisting of natural DNA, however, biocatalyst B2 does contains DNA comprised to 0.7% of foreign DNA as a result of the specific approach taken to engineer this organism for isobutanol production. The vessels are agitated and sampled until isobutanol yield is 90%. Tank B1 is complete in 36 hours and B2 is complete in 29 hours. At the end of their fermentations Tanks B1 and B2 fermentation broth is analyzed for isobutanol content. Analysis of the fermentation samples reveals the fermentation performance summarized in Table 6 for isobutanol titers, production rates and production yields. Fermenter B2 produced isobutanol at a higher rate compared to fermenter B1. Yield is defined as the actual amount of carbohydrate converted to butanol divided by the theoretical amount of butanol based on a 0.41 g butanol per g glucose theoretical yield.

TABLE 6

Summary of fermentation performance for fermentations B1 & B2 described above.

| | Fermenter B1 | Fermenter B2 |
|---|---|---|
| Production Organism | B1 (natural DNA) | B2 (foreign DNA) |
| Isobutanol Rate (g/l h) | 1.3 | 1.6 |
| Isobutanol Yield (% theoretical) | 90 | 90 |
| Isobutanol Titer (g/l) | 47 | 47 |
| Fermentation Time (hours) | 36 | 29 |

The spent biocatalyst from fermentation B1 is dried and added to DDGS sold for animal feed at current market rates. However the spent biocatalyst from fermenter B2 are dried to produce DDGS, which is burned for energy sold at current market rates. An economic analysis of the value of the DDGS sold as a feed in fermenter B1 compared to burning the DDGS from fermenter B2 was completed. Results of the economic analysis indicate that the co-product credit for selling the DDGS as animal feed results in a cost reduction of $0.14/gallon of isobutanol compared to burning the DDGS. The cost reduction as a result of the increased productivity in fermenter B2 is $0.012/gallon isobutanol. An economic analysis of the overall process costs for the two biocatalysts reveals that the economic advantages from the higher productivity in fermenter B2 is outweighed by the cost reduction due to the sale of DDGS from fermenter B1 as animal feed. This example illustrates the importance of producing a DDGS which can be sold into the feed markets.

Example 3

A cellulosic material consisting of 45% cellulose, 25% hemicellulose, 22% lignin and 8% other materials is pretreated to yield slurry of 8% insoluble cellulose with about 4% insoluble lignin, 1% glucose, 40 g/l xylose, 2 g/l mannose, 2 g/l galactose, 1 g/l arabinose, 5 g/l acetic acid in solution. For each experiment, equal portions of the pretreated cellulosic material are added into an agitated saccharification and fermentation vessel. All four experiments are charged with cellulase enzyme sufficient to hydrolyze 80% of the cellulose and are run in batch mode for over 72 hours. A biocatalyst known to convert glucose, xylose, mannose, galactose and arabinose to butanol is added to each of the four fermentations. The fermentation vessel is configured with an alkali and acid feed pH control system.

Fermentation C1 is controlled at pH 4.0. Fermentation C2 is controlled at pH 4.5. Fermentation C3 is controlled at pH 5.0. Fermentation C4 is controlled at pH 5.5. The vessels are agitated for 72 hours. At the end of 72 hours the fermentation broth is analyzed for butanol and organic acid content.

Fermentation C1 results in low butanol concentration of 30.5 g/L and low productivity of 0.42 g/L-hr. No organic acids are observed. Fermentation C2 results in 46.3 g/l butanol and productivity of 0.64 g/L-hr. No organic acids are observed in Fermentation C2. Fermentation C3 contains 45.7 g/l butanol resulting in a productivity of 0.63 g/L-hr and 1.2 g/l organic acids. Fermentation C4 produced 36.5 g/L butanol, a productivity of 0.51 g/L-hour and 6.0 g/L organic acids. The pH controlled fermentations at the higher pH range allowed for contaminant growth that produced carboxylic acid metabolic byproducts, resulting in butanol yield losses.

Economic analysis of the four batch fermentations indicates butanol recovered from fermentation 2 has the highest carbohydrate to butanol yield. Fermentation C1 has carbohydrate costs 51.8% greater than fermentation C2. Fermentations C3 and C4 carbohydrate costs are 1.3% and 26.9% higher compared to fermentation C2, respectively. The fermentation C2 process at pH 4.5 minimized carbohydrate costs relative to fermentations C1, C3 and C4. This example shows that production costs are minimized for fermentation C2 since substrate costs are the major raw material costs for such processing plants. Small swings in carbohydrate conversion can drastically impact economic viability and performance for high cash flow business such as the biofuels market. The results of these fermentations at various pH demonstrate the impact of utilization of a pH tolerant organism capable of reducing contamination growth of undesired byproducts.

Example 4 pH control impacts the ability of competing microorganisms to produce other metabolites such as organic acids, i.e., lactic acid. Dry corn is milled into a fine powder. The dry milled corn is slurried and heated to 99° C. and then alpha-amylase enzyme is added. After a short saccharification time the slurry is cooled to 30° C. The slurry solids concentration at this point is 361 g/kg, including insoluble & soluble solids. Three equal aliquots of the corn slurry are placed in three continuous fermenter tanks. Gluco-amylase enzyme and biocatalyst 2 are added to each of fermenter tanks D5, D6 & D7. Gluco-amylase and water sufficient to complete the saccharification at the designed dilution rate are added to each fermenter tank. The fermentation carbohydrate concentration is fed to an equivalent feed of 60 g/l. Calcium hydroxide and sulfuric acid are used as base and acid solutions pH controlled fermentations.

Fermentation D5 is uncontrolled and maintains at about pH 3.5. Fermentation D6 is controlled at pH 4.0. Fermentation D7 is controlled at pH 4.5. The fermentations are operated in a continuous mode and are agitated throughout the experiment. Once steady state, usually by 72 hours, the fermentation broth is analyzed for butanol and organic acid content. Continuous fermentation runs for fermenter D5, D6, & D7 are established at a dilution rate of 0.014/hr. Fermentations are monitored until cell density and residual glucose is stabilized.

The following steady state compositions are collected. Fermentation D5 samples show butanol concentration at 22.8 g/l and no lactic acid. Fermentation D6 results in 22.5 g/l butanol and 0.4 g/l lactic acid. Fermentation D7 results in 22.0 g/l butanol and 1.7 g/l lactic acid.

Economic analysis of the three continuous fermentations (D5, D6, & D7) indicates butanol recovered from fermentation D5 has the highest butanol yield and lowest carbohydrate costs. Fermentation D6 has carbohydrate costs 1.3% greater than Fermentation D5 performance. Fermentations D7 carbohydrate costs are 3.6% higher compared to Fermentation D5. Fermentation D5 operating at pH 3.5 minimized carbohydrate costs relative to other fermentations in the example and would minimize product costs as carbohydrate substrate costs are the major raw material costs for such processing plants. Small swings in carbohydrate conversion can drastically impact economic viability and performance for high cash flow business such as the biofuels market. The results of these fermentations at various pH demonstrate the impact of utilization of a pH tolerant organism capable of reducing contamination growth of undesired byproducts.

Economic analysis of example 4 also demonstrates an impact of pH on capital cost expenditures. Fermentation D5 produced the highest yield and lowest operating costs based on cost of the feedstock carbohydrates, but also did not require pH control. Lack of pH control means that no capital expenditures for equipment nor operating expenditures for acid and base are required to control pH of fermentation D5 and this lowers the overall process costs compared to fermentations D6 and D7. Product dilution and yield impact equipment sizes and energy consumption in corn processing, fermentation, and recovery equipment. Therefore, a biocatalyst that can produce biofuels at a low pH with no requirement for pH control yields a biofuel production process that is more economically competitive.

Example 5

A cellulosic material consisting of 45% cellulose, 25% hemicellulose, 22% lignin and 8% other materials is pretreated to yield slurry of 8% insoluble cellulose with about 4% insoluble lignin, 1% glucose, 40 g/l xylose, 2 g/l mannose, 2 g/l galactose, 1 g/l arabinose, 5 g/l acetic acid in solution. For each experiment, equal portions of the pretreated cellulosic material are added into an agitated saccharification and fermentation vessel. All four experiments are charged with cellulase enzyme sufficient to hydrolyze 80% of the cellulose and are run in batch mode over 72 hours. A biocatalyst known to convert glucose, xylose, mannose, galactose and arabinose to isobutanol is added to each of the four fermentations. The fermentation vessel is configured with an alkali and acid feed pH control system.

The fermentations are controlled at pH 6. The biocatalyst in fermenters E1 and E2 is able to recover from sudden changes in pH. The biocatalyst in fermenters E3 and E4 is not able to recover from sudden changes in pH. At time 36 hours the pH control of fermenter E1 and E3 malfunctions and the pH drops to pH 4 for 3 hours. At time 39 hours, the pH of fermenters E1 and E3 is returned to pH 6 for the remainder of the experiment. Fermenters E2 and E4 are controlled at pH 6 throughout the process. The vessels are agitated for a total of 72 hours. At the end of 72 hours the fermentation broth is analyzed for isobutanol.

Fermentations E2 and E4 result in an isobutanol concentration of 36 g/L and productivity of 0.5 g/L-hr. Fermentation E1 results in 34.5 g/L isobutanol and a productivity of 0.48 g/L-hr. Fermentation E3 contains 18 g/L isobutanol resulting in a productivity of 0.25 g/L-hour.

Economic analysis of the four batch fermentations indicates isobutanol recovered from fermentations E2 and E4 have the highest productivity and titer. Fermentation E1 produces isobutanol at a cost 4% higher than fermentations E2 and E4. Fermentation E3 produces isobutanol at a cost 100% higher than fermentation E2 and E4. The economic impact of the pH control malfunction has a far reduced impact for the fermenter with biocatalyst which recovers from sudden and sustained pH changes. Fluctuations in process condition can drastically impact economic viability and performance for high cash flow business such as the biofuels market. The results of these fermentations under control malfunction conditions demonstrate the positive impact of the use of a biocatalyst that recovers from fluctuations in pH on the economics of a biofuel production process.

Example 6

A cellulosic material consisting of 45% cellulose, 25% hemicellulose, 22% lignin and 8% other materials is pretreated to yield slurry of 8% insoluble cellulose with about 4% insoluble lignin, 1% glucose, 40 g/l xylose, 2 g/l mannose, 2 g/l galactose, 1 g/l arabinose, 5 g/l acetic acid in solution. Three equal portions of the pretreated cellulosic material are put into agitated saccharification and fermentation vessels. All three are charged with cellulase enzyme sufficient to hydrolyze 80% of the cellulose in 72 hours. At the same time the Fermentation F1, F2, & F3 are charged with biocatalyst with a temperature optimum at 50° C. and is known to convert glucose, xylose, mannose, galactose and arabinose to butanol is added to each of the three fermentations. The fermentations are operated at different temperatures. The fermentation vessel is configured with an alkali and acid feed pH control system and are maintained at pH 4.0. Titer, completion time and cell density are recorded at the completion of each of the three fermentations.

Fermentation F1 is operated at 40° C. Fermentation F2 is operated at 50° C. Fermentation F3 is operated at 60° C. The three fermentation experiments are monitored for completion by monitoring carbohydrate concentration and considered complete when less than 10% of the total fermentable sugar remains.

The vessels are monitored for carbohydrate level, cell density, and butanol titer over 72 hours. Fermentation F1 proceeds to completion in 45.2 hours with a cell density of 3 g CDW (cell dry weight)/kg and 44.5 g/L butanol. Fermentation F2 shows completion in 34.6 hours with a cell density of 3 g CDW/kg and 45.1 g/L butanol. Fermentation F3 does not go to completion within 72 hours with a cell density of 1 g CDW/kg and 40.2 g/L butanol. Fermentation F3 enzyme has essentially completed conversion of cellulose but greater than 10% of the total fermentable sugars of the original charge remained.

The three different operating temperatures of the enzyme and organism combine to impact the availability of carbohydrate, fermentation time and carbohydrate conversion. As the enzyme treatment temperature is optimized, fermentation productivity and economics are improved. Enzyme activity is optimized at 50° C. Fermentation F3 at 60° C. is detrimental to the biocatalyst metabolism and growth rate.

Economic analysis of the three fermentations shows that fermenter capital expenditures from butanol produced in fermenter F1 is 33% higher than the costs for butanol recovered from fermenter F2. The fermenter capital costs for butanol from fermentation F3 is 134% higher than the capital costs from butanol produced in fermentation F2. The revenue from butanol from fermentation F2 is 1.3% higher than fermentation F1. The revenue from fermentation F2 is 12.1% higher than fermentation F3 (assuming residual carbohydrate has no process value). Overall fermentation F2 is the preferred economic minimum as it matches enzyme activity and fermentation volumetric productivity relative to temperature.

The example also demonstrates the economic impact of the heat tolerant biocatalyst, which allows fermentation reactions at elevated temperatures optimal for degradation of the feedstock by digestive enzymes. These elevated temperatures allow better heat transfer and smaller heat transfer capital equipment, slower volumetric flows, and reduced capital and operating costs.

Example 7

A cellulosic material consisting of 45% cellulose, 25% hemicellulose, 22% lignin and 8% other materials is pretreated to yield slurry of 8% insoluble cellulose with about 4% insoluble lignin, 1% glucose, 40 g/l xylose, 2 g/l mannose, 2 g/l galactose, 1 g/l arabinose, 5 g/l acetic acid in solution. For each experiment, equal portions of the pretreated cellulosic material are added into four agitated saccharification and fermentation vessels. G1, G2, G3, and G4. All four experiments are charged with cellulase enzyme sufficient to hydrolyze 80% of the cellulose and are run in batch mode over 72 hours. A biocatalyst known to convert glucose, xylose, mannose, galactose and arabinose to isobutanol is added to each of the four fermentations. The fermentation vessel is configured with an alkali and acid feed pH control system and a thermostat-regulated temperature control device to maintain temperature at a preset value.

The temperature of the fermentations is controlled at 35° C. The biocatalyst in fermenters G1 and G2 is able to recover from sudden change in temperature. The biocatalyst in fermenters G3 and G4 is not able to recover from sudden change in temperature. At time 36 hours, the temperature control of fermenter G1 and G3 malfunctions and the temperature rises to 65° C. and is sustained at 65° C. for about 3 hours. At time 39 hours, the temperature of fermenters G1 and G3 is returned to 35° C. for the remainder of the experiment. Fermenters G2 and G4 are controlled at 35° C. throughout the process. The vessels are agitated for a total of 72 hours. At the end of 72 hours the fermentation broth is analyzed for isobutanol.

Fermentations G2 and G4 result in an isobutanol concentration of 36 g/L and productivity of 0.5 g/L-hour. Fermentation G1 results in 34.5 g/L isobutanol and productivity of 0.48 g/L-hour. Fermentation G3 contains 18 g/L isobutanol resulting in a productivity of 0.25 g/L-hour.

Economic analysis of the four batch fermentations indicates isobutanol recovered from fermentations G2 and G4 have the highest productivity and titer. Fermentation G1 produces isobutanol at a cost 4% higher than fermentations G2 and G4. Fermentation G3 produces isobutanol at a cost 100% higher than fermentation G2 and G4. The economic impact of the temperature control malfunction has a far reduced impact for the fermenter, G1, with a biocatalyst that recovers from sudden and sustained temperature changes. Fluctuations in process condition can drastically impact economic viability and performance for low profit margin business such as the biofuels market. The results of these fermentations under control malfunction conditions demonstrate the impact of the utilization of a biocatalyst that recovers from fluctuation of temperature on the economics of a biofuel production process.

Example 8

A cellulosic material consisting of 45% cellulose, 25% hemicellulose, 22% lignin and 8% other materials is pretreated to yield slurry of 8% insoluble cellulose with about 4% insoluble lignin, 1% glucose, 40 g/L xylose, 2 g/L mannose, 2 g/L galactose, 1 g/L arabinose, 5 g/L acetic acid in solution. For each experiment, equal portions of the pretreated cellulosic material are added into four agitated saccharification and fermentation vessels, H1, H2, H3, and H4. All four experiments are charged with cellulase enzyme sufficient to hydrolyze 80% of the cellulose and are run in batch mode for 72 hours. Four types of biocatalysts known to convert glucose, xylose, mannose, galactose and arabinose to butanol are individually added to each of the four fermentations. The fermentation vessel is configured with an alkali and acid feed pH control system and the pH is controlled at pH values optimal for each of the four organisms (in the range of 4.5-7).

The vessels are agitated for 72 hours. At the end of 72 hours, the fermentation broth is analyzed for butanol and byproducts content. Fermentation H1 results in low butanol concentration of 27.8 g/L and low productivity of 0.39 g/L-hr and low conversion yield of 0.25 g-butanol/g-total initial fermentable sugars. This organism produces substantial amounts of byproducts as detected in the broth (acetone, acetate, butyric acid and ethanol). Fermentation H2 results in 32.4 g/L butanol and productivity of 0.45 g/L-hr and a conversion yield of 0.29 g/g. As in fermentation H1, this organism also produces substantial amounts of byproducts as detected in the broth (acetone, acetate, butyric acid and ethanol), albeit at lower levels versus Fermenter H1. Fermentation H3 results in 37.1 g/L butanol and productivity of 0.52 g/L-hr and a conversion yield of 0.33 g/g. As in fermentation H1 and H2, this organism also produces substantial amounts of byproducts as detected in the broth (acetone, acetate, butyric acid and ethanol), albeit at lower levels versus fermentations H1 and H2. Fermentation H4 results in 41.7 g/L butanol and productivity of 0.58 g/L-hr and a conversion yield of 0.37 g/g. Unlike the previous fermentations, this fermentation produces no byproducts detectable in the fermentation broth.

Economic analysis of the four batch fermentations indicates butanol recovered from fermentation 4 has the highest carbohydrate to butanol yield. Fermentation H1 has carbohydrate costs 50.0% greater than Fermentation H4 performance. Fermentations H2 and H3 carbohydrate costs are 28.6% and 12.5% higher compared to Fermentation H4, respectively. The fermentation results demonstrate the significant impact of organism metabolite selectivity on carbohydrate and feedstock economics. Additionally, the creation of byproducts, such as acetate, increases capital costs and operating costs required to separate the byproducts from the more complex fermentation broth. This example demonstrates that a biocatalyst for the production of biofuel that has a high theoretical yield and also produces low or no levels of byproducts that require downstream separation and have low value, is the most economical for an economical biofuel production process.

Example 9

A cellulosic material consisting of 45% cellulose, 25% hemicellulose, 22% lignin and 8% other materials is pretreated to yield a slurry of 8% insoluble cellulose with about 4% insoluble lignin, 1% glucose, 40 g/L xylose, 2 g/L mannose, 2 g/L galactose, 1 g/L arabinose, 5 g/L acetic acid in solution. For each experiment equal portions of the pretreated cellulosic material are added into two agitated saccharification and fermentation vessels, I1 and I2. Both experiments are charged with cellulase enzyme sufficient to hydrolyze 80% of the cellulose and are run in batch mode for 72 hours. Two types of biocatalysts known to convert glucose, xylose, mannose, galactose and arabinose to isobutanol are used and individually added to either one of the two fermentations.

The vessels are agitated for 72 hours. At the end of 72 hours the fermentation broth is analyzed for isobutanol and byproducts content and the biofuel is recovered from the fermentation broth. Both fermentations yield similar isobutanol amounts. Fermentation I1 results in low (less than 0.01% (w/w)) amounts of byproducts such as butyrate, acetate, and isobutyraldehyde in the biofuel product. The small amounts of these byproducts cause the biofuel to not meet ASTM specifications (ASTM D4814) for copper corrosion test (ASTM D130) and oxidation stability (ASTM D525). Fermentation I2 results in no byproducts and the biofuel meets the ASTM specifications. The biofuel produced in fermentation I1 is treated with an additional purification step to remove the impurities, adding an additional cost of 5% to the overall process cost compared to the cost of fermentation I2. Therefore, this example demonstrates that the biocatalyst that produces less trace byproducts yields a biofuel that is more economical.

Example 10

Corn grain is milled into a fine powder. The dry milled corn is slurried and heated to 99° C. and then alpha-amylase enzyme is added. After a short saccharification time of about 5-6 hours, the slurry is cooled to about 32° C. The slurry solids concentration at this point is about 361 g/kg, including insoluble & soluble solids. Three equal aliquots of the corn slurry are placed in three identical fermenter tanks, labeled fermenters J4, J5 & J6. Gluco-amylase enzyme is added to all tanks, and biocatalysts J4, J5 & J6 are added to tanks J4, J5, & J6, respectively. Gluco-amylase sufficient to complete the saccharification in 32 hours is also added to each tank.

Biocatalysts J4, J5, and J6 have a specific butanol productivity of 0.5 g butanol per g cells per hr and reach a final cell density of 3 g cells per liter. Biocatalysts J4, J5, and J6 show a linear reduction in their specific productivity above their tolerance level for butanol. Beyond this level the specific productivity is reduced by 10% for every increase in titer of 10 g/L. Biocatalyst J4 is tolerant to butanol up to a concentration of 20 g/L. Biocatalyst J5 is tolerant to butanol up to a final concentration of 30 g/L. Biocatalyst J6 is tolerant to butanol up to a final concentration of 40 g/L. This results in a fermentation process time of about 112 hours for biocatalyst 4, 95 hours for biocatalyst J5, and 83 hours for biocatalyst J6, respectively, to permit consumption of greater than 98% of the total fermentable sugars added in the original charge and liberated by the digestive enzymes.

A commercial facility using biocatalyst J4, producing 100 million gallons of butanol per year using batch fermentations with a turnaround time between subsequent fermentations of 10 hours, and operating 350 days per year requires total fermentation volume of 10.3 million gallons total. Commercial processes for biocatalyst J5 and biocatalyst J6 require 8.9 and 7.8 million gallons of fermentation capacity, respectively. The capital cost for the fermentation portion using biocatalyst J6 compared to using biocatalyst J4 is 17% less. The capital cost for the fermentation portion of the butanol process using biocatalyst J5 is 10% less when compared to utilizing biocatalyst J4. Finally, the capital cost for the fermentation portion of the butanol process using biocatalyst J6 is 8% less when compared to utilizing biocatalyst J5. Using a depreciation and capital charge totaling 20% of the invested capital per year, similar to a 10% Internal Rate of Return, biocatalyst J6 is 1.3 cents per gallon lower in cost than biocatalyst J4, and 0.5 cents per gallon lower in cost than biocatalyst J5.

Overall, the high tolerance of biocatalyst J6 is favored compared to biocatalyst J5 or biocatalyst J4. This example demonstrates that the higher the tolerance of the biocatalyst for the production of biofuel, the lower the cost of fermentation capital. Higher tolerance and higher volumetric productivities are economically favored.

Example 11

Corn grain is milled into a fine powder. The dry milled corn is slurried and heated to 99° C. and then alpha-amylase enzyme is added. After a short saccharification time of about 5-6 hours the slurry is cooled to about 32° C. The slurry solids concentration at this point is about 361 g/kg, including insoluble & soluble solids. Three equal aliquots of the corn slurry are placed into three identical fermenter tanks labeled fermenters K14, K15 & K16. Gluco-amylase enzyme is added to all tanks, and biocatalysts K14, K15 & K16 are added to fermentation tanks K14, K15, & K16, respectively. Gluco-amylase sufficient to complete the saccharification in 32 hours is also added to each tank.

Biocatalysts K14, K15, and K16 have a specific butanol productivity of 0.5 g butanol per g cells per hr and reach a final cell density of 3 g cells per liter. Biocatalyst K14, K15 and K16 are tolerant to butanol up to a concentration of 50 g/L. Biocatalysts K14, K15, and K16 show a linear reduction in their specific productivity above the inhibitory concentration for butanol. The rate of inhibition is different for the three biocatalysts. Beyond the inhibitory concentration the specific productivity is reduced by 20% for every increase in titer of 10 g/L for biocatalyst K14. Beyond the inhibitory concentration, the specific productivity is reduced by 15% for every increase in titer of 10 g/L for biocatalyst K15. Beyond the inhibitory concentration, the specific productivity is reduced by 10% for every increase in titer of 10 g/L for biocatalyst K16.

A commercial facility using biocatalyst K14, producing 100 million gallons of butanol per year using batch fermentations with a turnaround time between subsequent fermentations of 10 hours, and operating 350 days per year requires total fermentation volume of 12.0 million gallons total. Commercial processes for biocatalyst K15 and biocatalyst K16 require 8.3 and 7.2 million gallons of fermentation capacity, respectively. The capital cost for the fermentation portion using biocatalyst K16 is 30% less when compared to using biocatalyst K14. The capital cost for the fermentation portion of the butanol process using biocatalyst K15 is 23% less when compared to utilizing biocatalyst K14. Finally, the capital cost for the fermentation portion of the butanol process using biocatalyst K16 is 9% less when compared to utilizing biocatalyst K15. Using a depreciation and capital charge totaling 20% of the invested capital per year, similar to a 10% Internal Rate of Return, biocatalyst K16 is 2.5 cents per gallon lower in cost than biocatalyst K14, and 0.6 cents per gallon lower in cost than biocatalyst K15.

Overall, the low rate of inhibition of biocatalyst K16 is favored compared to biocatalyst K15 or biocatalyst K14. This example demonstrates that the higher the specific productivity at the same cell density and at higher titers of biofuel, the lower the cost of fermentation capital. Lower rates of inhibition of the biocatalyst by the biofuel and higher volumetric productivities are economically favored and lead to a more economical biofuel production process.

Example 12

Corn grain is milled into a fine powder. The dry milled corn is slurried and heated to 99° C. and then alpha-amylase enzyme is added. After a short saccharification time of about 5-6 hours the slurry is cooled to about 32° C. The slurry solids concentration at this point is about 361 g/kg, including insoluble & soluble solids. Three equal aliquots of the corn slurry are placed in four identical fermenter tanks labeled fermenters L23, L24, L25 & L26. Gluco-amylase enzyme is added to all tanks, and biocatalysts L23, L24, L25 & L26 are added to tanks L23, L24, L25, & L26, respectively. Gluco-amylase sufficient to complete the saccharification in 32 hours is also added to each tank.

Biocatalysts L23, L24, L25, and L26 have a specific butanol productivity of 0.5 g butanol per g cells per hr, and reach a final cell density of 3 g cells per liter. Biocatalyst L23, L24, L25 and L26 are not tolerant to butanol. Biocatalysts L23, L24, L25, and L26 show a linear reduction in their specific productivity with increasing concentration of butanol. The rate of inhibition is different for the four biocatalysts and inhibition begins at 0 g/L isobutanol for each of the biocatalysts. The specific productivity is reduced by 5% for every increase in titer of 10 g/L for biocatalyst L23. The specific productivity is reduced by 10% for every increase in titer of 10 g/L for biocatalyst L24. The specific productivity is reduced by 20% for every increase in titer of 10 g/L for biocatalyst L25. The specific productivity is reduced by 40% for every increase in titer of 10 g/L for biocatalyst L26.

A commercial facility using biocatalyst L23 reaches an economically feasible titer of greater than 80 g/l after 68 hours. Using biocatalyst L24, in the same process time, the titer would be 64 g/l. Biocatalyst L25 reaches a titer of 43 g/l, and biocatalyst L26 has a titer of 25 g/l. This example shows that biocatalyst L23 has a 25% higher titer when compared to biocatalyst L24, leading to smaller capital costs and smaller downstream processing costs. This example demonstrates that biocatalysts that produce biofuel with lower rates of inhibition due to the biofuel, resulting in higher titers of biofuel due to increased resistance of biocatalysts, are economically favored.

Example 13

Corn is fed into holding tanks and steeped in preparation for processing into germ, fiber and starch. The corn is processed and the starch is recovered and saccharified with alpha-amylase and gluco-amylase enzymes with the resulting sugar solution being 97% dextrose at a total solids concentration of about 30 weight %. Three equal aliquots of this sugar are put into three separate fermentation vessels. Biocatalysts M35, M36, & M37, which convert dextrose to isobutanol, are inoculated into fermentation vessels MA, MB, & MC, respectively. The fermentations utilizing biocatalysts M35, M36 & M37 are finished converting sugar after 30 hours, 42 hours, and 56 hours, respectively. The final isobutanol concentrations for fermentation M35, M36 & M37 are 80 g/l, 63 g/l, and 47 g/l, respectively.

Biocatalyst M35 clearly offers superior fermentation performance because it is tolerant of higher isobutanol concentrations resulting in higher final titers and higher volumetric productivities. The results of biocatalyst M35 support a business system with lower energy costs for recovery and spent fermentation broth drying. Additionally, biocatalyst M35 has lower fermentation capital cost because of the higher productivities. For the purposes of the economic analysis, the excess sugar left after the fermentation stops are not considered in results analysis. The reason is that the initial sugar concentration will be diluted to provide only the quantity of sugar that the biocatalyst can consume. Economic analysis of the results shows that the cost per gallon for biocatalyst M36 is increased by 5.7 cents per gallon of isobutanol compared to biocatalyst M35. Economic analysis of the results shows the cost per gallon of butanol is increased by 15.3 cents for biocatalyst M37 compared to biocatalyst M35. The cost increases include the cost of natural gas to make steam and extra depreciation for larger fermentation vessels to make the same quantity of product. The depreciation charge was calculated on a straight line, 10-year basis. This example demonstrates that the business system and method of producing biofuel benefits from use of biocatalysts with greater biofuel,

Example 14

Biocatalysts N7 & N8 both have high 2-propanol specific and volumetric productivity, high yield, and high final concentration when grown on dry milled corn feedstock. Biocatalyst N7 produces an endotoxin, toxic to humans and cattle, while biocatalyst N8 does not.

Dry milled corn is prepared and put into two fermenter tanks, N7 and N8. Dry milled corn is prepared by first milling into a fine powder. The dry milled corn is then slurried and heated to 99° C. and then alpha-amylase enzyme is added. After a short saccharification time the slurry is cooled to 30° C. The slurry solids concentration at this point is about 361 g/kg (insoluble & soluble solids). Fermentation tank N7 is charged with biocatalyst N7. Fermentation tank N8 is charged with biocatalyst N8. The residue from fermentation tank N7, after stripping off the 2-propanol, is dried and used to fire a boiler, providing a value of about $40/ton. The residue from fermentation tank N8 is dried and sold as animal feed for $90/ton because it contains no endotoxin. Based on a $50/ton difference in value for the residual solids from the spent fermentation stream, the 2-propanol produced by biocatalyst N8 costs 17 cents per gallon less to produce than the 2-propanol produced using biocatalyst N7. This example demonstrates that biocatalysts that do not produce endotoxin or compounds harmful to cattle provide a lower cost biofuel, and here specifically, 2-propanol, because co-product value is enhanced.

Example 15

Biocatalysts O9 & O10 both have high isobutanol specific and volumetric productivity, high yield, and high final concentration when grown on dry milled corn feedstock. Biocatalyst O9 produces an exotoxin, toxic to humans and cattle, while biocatalyst O10 does not. Dry milled corn is prepared as described in example 14 and put into two fermenter tanks. Fermentation tank O9 is charged with biocatalyst O9. Fermentation tank O10 is charged with biocatalyst O10. The residue from fermentation tank O9, after stripping off the isobutanol, can be dried and used to fire a boiler, providing a value of about $40/ton. The residue from fermentation tank O10 is dried and sold as animal feed for $90/ton because it contains no exotoxin. Based on a $50/ton difference in value for the residual solids from the spent fermentation stream, the isobutanol utilizing biocatalyst O10 costs 17 cents per gallon less to produce than the isobutanol produced using biocatalyst O9. This example demonstrates that biocatalysts that do not produce exotoxin or compounds harmful to cattle provide a lower cost biofuel, and here specifically isobutanol, because co-product value is enhanced.

Example 16

Corn grain is milled into a fine powder. The dry milled corn is slurried and heated to about 105° C. and then alpha-amylase enzyme is added. After a short saccharification time of about 5-6 hours the slurry is cooled to about 32° C. The slurry solids concentration at this point is about 361 g/kg (insoluble & soluble solids). Five equal aliquots of the corn slurry are placed in five identical fermenter tanks labeled fermenters P10, P11, P12, P13 & P14. Gluco-amylase enzyme is added to all tanks and biocatalysts P10, P11, P12, P13, & P14 are added to tanks P10, P11, P12, P13, & P14, respectively. Gluco-amylase sufficient to complete the saccharification in 48 hours is also added to each tank.

Biocatalysts P10, P11, P12, P13 & P14 are all engineered to produce butanol from glucose and in 48 hours time have converted all sugar to produce 84.7 g/L, 90.0 g/L, 95.3 g/L, 97.4 g/L and 99.5 g butanol/L fermentation broth respectively. Biocatalysts P10, P11, P12, P13, & P14 have theoretical weight yields of butanol on sugar consumed of 80, 85, 90, 92 & 94% respectively.

The difference in yields shown by biocatalysts P10, P11, P12, P13, and P14 impact the quantity of feedstock, the operating cost, and the capital cost needed to make a gallon of butanol. This example demonstrates that lower yield increases the cost of feedstock and other operating costs and capital cost in a fermentation for the production of biofuel. Therefore, this example demonstrates that a biocatalyst that produces a biofuel at high yields is more economical compared to a biocatalyst that produces a biofuel at a lower yield.

Example 17

A cellulosic material consisting of 45% cellulose, 25% hemicellulose, 22% lignin and 8% other materials is pretreated to yield slurry of 8% insoluble cellulose with about 4% insoluble lignin, 1% glucose, 40 g/l xylose, 2 g/l mannose, 2 g/l galactose, 1 g/l arabinose, 5 g/l acetic acid in solution. Three equal portions of the pretreated cellulosic material are put into agitated saccharification and fermentation vessels. All three are charged with cellulase enzyme sufficient to hydrolyze 80% of the cellulose in 72 hours. Three equal sized samples of the slurry are put into identical saccharification and fermentation vessels labeled Q7, Q8, and Q9.

Biocatalysts Q7, Q8 & Q9 were each used to inoculate one of the saccharification and fermentation vessels with the corresponding label Q7, Q8, and Q9, respectively.

Biocatalysts Q7, Q8, and Q9 are all engineered to produce butanol from pretreated cellulosic material (hydrolysate) and in 48 hours time have converted all sugar to produce 10 g/L, 12.5 g/L, and 15 g butanol/L fermentation broth respectively.

The difference in yields shown by biocatalysts Q7, Q8, and Q9 impact the quantity of feedstock, the operating cost, and the capital cost needed to make a gallon of butanol. This example demonstrates that lower yield increases the cost of feedstock and other operating costs and capital cost in a fermentation for the production of biofuel. Therefore, this example demonstrates that a biocatalyst that produces a biofuel at high yields is more economical compared to a biocatalyst that produces a biofuel at a lower yield.

Example 18

A cellulosic material consisting of 45% cellulose, 25% hemicellulose, 22% lignin and 8% other materials is pretreated to yield slurry of 8% insoluble cellulose with about 4% insoluble lignin, 1% glucose, 40 g/l xylose, 2 g/l mannose, 2 g/l galactose, 1 g/l arabinose, 5 g/l acetic acid in solution. For each experiment, equal portions of the pretreated cellulosic material are added into an agitated saccharification and fermentation vessel. All four experiments are charged with cellulase enzyme sufficient to hydrolyze 80% of the cellulose and are run in batch mode over 72 hours. A biocatalyst known to convert glucose, xylose, mannose, galactose and arabinose to butanol is added to each of the four fermentations. The fermentation vessels are configured with an alkali and acid feed pH control system. Furthermore, each of the four vessels is supplemented with additional nutrients, as shown in Table 7.

TABLE 7

Media supplementations for fermenters R1-R4 listed in g/L.

| | Fermenter R1 | Fermenter R2 | Fermenter R3 | Fermenter R4 |
|---|---|---|---|---|
| Yeast Extract | 10 | 0 | 5 | 2.5 |
| Peptone | 20 | 0 | 10 | 5 |
| Ammonium Sulfate | 0 | 5 | 5 | 5 |
| Potassium Phosphate Monobasic | 0 | 1 | 1 | 1 |
| Magnesium Sulfate | 0 | 0.5 | 0.5 | 0.5 |
| Sodium Chloride | 0 | 0.1 | 0.1 | 0.1 |
| Calcium Chloride | 0 | 0.1 | 0.1 | 0.1 |
| Biotin | 0 | 0.000002 | 0 | 0 |
| D-Pantothenic Acid•Ca | 0 | 0.0004 | 0 | 0 |
| Folic Acid | 0 | 0.00002 | 0 | 0 |
| Inositol | 0 | 0.002 | 0 | 0 |
| Niacin | 0 | 0.0004 | 0 | 0 |
| p-Aminobenzoic Acid | 0 | 0.0002 | 0 | 0 |
| Pyridoxine HCl | 0 | 0.0004 | 0 | 0 |
| Riboflavin | 0 | 0.0002 | 0 | 0 |
| Thiamine HCl | 0 | 0.0004 | 0 | 0 |

The vessels are agitated for 72 hours. At the end of 72 hours, the fermentation broth is analyzed for butanol and carbon sources. Analysis of the fermentation samples reveals the fermentation performance summarized in Table 8 for butanol titers, production rates and production yields.

TABLE 8

Summary of fermentation performance for fermentations 1-4 described above.

| | Fermenter R1 | Fermenter R2 | Fermenter R3 | Fermenter R4 |
|---|---|---|---|---|
| Butanol Rate (g/L/h) | 1 | 0.5 | 0.8 | 0.7 |
| Butanol Yield (% theoretical) | 90 | 72 | 81 | 72 |
| Butanol Titer (g/L) | 45 | 22.5 | 36 | 31.5 |

Fermentation R2 on salts plus vitamins defined medium, results in relatively low butanol rate, titer and yield, whereas the fermentation of fermenter R1, on rich complex media, achieves the highest performance (Table 8). The fermentations of fermenters R3 and R4 achieve intermediate rates, titers and yields.

Economic analysis of the four batch fermentations indicates butanol recovered from the fermentation of fermenter R1 has the highest butanol to carbohydrate yield. The fermentation of fermenter R2 has 60% greater carbohydrate costs than the fermentation of fermenter R1, relative to the amount of butanol produced. The fermentations of fermenters R3 and R4 carbohydrate have 12.5% and 14.3% higher costs when compared to the fermentation of fermenter R1, respectively, and relative to the amount of butanol produced. The economic comparison of nutrient costs reveals that the fermentation of fermenter R2 is the most economical nutrient composition of all four examples. The fermentation of fermenter R1 has nutrient costs of almost 600% more that of the fermentation of fermenter R2. The fermentations of fermenters R3 and R4 have nutrient costs of 380% and 220% when compared to the fermentation of fermenter R2. When economic costs for carbohydrate and nutrients are combined, the experiments show the fermentation of fermenter R2 to be the most cost effective. Carbohydrate and nutrient costs for the fermentation of fermenter R1 is 312% greater than that of the fermentation of fermenter R2. Carbohydrate and nutrient costs for the fermentations of fermenters R3 and R4 are 199% and 141% greater than that of the fermentation of fermenter R2, respectively.

This example demonstrates that economic production of butanol must consider both the efficiency of carbohydrate conversion by the biocatalysts, as well as nutrient cost and biocatalyst performance as a system. Selection of a biocatalyst that can convert carbohydrate on a defined medium with average productivity and yield can lead to better economics than selection of a biocatalyst that functions at higher productivity and yields on complex media.

Example 19

Dry corn is milled into a fine powder. The dry milled corn is slurried and jet cooked at temperature of about 105° C. and then alpha-amylase enzyme is added. The stream is cooled and gluco-amylase is added. After a short saccharification time of about 5-6 hours, the slurry is cooled to about 32° C. The slurry solids concentration at this point is about 361 g/kg, insoluble and soluble solids. Three equal aliquots of the corn slurry are placed in three identical batch fermenter tanks. A biocatalyst that can convert dextrose to isobutanol is added to all tanks. Furthermore, each of the three vessels is supplemented with additional nutrients, as shown in Table 9.

TABLE 9

Media supplementations for fermenters S1-S3 listed in g/L.

| | Fermenter S1 | Fermenter S2 | Fermenter S3 |
|---|---|---|---|
| Yeast Extract | 0 | 5 | 2.5 |
| Peptone | 0 | 10 | 5 |
| Ammonium Sulfate | 5 | 5 | 5 |
| Potassium Phosphate Monobasic | 1 | 1 | 1 |
| Magnesium Sulfate | 0.5 | 0.5 | 0.5 |
| Sodium Chloride | 0.1 | 0.1 | 0.1 |
| Calcium Chloride | 0.1 | 0.1 | 0.1 |
| Biotin | 0.000002 | 0 | 0 |
| D-Pantothenic Acid•Ca | 0.0004 | 0 | 0 |
| Folic Acid | 0.00002 | 0 | 0 |
| Inositol | 0.002 | 0 | 0 |
| Niacin | 0.0004 | 0 | 0 |
| p-Aminobenzoic Acid | 0.0002 | 0 | 0 |
| Pyridoxine HCl | 0.0004 | 0 | 0 |
| Riboflavin | 0.0002 | 0 | 0 |
| Thiamine HCl | 0.0004 | 0 | 0 |

The vessels are agitated for 52 hours. At the end of 52 hours, the fermentation broth is analyzed for isobutanol content and carbon sources. Analysis of the fermentation samples reveals the fermentation performance summarized in Table 10 for isobutanol titers, production rates, and production yields.

TABLE 10

Summary of fermentation performance for fermentations S1-S3 described above.

| | Fermenter S1 | Fermenter S2 | Fermenter S3 |
|---|---|---|---|
| Isobutanol Production Rate (g/L/h) | 1.05 | 1.5 | 1.35 |
| Isobutanol Yield (% theoretical) | 81 | 90 | 90 |
| Isobutanol Titer (g/L) | 66.5 | 95 | 85.5 |

The fermentation of fermenter S1 utilizes a defined media consisting of salts plus vitamins results in relatively low isobutanol rates, titers and yields, whereas fermentation S2 on rich complex media achieves the highest performance. The fermentation of fermenter S3 achieves results between the fermentation of fermenter S1 and the fermentation of fermenter S2 in volumetric rate, titer and yield.

Economic analysis of the three batch fermentations indicates isobutanol recovery from the fermentation of fermenter S2 has the highest isobutanol yield on carbohydrate. The fermentation of fermenter S1 has carbohydrate costs 29% greater than the fermentation of fermenter S2 on a unit of biofuels production basis. The fermentation of fermenter S3 shows carbohydrate cost 11% higher than the fermentation of fermenter S2. The economic comparison of nutrient costs reveals that the fermentation of fermenter S1 is the most economical nutrient composition of all three examples. The fermentation of fermenter S2 has nutrient costs more than 40 times the cost of nutrients for the fermentation of fermenter S1. The fermentation of fermenter S3 has nutrients costing 24 times those of the fermentation of fermenter S1. In this example, the fermentation of fermenter S1 has the lowest biofuel cost even though the fermentations of fermenters S2 and S3 show better fermentation performance. Carbohydrate and nutrient cost for the fermentation of fermenter S2 is 52.5% greater than the fermentation of fermenter S1. Carbohydrate and nutrient costs for the fermentation of fermenter S3 are 27.8% more expensive than the fermentation of fermenter S1.

This example demonstrates that economic production of a biofuel, and here isobutanol, must consider the biocatalyst efficiency at carbohydrate conversion, as well as the nutrient cost and biocatalyst performance as a system. Selection of a biocatalyst that can convert carbohydrate utilizing a low cost minimal medium consisting of a low cost nutrient package with average productivity and yield can provide a lower cost biofuel production compared to complex media producing higher productivities or concentrations. The low cost nutrient package needs to be chosen to provide the low cost biofuel production and must take into account the feed stock, fermentation performance and downstream recovery and purification.

Example 20

A cellulosic material consisting of 45% cellulose, 25% hemicellulose, 22% lignin and 8% other materials is pretreated to yield slurry of 8% insoluble cellulose with about 4% insoluble lignin, 1% glucose, 40 g/l xylose, 2 g/l mannose, 2 g/l galactose, 1 g/l arabinose, 5 g/l acetic acid in solution. For each experiment, equal portions of the pretreated cellulosic material are added into four agitated saccharification and fermentation vessels. All four experiments are charged with cellulase enzyme sufficient to hydrolyze 80% of the cellulose, and are run in batch mode over 72 hours. Biocatalysts TA and TB are known to convert glucose, xylose, mannose, galactose and arabinose to butanol. Biocatalyst TA is added to the fermentations of fermenters T1 and T2. Biocatalyst TB is added to the fermentations of fermenters T3 and T4. The fermentation vessels are configured with an alkali and acid feed pH control system. Furthermore, each of the four vessels is supplemented with additional nutrients, as shown in Table 11.

TABLE 11

Media supplementations for fermenters T1-T4 listed in g/L.

| | Fermenter T1 and T3 | Fermenter T2 and T4 |
|---|---|---|
| Yeast Extract | 10 | 0 |
| Peptone | 20 | 0 |
| Ammonium Sulfate | 0 | 5 |
| Potassium Phosphate Monobasic | 0 | 1 |
| Magnesium Sulfate | 0 | 0.5 |
| Sodium Chloride | 0 | 0.1 |
| Calcium Chloride | 0 | 0.1 |
| Biotin | 0 | 0.000002 |
| D-Pantothenic Acid•Ca | 0 | 0.0004 |
| Folic Acid | 0 | 0.00002 |
| Inositol | 0 | 0.002 |
| Niacin | 0 | 0.0004 |
| p-Aminobenzoic Acid | 0 | 0.0002 |
| Pyridoxine HCl | 0 | 0.0004 |
| Riboflavin | 0 | 0.0002 |
| Thiamine HCl | 0 | 0.0004 |

The vessels are agitated for 72 hours. At the end of 72 hours the fermentation broth is analyzed for butanol and carbon sources. Analysis of the fermentation samples reveals the fermentation performance summarized in Table 12 for butanol titers, production rates and production yields.

TABLE 12

Summary of fermentation performance for fermentations T1-T4 described above.

| | Fermenter T1, Biocatalyst TA | Fermenter T2, Biocatalyst TA | Fermenter T3, Biocatalyst TB | Fermenter T4, Biocatalyst TB |
|---|---|---|---|---|
| Butanol Rate (g/L/h) | 1 | 0.5 | 1 | 0.25 |
| Butanol Yield (% theoretical) | 90 | 72 | 90 | 36 |
| Butanol Titer (g/L) | 45 | 22.5 | 45 | 11 |

The fermentation of fermenter T1 and the fermentation of fermenter T3 on rich, complex media achieved the highest performance. The fermentation of fermenter T2 with Biocatalyst TA on salts plus vitamins defined media results in intermediate butanol rates, titers and yields, whereas the fermentation of fermenter T4 with Biocatalyst TB achieved a low rate, titer and yield.

Economic analysis of the four batch fermentations indicates butanol recovered from the fermentation of fermenter T1 and T3 have the highest butanol to carbohydrate yield. The fermentation of fermenter T2 has 60% greater carbohydrate costs than the fermentation of fermenter T1 and T3. The fermentation of fermenter T4 carbohydrate costs are 120% higher compared to the fermentations of fermenters T1 and T3. The economic comparison of nutrient costs reveals that the fermentations of fermenters T2 and T4 are the most economical nutrient compositions of all four experiments. The fermentations of fermenters T1 and T3 have nutrient costs at almost 600% that of the fermentation of fermenter T2. The fermentation of fermenter T4 has nutrient costs similar to that of the fermentation of fermenter T2. When economic costs for carbohydrate and nutrients are combined, the experiments show the fermentation of fermenter T2 to be the most cost effective. Carbohydrate and nutrient costs for the fermentations of fermenters T1 and T3 are the same. Carbohydrate and nutrient costs for the fermentations of fermenters T1 and T3 are 312% that of the fermentations of fermenters T2. Carbohydrate and nutrient costs for the fermentation of fermenter T4 is about 200% greater than for the fermentation of fermenter T2.

This example demonstrates that economic production of biofuel, and here butanol, must consider both the efficiency of carbohydrate conversion by the biocatalysts and nutrient cost and performance as a biofuel fermentation system. As Biocatalyst TA operates with better performance on a defined medium, relative to the performance of Biocatalyst TB, whereas in complex medium, Biocatalyst TA and Biocatalyst TB have the same performance. Therefore, Biocatalyst TA is economically superior to Biocatalyst TB. Selection of an organism that can convert carbohydrate into biofuel on low-cost, defined medium with sufficient productivity and yield can lead to better economics than selection of a biocatalyst that leads to insufficient productivity and yield of biofuel on low-cost, defined medium and, therefore, requires complex medium for economical productivity and yield.

Example 21

A cellulosic material consisting of 45% cellulose, 25% hemicellulose, 22% lignin and 8% other materials is pretreated to yield slurry of 8% insoluble cellulose with about 4% insoluble lignin, 1% glucose, 40 g/l xylose, 2 g/l mannose, 2 g/l galactose, 1 g/l arabinose, 5 g/l acetic acid in solution. For each experiment, equal portions of the pretreated cellulosic material are added into an agitated saccharification and fermentation vessel. All four experiments are charged with cellulase enzyme sufficient to hydrolyze 80% of the cellulose and are run in batch mode over 72 hours. Biocatalysts UA and UB are known to convert glucose, xylose, mannose, galactose and arabinose to butanol. Biocatalyst UA is added to fermentations U1 and U2. Biocatalyst UB is added to fermentations U3 and U4. The fermentation vessels are configured with an alkali and acid feed pH control system. Furthermore, each of the four vessels is supplemented with additional nutrients, as shown in Table 13.

TABLE 13

Media supplementations for fermenters U1-U4 listed in g/L.

|  | Fermenter U1 and U3 | Fermenter U2 and U4 |
|---|---|---|
| Yeast Extract | 0 | 0 |
| Peptone | 0 | 0 |
| Ammonium Sulfate | 5 | 5 |
| Potassium Phosphate Monobasic | 1 | 1 |
| Magnesium Sulfate | 0.5 | 0.5 |
| Sodium Chloride | 0.1 | 0.1 |
| Calcium Chloride | 0.1 | 0.1 |
| Iron Sulfate | 0.1 | 0.1 |
| Biotin | 0.000002 | 0 |
| D-Pantothenic Acid•Ca | 0.0004 | 0 |
| Folic Acid | 0.00002 | 0 |
| Inositol | 0.002 | 0 |
| Niacin | 0.0004 | 0 |
| p-Aminobenzoic Acid | 0.0002 | 0 |
| Pyridoxine HCl | 0.0004 | 0 |
| Riboflavin | 0.0002 | 0 |
| Thiamine HCl | 0.0004 | 0 |

The vessels are agitated for 72 hours. At the end of 72 hours the fermentation broth is analyzed for butanol and carbon sources. Analysis of the fermentation samples reveals the fermentation performance summarized in Table 14 for butanol titers, production rates and production yields.

TABLE 14

Summary of fermentation performance for fermentations U1-U4 described above

|  | Fermenter U1, Biocatalyst UA | Fermenter U2, Biocatalyst UA | Fermenter U3, Biocatalyst UB | Fermenter U4, Biocatalyst UB |
|---|---|---|---|---|
| Butanol Rate (g/L/h) | 1 | 1 | 1 | 0.5 |
| Butanol Yield (% theoretical) | 90 | 90 | 90 | 45 |
| Butanol Titer (g/L) | 45 | 45 | 45 | 22.5 |

The fermentation of fermenter U1 and the fermentation of fermenter U3 on minimal medium plus vitamins result in equal butanol rates, titers and yields. The fermentation of fermenter U2 with Biocatalyst UA on salts defined media results in equal butanol rate, titer and yield when compared to Fermentations U1 and U3. However, the fermentation of fermenter U4 with Biocatalyst UB achieved a lower rate, titer and yield, relative to the fermentations of fermenters U1, U2, and U3.

Economic analysis of the four batch fermentations indicates butanol recovered from the fermentations of fermenters U1, U2, and U3 have the highest butanol to carbohydrate yield. The fermentation of fermenter U4 has 60% greater carbohydrate costs than the fermentations of fermenters U1, U2, and U3. The fermentations of fermenters U2 and U4 use the most economical nutrient composition of all four fermentations. The fermentations of fermenters U1 and U3 have nutrient costs at almost 150% that of the fermentation of fermenter U2. The fermentation of fermenter U4 has nutrient costs at almost 200% that of the fermentation of fermenter U2. When economic costs for carbohydrate and nutrients are combined, the experiments show the fermentation of fermenter U2 to be the most cost effective. Carbohydrate and nutrient costs for the fermentations of fermenters U1 and U3 are the same. Carbohydrate and nutrient costs for the fermentations of fermenters U1 and U3 are 150% that of the fermentation of fermenter U2. Carbohydrate and nutrient costs for the fermentation of fermenter U4 is about 200% that of the fermentation of fermenter U2. The biocatalyst UA is able to produce butanol with only mineral salts composed of major and minor bioelements, whereas the biocatalyst UB requires addition of vitamins and other nutrients. Therefore, since the fermentation in fermenter U2 using biocatalyst UA is the most economical for production of butanol, the biocatalyst UA is economically superior to biocatalyst UB and is thus the preferred biocatalyst.

This example demonstrates that economic production of biofuel must consider both the efficiency of carbohydrate conversion by the biocatalysts, nutrient cost, and biocatalyst performance as a biofuel fermentation system. Biocatalyst UA operates with better performance on a minimal medium, relative to the performance of Biocatalyst UB, whereas in minimal medium plus vitamins, Biocatalyst UA and Biocatalyst UB have the same performance. Therefore, Biocatalyst UA is economically superior to Biocatalyst UB. Selection of an organism that can convert a feedstock like carbohydrate into biofuel on low-cost, minimal medium of mineral salts comprised of major and minor bioelements in addition to the feedstock, and with sufficient productivity and yield, can lead to better economics than selection of a biocatalyst that leads to insufficient productivity and yield on low-cost, minimal medium and, therefore, requires vitamins for economically-viable productivity and yield.

Example 22

A cellulosic material consisting of 45% cellulose, 25% hemicellulose, 22% lignin and 8% other materials is pretreated to yield slurry of 8% insoluble cellulose with about 4% insoluble lignin, 1% glucose, 40 g/l xylose, 2 g/l mannose, 2 g/l galactose, 1 g/l arabinose, 5 g/l acetic acid in solution. For each experiment, equal portions of the pretreated cellulosic material are added into four agitated saccharification and fermentation vessels. All four experiments are charged with cellulase enzyme sufficient to hydrolyze 80% of the cellulose and are run in batch mode over 72 hours. Biocatalysts VA and VB are known to convert glucose, xylose, mannose, galactose and arabinose to butanol. Biocatalyst VA is added to the fermentations of fermenters V1 and V2. Biocatalyst VB is added to the fermentations of fermenters V3 and V4. The fermentation vessels are configured with an alkali and acid feed pH control system. Furthermore, each of the four vessels is supplemented with additional nutrients, as shown in Table 15.

TABLE 15

Media supplementations for fermenters V1-V4 listed in g/L.

| | Fermenter V1 and V3 | Fermenter V2 and V4 |
|---|---|---|
| Yeast Extract | 0 | 0 |
| Peptone | 0 | 0 |
| Ammonium Sulfate | 5 | 5 |
| Potassium Phosphate Monobasic | 1 | 1 |
| Magnesium Sulfate | 0.5 | 0.5 |
| Sodium Chloride | 0.1 | 0 |
| Calcium Chloride | 0.1 | 0 |
| Sodium Sulfate | 0 | 0.1 |
| Calcium Phosphate | 0 | 0.1 |
| Iron Sulfate | 0.1 | 0.1 |

The vessels are agitated for 72 hours. At the end of 72 hours, the fermentation broth is analyzed for butanol and carbon sources. Analysis of the fermentation samples reveals the fermentation performance summarized in Table 16 for butanol titers, production rates and production yields.

TABLE 16

Summary of fermentation performance for fermentations V1-V4 described above.

| | Fermenter V1, Biocatalyst VA | Fermenter V2, Biocatalyst VA | Fermenter V3, Biocatalyst VB | Fermenter V4, Biocatalyst VB |
|---|---|---|---|---|
| Butanol Rate (g/L/h) | 1 | 1 | 1 | 0.5 |
| Butanol Yield (% theoretical) | 90 | 90 | 90 | 45 |
| Butanol Titer (g/L) | 45 | 45 | 45 | 22.5 |

The fermentation of fermenter V1 and the fermentation of fermenter V3 on minimal medium with chloride salts result in equal butanol rates, titers and yields. The fermentation of fermenter V2 with Biocatalyst VA on minimal medium without chloride salts results in equal butanol rate, titer and yield when compared to the fermentations of fermenters V1 and V3. However, the fermentation of fermenter V4 with Biocatalyst VB achieved a lower rate, titer and yield, relative to Fermenters V1, V2, and V3.

Economic analysis of the four batch fermentations indicates butanol recovered from the fermentations of fermenters V1, V2, and V3 have the highest butanol to carbohydrate yield. The fermentation of fermenter V4 has carbohydrate costs 200% that of the fermentations of fermenters V1, V2, and V3. The fermentation of fermenter V4 has nutrient costs almost 150% that of the fermentations of fermenters V1, V2, and V3 relative to butanol produced. When economic costs for carbohydrate and nutrients are combined, the experiments show the fermentations of fermenters V1, V2, and V3 to be the most cost effective. Carbohydrate and nutrient costs for the fermentation of fermenter V4 are about 250% than the costs of the fermentations of fermenters V1, V2, and V3. Capital costs for the fermentations of fermenters V2 and V4 are less than the capital costs for the fermentations of fermenters V1 and V3. The presence of chloride salts in the fermentation of fermenter V1 and V3 make it necessary to use stainless steel to build the fermentation vessels and the downstream equipment for these fermentations. However, the lack of chloride salts in the added nutrients in the fermentations of fermenters V2 and V4 permit the use of carbon steel. Carbon steel is much less expensive than stainless steel, and therefore the capital costs for the fermentations of fermenters V2 and V4 are lower. However, for the fermentations of fermenters V4, the lower performance of the biocatalyst without chloride in the nutrients added leads to an increase in capital costs relative to fermentation V2 because a larger vessel size is needed to compensate for the lower performance of Biocatalyst VB. In summary, Biocatalyst VA is superior to Biocatalyst VB because capital and operating costs are lower.

This example demonstrates that economic production of biofuel must consider both the efficiency of carbohydrate conversion by the biocatalysts, nutrient cost, biocatalyst performance as a biofuel fermentation system and capital cost requirements. Biocatalyst VA operates with better performance on a minimal medium excluding chloride salts, relative to the performance of Biocatalyst VB, whereas in minimal medium including chloride salts, Biocatalyst VA and Biocatalyst VB have the same performance. Therefore, Biocatalyst VA is economically superior to Biocatalyst VB. Selection of an organism that can convert a feedstock like carbohydrate into biofuel like butanol on minimal medium excluding chloride salts with sufficient productivity and yield can lead to better economics than selection of a biocatalyst that leads to insufficient productivity and yield on minimal medium without chloride salts and, therefore, requires chloride salts for economical productivity and yield.

Example 23

A cellulosic material consisting of 45% cellulose, 25% hemicellulose, 22% lignin and 8% other materials is pretreated to yield slurry of 8% insoluble cellulose with about 4% insoluble lignin, 1% glucose, 40 g/l xylose, 2 g/l mannose, 2 g/l galactose, 1 g/l arabinose, 5 g/l acetic acid in solution. For each experiment, equal portions of the pretreated cellulosic material are added into an agitated saccharification and fermentation vessel. All six experiments are charged with cellulase enzyme sufficient to hydrolyze 80% of the cellulose and are run in batch mode over 72 hours. Biocatalysts WA, WB, and WC are anaerobes known to convert glucose, xylose, mannose, galactose and arabinose to butanol. Biocatalyst WA does not function in the presence of oxygen, but recovers from oxygen exposure and regains its original butanol specific productivity when oxygen is removed. When exposed to oxygen for 3 hours, Biocatalyst WB is damaged such that it loses 50% of its butanol specific productivity. When exposed to oxygen for 3 hours, Biocatalyst WC is damaged such that it loses all of its butanol specific productivity. All three biocatalysts continue to consume feedstock when exposed to oxygen. Biocatalyst WA is added to Fermenter W1 and Fermenter W2. Biocatalyst WB is added to Fermenter W3 and Fermenter W4. Biocatalyst WC is added to Fermenter W5 and Fermenter W6. All six fermenters contain 3 g/cell dry weight of throughout the experiment.

At the beginning of the fermentations, all fermenters are controlled to exclude oxygen completely. Fermenters W1, W3 and W5 remain completely without oxygen throughout the fermentation. Fermenters W2, W4, and W6 are exposed to oxygen at a dissolved oxygen concentration of about 10% air saturation at 36 hours into the fermentation. The oxygen exposure lasts for about 3 hours and then oxygen is removed completely from Fermenters W2, W4, and W6 for the remainder of the fermentations. The vessels are operated for 72 hours. At the end of 72 hours the fermentation broth is analyzed for butanol.

Fermentations W1, W3, and W5 produce the same amount of butanol after 72 hours. Fermentation W2 produces 4% less butanol than Fermentations W1, W3, and W5. Fermentation W4 produces 16.5% less butanol than Fermentations W1, W3, and W5. Fermentation W6 produces 50% less butanol than Fermentations W1, W3, and W5.

Economic analysis of the six batch fermentations indicates butanol recovered from Fermentations W1, W3, and W5, which have the highest volumetric productivity, can be produced at a lower cost. The cost of butanol produced in Fermentation W2 is slightly more expensive than butanol produced in Fermentations W1, W3, and W5. The cost of butanol produced in Fermentation W4 is more expensive than butanol produced in Fermentation W2. The cost of butanol produced in Fermentation W6 is significantly more expensive than butanol produced in Fermentation W2. The reduced butanol titer of fermentations W2, W4, and W6 results in higher operating costs since less butanol is produced from the same amount of feedstock consumed and in the same amount of time. Furthermore, the lower titer reached in these fermentations requires higher energy input during downstream separation and processing, thus further increasing the costs of fermentations W2, W4, and W6. However, the additional operating costs incurred using biocatalyst WA are less than the operating costs incurred through the use of biocatalysts WB and WC. Therefore, biocatalyst WA is the most economical biocatalyst when introduction of oxygen occurs during an anaerobic fermentation because biocatalyst WA can tolerate brief exposure to oxygen and regains 100% of the specific butanol productivity once the oxygen is removed.

If consistent costs for butanol production are to be achieved and to compensate for differences in performance of biocatalysts WA, WB, and WC under the conditions of this example, a manufacturing facility must build fermentation vessels of different sizes to ensure equal overall productivity of the manufacturing facility. The reduced productivity in fermenter W2 results in a slight increase in capital costs, relative to Fermenters W1, W3, and W5. The reduced productivity in fermenter W4 results in a moderate increase in capital costs, relative to Fermenter W2. The reduced productivity in fermenter W6 results in a significant increase in capital costs, relative to Fermenter W2. In order to reach the same overall productivity that is reached in fermentation W2 and by biocatalyst WA, a biofuel manufacturing facility operating fermenters W4 and W6 requires larger volume fermentation vessels built at a higher capital expense. The results of these fermentations at various levels of oxygen contamination demonstrate the impact of utilization of an oxygen tolerant biocatalyst capable of recovering from exposure to oxygen on the capital costs of the biofuel production process.

Example 24

A cellulosic material consisting of 45% cellulose, 25% hemicellulose, 22% lignin and 8% other materials is pretreated to yield slurry of 8% insoluble cellulose with about 4% insoluble lignin, 1% glucose, 40 g/l xylose, 2 g/l mannose, 2 g/l galactose, 1 g/l arabinose, 5 g/l acetic acid in solution. For each experiment, equal portions of the pretreated cellulosic material are added into four agitated saccharification and fermentation vessels. All four experiments are charged with cellulase enzyme sufficient to hydrolyze 80% of the cellulose and are run in batch mode over 72 hours. Biocatalysts XA and XB are anaerobes known to convert glucose, xylose, mannose, galactose and arabinose to isobutanol. Biocatalyst XA functions in the presence of small amounts of oxygen. When exposed to oxygen, Biocatalyst XB is damaged such that it loses 50% of its specific productivity. Biocatalyst XA is added to Fermenter X1 and Fermenter X2. Biocatalyst XB is added to Fermenter X3 and Fermenter X4. All four fermenters contain 3 g/cell dry weight of throughout the experiment.

Fermenters X1 and X3 remain completely without oxygen throughout the fermentation. Fermenters X2 and X4 are exposed to oxygen at a dissolved oxygen concentration of 0.1% saturation throughout the fermentation. The vessels are operated for 72 hours. At the end of 72 hours the fermentation broth is analyzed for isobutanol. Fermentations X1, X2 and X3 produce the same amount of isobutanol after 72 hours. Fermentation X4 produces 50% less isobutanol than Fermentations X1, X2, and X3.

Economic analysis of the four batch fermentations indicates isobutanol recovered from Fermentations X1, X2, and X3, which have the highest volumetric productivity, can be produced at a lower cost. However, the overall cost of isobutanol produced in Fermenter X2, using Biocatalyst XA, is less expensive than isobutanol produced in Fermenters X1 and X3. The operating costs of Fermenter X2 are lower, since less heat in the form of steam and oxygen-free gas must be used to remove oxygen from the fermenter. The cost of isobutanol produced in Fermentation X4 is significantly more expensive than isobutanol produced in Fermentations X1, X2, and X3. Therefore, a biofuel manufacturing facility operating a process that uses Biocatalyst XA can operate a fermentation setup that permits small amounts of oxygen to be present in the fermentation broth without sacrificing the overall productivity of the process. To compensate for differences in performance of biocatalysts XA and XB under the conditions of this example, a biofuel manufacturing facility must build fermentation vessels of increased size or of material composition that exclude oxygen completely to ensure equal overall productivity of the biofuel manufacturing facility. The reduced productivity of Biocatalyst XB in fermenter X4 results in a significant increase in capital costs, relative to Biocatalyst XA in Fermenter X2. The results of these fermentations at various levels of oxygen contamination demonstrate the impact of utilization of an oxygen tolerant organism capable of recovering from exposure to oxygen on the capital costs of the biofuel production process.

Example 25

A cellulosic material consisting of 45% cellulose, 25% hemicellulose, 22% lignin and 8% other materials is pretreated to yield slurry of 8% insoluble cellulose with about 4% insoluble lignin, 1% glucose, 40 g/l xylose, 2 g/l mannose, 2 g/l galactose, 1 g/l arabinose, 5 g/l acetic acid in solution. For each experiment, equal portions of the pretreated cellulosic material are added into an agitated saccharification and fermentation vessel. All four experiments are charged with cellulase enzyme sufficient to hydrolyze 80% of the cellulose and are run in batch mode over 72 hours. Biocatalysts YA and YB are facultative anaerobes known to convert glucose, xylose, mannose, galactose and arabinose to butanol. Biocatalyst YA is modified such that it does not consume oxygen through respiration, but instead in the presence of oxygen, the biocatalyst still produces butanol at undiminished productivity. When exposed to oxygen, Biocatalyst YB activates aerobic pathways that lead to byproducts that reduce the yield of butanol. Biocatalyst YA is added to Fermenter Y1 and Fermenter Y2. Biocatalyst YB is added to Fermenter Y3 and Fermenter Y4. All four fermenters contain 3 g/cell dry weight of throughout the experiment.

Fermenters Y1 and Y3 remain completely without oxygen throughout the fermentation. Oxygen levels in Fermenters Y2 and Y4 are maintained at 0.1% air saturation dissolved oxygen concentration. The vessels are operated for 72 hours. At the end of 72 hours the fermentation broth is analyzed for butanol. Fermentations Y1, Y2 and Y3 produce the same amount of butanol after 72 hours. Fermentation Y4 produces 50% less butanol than Fermentations Y1, Y2, and Y3. All four fermenters consume the same amount of feedstock. Economic analysis of the four batch fermentations indicates butanol recovered from Fermentations Y1, Y2, and Y3, which have the highest titers of butanol, can be produced at a lower cost. However, the overall cost of butanol produced in Fermenter Y2, using Biocatalyst YA, is less expensive than butanol produced in Fermenters Y1 and Y3. The operating costs of Fermenter Y2 are lower, since less heat in the form of steam and oxygen-free gas must be used to remove oxygen from the fermenter. The cost of butanol produced in Fermentation Y4 is significantly more expensive than butanol produced in Fermentations Y1, Y2, and Y3, due to the lower yield of butanol and the increased cost of feedstock relative to the amount of butanol produced. Therefore, a biofuel manufacturing facility operating a process that uses Biocatalyst YA can operate a biofuel fermentation setup that permits small amounts of oxygen to be present in the fermentation broth without sacrificing the overall productivity of the process. To compensate for differences in performance of biocatalysts YA and YB under the conditions of this example, a biofuel manufacturing facility must build fermentation vessels of increased size or of material composition that exclude oxygen completely to ensure equal overall productivity of the manufacturing facility. The reduced productivity of Biocatalyst YB in fermenter Y4 results in a significant increase in capital costs, relative to Biocatalyst YA in Fermenter Y2. The results of these biofuel fermentations at various levels of oxygen contamination demonstrate the impact of utilization of an oxygen tolerant biocatalyst capable of recovering from exposure to oxygen on the capital costs of the process.

Example 26

Dry corn is milled into a fine powder. The dry milled corn is slurried and jet cooked at temperature of about 105° C. and then alpha-amylase enzyme is added. The stream is cooled and gluco-amylase is added. After a short saccharification time of about 5-6 hours the slurry is cooled to about 30° C. The slurry solids concentration at this point is about 361 g/kg (insoluble & soluble solids). Two equal aliquots of the corn slurry are placed in two identical batch fermenter tanks. No additional nutrients are added to fermentation tank Z1, whereas fermentation tank Z2 receives additional mineral salts and vitamins, as required by the properties of the biocatalysts ZA and ZB used in each tank (Table 17). Both tanks are inoculated with biocatalysts that can convert dextrose to isobutanol: Tank Z1 is inoculated with biocatalyst ZA and Tank Z2 is inoculated with biocatalyst ZB. Fermenter tanks Z1 and Z2 are operated under different conditions as required by the properties of the biocatalysts ZA and ZB used in each tank (Table 17). Both biocatalysts ZA and ZB are genetically engineered to convert dextrose to isobutanol. Biocatalyst ZA is engineered in a way such that it contains DNA consisting of natural DNA, however, biocatalyst ZB contains DNA comprised to 2% of foreign DNA, in the form of a DNA marker, as a result of the specific approach taken to engineer this organism for isobutanol production. Both tank Z1 and tank Z2 contain 1 g/L cell dry weight. Fermenter Z1 is temperature controlled at 30° C. and fermenter Z2 is controlled at 25° C. Fermenter Z1 is controlled at a pH of 5 and fermenter Z2 is controlled at a pH of 8. Both fermenter Z1 and fermenter Z2 experience equipment malfunctions that cause a 10° C. increase in temperature of the fermentation for a brief period of time. After this time, the fermenters are restored to their original temperature. Also, during the fermentation, both fermenter Z1 and fermenter Z2 experience equipment malfunctions that cause a one unit increase of pH in the fermentation for a brief period of time. After this time, the fermenters are restored to their original pH. The vessels are agitated until maximum titer is reached. At the point of maximum titer, the fermentation broth of each fermenter is analyzed for isobutanol content, byproducts, and dextrose. DDG product comprising spent biocatalyst ZA and spent biocatalyst ZB are analyzed for toxicity.

Analysis of the fermentation samples reveals the fermentation performance parameters summarized in Table 17 for isobutanol titers, production rates, production yields, toxicity of DDG, and growth rates. Fermenter Z1 produces isobutanol at a higher rate, titer, yield, compared to fermenter Z2 (Table 17). Biocatalyst ZA has a higher growth rate and lower toxicity compared to biocatalyst ZB (Table 17). The spent biocatalyst from fermentation Z1 is dried and added to DDGS sold for animal feed at current market rates. However the spent biocatalyst from fermenter Z2 are dried and burned for energy sold at current market rates.

TABLE 17

Summary of biocatalyst parameters and fermentation results for fermentations Z1 & Z2.

|  | Fermenter Z1 | Fermenter Z2 |
| --- | --- | --- |
| Production Biocatalyst | ZA | ZB |
| Isobutanol titer | 2% (w/w) | 1% (w/w) |
| Isobutanol Rate (g/l h) | 0.5 | 0.4 |
| DDG toxicity of 1 kg | 1/1000 of $LD_{50}$ | 1/250 of $LD_{50}$ |
| Isobutanol Yield (% theoretical) | 80 | 70 |
| Byproduct concentration | None | 5% |
| DNA content | Natural DNA | 2% foreign DNA |
| Operating pH | 5 | 8 |
| pH fluctuation | ±1 pH | ±1 pH |
| Operating temperature | 30° C. | 25° C. |

TABLE 17-continued

Summary of biocatalyst parameters and fermentation results for fermentations Z1 & Z2.

|  | Fermenter Z1 | Fermenter Z2 |
|---|---|---|
| Temperature fluctuation | ±10° C. | ±10° C. |
| Additional nutrients provided | None | Mineral salts and vitamins |
| Biocatalyst growth rate | 0.3 per h | 0.17 per h |

An economic analysis of the value of the DDGS sold as a feed in fermenter Z1 compared to burning the spent biocatalyst from fermenter Z2 is performed. Additionally, an economic analysis of the cost of the isobutanol produced from fermenter Z1 with biocatalyst ZA and fermenter Z2 with biocatalyst ZB is performed. Results of the economic analyses indicate that the co-product credit for selling the DDGS as animal feed results in a cost reduction of isobutanol compared to burning the spent biocatalyst. There is also a cost reduction of isobutanol per gallon as a result of the increased productivity, titer, yield, and biocatalyst ZA growth rate in fermenter Z1. Additionally, fermenter Z1 and biocatalyst ZA results in lower operating costs than fermenter Z2 and biocatalyst ZB, since no nutrients in addition to the feedstock are added. Further still, fermenter Z1 does not require as much energy for cooling as fermenter Z2 and thus energy costs for fermenter Z1 are less than for fermenter Z2. An economic analysis of the overall process costs for the two biocatalysts reveals that fermenter Z1 costs are 10% less than fermenter Z2. Thus, fermenter Z1 and biocatalyst ZA provide an economic advantage. This example illustrates the importance of economically superior performance parameters and properties of a biocatalyst in a biofuel production process, as shown in Table 17.

Example 27

A cellulosic material consisting of 45% cellulose, 25% hemicellulose, 22% lignin and 8% other materials is pretreated to yield slurry of 8% insoluble cellulose with about 4% insoluble lignin, 1% glucose, 40 g/l xylose, 2 g/l mannose, 2 g/l galactose, 1 g/l arabinose, 5 g/l acetic acid in solution. For each experiment, equal portions of the pretreated cellulosic material are added into an agitated saccharification and fermentation vessel. All fermenters are charged with cellulase enzyme sufficient to hydrolyze 80% of the cellulose. This results in about 119 g fermentable carbon source per kg dry feed used. Biocatalysts known to convert glucose, xylose, mannose, galactose and arabinose to butanol are added to each of nine fermentation vessels, but all nine biocatalysts exhibit different performance characteristics. Each fermentation vessel is configured with an alkali and acid feed pH control system. Biocatalyst AA1 shows a combination of optimal performance characteristics. All eight other biocatalysts are compared to AA1. Biocatalyst AA1 exhibits improved productivity, compared to biocatalyst AA2. Biocatalyst AA1 exhibits a higher titer due to lack of inhibition, compared to biocatalyst AA3. Biocatalyst AA1 exhibits a higher yield, compared to biocatalyst AA4. Biocatalyst AA1 exhibits a higher yield due to the lack of production of byproducts, compared to biocatalyst AA5. Biocatalyst AA1 exhibits a higher productivity due to lack of inhibition at process pH, compared to biocatalyst AA6, which exhibits partial inhibition at process pH. Biocatalyst AA1 exhibits a higher productivity than biocatalyst AA7 because biocatalyst AA7 exhibits partial inhibition at the process temperature. Biocatalyst AA8 shows the same performance as biocatalyst AA1, except only in the presence of 10 g/L complex nutrients (5 g/L of yeast extract and 5 g/L of peptone). Thus, 10 g/L complex nutrients are also added along with the feedstock to fermenter AA8. Biocatalyst AA9 combines all reduced performance characteristics of biocatalyst AA2 through biocatalyst AA8.

Fermentations are run and at the point of maximum titer, the runs are ended. Samples are taken from each fermenter and analyzed for butanol concentration. Analysis of the fermentation samples reveals the fermentation performance summarized in Table 18 for butanol titers, production rates and production yields. Resulting costs are based on a feedstock cost of $0.22/kg butanol. The butanol plant has a capacity of 100 million gallons per year. The capital costs for this plant are $8 million per million gallon fermenter capacity.

TABLE 18

Summary of performance for fermentations using biocatalysts AA1-AA9 and resulting costs.

| | Biocatalyst/Fermenter | | | | | | | | |
|---|---|---|---|---|---|---|---|---|---|
| | AA1 | AA2 | AA3 | AA4 | AA5 | AA6 | AA7 | AA8 | AA9 |
| Approximate medium cost (cents/L) | 0.1 | 0.1 | 0.1 | 0.1 | 0.1 | 0.1 | 0.1 | 5.1 | 5.1 |
| Butanol Rate (g/L h) | 1.0 | 0.8 | 1.0 | 1.0 | 1.0 | 0.6 | 0.4 | 1.0 | 0.2 |
| Butanol Yield (% theoretical) | 90.0 | 90.0 | 90.0 | 72.0 | 54.0 | 90.0 | 90.0 | 90.0 | 43.2 |
| Butanol Titer (g/L) | 45.0 | 45.0 | 22.5 | 45.0 | 45.0 | 45.0 | 45.0 | 45.0 | 22.5 |
| Capital cost for fermenter System (million $) | 72.3 | 90.3 | 72.3 | 72.3 | 72.3 | 120.4 | 180.6 | 72.3 | 380.3 |
| Capital costs compared to Biocatalyst AA1 (%) | 100 | 125 | 100 | 100 | 100 | 167 | 250 | 100 | 526 |
| Total Feedstock & Medium Costs Annually (million $) | 184.3 | 184.3 | 191.1 | 228.7 | 302.6 | 184.3 | 184.3 | 525.0 | 1064.7 |
| Sugar and nutrient costs ratio compared to biocatalyst AA1 (%) | 100 | 100 | 104 | 124 | 164 | 100 | 100 | 285 | 578 |

Economic analysis of the batch fermentations indicates butanol recovered from fermentation AA1 shows the best economics. Compared to fermentation AA1, fermentations AA2, AA6 and AA7 show higher capital costs of 125%, 167% and 250%, respectively. Compared to fermentation AA1, fermentations AA3, AA4, AA5 and AA8 show higher operating costs of 104%, 124%, 164% and 385%, respectively. Fermentation AA9 has a higher capital cost of 526% and a higher operating cost of 578% compared to fermentation AA1. In addition to the cost considerations of this model, increased down-stream recovery costs for processes based on less efficient biocatalysts also affect the overall process economics. Biocatalyst AA1 has favorable and economic down-stream recovery costs.

This example demonstrates that economic production of biofuel must consider a broad range of biocatalyst performance characteristics for the efficient conversion of a feedstock, such as carbohydrate, into a biofuel. Further, this example demonstrates that use of a biocatalyst with lower performance characteristics negatively impacts capital and operating costs of a biofuel production process. Selection and use of a biocatalyst that shows the best performance of a combination of characteristics for biofuel production is crucial for economic success.

Example 28

General Methods Used in this Disclosure

Sample Preparation:

All Samples (2 mL) from fermentation experiments performed in shake flasks were stored at −20° C. for later substrate and product analysis. Prior to analysis, samples were thawed, mixed well, and then centrifuged at 14,000×g for 10 min. The supernatant was filtered through a 0.2 µm filter. Analysis by HPLC or GC of substrates and products was performed using authentic standards (>99%, obtained from Sigma-Aldrich), and a five-point calibration curve (with 1-pentanol as an internal standard for analysis by gas chromatography).

Determination of Optical Density and Cell Dry Weight:

The optical density of cultures was determined at 600 nm using a DU 800 spectrophotometer (Beckman-Coulter, Fullerton, Calif., USA). Samples were diluted as necessary to yield an optical density of between 0.1 and 0.8. The cell dry weight was determined by centrifuging 50 mL of culture prior to decanting the supernatant. The cell pellet was washed once with 50 mL of milliQ $H_2O$, centrifuged and the pellet was washed again with 25 mL of milliQ $H_2O$. The cell pellet was then dried at 80° C. for at least 72 hours. The cell dry weight was calculated by subtracting the weight of the centrifuge tube from the weight of the centrifuge tube containing the dried cell pellet. For $E.$ $coli$ cultures, an OD600 to cell dry weight conversion factor of 0.25 was used.

Gas Chromatography:

Analysis of volatile organic compounds, including ethanol and isobutanol, was performed on a HP 5890 gas chromatograph fitted with an HP 7673 Autosampler, a DB-FFAP column (J&W; 30 m length, 0.32 mm ID, 0.25 µM film thickness) or equivalent connected to a flame ionization detector (FID). The temperature program was as follows: 200° C. for the injector, 300° C. for the detector, 100° C. oven for 1 minute, 70° C./minute gradient to 235° C., and then hold for 2.5 min. Analysis was performed using authentic standards (>99%, obtained from Sigma-Aldrich), and a 5-point calibration curve with 1-pentanol as the internal standard.

High Performance Liquid Chromatography:

Analysis of glucose and organic acids was performed on a HP-1100 High Performance Liquid Chromatography system equipped with a Aminex HPX-87H Ion Exclusion column (Bio-Rad, 300×7.8 mm) or equivalent and an $H^+$ cation guard column (Bio-Rad) or equivalent. Organic acids were detected using an HP-1100 UV detector (210 nm, 8 nm 360 nm reference) while glucose was detected using an HP-1100 refractive index detector. The column temperature was 60° C. This method was isocratic with 0.008N sulfuric acid in water as mobile phase. Flow was set at 0.6 mL/min. Injection size was 20 µL and the run time was 30 minutes.

Molecular Biology and Bacterial Cell Culture:

Standard molecular biology methods for cloning and plasmid construction were generally used, unless otherwise noted (Sambrook, J., Russel, D. W. *Molecular Cloning, A Laboratory Manual*. 3 ed. 2001, Cold Spring Harbor, N.Y.: Cold Spring Harbor Laboratory Press).

Standard recombinant DNA and molecular biology techniques used in the Examples are well known in the art and are described by Sambrook, J., Russel, D. W. *Molecular Cloning, A Laboratory Manual*. 3 ed. 2001, Cold Spring Harbor, N.Y.: Cold Spring Harbor Laboratory Press; and by T. J. Silhavy, M. L. Bennan, and L. W. Enquist, *Experiments with Gene Fusions*, Cold Spring Harbor Laboratory Press, Cold Spring Harbor, N.Y. (1984) and by Ausubel, F. M. et al., *Current Protocols in Molecular Biology*, pub. by Greene Publishing Assoc. and Wiley-Interscience (1987).

General materials and methods suitable for the routine maintenance and growth of bacterial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, eds.), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989).

Preparation of Electrocompetent Cells and Transformation:

The acceptor strain culture was grown in SOB-medium (Sambrook, J., Russel, D. W. *Molecular Cloning, A Laboratory Manual*. 3 ed. 2001, Cold Spring Harbor, N.Y.: Cold Spring Harbor Laboratory Press) to an $OD_{600}$ of about 0.6 to 0.8. The culture was concentrated 100-fold, washed once with ice cold water and 3 times with ice cold 10% glycerol. The cells were then resuspended in 150 µL of ice-cold 10% glycerol and aliquoted into 50 µL portions. These aliquots were used immediately for standard transformation or stored at −80° C. These cells were transformed with the desired plasmid(s) via electroporation. After electroporation, SOC medium (Sambrook, J., Russel, D. W. *Molecular Cloning, A Laboratory Manual*. 3 ed. 2001, Cold Spring Harbor, N.Y.: Cold Spring Harbor Laboratory Press) was immediately added to the cells. After incubation for an hour at 37° C. the cells were plated onto LB-plates containing the appropriate antibiotics and incubated overnight at 37° C.

Example 29

Construction of Strains and Plasmids:

GEVO1748 and GEVO1749 are derivatives of JCL260 ((WO 2008/098227) BIOFUEL PRODUCTION BY RECOMBINANT MICROORGANISMS). For the construction of GEVO1748 PLlacO1::kivd::ilvDco was integrated into the ilvC locus on the $E.$ $coli$ chromosome. In particular primers 869 and 1030 were used to amplify the kanamycin resistance cassette (Kan) from pKD13, and primers 1031 and 1032 were used to amplify PLlacO1::kivd::ilvDco from pGV1655. For the construction of GEVO1749 PLlacO1:: kivd::ilvDco was integrated into the adhE locus on the $E.$ $coli$ chromosome. In particular primers 50 and 1030 were used to amplify the kanamycin resistance cassette from pKD13, and primers 1031 and 1205 were used to amplify PLlacO1::kivd::ilvDco from pGV1655. Afterwards, SOE (splicing by overlap extension) (Horton, R M, Cai, Z L, Ho, S N, et al. Biotechniques Vol. 8 (1990) pp 528) reactions were done to connect the gene expression cassettes to the resistance cassette using primers 1032 and 869 for the ilvC locus and primers 1205 and 50 for the adhE locus.

The linear PCR products were transformed into W3110 pKD46 electro competent cells and the knock ins of PLlacO1::kivd::ilvDco::FRT::Kan::FRT were verified by PCR. The knock ins were further verified by sequencing. Lysates of the new strains E. coli W3110, ΔilvC::PLlacO1::kivd::ilvDco::FRT::Kan::FRT) and E. coli W3110, ΔadhE::PLlacO1::kivd::ilvDco::FRT::Kan::FRT) were prepared and the knock ins were transferred to JCL260 by P1 transduction. Removal of the Kan resistance cassette from this strain using expression of FLP recombinase yielded GEVO1748 and GEVO1749.

GEVO1844 is a derivative of GEVO1748 and was constructed by P1 transduction of the sthA gene deletion from the Keio collection strain CGSC11459 (E. coli BW25113, ΔsthA::FRT-kan-FRT) into GEVO1748. Removal of the Kan resistance cassette from this strain using expression of FLP recombinase yielded GEVO1844.

GEVO1859 was constructed according to the standard protocol for gene integration using the Wanner method (Datsenko, K. and Wanner, B. One-step Inactivation of chromosomal genes in Escherichia coli K-12 using PCR products. PNAS 2000). Primers 1219 and 1485 were used to amplify PLlacO1::alsS::ilvC co from pGV1698. Primers 1218 and 1486 were used to amplify the kan resistance cassette from pKD13. SOE (splicing by overlap extension) was used to combine the two pieces to one integration cassette. The linear PCR product was transformed into E. coli W3110 pKD46 electro competent cells and the knock in of PLlacO1::alsS::ilvC co::FRT::Kan::FRT into the pflB locus was verified by PCR. The knock in was further verified by sequencing. Lysate of the new strain (E. coli W3110, ΔpflB::PLlacO1::alsS::ilvC co::FRT::Kan::FRT) was prepared and the knock in was transferred into GEVO1749 by P1 transduction. Removal of the Kan resistance cassette from this strain using expression of FLP recombinase yielded GEVO1859.

GEVO1886 (E. coli BW25113, ΔldhA-fnr::FRT, Δfrd::FRT, Δpta::FRT, (laclq+), ΔadhE::[pLlacO1::kivd::ilvDco::FRT], ΔpflB::[pLlacO1::alsS::ilvCco::FRT] ΔsthA::[pLlacO1::pntA::pntB::FRT]) was constructed according to the standard protocol for gene integration using the Wanner method (Datsenko, K. and Wanner, B. One-step Inactivation of chromosomal genes in Escherichia coli K-12 using PCR products. PNAS 2000). Primers 1562 and 1539 were used to amplify PLlacO1::pntAB from pGV1745. Primers 1479 and 1561 were used to amplify the kan resistance cassette from pKD13. SOE was used to combine the two pieces to one integration cassette. The linear PCR product was transformed into E. coli W3110 pKD46 electro competent cells and the knock in of PLlacO1::pntAB::FRT::Kan::FRT into the sthA locus was verified by PCR. The knock in was further verified by sequencing. Lysate of the new strain (E. coli W3110, ΔsthA::PLlacO1::pntAB::FRT::Kan::FRT) was prepared and the knock in was transferred into GEVO1859 by P1 transduction. Removal of the Kan resistance cassette from this strain using expression of FLP recombinase yielded GEVO1886.

GEVO1530 is a derivative of JCL260 and was constructed by deletion of aceF and mdh from the E. coli chromosome.

The gene aceF was deleted according to the standard protocol for gene integration using the Wanner method (Datsenko, K. and Wanner, B. One-step Inactivation of chromosomal genes in Escherichia coli K-12 using PCR products. PNAS 2000). Primers 1026 and 1027 were used to amplify the Kan resistance cassette from pKD13. The linear PCR product was transformed into E. coli W3110 pKD46 electro competent cells and the knockout of aceF was verified by PCR. Lysate of the new strain (E. coli W3110, ΔaceF::FRT::Kan::FRT) was prepared and the knock out was transferred into JCL260 by P1 transduction. The Kan resistance cassette was removed from this strain using expression of FLP recombinase. The gene mdh was deleted according to the standard protocol for gene integration using the Wanner method (Datsenko, K. and Wanner, B. One-step Inactivation of chromosomal genes in Escherichia coli K-12 using PCR products. PNAS 2000). Primers 226 and 227 were used to amplify the Kan resistance cassette from pKD13. The linear PCR product was transformed into E. coli W3110 pKD46 electro competent cells and the knockout of mdh was verified by PCR. Lysate of the new strain (E. coli W3110, Δmdh::FRT::Kan::FRT) was prepared and the knock out was transferred into JCL260, aceF by P1 transduction. Removal of the Kan resistance cassette from this strain using expression of FLP recombinase yielded GEVO1530.

GEVO1627 is a derivative of E. coli B (USDA, NRRL B-14943). To create an isobutanol production strain based on E. coli B the main competing pathway to the isobutanol pathway was deleted by deletion of the adhE gene coding for the alcohol dehydrogenase. Also to render the expression of the isobutanol pathway genes from plasmids inducible the Z1 module which contains the laclq expression cassette was integrated into this strain. E. coli B is known to have less catabolite repression than E. coli K12 which enables this strain to convert several carbon sources at the same time. Also the B strain is known to maintain low acetate levels during fermentation. Both characteristics are advantageous for an isobutanol production strain. In particular the adhE gene was deleted according to the standard protocol for gene integration using the Wanner method (Datsenko, K. and Wanner, B. One-step Inactivation of chromosomal genes in Escherichia coli K-12 using PCR products. PNAS 2000). Primers 49 and 50 were used to amplify the Kan resistance cassette from pKD13. The linear PCR product was transformed into E. coli WA837 pKD46 electro competent cells and the knockout of adhE was verified by PCR. Lysate of the new strain (E. coli WA837, ΔadhE::FRT::Kan::FRT) was prepared and the knock out was transferred into E. coli B by P1 transduction. The Z1 module was integrated into the chromosome of E. coli B ΔadhE::FRT::Kan::FRT by P1 transduction from the strain E. coli W3110,Z1 (Lutz, R, Bujard, H Nucleic Acids Research (1997) 25, 1203-1210). The resulting strain was GEVO1627.

Table 19 details the genotype of strains disclosed herein:

| Strain | Genotype |
| --- | --- |
| GEVO1530 | E. coli BW25113, ΔldhA-fnr::FRT, ΔadhE::FRT, Δfrd::FRT, Δpta::FRT, pflB::FRT, Δmdh::FRT, ΔaceF::FRT F' (laclq+) |
| GEVO1627 | E. coli B, ΔadhE::FRT-kan-FRT, attB::(Sp+ laclq+ tetR+) |

-continued

| Strain | Genotype |
|---|---|
| GEVO1748 | E. coli BW25113, ΔldhA-fnr::FRT, ΔadhE::FRT, Δfrd::FRT, Δpta::FRT, pflB::FRT, F' (lacIq+), ΔilvC::[PLlacO1::kivd::ilvDco::FRT] |
| GEVO1749 | E. coli BW25113, ΔldhA-fnr::FRT, Δfrd::FRT, Δpta::FRT, pflB::FRT, F' (lacIq+), ΔadhE::[PLlacO1::kivd::ilvDco::FRT] |
| GEVO1780 | E. coli BW25113, ΔldhA-fnr::FRT, ΔadhE::FRT, Δfrd::FRT, Δpta::FRT, pflB::FRT, F' (lacIq+), pGV1655, pGV1698 |
| GEVO1821 | E. coli B, ΔadhE::FRT-kan-FRT, attB::(Sp+ lacIq+ tetR+), pSA55, pGV1609 |
| GEVO1844 | E. coli BW25113, ΔldhA-fnr::FRT, ΔadhE::FRT, Δfrd::FRT, ΔpflB::FRT, Δpta::FRT, F' (lacIq+), ΔilvC::[PLlacO1::kivd::ilvDco::FRT], ΔsthA::FRT |
| GEVO1846 | GEVO1748, pGV1745, pGV1698 |
| GEVO1859 | E. coli BW25113, ΔldhA-fnr::FRT, Δfrd::FRT, Δpta::FRT, F' (lacIq+), ΔadhE::[pLlacO1::kivd::ilvDco::FRT], pflB::[pLlacO1::alsS::ilvCco::FRT] |
| GEVO1886 | E. coli BW25113, ΔldhA-fnr::FRT, Δfrd::FRT, Δpta::FRT, F' (lacIq+), ΔadhE::[pLlacO1::kivd::ilvDco::FRT], ΔpflB::[pLlacO1::alsS::ilvCco::FRT] ΔsthA::[pLlacO1::pntA::pntB::FRT] |
| GEVO1948 | E. coli BW25113, ΔldhA-fnr::FRT, Δfrd::FRT, Δpta::FRT, ΔadhE::[pLlacO1::kivd::ilvDco::FRT], ΔpflB::[pLlacO1::alsS::ilvCco::FRT] ΔsthA::[pLlacO1::pntA::pntB::FRT] |

Table 20 provides a list of plasmids:

| Plasmid | Genotype |
|---|---|
| pSA55* | pLlacO1::kivd::adh2, ColE1, Amp |
| pSA69* | pLlacO1::alsS::ilvC::ilvD, p15A, Kan |
| pGV1609 | pLlacO1::alsS::ilvC::ilvD, p15A, Cm |
| pGV1655 | pLlacO1:: kivd::ilvDco, pSC101, Kan |
| pGV1698 | PLlacO1::alsS::ilvCco, ColE1, Amp |
| pGV1720 | pLlacO1::empty, pSC101, Kan |
| pGV1745 | pLlacO1::pntAB, pSC101, Kan |

*pSA55 and pSA69 plasmids are described in the prior art ((WO 2008/098227) BIOFUEL PRODUCTION BY RECOMBINANT MICROORGANISMS)

Table 21 provides a list of primer sequences:

| Primer No. | Sequence |
|---|---|
| 49 | GTTATCTAGTTGTGCAAAACATGCTAATGTAGCCACCAAATCGTGTAGGCTGGAG CTGCTTC (SEQ ID NO: 1) |
| 50 | GCAGTTTCACCTTCTACATAATCACGACCGTAGTAGGTATCATTCCGGGGATCCG TCGACC (SEQ ID NO: 2) |
| 226 | TTGGCTGAACGGTAGGGTATATTGTCACCACCTGTTGGAATGTTGGTGTAGGCT GGAGCTGCTTC (SEQ ID NO: 3) |
| 227 | GTATCCAGCATACCTTCCAGCGCGTTCTGTTCAAATGCGCTCAGGATTCCGGGG ATCCGTCGACC (SEQ ID NO: 4) |
| 869 | CTTAACCCGCAACAGCAATACGTTTCATATCTGTCATATAGCCGCATTCCGGGGA TCCGTCGACC (SEQ ID NO: 5) |
| 1026 | CACCGAGATCCTGGTCAAAGTGGGCGACAAAGTTGAAGCCGTGTAGGCTGGAG CTGCTTC (SEQ ID NO: 6) |
| 1027 | GCGGTGGTCGAAGGAGAGAGAAATCGGCAGCATCAGACGCATTCCGGGGATCC GTCGACC (SEQ ID NO: 7) |
| 1030 | GTCGGTGAACGCTCTCCTGAGTAGGGTGTAGGCTGGAGCTGCTTC (SEQ ID NO: 8) |
| 1031 | GAAGCAGCTCCAGCCTACACCCTACTCAGGAGAGCGTTCACCGAC (SEQ ID NO: 35) |
| 1032 | CACAACATCACGAGGAATCACCATGGCTAACTACTTCAATACACCACGAGGCCC TTTCGTCTTCACCTC (SEQ ID NO: 9) |
| 1205 | GTTATCTAGTTGTGCAAAACATGCTAATGTAGCCACCAAATCCACGAGGCCCTTT CGTCTTCACCTC (SEQ ID NO: 10) |
| 1214 | TTAAGGTACCATGCGAATTGGCATACCAAG (SEQ ID NO: 11) |
| 1215 | TAATGTCGACGCAATCCTGAAAGCTCTGTAA (SEQ ID NO: 12) |
| 1218 | GCTCACTCAAAGGCGGTAATACGTGTAGGCTGGAGCTGCTTC (SEQ ID NO: 13) |
| 1219 | GAAGCAGCTCCAGCCTACACGTATTACCGCCTTTGAGTGAGC (SEQ ID NO: 14) |

| Primer No. | Sequence |
|---|---|
| 1478 | CCATTCTGTTGCTTTTATGTATAAGAACAGGTAAGCCCTACCATGATTCCGGGGA TCCGTCGACC (SEQ ID NO: 15) |
| 1479 | CCGATAGGCTTCCGCCATCGTCGGGTAGTTAAAGGTGGTGTTGAGTGTAGGCTG GAGCTGCTTC (SEQ ID NO: 16) |
| 1485 | GCCTTTATTGTACGCTTTTTACTGTACGATTTCAGTCAAATCTAACACGAGGCCCT TTCGTCTTCACCTC (SEQ ID NO: 17) |
| 1486 | AAGTACGCAGTAAATAAAAAATCCACTTAAGAAGGTAGGTGTTACATTCCGGGGA TCCGTCGACC (SEQ ID NO: 18) |
| 1539 | CCATTCTGTTGCTTTTATGTATAAGAACAGGTAAGCCCTACCATGGAGAATTGTG AGCGGATAAC (SEQ ID NO: 19) |
| 1561 | GCAATCCTGAAAGCTCTGTAACATTCCGGGGATCCGTCGACC (SEQ ID NO: 20) |
| 1562 | GGTCGACGGATCCCCGGAATGTTACAGAGCTTTCAGGATTGC (SEQ ID NO: 21) |

Example 30

High Titer and High Volumetric Productivity Example: Two 400 mL DasGip fermenter vessels containing 200 mL each of EZ Rich medium (Neidhardt, F. C., P. L. Bloch, and D. F. Smith. 1974. Culture medium for enterobacteria. J. Bacteriol. 119:736-47) containing 72 g/L glucose and 10 g/L yeast extract were inoculated with Gevo1530 containing the two plasmids pSA55 and pSA69 from which the isobutanol pathway genes were expressed. Cells from a fresh transformation plate were used. GEVO1530 is a modified bacterial biocatalyst that contains genes on two plasmids which encode a pathway of enzymes that convert pyruvate into isobutanol. When the biocatalyst GEVO1530 was contacted with glucose in a medium suitable for growth of the biocatalyst, at about 30° C., the biocatalyst produced isobutanol from the glucose. The fermenter vessels were attached to a computer control system to monitor and control pH at 6.5 through addition of base, temperature at about 30° C., dissolved oxygen, and agitation. The vessels were agitated, with a minimum agitation of 300 rpm and agitation was varied to maintain a dissolved oxygen content of about 50% using a 12 sL/h air sparge until the $OD_{600}$ was about 1.0. The vessels were then induced with 0.1 mM IPTG. The vessels were operated under these conditions for about 12 hours. At about 12 hours, the contents of the fermenter vessels were then poured into 500 ml sterile graduated plastic bottles and centrifuged for 20 minutes at 4500 rpm. The cells were resuspended in 50 ml total volume of EZ Rich medium. A 400 ml DasGip vessel containing 150 ml of EZ Rich medium containing 72 g/L glucose and 10 g/L yeast extract was inoculated with 50 ml of the cell containing medium and then induced with 0.1 mM IPTG. Constant dissolved oxygen content of 5% was maintained using a 2.5 sL/h air sparge with variable agitation automatically controlled from 300 to 1200 rpm and a variable oxygen concentration ranging from 21% to about 30%. Measurement of the fermentor vessel off-gas by trapping in an octanol bubble trap then analysis by GC was performed for isobutanol and ethanol. Continuous measurement of off-gas concentrations of carbon dioxide and oxygen were also measured by a DasGip off-gas analyzer throughout the experiment. Samples were aseptically removed from the fermenter vessel throughout the experiment and used to measure $OD_{600}$, glucose concentration and isobutanol concentration in the broth. Isobutanol production reached a maximum at around 42 hours with a titer of about 22.9 g/L and with a yield of approximately 79% maximum theoretical. Volumetric productivity of the fermentation, calculated when the titer of isobutanol was between 1 g/L and 15 g/L, was about 2.8 g/L/h.

Example 31

High Titer Example 2: GEVO1780 is a modified bacterial biocatalyst that contains genes on two plasmids which encode a pathway of enzymes that convert pyruvate into isobutanol. When the biocatalyst GEVO1780 was contacted with glucose in a medium suitable for growth of the biocatalyst, at about 30° C., the biocatalyst produced isobutanol from the glucose. An overnight starter culture was started in a 250 mL Erlenmeyer flask with GEVO1780 cells from a freezer stock with a 40 mL volume of modified M9 medium consisting of 85 g/L glucose, 20 g/L yeast extract, 20 µM ferric citrate, 5.72 mg/L $H_3BO_3$, 3.62 mg/L $MnCl_2.4H_2O$, 0.444 mg/L $ZnSO_4.7H_2O$, 0.78 mg/L $Na_2MnO_4.2H_2O$, 0.158 mg/L $CuSO_4.5H_2O$, 0.0988 mg/L $CoCl_2.6H_2O$, $NaHPO_4$ 6.0 g/L, $KH_2PO_4$ 3.0 g/L, NaCl 0.5 g/L, $NH_4Cl$ 2.0 g/L, $MgSO_4$ 0.0444 g/L and $CaCl_2$ 0.00481 g/L and at a culture $OD_{600}$ of about 0.05. The starter culture was grown for approximately 14 hrs in a 30° C. shaker at 250 rpm. Some of the starter culture was then transferred to a 2000 mL DasGip fermenter vessel containing about 1500 mL of modified M9 medium to achieve an initial culture $OD_{600}$ of about 0.1. The fermenter vessel was attached to a computer control system to monitor and control pH at 6.5 through addition of base, temperature at about 30° C., dissolved oxygen, and agitation. The vessel was agitated, with a minimum agitation of 400 rpm and agitation was varied to maintain a dissolved oxygen content of about 50% using a 25 sL/h air sparge until the $OD_{600}$ was about 1.0. The vessel was then induced with 0.1 mM IPTG. After continuing growth for approximately 8-10 hrs, the dissolved oxygen content was decreased to 5% with 400 rpm minimum agitation and 10 sl/h airflow. Continuous measurement of the fermentor vessel off-gas by GC-MS analysis was performed for oxygen, isobutanol, ethanol, and carbon dioxide throughout the experiment. Samples were aseptically removed from the fermenter vessel throughout the experiment and used to measure $OD_{600}$, glucose concentration and isobutanol concentration in the broth. Throughout the experiment, supplements of pre-grown and pre-induced biocatalyst cells were added as a concentrate three times since the start of the experiment: at 21 h, 38 h, and 46.3 h. These cells were the same strain and plasmids shown above and used in the fermenter. Supplemented cells were grown as 1 L cultures in 2.8 L Fernbach flasks and incubated at 30° C., 250 RPM in Modified M9 Medium with 85 g/L of glucose. Cultures were induced upon inoculation with 0.1 mM IPTG. When the cells had reached an $OD_{600}$ of about 4.0-5.0, the culture was concentrated by centrifugation and then added to the fermenter. A sterile glucose feed of 500 g/L glucose in DI water was used intermittently during the production phase of the experiment at time points great than 12 h to maintain glucose concentration in the fermenter of about 30 g/L or above.

The fermenter vessel was attached by tubing to a smaller 400 mL fermenter vessel that served as a flash tank and operated in a recirculation loop with the fermenter. The biocatalyst cells within the fermenter vessel were isolated from the flash tank by means of a cross-flow filter placed in-line with the fermenter/flash tank recirculation loop. The filter only allowed cell-free fermentation broth to flow from the fermenter vessel into the flash tank. The volume in the flash tank was approximately 100 mL and the hydraulic retention time was about 10 minutes. Heat and vacuum were applied to the flash tank. The vacuum level applied to the flash tank was initially set at 45 mBar and the flash tank was set at about 45° C. These parameters were adjusted to maintain approximately 6-10 g/L isobutanol in the fermenter throughout the experiment. Generally, the vacuum ranged from 45-100 mBar and the flash tank temperature ranged from 43° C. to 45° C. throughout the experiment. Vapor from the heated flash tank was condensed into a collection vessel as distillate. Cell-free fermentation broth was continuously returned from the flash tank to the fermentation vessel.

The distillate recovered in the experiment was strongly enriched for isobutanol. Isobutanol formed an azeotrope with water and usually lead to a two phase distillate: an isobutanol rich top phase and an isobutanol lean bottom phase. Distillate samples were analyzed by GC for isobutanol concentration. Isobutanol production reached a maximum at around 95 hrs with a total titer of about 63 g/L. As used herein, the term "titer" is defined as the strength of a solution or the concentration of a substance in solution plus the substance in the gas phase. For example, the titer of a biofuel in a fermentation is described as g of biofuel in solution plus the g of biofuel in the gas phase per liter of fermentation broth. The term "titre" is used interchangeably throughout with the term "titer". The isobutanol production rate was about 0.64 g/L/h and the percent theoretical yield was approximately 86%.

Example 32

High Yield Example: The modified biocatalyst GEVO1530 was transformed with the two plasmids pSA69 and pSA55, which encode a pathway of enzymes that convert pyruvate into isobutanol. When the biocatalyst Gevo1530 (pSA69, pSA55) was contacted with glucose in a medium suitable for growth of the biocatalyst, at about 30° C., the biocatalyst produced isobutanol from the glucose. An overnight starter culture was started in a 250 mL Erlenmeyer flask with GEVO1530 cells from a fresh transformation plate with a 40 mL volume of EZ Rich medium (Neidhardt, F. C., P. L. Bloch, and D. F. Smith. 1974. Culture medium for enterobacteria. J. Bacteriol. 119:736-47) containing 72 g/L glucose and 10 g/L yeast extract and at a culture $OD_{600}$ of about 0.05. The starter culture was grown for approximately 14 hrs in a 37° C. shaker at 250 rpm. Some of the starter culture was then transferred to a 2 L DasGip fermenter vessel containing about 1000 mL of EZ Rich medium containing 72 g/L glucose and 10 g/L yeast extract to achieve a 1% v/v inoculum. The fermenter vessel was attached to a computer control system to monitor and control pH at 6.5 through addition of base, temperature at 30° C., dissolved oxygen, and agitation. The vessel was agitated, with a minimum agitation of 300 rpm and agitation was varied to maintain a dissolved oxygen content of about 50% using a 25 sL/h air sparge until the $OD_{600}$ was about 1.0. The vessel was then induced with 0.1 mM IPTG. After continuing growth for approximately 8-10 hrs, the dissolved oxygen content was decreased to 5% with 300 rpm minimum agitation and 5 sl/h airflow. Measurement of the fermentor vessel off-gas by trapping in an octanol bubble trap and then measurement by GC was performed for isobutanol and ethanol. Continuous measurement of off gas concentrations of carbon dioxide and oxygen were also measured by a DasGip off-gas analyzer throughout the experiment. Samples were aseptically removed from the fermenter vessel throughout the experiment and used to measure $OD_{600}$, glucose concentration by HPLC, and isobutanol concentration in the broth by GC. Isobutanol production reached a maximum at around 48 hrs with a titer of about 18 g/L. Yield of the fermentation, calculated when the titer of isobutanol was between 1 g/L and 15 g/L, was approximately 83% maximum theoretical.

Example 33

High Volumetric Productivity Example: GEVO1780 is a modified bacterial biocatalyst that contains genes on two plasmids which encode a pathway of enzymes that convert pyruvate into isobutanol. When the biocatalyst GEVO1780 was contacted with glucose in a medium suitable for growth of the biocatalyst, at about 30° C., the biocatalyst produced isobutanol from the glucose. Two 400 mL DasGip fermenter vessels containing 200 mL each of modified M9 medium consisting of 85 g/L glucose, 20 g/L yeast extract, 20 µM ferric citrate, 5.72 mg/L $H_3BO_3$, 3.62 mg/L MnCl2.4H2O, 0.444 mg/L ZnSO4.7H2O, 0.78 mg/L Na2MnO4.2H2O, 0.158 mg/L CuSO4.5$H_2$O, 0.0988 mg/L CoCl2.6$H_2$O, NaHPO4 6.0 g/L, KH2PO4 3.0 g/L, NaCl 0.5 g/L, NH4Cl 2.0 g/L, MgSO4 0.0444 g/L and CaCl2 0.00481 g/L were inoculated with GEVO1780 cells from frozen stocks. The fermenter vessels were attached to a computer control system to monitor and control pH at 6.5 through addition of base, temperature at 30° C., dissolved oxygen, and agitation. The vessels were agitated, with a minimum agitation of 300 rpm and agitation was varied to maintain a dissolved oxygen content of about 50% using a 12 sL/h air sparge until the $OD_{600}$ was about 1.0. The vessels were then induced with 0.1 mM IPTG. The vessels were operated under these conditions for about 12 hours. At about 12 hours, the contents of the fermenter vessels were then poured into 500 ml sterile graduated plastic bottles and centrifuged for 20 minutes at 4500 rpm. The cells were resuspended in 50 ml total volume of modified M9 medium. A 400 ml DasGip vessel containing 150 ml of modified M9 medium was inoculated with 50 ml of the cell containing medium and then induced with 0.1 mM IPTG. Constant dissolved oxygen content of 5% was maintained using a 2.5 sL/h air sparge with variable agitation automatically controlled from 300 to 1200 rpm. Continuous measurement of the fermentor vessel off gas by GC-MS analysis was performed for oxygen, isobutanol, ethanol, carbon dioxide, and nitrogen throughout the experiment. Samples were aseptically removed from the fermenter vessel throughout the experiment and used to measure $OD_{600}$, glucose concentration by HPLC, and isobutanol concentration in the broth by GC. Isobutanol production reached a maximum at around 22 hours with a titer of about 22 g/L and with a yield of approximately 80% maximum theoretical. Volumetric productivity of the fermentation, calculated when the titer of isobutanol was between 1 g/L and 15 g/L, was about 2.3 g/L/h.

Example 34

Inexpensive Nutrients and Biomass Example (Corn Liquefact): GEVO1780 is a modified bacterial biocatalyst that contains genes on two plasmids which encode a pathway of enzymes that convert pyruvate into isobutanol. When the biocatalyst GEVO1780 was contacted with glucose in a medium suitable for growth of the biocatalyst, at about 30° C., the biocatalyst produced isobutanol from the glucose. An overnight starter culture was started in a 250 mL Erlenmeyer flask with GEVO1780 cells from a freezer stock with a 40 mL volume of modified M9 medium consisting of 85 g/L glucose, 10 g/L yeast extract, 10 μM ferric citrate, 2.86 mg/L H3BO3, 1.81 mg/L MnCl2.4H2O, 0.222 mg/L ZnSO4.7H2O, 0.39 mg/L Na2MnO4.2H2O, 0.079 mg/L CuSO4.5H2O, 0.0494 mg/L CoCl2.6H2O, NaHPO4 6.0 g/L, KH2PO4 3.0 g/L, NaCl 0.5 g/L, NH4Cl 2.0 g/L, MgSO4 0.0222 g/L and CaCl2 0.00241 g/L and at a culture $OD_{600}$ of 0.02 to 0.05. The starter culture was grown for approximately 14 hrs in a 30° C. shaker at 250 rpm. Some of the starter culture was then transferred to two 400 mL DasGip fermenter vessels to achieve an inoculum of about 0.1 OD600. One fermenter vessel, A, contained about 200 mL of medium consisting of liquefact hydrolyzed corn substrate, deionized water, and 2.5 g/L (NH4)2SO4. A second fermenter vessel, B, contained about 200 mL of medium consisting of liquefact hydrolyzed corn substrate and deionized water with no additional supplements. The liquefact hydrolyzed corn substrate was generated by traditional corn-ethanol dry mill processing methods known to one skilled in the art. At inoculation, glucoamylase sufficient to hydrolyze the starch present in the liquefact to available glucose was added to each fermenter vessel. The vessels were attached to a computer control system to monitor and control pH at 6.5 through addition of base, temperature at about 30° C., dissolved oxygen, and agitation. The vessels were agitated, with a minimum agitation of 200 rpm and agitation was varied to maintain a dissolved oxygen content of about 50% using a 12 sL/h air sparge for about 2 hours. The vessels were then induced with 0.1 mM IPTG. After continuing growth for approximately 7 hours, the dissolved oxygen content was decreased to 5% with 200 rpm minimum agitation and 2.5 sL/h airflow. Continuous measurement of fermentor vessel off-gas by GC-MS analysis was performed for oxygen, isobutanol, ethanol, carbon dioxide, and nitrogen throughout the experiment for each vessel. Samples were aseptically removed from each fermenter vessel throughout the experiment and used to measure free glucose concentration by HPLC and isobutanol concentration in the broth by GC. In fermenter vessel A, isobutanol production reached a maximum at around 52 hrs with a titer of about 8 g/L and a volumetric productivity of about 0.2 g/L/h. In fermenter vessel B, isobutanol production reached a maximum at around 52 hrs with a titer of about 4 g/L and a volumetric productivity of about 0.1 g/L/h. The complete fermentation results for each vessel are found in Table 22, below. Yield was not determined.

Table 22 provides exemplary fermentation data:

| Vessel | Elapsed Fermentation Time (h) | Isobutanol Concentration (g/L) |
|---|---|---|
| A | 0.0 | 0.03 |
| A | 2.0 | 0.03 |
| A | 7.0 | 0.08 |
| A | 24.0 | 3.44 |
| A | 28.0 | 4.90 |
| A | 31.0 | 5.67 |
| A | 48.0 | 7.43 |
| A | 52.0 | 7.65 |
| B | 0.0 | 0.17 |
| B | 2.0 | 0.11 |
| B | 7.0 | 0.24 |
| B | 24.0 | 2.47 |
| B | 28.0 | 3.10 |
| B | 31.0 | 3.17 |
| B | 48.0 | 3.93 |
| B | 52.0 | 4.09 |

Example 35

Cheap Nutrients and Biomass Example—Acid Pretreated Corn Stover Hydrolysate: Corn stover hydrolysate was conditioned with ammonium hydroxide by adjusting the pH to 8.5, incubating for 30 minutes with stirring at room temperature (about 23° C.), then adjusting the pH to 6.5 with concentrated sulfuric acid. The conditioned corn stover hydrolysate was then filtered through a 0.2 μm filter and the permeate was used in the experiment.

GEVO1780 is a modified bacterial biocatalyst that contains genes on two plasmids which encode a pathway of enzymes that convert pyruvate into isobutanol. When the biocatalyst GEVO1780 was contacted with glucose in a medium suitable for growth of the biocatalyst, at about 30° C., the biocatalyst produced isobutanol from the glucose. An overnight starter culture was started in a 250 mL Erlenmeyer flask with GEVO1780 cells from a freezer stock with a 40 mL volume of LB medium (5 g/L yeast extract, 10 g/L tryptone, 10 g/L NaCl in dionized water) and at a culture OD600 of 0.02 to 0.05. The starter culture was grown for approximately 14 hrs in a 37° C. shaker at 250 rpm. Some of the starter culture was then transferred to 20 mL volume of modified M9 medium in a 250 mL Erlenmeyer flask consisting of 10% v/v, 20% v/v, 30% v/v, 40% v/v, or 50% v/v conditioned corn stover hydrolysate, 10 g/L yeast extract, 10 μM ferric citrate, 2.86 mg/L $H_3BO_3$, 1.81 mg/L $MnCl_2.4H_2O$, 0.222 mg/L $ZnSO_4.7H_2O$, 0.39 mg/L $Na_2MnO_4.2H_2O$, 0.079 mg/L $CuSO_4.5H_2O$, 0.0494 mg/L $CoCl_2.6H_2O$, $NaHPO_4$ 6.0 g/L, $KH_2PO_4$ 3.0 g/L, NaCl 0.5 g/L, $NH_4Cl$ 2.0 g/L, $MgSO_4$ 0.0222 g/L and $CaCl_2$ 0.00241 g/L and at a culture OD600 of about 0.1. The flasks were incubated for about 4 hours in a 37° C. shaker at 250 rpm. The flasks were then induced with 0.1 mM IPTG and transferred to 30° C. shaker at 250 rpm. Incubation continued for about 50 hours with periodic sampling to measure $OD_{600}$, isobutanol concentration by GC, and sugar concentrations by HPLC.

The biocatalyst GEVO1780 produced isobutanol from the conditioned corn stover hydrolysate (20% by volume), with two independent replicates producing about 5.2 g/L and 5.0 g/L isobutanol, respectively, in 52 h. In an experiment that contained 10% by volume conditioned corn stover hydrolysate, the biocatalyst GEVO1780 produced about 3.2 g/L and 3.2 g/L isobutanol, respectively, in 52 h in two independent replicates. In an experiment that contained 30% by volume conditioned corn stover hydrolysate, the biocatalyst GEVO1780 produced about 3.4 g/L isobutanol in 52 h. The complete fermentation results for each experiment are found in Table 23, below.

Table 23 provides data for isobutanol produced from hydrolyzed corn stover:

| Elapsed Fermentation Time (h) | Isobutanol Concentration (g/L) | | | | | |
|---|---|---|---|---|---|---|
| | 10% Hydrolysate Replicate 1 | 10% Hydrolysate Replicate 2 | 20% Hydrolysate Replicate 1 | 20% Hydrolysate Replicate 2 | 30% Hydrolysate Replicate 1 | 30% Hydrolysate Replicate 2 |
| 0.0 | 0.01 | 0.01 | 0.00 | 0.00 | 0.00 | 0.00 |
| 2.0 | 0.01 | 0.01 | 0.00 | 0.00 | 0.00 | 0.00 |
| 3.5 | 0.04 | 0.04 | 0.02 | 0.02 | 0.01 | 0.00 |
| 5.0 | 0.20 | 0.21 | 0.07 | 0.07 | 0.03 | 0.02 |
| 7.0 | 3.18 | 3.14 | 3.85 | 3.62 | 0.44 | 0.44 |
| 24.0 | 3.25 | 3.17 | 3.23 | 3.10 | 1.14 | 1.13 |
| 52.0 | 3.16 | 3.16 | 5.20 | 5.04 | 3.42 | 3.42 |

Example 36

Cheap Nutrients and Biomass Example: Isobutanol Production from Cellulose: GEVO1780 is a modified bacterial biocatalyst that contains genes on two plasmids which encode a pathway of enzymes that convert pyruvate into isobutanol. When the biocatalyst GEVO1780 was contacted with glucose in a medium suitable for growth of the biocatalyst, at about 30° C., the biocatalyst produced isobutanol from the glucose. An overnight starter culture was started in a 250 mL Erlenmeyer flask with GEVO1780 cells from a freezer stock with a 40 mL volume of LB medium (5 g/L yeast extract, 10 g/L tryptone, 10 g/L NaCl in dionized water) and at a culture $OD_{600}$ of about 0.05. The starter culture was grown for approximately 14 hrs in a 37° C. shaker at 250 rpm. Some of the starter culture was then transferred to 20 mL volume of modified M9 medium in a 250 mL Erlenmeyer flask consisting of 77 g/L purified cellulose (Sigmacell 50, Sigma Aldrich Chemical Company), 10 g/L yeast extract, 10 µM ferric citrate, 2.86 mg/L H3BO3, 1.81 mg/L MnCl2.4H2O, 0.222 mg/L ZnSO4.7H2O, 0.39 mg/L Na2MnO4.2H2O, 0.079 mg/L CuSO4.5H2O, 0.0494 mg/L CoCl2.6H2O, NaHPO4 6.0 g/L, KH2PO4 3.0 g/L, NaCl 0.5 g/L, NH4Cl 2.0 g/L, MgSO4 0.0222 g/L and CaCl2 0.00241 g/L and at a culture $OD_{600}$ of about 0.1. Cellulase enzyme (Genencor Accelerase) sufficient to hydrolyze the purified cellulose into monomeric glucose was added to each flask at the time of inoculation. The flasks were incubated for about 4 hours in a 37° C. shaker at 250 rpm. The flasks were then induced with 0.1 mM IPTG and transferred to 30° C. shaker at 250 rpm. Incubation continued for about 50 hours with periodic sampling to measure OD600, isobutanol concentration by GC, and sugar concentration by HPLC.

The biocatalyst GEVO1780 produced isobutanol from 77 g/L cellulose, with three independent replicates producing about 5.6 g/L, 5.4 g/L, and 4.7 g/L isobutanol, respectively, in 52 h. The complete fermentation results for each experiment are found in Table 24 below.

Table 24 provides data for isobutanol production from cellulose:

| Elapsed Fermentation Time (h) | Isobutanol Concentration (g/L) | | |
|---|---|---|---|
| | Replicate 1 | Replicate 2 | Replicate 3 |
| 0.0 | 0.04 | 0.03 | 0.03 |
| 2.0 | 0.02 | 0.01 | 0.01 |
| 3.5 | 0.03 | 0.03 | 0.03 |
| 5.0 | 0.29 | 0.28 | 0.19 |
| 7.0 | 4.17 | 4.04 | 3.58 |
| 24.0 | 3.53 | 3.35 | 3.10 |
| 52.0 | 5.57 | 5.38 | 4.68 |

Example 37

Growth of Biocatalyst on Biomass Sugars Example: To assess growth on different carbon sources GEVO1627, a modified bacterial biocatalyst, was streaked onto a LB (5 g/L yeast extract, 10 g/L tryptone, 10 g/L NaCl in dionized water) plate from a frozen stock. A colony from this plate was used to start two overnight starter cultures from the same colony in 3 mL modified M9 medium consisting of 40 g/L glucose, 10 g/L yeast extract, 10 µM ferric citrate, 2.86 mg/L H3BO3, 1.81 mg/L MnCl2.4H2O, 0.222 mg/L ZnSO4.7H2O, 0.39 mg/L Na2MnO4.2H2O, 0.079 mg/L CuSO4.5H2O, 0.0494 mg/L CoCl2.6H2O, NaHPO4 6.0 g/L, KH2PO4 3.0 g/L, NaCl 0.5 g/L, NH4Cl 2.0 g/L, MgSO4 0.0222 g/L and CaCl2 0.00241 g/L and the antibiotics chloramphenicol and ampicillin in a snap cap tube. The cultures were incubated for about 14 h at 37° C. and 250 rpm. Cultures were used to inoculate baffled 250 mL flasks containing 40 mL modified M9 medium containing 40 g/L of the desired sugar (glucose, galactose, mannose, arabinose, xylose, lactose or sucrose) and the antibiotics chloramphenicol and ampicillin and at a culture OD600 of about 0.1. The cells were incubated at 37° C. and 250 rpm and OD600 measurements were taken at 1.5, 3, 5, and 6.5 h after inoculation. GEVO1627 grew on all the tested sugars (Table 25). All cultures grew to an OD600 of between 11.5 and 11.7 with the exception of the cultures supplemented with arabinose, which reached an OD of 9.6, and the cultures supplemented with sucrose, which reached an OD of 7.3. The initial growth rate of GEVO1627 was the same independent of the carbon source used.

Table 25 provides OD values for GEVO1627 grown in fermentation medium supplemented with different sugars (40 g/L):

| time [h] | OD values | | | | | | |
|---|---|---|---|---|---|---|---|
| | lactose | sucrose | mannose | xylose | arabinose | galactose | glucose |
| 1.5 | 0.39 | 0.40 | 0.35 | 0.38 | 0.37 | 0.38 | 0.40 |
| 3 | 4.3 | 4.4 | 4.0 | 4.2 | 4.1 | 4.2 | 4.2 |
| 5 | 10.2 | 7.0 | 10.6 | 11.1 | 9.1 | 11.0 | 10.2 |
| 6.5 | 11.1 | 7.3 | 11.7 | 11.2 | 9.6 | 10.4 | 11.5 |

Example 38

Conversion of Biomass Sugars to Isobutanol Example: The plasmids pGV1609 (PLlacO1::alsS::ilvC::ilvD, p15A, Cm) and pSA55 (pLlacO1::kivd::ADH2, ColE1, Amp) were introduced into the strain GEVO1627 yielding strain GEVO1821. In particular, a culture of GEVO1627 was grown in SOB medium (Sambrook, J. and Russell, D. 2001. Molecular Cloning: A Laboratory Manual, Third Edition. ISBN 978-087969577-4) to an OD600 of about 0.6 to 0.8. The strain was then made electro-competent by concentrating it 100-fold, washing once with ice cold water and 3 times with ice cold 10% glycerol. The cells were then resuspended in 150 µL of ice-cold 10% glycerol. The electro-competent cells were transformed with the plasmids pGV1609 and pSA55 using an electroporator set to 25° F., 2.5 kV and the pulse controller at 200Ω. After the electroporation, SOC medium (Sambrook, J. and Russell, D. 2001. Molecular Cloning: A Laboratory Manual, Third Edition. ISBN 978-087969577-4) was immediately added to the cells. After incubation for an hour at 37° C., the cells were plated onto LB (5 g/L yeast extract, 10 g/L tryptone, 10 g/L NaCl in dionized water) plates containing the antibiotics chloramphenicol and ampicillin and incubated for about 18 h at 37° C. Plates were removed from the incubator and stored at room temperature until further use.

GEVO1821 is a modified bacterial biocatalyst that contains genes on two plasmids which encode a pathway of enzymes that convert pyruvate into isobutanol. When the biocatalyst GEVO1821 was contacted with glucose in a medium suitable for growth of the biocatalyst, at about 30° C., the biocatalyst produced isobutanol from the glucose. Starter cultures of GEVO1821 were inoculated in 3 mL LB medium and the antibiotics chloramphenicol and ampicillin in snap cap tubes. The cultures were incubated for about 14 h at 37° C. and 250 rpm. Isobutanol fermentations were carried out in modified M9 medium consisting of 40 g/L of the desired sugar (glucose, galactose, mannose, arabinose, xylose, lactose or sucrose), 10 g/L yeast extract, 10 µM ferric citrate, 2.86 mg/L H3B03, 1.81 mg/L MnCl2.4H2O, 0.222 mg/L ZnSO4.7H2O, 0.39 mg/L Na2MnO4.2H2O, 0.079 mg/L CuSO4.5H2O, 0.0494 mg/L CoCl2.6H2O, NaHPO4 6.0 g/L, KH2PO4 3.0 g/L, NaCl 0.5 g/L, NH4Cl 2.0 g/L, MgSO4 0.0222 g/L and CaCl2 0.00241 g/L and the antibiotics chloramphenicol and ampicillin in 250 mL screw cap flasks with 20 mL fermentation medium, inoculated with about 0.1 OD600 of the grown starter cultures. The cells were incubated at 37° C. and 250 rpm until the strains reached an OD600 of between 0.6 and 0.8 and were then induced with IPTG at 1 mM final concentration. Samples were taken from the cultures at 24 h and 48 h after inoculation, centrifuged at 22000 g to separate the cell pellet from the supernatant and the supernatant stored frozen at −20° C. until analysis. The samples were analyzed for sugar concentration by HPLC and isobutanol concentration by GC.

GEVO1821 was tested in an isobutanol fermentation using modified M9 medium with seven different sugars. All samples grew to an OD600 of about 7 to 8 with the exception of the cultures with sucrose. Sucrose cultures grew to an OD600 of about 3. Over the course of the fermentation, some cultures produced acid, and were neutralized at the 24 h time point, as they were at a pH of 5.0 or below. The pH was adjusted to 7 using 2 M NaOH as needed. All hexose sugars (galactose and mannose) and the disaccharide lactose yielded isobutanol production similar to isobutanol production from glucose (Table 26). The cultures grown on pentose sugars reached isobutanol titers of about 5 g/L for xylose and about 4 g/L for arabinose. The cultures grown on sucrose produced 0.41 g/L isobutanol. Maximal titers were seen at the 48 h time point. Volumetric productivity was calculated from zero to 24 h and is indicated in Table 26 for each sugar. Yields were calculated at 48 h and are shown as a percentage of theoretical yield. No yield was determined for lactose and sucrose fermentations.

Table 26 provides the results for volumetric productivity, titer and yield for the tested sugar fermentations to isobutanol using biocatalyst GEVO1821:

| samples | Volumetric Productivity (0-24 h) [g/L/h] | Maximum Titer (48 h) [g/L] | Yield [% theoretical] |
|---|---|---|---|
| glucose | 0.255 | 8.72 | 60.8 |
| galactose | 0.320 | 8.11 | 59.8 |
| mannose | 0.221 | 8.41 | 63 |
| xylose | 0.144 | 5.17 | 42.1 |
| arabinose | 0.178 | 4.67 | 34.1 |
| lactose | 0.337 | 8.90 | Not determined |
| sucrose | 0.019 | 0.43 | Not determined |

Example 39

No-byproducts Example: An isobutanol fermentation was carried out using a biocatalyst that produces isobutanol from glucose. During the course of the fermentation, isobutanol was removed from the fermenter using vacuum distillation directly applied to the fermenter. As a result, 20 liters of a two-phase solution of isobutanol in water was recovered from the fermentation broth. The solution contained approximately 8% v/v isobutanol. An initial distillation was conducted at moderate vacuum (0.5 bar) and 40-50° C. where a low boiling azeotrope of isobutanol/water boiled and was condensed in the recovery vessel. The condensed mixture phase separated into an isobutanol rich phase (of approximate composition of 85% volume/volume isobutanol and 15% water) and an aqueous phase (of approximate composition of 8% volume/volume) isobutanol in water). Distillation continued until the initial aqueous broth contained less than 2 g/L isobutanol (<0.2% weight/volume). The recovered two-phase mixture was transferred to a separation funnel where the two liquids were separated. The aqueous phase was recycled into the next batch for distillation and distillation continued until the initial aqueous broth contained less than 2 g/L isobutanol fuel additive, but the purified isobutanol also met portions of the specification for ethanol as a fuel ASTM D4806-07, such as water content, acidity, and nonvolatile matter (g/100 mL) (Table 27) and would likely meet a newly-developed specification for isobutanol as a fuel or fuel additive.

Exemplary specifications are provided in Table 27:

| Test | Method | Specification | Results for This Lot |
|---|---|---|---|
| Appearance | Visual | Clear and Bright | Clear and Bright |
| Color by Pt-Co Scale | ASTM D1209 | 10 max[1] | Colorless |
| Water by Karl Fischer (ppm/%) | ASTM E1064 | 0.2%[1] or 1.0%[2] max | 0.13% |
| Isobutanol (%) | GC method | 98% min | 99.1% |
| Apparent Specific Gravity 25/25° C. | ASTM D891 B | 0.794 to 0.801 | 0.7997 |
| Acidity (weight %) | ASTM D1613 | 0.003%[1] or 0.007%[2] max | 0.002% |
| Nonvolatile Matter (g/100 mL) | ASTM D1353 | 0.005[1,2] | 0.001 |
| Organic Impurities by GC: | GC method | — | — |
| Ethanol (ppm/%) | GC method | Report | 606 ppm/0.06% |
| Acetic Acid (ppm/%) | GC method | Report | <10 ppm |
| Propanols (ppm/%) | GC method | Report Each | <10 ppm |
| Propionic Acid (ppm/%) | GC method | Report | <10 ppm |
| Acetone (ppm/%) | GC method | Report | 15 ppm/0.0015% |
| 1- and 2-Butanols (ppm/%) | GC method | Report Each | <10 ppm |
| Butyraldehydes (ppm/%) | GC method | Report Each | <10 ppm |
| Butyric Acids (ppm/%) | GC method | Report Each | <10 ppm |
| Pentanols (ppm/%) | GC method | Report Each | Isopentanol 3483 ppm/ 0.35% <10 ppm others detected |
| Pentaldehydes (ppm/%) | GC method | Report Each | <10 ppm |
| Pentanoic Acids (ppm/%) | GC method | Report Each | <10 ppm |
| Sulfur Content (ppm)[3] | ASTM D3120 | 30 max[1] | <1 |
| Nitrogen Content (ppm)[3] | ASTM D5762 | Report | <40 |

[1]ASTM D1719-05 specification for solvent isobutanol.
[2]ASTM D4806-07 specification for fuel grade ethanol for blending with gasoline.
[3]Tests were performed by Core Lab, 8210 Mosley Rd., Houston, TX 77075; Ph: 713-943-9776.

(<0.2%/weight/volume). About 1.6 liters of the isobutanol-rich phase were recovered.

The isobutanol-rich phase was then fed into a second stage distillation apparatus. In the second distillation, the azeotrope was boiled overhead, leaving a relatively dry isobutanol in the flask. The solution was distilled at atmospheric pressure and temperature from 85-100° C. The boiled mixture was collected in a recovery flask where it phase separated as described previously in this example. The two-phase mixture was transferred to separation funnel and decanted as previously described above. The aqueous phase was recycled into the feed of the next batch for initial distillation. The isobutanol-rich phase was recycled into the subsequent batch of second-stage distillation. One liter of isobutanol was recovered with approximately 0.13% weight/volume water.

The isobutanol recovered from such a process was assigned a lot identifier of 05E08C3N00P and was then subjected to several tests for purity and compositional analysis. Tests are described below and methods used were known to one skilled in the art and from the ASTM International specifications ASTM D3120, ASTM D5453, ASTM 4629, ASTM D5762, and ASTM E-1064. ASTM specifications were met or exceeded by the purified isobutanol (Table 27). The ASTM specification for isobutanol as a solvent, ASTM D1719-05 was met with the purified isobutanol (Table 27). There is currently no specification for isobutanol for use as a fuel or a Example 40

Isotope Fractionation Example—Detection of isobutanol made from renewable feedstock: Isobutanol obtained from a method described herein was analyzed by mass spectrometry to compare its carbon isotope distribution with the distribution of petroleum-derived isobutanol. To determine the isotope ratio of both materials, 0.5 μL of neat isobutanol was injected into a Varian CP-3800 Gas Chromatograph configured with a Varian 320-MS single quadrupole Mass Spectrometer detector, a CTC Analytics CombiPAL autosampler, a Varian 1079 split/splitless injector configuration, and a Varian FactorFour VF-5 ms capillary column (30M×0.25 mm internal diameter×0.25 μM film thickness) under the following conditions: 250° C. injector temperature, 100:1 split ratio, helium carrier gas at 1.0 mL/min constant flow, 35° C. isothermal oven temperature, and mass spectrometer operated in Electron Ionization mode at 70 eV. Isobutanol eluted at 2.7 minutes and a mass intensity table from the apex of this peak was measured. Three samples of each type of isobutanol were injected, and the isotope distribution ratios were averaged.

The intensity of the following mass peaks were measured for each sample: 74.1 (corresponding to C12-based isobutanol), 75.1 (corresponding to C12-isobutanol with one C13), and 76.1 (corresponding to one C14 or two C13 per renewable molecule or two C13 per petroleum-based molecule). The ratios of the intensity of the 75.1 and 76.1 peaks to the intensity of the 74.1 peak were calculated for each sample and each ratio from the three replicates was averaged for each type of sample. Based upon the natural abundance of the carbon 13 isotope (carbon 14 decays rapidly on a geological time scale and is generally not present in petroleum products), the 75.1/74.1 ratio should be 0.046 and the 76.1/74.1 ratio should be 0.0027 for a petroleum based sample. Material that is produced by a biological process will be different due to cumulative kinetic isotope effects inside the organism that produces the material. The petroleum based material exhibited an average 75.1/74.1 ratio of 0.045 and an average 76.1/74.1 ratio of 0.0027. The renewable isobutanol obtained by a method provided herein exhibited an average 75.1/74.1 ratio of 0.0060 and an average 76.1/74.1 ratio of 0.0060, a 30% increase in C13 over the petroleum based material and a measurable amount of C14 not present in the non-renewable isobutanol.

Example 41

High Volumetric Productivity Example 2: The modified biocatalyst Gevo1530 was transformed with the two plasmids pSA69 and pSA55, which encode a pathway of enzymes that convert pyruvate into isobutanol. When the biocatalyst Gevo1530 (pSA69, pSA55) was contacted with glucose in a medium suitable for growth of the biocatalyst, at about 30° C., the biocatalyst produced isobutanol from the glucose. Two 400 mL DasGip fermenter vessels containing 200 mL each of EZ Rich medium (Neidhardt, F. C., P. L. Bloch, and D. F. Smith. 1974. Culture medium for enterobacteria. J. Bacteriol. 119:736-47) containing 72 g/L glucose and 10 g/L yeast extract were inoculated with Gevo1530 (pSA69, pSA55) cells. The vessels were attached to a computer control system to monitor and control pH at 6.5 through addition of base, temperature at about 30° C., dissolved oxygen, and agitation. The vessels were agitated, with a minimum agitation of 300 rpm and agitation was varied to maintain a dissolved oxygen content of about 50% using a 12 sL/h air sparge until the $OD_{600}$ was about 1.0. The vessels were then induced with 0.1 mM IPTG. The vessels were operated under these conditions for about 11 hours. At about 11 hours, the contents of the fermenter vessels were then poured into 500 ml sterile graduated plastic bottles and centrifuged for 20 minutes at 4500 rpm. The cells were resuspended in 50 ml total volume of modified M9 medium. A 400 ml DasGip vessel containing 150 ml of EZ Rich medium containing 72 g/L glucose and 10 g/L yeast extract was inoculated with 50 ml of the cell containing medium and then induced with 0.1 mM IPTG. Cell concentration was approximately 6 g CDW per L. Constant dissolved oxygen content of 5% was maintained using a 2.5 sL/h air sparge with variable agitation automatically controlled from 300 to 1200 rpm. Measurement of the fermentor vessel off-gas by trapping in an octanol bubble trap and then measurement by GC was performed for isobutanol and ethanol. Continuous measurement of off-gas concentrations of carbon dioxide and oxygen were also measured by a DasGip off-gas analyzer throughout the experiment. Samples were aseptically removed from the fermenter vessel throughout the experiment and used to measure $OD_{600}$, glucose concentration by HPLC, and isobutanol concentration in the broth by GC. Isobutanol production reached a maximum at around 4 hours with a titer of 15 g/L and with a yield of approximately 86% maximum theoretical. Volumetric productivity of the fermentation, calculated from the inception of the fermentation at time 0 h to an elapsed fermentation time of about 4 h, was about 3.5 g/L/h.

Example 42

High Volumetric Productivity Example 3: The modified biocatalyst Gevo1530 was transformed with the two plasmids pSA69 and pSA55, which encode a pathway of enzymes that convert pyruvate into isobutanol. When the biocatalyst Gevo1530 (pSA69, pSA55) was contacted with glucose in a medium suitable for growth of the biocatalyst, at about 30° C., the biocatalyst produced isobutanol from the glucose. Two 400 mL DasGip fermenter vessels containing 200 mL each of EZ Rich medium (Neidhardt, F. C., P. L. Bloch, and D. F. Smith. 1974. Culture medium for enterobacteria. J. Bacteriol. 119:736-47) containing 72 g/L glucose and 10 g/L yeast extract were inoculated with Gevo1530 (pSA69, pSA55) cells. The vessels were attached to a computer control system to monitor and control pH at 6.5 through addition of base, temperature at about 30° C., dissolved oxygen, and agitation. The vessels were agitated, with a minimum agitation of 300 rpm and agitation was varied to maintain a dissolved oxygen content of about 50% using a 12 sL/h air sparge until the $OD_{600}$ was about 1.0. The vessels were then induced with 0.1 mM IPTG. The vessels were operated under these conditions for about 11 hours. At about 11 hours, the contents of the fermenter vessels were then poured into 500 ml sterile graduated plastic bottles and centrifuged for 20 minutes at 4500 rpm. The cells were resuspended in 50 ml total volume of modified M9 medium. A 400 ml DasGip vessel containing 150 ml of EZ Rich medium containing 72 g/L glucose and 10 g/L yeast extract was inoculated with 50 ml of the cell containing medium and then induced with 0.1 mM IPTG. Cell concentration was approximately 6 g CDW per L. Constant dissolved oxygen content of 5% was maintained using a 1 sL/h air sparge with variable agitation automatically controlled from 300 to 1200 rpm. Measurement of the fermentor vessel off-gas by trapping in an octanol bubble trap and then measurement by GC was performed for isobutanol and ethanol. Continuous measurement of off-gas concentrations of carbon dioxide and oxygen were also measured by a DasGip off-gas analyzer throughout the experiment. Samples were aseptically removed from the fermenter vessel throughout the experiment and used to measure $OD_{600}$, glucose concentration by HPLC, and isobutanol concentration in the broth by GC. Isobutanol production reached a maximum at around 4 hours with a titer of about 13.7 g/L and with a yield of approximately 87% maximum theoretical. Volumetric productivity of the fermentation, calculated from the inception of the fermentation at time 0 h to an elapsed fermentation time of about 4 h, was about 3.2 g/L/h.

Example 43

High Titer Example 4: GEVO1780 is a modified bacterial biocatalyst that contains genes on two plasmids which encode a pathway of enzymes that convert pyruvate into isobutanol. When the biocatalyst GEVO1780 was contacted with glucose in a medium suitable for growth of the biocatalyst, at about 30° C., the biocatalyst produced isobutanol from the glucose. An overnight starter culture was started in a 250 mL Erlenmeyer flask with GEVO1780 cells from a freezer stock with a 40 mL volume of modified M9 medium consisting of 85 g/L glucose, 20 g/L yeast extract, 20 µM ferric citrate, 5.72 mg/L $H_3BO_3$, 3.62 mg/L $MnCl_2.4H_2O$, 0.444 mg/L $ZnSO_4.7H_2O$, 0.78 mg/L $Na_2MnO_4.2H_2O$, 0.158 mg/L $CuSO_4.5H_2O$, 0.0988 mg/L $CoCl_2.6H_2O$, $NaHPO_4$ 6.0 g/L, $KH_2PO_4$ 3.0 g/L, NaCl 0.5 g/L, $NH_4Cl$ 2.0 g/L, $MgSO_4$ 0.0444 g/L and $CaCl_2$ 0.00481 g/L and at a culture OD600 of 0.02 to 0.05. The starter culture was grown for approximately 14 hrs in a 30° C. shaker at 250 rpm. Some of the starter culture was then transferred to a 2000 mL DasGip fermenter vessel containing about 1500 mL of modified M9 medium to achieve an initial culture OD600 of about 0.1. The vessel was attached to a computer control system to monitor and control pH at 6.5 through addition of base, temperature at about 30° C., dissolved oxygen, and agitation. The vessel was agitated, with a minimum agitation of 400 rpm and agitation was varied to maintain a dissolved oxygen content of about 50% using a 25 sL/h air sparge until the OD600 was about 1.0. The vessel was then induced with 0.1 mM IPTG. After continuing growth for approximately 8-10 hrs, the dissolved oxygen content was decreased to 5% with 400 rpm minimum agitation and 10 sl/h airflow. Continuous measurement of the fermentor vessel off-gas by GC-MS analysis was performed for oxygen, isobutanol, ethanol, and carbon dioxide throughout the experiment. Samples were aseptically removed from the fermenter vessel throughout the experiment and used to measure OD600, glucose concentration, and isobutanol concentration in the broth. Throughout the experiment, supplements of pre-grown and pre-induced biocatalyst cells were added as a concentrate two times after the start of the experiment: at 40 h and 75 h. These cells were the same strain and plasmids shown above and used in the fermenter. Supplemented cells were grown as 1 L cultures in 2.8 L Fernbach flasks and incubated at 30° C., 250 RPM in Modified M9 Medium with 85 g/L glucose. Cultures were induced upon inoculation with 0.1 mM IPTG. When the cells had reached an $OD_{600}$ of about 4.0-5.0, the culture was concentrated by centrifugation and then added to the fermenter. A glucose feed of about 500 g/L glucose in DI water was used intermittently during the production phase of the experiment at time points greater than 12 h to maintain glucose concentration in the fermenter of about 30 g/L or above.

The fermenter vessel was attached by tubing to a smaller 400 mL fermenter vessel that served as a flash tank and operated in a recirculation loop with the fermenter. The biocatalyst cells within the fermenter vessel were isolated from the flash tank by means of a cross-flow filter placed in-line with the fermenter/flash tank recirculation loop. The filter only allowed cell-free fermentation broth to flow from the fermenter vessel into the flash tank. The volume in the flash tank was approximately 100 mL and the hydraulic retention time was about 10 minutes. Heat and vacuum were applied to the flash tank. The vacuum level applied to the flash tank was initially set at about 50 mBar and the flash tank was set at about 45° C. These parameters were adjusted to maintain approximately 6-13 g/L isobutanol in the fermenter throughout the experiment. Generally, the vacuum ranged from 45-100 mBar and the flash tank temperature ranged from 43° C. to 45° C. throughout the experiment. Vapor from the heated flash tank was condensed into a collection vessel as distillate. Cell-free fermentation broth was continuously returned from the flash tank to the fermentation vessel.

The distillate recovered in the experiment was strongly enriched for isobutanol. Isobutanol formed an azeotrope with water and usually lead to a two phase distillate: an isobutanol rich top phase and an isobutanol lean bottom phase. Distillate samples were analyzed by GC for isobutanol concentration. Isobutanol production reached a maximum at around 118 hrs with a total titer of about 87 g/L. The isobutanol production rate was about 0.74 g/L/h on average over the course of the experiment. The percent theoretical yield of isobutanol was approximately 90.4% at the end of the experiment.

Example 44

High Titer Example 5: GEVO1780 is a modified bacterial biocatalyst that contains genes on two plasmids which encode a pathway of enzymes that convert pyruvate into isobutanol. When the biocatalyst GEVO1780 was contacted with glucose in a medium suitable for growth of the biocatalyst, at about 30° C., the biocatalyst produced isobutanol from the glucose. An overnight starter culture was started in a 250 mL Erlenmeyer flask with GEVO1780 cells from a freezer stock with a 40 mL volume of modified M9 medium consisting of 85 g/L glucose, 20 g/L yeast extract, 20 μM ferric citrate, 5.72 mg/L $H_3BO_3$, 3.62 mg/L $MnCl_2.4H_2O$, 0.444 mg/L $ZnSO_4.7H_2O$, 0.78 mg/L $Na_2MnO_4.2H_2O$, 0.158 mg/L $CuSO_4.5H_2O$, 0.0988 mg/L $CoCl_2.6H_2O$, $NaHPO_4$ 6.0 g/L, $KH_2PO_4$ 3.0 g/L, NaCl 0.5 g/L, $NH_4Cl$ 2.0 g/L, $MgSO_4$ 0.0444 g/L and $CaCl_2$ 0.00481 g/L and at a culture $OD_{600}$ of about 0.05. The starter culture was grown for approximately 14 hrs in a 30° C. shaker at 250 rpm. Some of the starter culture was then transferred to a 2000 mL DasGip fermenter vessel containing about 1500 mL of modified M9 medium to achieve an initial culture $OD_{600}$ of about 0.1. The vessel was attached to a computer control system to monitor and control pH at 6.5 through addition of base, temperature at about 30° C., dissolved oxygen, and agitation. The vessel was agitated, with a minimum agitation of 400 rpm and agitation was varied to maintain a dissolved oxygen content of about 50% using a 25 sL/h air sparge until the $OD_{600}$ was about 1.0. The vessel was then induced with 0.1 mM IPTG. After continuing growth for approximately 8-10 hrs, the dissolved oxygen content was decreased to 5% with 400 rpm minimum agitation and 10 sl/h airflow. Continuous measurement of the fermentor vessel off-gas by GC-MS analysis was performed for oxygen, isobutanol, ethanol, and carbon dioxide throughout the experiment. Samples were aseptically removed from the fermenter vessel throughout the experiment and used to measure $OD_{600}$, glucose concentration, and isobutanol concentration in the broth. Throughout the experiment, supplements of pre-grown and pre-induced biocatalyst cells were added as a concentrate after the start of the experiment: at 62.5 h, 87 h, 113 h, and 142 h. These cells were the same strain and plasmids shown above and used in the fermenter. Supplemented cells were grown as 1 L cultures in 2.8 L Fernbach flasks and incubated at 30° C., 250 RPM in Modified M9 Medium. Cultures were induced upon inoculation with 0.1 mM IPTG. When the cells had reached an $OD_{600}$ of about 4.0-5.0, the culture was concentrated by centrifugation and then added to the fermenter. A glucose feed of about 500 g/L glucose in DI water was used intermittently during the production phase of the experiment at time points greater than 12 h to maintain glucose concentration in the fermenter of about 30 g/L or above.

The fermenter vessel was attached by tubing to a smaller 400 mL fermenter vessel that served as a flash tank and operated in a recirculation loop with the fermenter. The volume in the flash tank was approximately 100 mL and the hydraulic retention time was about 5-10 minutes. Heat and vacuum were applied to the flash tank. The vacuum level applied to the flash tank was initially set at about 40 mBar and the flash tank was set at about 36° C. These parameters were adjusted to maintain approximately 5-10 g/L isobutanol in the fermenter throughout the experiment. Generally, the vacuum ranged from about 20-50 mBar and the flash tank temperature of about 36° C. throughout the experiment. Vapor from the heated flash tank was condensed into a collection vessel as distillate. The fermentation broth was continuously returned from the flash tank to the fermentation vessel.

The distillate recovered in the experiment was strongly enriched for isobutanol. Isobutanol formed an azeotrope with water and usually lead to a two phase distillate: an isobutanol rich top phase and an isobutanol lean bottom phase. Distillate samples were analyzed by GC for isobutanol concentration.

Isobutanol production reached a maximum at around 166 hrs with a total titer of about 106 g/L. The isobutanol production rate was about 0.64 g/L/h and the percent theoretical yield was approximately 91% at the end of the experiment.

Example 45

High Titer Example 6: GEVO1780 is a modified bacterial biocatalyst that contains genes on two plasmids which encode a pathway of enzymes that convert pyruvate into isobutanol. When the biocatalyst GEVO1780 was contacted with glucose in a medium suitable for growth of the biocatalyst, at about 30° C., the biocatalyst produced isobutanol from the glucose. Overnight starter cultures were started in four 2.8 L Fernbach flasks with GEVO1780 cells from freezer stocks with four 1000 mL volumes of modified M9 medium consisting of 85 g/L glucose, 20 g/L yeast extract, 20 µM ferric citrate, 5.72 mg/L $H_3BO_3$, 3.62 mg/L $MnCl_2.4H_2O$, 0.444 mg/L $ZnSO_4.7H_2O$, 0.78 mg/L $Na_2MnO_4.2H_2O$, 0.158 mg/L $CuSO_4.5H_2O$, 0.0988 mg/L $CoCl_2.6H_2O$, $NaHPO_4$ 6.0 g/L, $KH_2PO_4$ 3.0 g/L, NaCl 0.5 g/L, $NH_4Cl$ 2.0 g/L, $MgSO_4$ 0.0444 g/L and $CaCl_2$ 0.00481 g/L and at a culture $OD_{600}$ of about 0.05. The cultures were induced with 1 mM IPTG at the point of inoculation and grown for approximately 14 hrs in a 30° C. shaker at 250 rpm. At about 14 hours, the contents of the flasks were then poured into 500 ml sterile graduated plastic bottles and centrifuged for 20 minutes at 4500 rpm. The cells were resuspended in about 100 ml total volume of modified M9 medium without glucose, then transferred to a 2000 mL DasGip fermenter vessel containing about 1500 mL of modified M9 medium, wherein the glucose was replaced by clarified corn liquefact to give an approximate glucose concentration of about 100 g/L and to achieve an initial culture $OD_{600}$ of about 10. Clarified corn liquefact was prepared by incubating a slurry of ground corn at about 60° C. for about 24 hrs to which alpha-amyalse and gluco-amalyase enzymes had been added in sufficient amounts to liberate free glucose from the corn starch. After about 24 hours of treatment as described above, the corn liquefact was clarified by centrifugation and filtration to remove most of the solids and generate a clarified corn liquefact solution of about 250 g/L glucose. The fermenter vessel was attached to a computer control system to monitor and control pH at 6.5 through addition of base, temperature at about 30° C., dissolved oxygen, and agitation. The vessel was agitated, with a minimum agitation of 400 rpm and agitation was varied to maintain a dissolved oxygen content of about 5% using a 10 sL/h air sparge. Continuous measurement of the fermentor vessel off-gas by GC-MS analysis was performed for oxygen, isobutanol, ethanol, and carbon dioxide throughout the experiment. Samples were aseptically removed from the fermenter vessel throughout the experiment and used to measure $OD_{600}$, glucose concentration, and isobutanol concentration in the broth. Supplements of pre-grown and pre-induced biocatalyst cells were added as a concentrate throughout this experiment. These cells were the same strain and plasmids shown above and used in the fermenter. Supplemented cells were grown as 1 L cultures in 2.8 L Fernbach flasks and incubated at 30° C., 250 RPM in Modified M9 Medium using glucose as the main carbon source. Cultures were induced upon inoculation with 1 mM IPTG. When the cells had reached an $OD_{600}$ of about 2.0-5.0, the culture was concentrated by centrifugation and then added to the fermenter. A feed of clarified corn liquefact containing about 250 g/L glucose was used intermittently during the experiment to maintain glucose concentration in the fermenter of about 30 g/L or above.

The fermenter vessel was attached by tubing to a smaller 400 mL fermenter vessel that served as a flash tank and operated in a recirculation loop with the fermenter. The volume in the flash tank was approximately 100 mL and the hydraulic retention time was about 5-10 minutes. Heat and vacuum were applied to the flash tank. The vacuum level applied to the flash tank was initially set at about 40 mBar and the flash tank was set at about 36° C. These parameters were adjusted to maintain approximately 5-10 g/L isobutanol in the fermenter throughout the experiment. Generally, the vacuum ranged from about 20-50 mBar and the flash tank temperature of about 36° C. throughout the experiment. Vapor from the heated flash tank was condensed into a collection vessel as distillate. The fermentation broth was continuously returned from the flash tank to the fermentation vessel.

The distillate recovered in the experiment was strongly enriched for isobutanol. Isobutanol formed an azeotrope with water and usually lead to a two phase distillate: an isobutanol rich top phase and an isobutanol lean bottom phase. Distillate samples were analyzed by GC for isobutanol concentration. Isobutanol production reached a maximum at around 217 hrs with a total titer of about 124 g/L. The isobutanol production rate was about 0.57 g/L/h on average over the course of the experiment, but a maximum isobutanol production rate of about 1.3 g/L/h was achieved in the experiment. The percent theoretical yield was approximately 74% at the end of the experiment, but a maximum theoretical yield of about 88% theoretical yield was achieved during the experiment.

Example 46

High Titer Example 7: GEVO1780 is a modified bacterial biocatalyst that contains genes on two plasmids which encode a pathway of enzymes that convert pyruvate into isobutanol. When the biocatalyst GEVO1780 was contacted with glucose in a medium suitable for growth of the biocatalyst, at about 30° C., the biocatalyst produced isobutanol from the glucose. An overnight starter culture was started in a 2.8 L Fernbach flask with GEVO1780 cells from a freezer stock with a 1000 mL volume of modified M9 medium consisting of 85 g/L glucose, 20 g/L yeast extract, 20 µM ferric citrate, 5.72 mg/L $H_3BO_3$, 3.62 mg/L $MnCl_2.4H_2O$, 0.444 mg/L $ZnSO_4.7H_2O$, 0.78 mg/L $Na_2MnO_4.2H_2O$, 0.158 mg/L $CuSO_4.5H_2O$, 0.0988 mg/L $CoCl_2.6H_2O$, $NaHPO_4$ 6.0 g/L, $KH_2PO_4$ 3.0 g/L, NaCl 0.5 g/L, $NH_4Cl$ 2.0 g/L, $MgSO_4$ 0.0444 g/L and $CaCl_2$ 0.00481 g/L and at a culture $OD_{600}$ of about 0.05. The culture was induced with 1 mM IPTG at the point of inoculation and grown for approximately 14 hrs in a 30° C. shaker at 250 rpm. At about 14 hours, the contents of the flask was then poured into 500 ml sterile graduated plastic bottles and centrifuged for 20 minutes at 4500 rpm. The cells were resuspended in about 40 ml total volume of modified M9 medium, then transferred to a 2000 mL DasGip fermenter vessel containing about 1500 mL of modified M9 medium, wherein the glucose was replaced by corn liquefact with about 17% dry solids concentration and to achieve an initial calculated culture $OD_{600}$ of about 3. Corn liquefact, which was treated with alpha-amyalse, was prepared by diluting sterilized corn liquefact with a dry solids concentration of about 35% with sterile dionized water to a final dry solids concentration of about 17%. The diluted corn liquefact was then added to the modified M9 medium components described above without additional glucose and placed in the 2000 mL fermenter vessel. At the point of inoculation, a dose of gluco-amylase was added to the fermenter vessel in sufficient quantity to hydrolyse the corn starch oligomers present in the corn liquefact to monomeric glucose. The vessel was attached to a computer control system to monitor and control pH at about 6.5 through addition of base, temperature at about 30° C., dissolved oxygen, and agitation. The vessel was agitated, with a minimum agitation of 400 rpm and agitation was varied to maintain a dissolved oxygen content of about 5% using a 10 sL/h air sparge. Continuous measurement of the fermentor vessel off-gas by GC-MS analysis was performed for oxygen, isobutanol, ethanol, and carbon dioxide throughout the experiment. Samples were aseptically removed from the fermenter vessel throughout the experiment and used to measure glucose concentration and isobutanol concentration in the broth. Supplements of pre-grown and pre-induced biocatalyst cells were added as a concentrate throughout this experiment. These cells were the same strain shown above and used in the fermenter. Supplemented cells were grown as 1 L cultures in 2.8 L Fernbach flasks and incubated at 30° C., 250 RPM in Modified M9 Medium using glucose as the main carbon source. Cultures were induced upon inoculation with 1 mM IPTG. When the cells had reached an $OD_{600}$ of about 2.0-5.0, the culture was concentrated by centrifugation and then added to the fermenter. A feed of corn liquefact was prepared by adding dose of gluco-amylase in sufficient quantity to hydrolyse the corn starch oligomers present in the corn liquefact to monomeric glucose and incubation at about 50° C. for 24 hrs prior to use. The resulting solution contained about 188 g/L glucose and was used intermittently during the experiment to maintain glucose concentration in the fermenter of about 40 g/L or above.

The fermenter vessel was attached by tubing to a smaller 400 mL fermenter vessel that served as a flash tank and operated in a recirculation loop with the fermenter. The volume in the flash tank was approximately 100 mL and the hydraulic retention time was about 5-10 minutes. Heat and vacuum were applied to the flash tank. The vacuum level applied to the flash tank was initially set at about 40 mBar and the flash tank was set at about 36° C. These parameters were adjusted to maintain approximately 5-10 g/L isobutanol in the fermenter throughout the experiment. Generally, the vacuum ranged from about 20-50 mBar and the flash tank temperature was about 36° C. throughout the experiment. Vapor from the heated flash tank was condensed into a collection vessel as distillate. The fermentation broth was continuously returned from the flash tank to the fermentation vessel.

The distillate recovered in the experiment was strongly enriched for isobutanol. Isobutanol formed an azeotrope with water and usually lead to a two phase distillate: an isobutanol rich top phase and an isobutanol lean bottom phase. Distillate samples were analyzed by GC for isobutanol concentration. Isobutanol production reached a maximum at around 166 hrs with a total titer of about 30 g/L. The isobutanol production rate was about 0.31 g/L/h on average over the course of the experiment. The percent theoretical yield was not determined in this experiment.

Example 47

Low-Level Anaerobic Production of Isobutanol: This example illustrates that a microorganism which is metabolically engineered to overexpress an isobutanol producing pathway produces a low amount of isobutanol under anaerobic conditions.

Overnight cultures of GEVO1859 were started from glycerol stocks stored at −80° C. of previously transformed strains. These cultures were started in 3 mL M9 minimal medium (Sambrook, J., Russel, D. W. Molecular Cloning, A Laboratory Manual. 3 ed. 2001, Cold Spring Harbor, N.Y.: Cold Spring Harbor Laboratory Press), supplemented with 10 g/L yeast extract, 10 µM ferric citrate and trace metals, containing 8.5% glucose and the appropriate antibiotics in snap cap tubes about 14 h prior to the start of the fermentation. Isobutanol fermentations were then carried out in screw cap flasks containing 20 mL of the same medium that was inoculated with 0.2 mL of the overnight culture. The cells were incubated at 37° C./250 rpm until the strains had grown to an OD600 of 0.6-0.8 and were then induced with Isopropyl β-D-1-thiogalactopyranoside at 1 mM final concentration.

Three hours after induction the cultures were either kept under the current conditions (micro-aerobic conditions) or shifted to anaerobic conditions by loosening the cap of the flasks and placing the flasks into to a Coy Laboratory Products Type B Vinyl anaerobic chamber (Coy Laboratory Products, Grass Lakes, Mich.) through an airlock in which the flasks were cycled three times with nitrogen and vacuum, and then filled with the a hydrogen gas mix (95% Nitrogen, 5% Hydrogen).

Once the flasks were inside the anaerobic chamber, the flasks were closed again and incubated without shaking at 30° C. The flasks in the anaerobic chamber were swirled twice a day. Samples (2 mL) were taken at the time of the shift and at 24 h and 48 h after inoculation, spun down at 22000 g for 1 min to separate the cell pellet from the supernatant and stored frozen at −20° C. until analysis. The samples were analyzed using High performance liquid chromatography (HPLC) and gas chromatography GC. All experiments were performed in duplicate.

Figure 6:
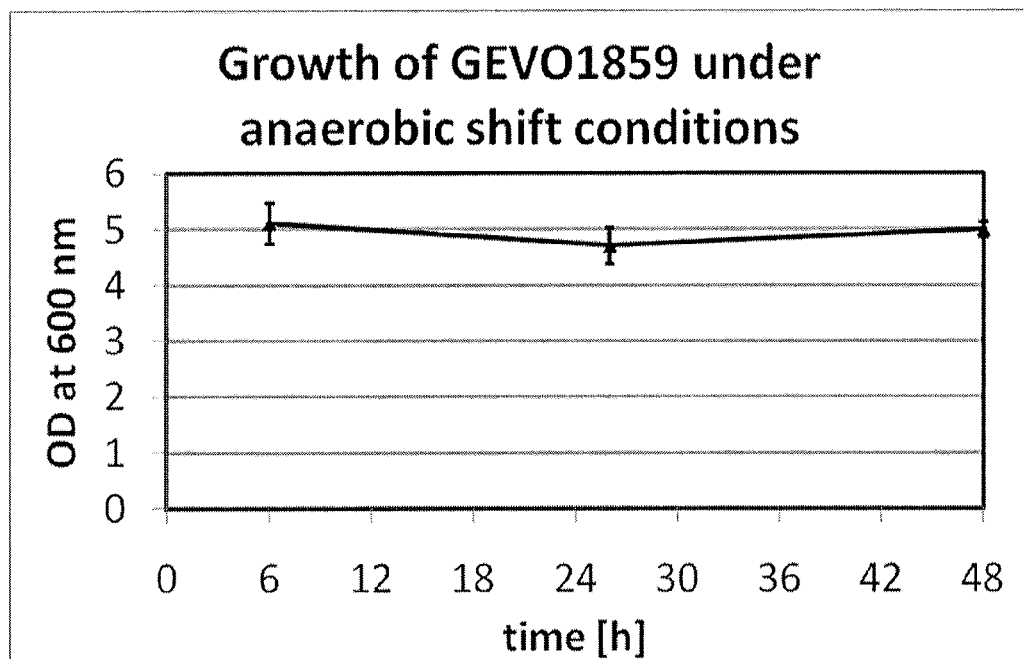
FIG. 6 illustrates the growth of an exemplary biocatalyst under anaerobic shift conditions.

GEVO1859 was run in triplicate. Stable OD values can be observed for all strains under anaerobic shift conditions over the course of the fermentation. FIG. 6 illustrates the growth of Gevo 1859 under anaerobic shift conditions over the course of the fermentation.

Figure 7:
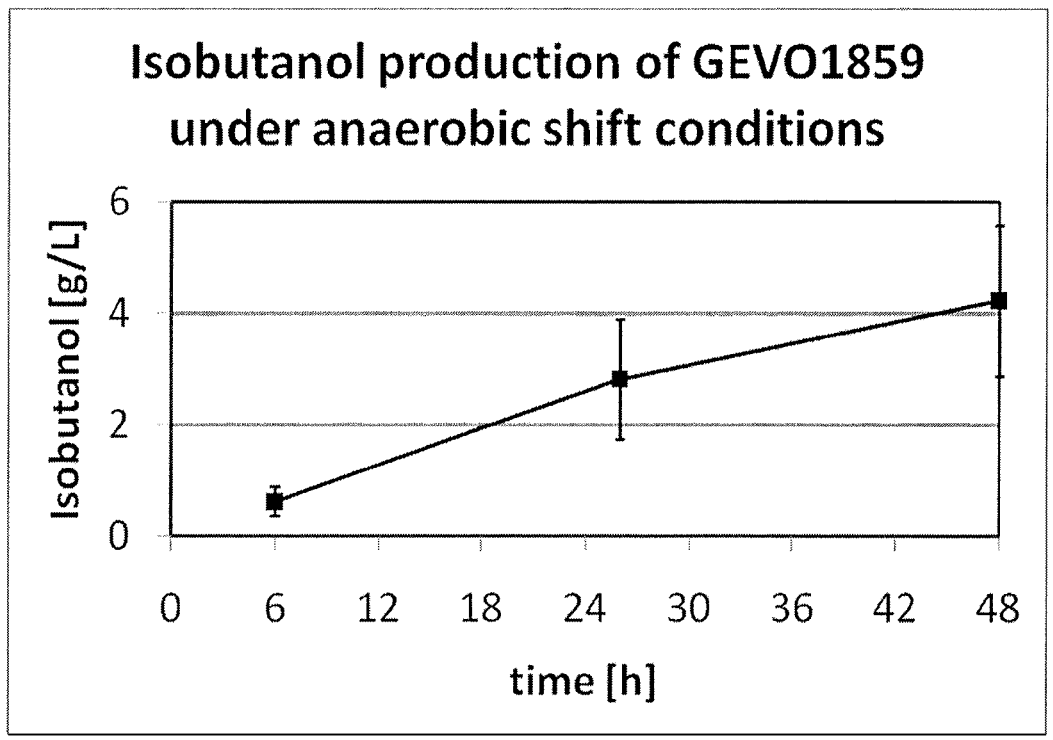
FIG. 7 illustrates biofuel production by an exemplary biocatalyst under microaerobic conditions.

A complete pathway integrant strain showed low-level anaerobic isobutanol production over the course of the fermentation (see FIG. 7 and Table 28 below). FIG. 7 illustrates isobutanol production by Gevo 1859 under microaerobic conditions over the course of the fermentation.

Table 28 provides results for volumetric productivity, specific productivity titer and yield reached in an anaerobic fermentation for the tested strains and plasmid systems:

| Samples | Volumetric Productivity [g/L/h] | ± | Specific Productivity [g/L/h/OD] | ± | Titer [g/L] | ± | Yield [g/g] | ± |
|---|---|---|---|---|---|---|---|---|
| GEVO1859 | 0.088 | 0.028 | 0.019 | 0.005 | 4.22 | 1.35 | 0.140 | 0.029 |

As shown in Table 29 below, in the period from 6 to 48, i.e. under anaerobic conditions GEVO1859 demonstrated limited production of isobutanol.

Table 29 provides results for volumetric productivity, specific productivity titer and yield reached in the period from 6 to 48 h for the tested strains and plasmid systems:

| Samples | Condition | Volumetric Productivity [g/L/h] | ± | Specific Productivity [g/L/h/OD] | ± | Titer [g/L] | ± | Yield [g/g] | ± |
|---|---|---|---|---|---|---|---|---|---|
| GEVO1859 | Micro-aerobic | 0.266 | 0.010 | 0.040 | 0.004 | 11.2 | 0.4 | 0.33 | 0.016 |
| GEVO1859 | Anaerobic | 0.086 | 0.026 | 0.019 | 0.005 | 3.60 | 1.1 | 0.14 | 0.032 |

Example 48

Overexpression of pntAB improves isobutanol fermentation performance: This example illustrates that overexpression of a transhydrogenase, exemplified by the E. coli pntAB operon product, on a low copy plasmid improves isobutanol production under anaerobic conditions.

GEVO1748 was transformed with plasmids pGV1698 one of either pGV1720 (control) or pGV1745 (pntAB).

The aforementioned strains were plated on LB-plates containing the appropriate antibiotics and incubated overnight at 37° C. Overnight cultures were started in 3 mL EZ-Rich medium (Neidhardt, F. C., P. L. Bloch, and D. F. Smith. 1974. Culture medium for enterobacteria. J. Bacteriol. 119:736-47) containing 5% glucose and the appropriate antibiotics in snap cap tubes about 14 h prior to the start of the fermentation. Isobutanol fermentations were then carried out in EZ-Rich Medium containing 5% glucose and the appropriate antibiotics. Screw cap flasks with 20 mL EZ-Rich medium containing 5% glucose and the appropriate antibiotics were inoculated with 1% of the grown overnight culture. The cells were incubated at 37° C./250 rpm until they reached an OD600 of 0.6-0.8 followed by induction with Isopropyl β-D-1-thiogalactopyranoside (IPTG, 1 mM) and anhydrotetracycline (aTc, 100 ng/mL). Samples (2 mL) were taken 24 h and 48 h post inoculation, centrifuged at 22,000×g for 1 min and stored frozen at −20° C. until via Gas Chromatography (GC) and High Performance Liquid Chromatography (HPLC). Fermentations were run with two biological replicates.

All cultures grew to an OD of 5.5 to 6.5. Volumetric productivity and titer were improved by 45%, specific productivity improved by 51%. Yield was improved by 8% (Table 30).

Table 30 provides data indicating that overexpression of pntAB improves isobutanol fermentation performance:

Example 49

Overexpression of pntAB enables anaerobic isobutanol production: This example illustrates that overexpression of a transhydrogenase, exemplified by the E. coli pntAB operon product, improves anaerobic isobutanol.

GEVO1844 was transformed with plasmids pGV1698 and one of either pGV1720 (control) or pGV1745 (pntAB). GEVO1748 was transformed with plasmids pGV1698 and pGV1720 (control) or pGV1745 (pntAB).

Overnight cultures of the aforementioned strains were started from glycerol stocks stored at −80° C. of previously transformed strains. These cultures were started in 3 mL M9 minimal medium (Sambrook, J., Russel, D. W. Molecular Cloning, A Laboratory Manual. 3 ed. 2001, Cold Spring Harbor, N.Y.: Cold Spring Harbor Laboratory Press), supplemented with 10 g/L yeast extract, 10 µM ferric citrate and trace metals, containing 8.5% glucose and the appropriate antibiotics in snap cap tubes about 14 h prior to the start of the fermentation. Isobutanol fermentations were then carried out in screw cap flasks containing 20 mL of the same medium that was inoculated with 0.2 mL of the overnight culture. The cells were incubated at 37° C./250 rpm until the strains had grown to an OD600 of 0.6-0.8 and were then induced with Isopropyl β-D-1-thiogalactopyranoside at 1 mM final concentration.

Three hours after induction the cultures were shifted to anaerobic fermentation conditions by loosening the cap of the flasks and placing the flasks into to a Coy Laboratory Products Type B Vinyl anaerobic chamber (Coy Laboratory Products, Grass Lakes, Mich.) through an airlock in which the flasks were cycled three times with nitrogen and vacuum, and then filled with the a hydrogen gas mix (95% Nitrogen, 5% Hydrogen). Once the flasks were inside the anaerobic chamber, the flasks were closed again and incubated without shaking at 30° C. Inside the chamber, an anaerobic atmosphere (less than 5 ppm oxygen) was maintained through the hydrogen gas mix (95% Nitrogen, 5% Hydrogen) reacting with a palladium catalyst to remove oxygen. The flasks in the anaerobic chamber were swirled twice a day. Samples (2 mL) were taken at the time of the shift and at 24 h and 48 h after inoculation, spun down at 22000 g for 1 min to separate the

| Strain | Volumetric Productivity [g/L/h] | ± | Specific Productivity [g/L/h/OD] | ± | Titer [g/L] | ± | Yield [g/g] | ± |
|---|---|---|---|---|---|---|---|---|
| GEVO1748 + pGV1698 + pGV1720 (control) | 0.205 | 0.001 | 0.035 | 0.001 | 9.86 | 0.04 | 0.311 | 0.001 |
| GEVO1748 + pGV1698 + pGV1745 (pntAB) | 0.298 | 0.006 | 0.053 | 0.003 | 14.29 | 0.28 | 0.337 | 0.001 | cell pellet from the supernatant and stored frozen at −20° C. until analysis. The samples were analyzed using High performance liquid chromatography (HPLC) and gas chromatography GC. All experiments were performed in duplicate.

Figure 8:
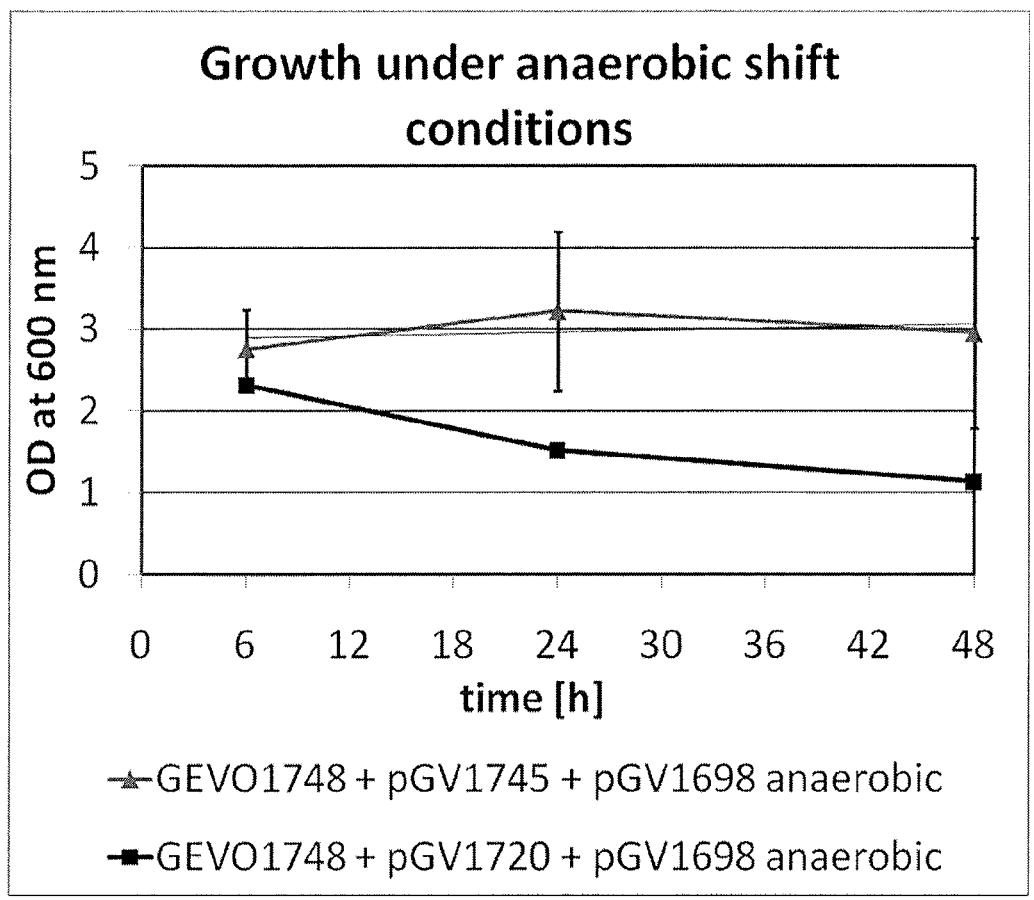
FIG. 8 illustrates the growth of exemplary biocatalysts under anaerobic conditions.

At the time of shifting the cultures to anaerobic conditions all samples had an OD600 ranging between 2.3 and 3.3. All samples featuring an overexpressed pntAB operon (pGV1745) increased in OD600 from 6 h to 24 h by 0.2-1.1, all samples lacking pntAB (pGV1720) decreased in OD600 by 0.5-1.2 (FIG. 8), indicating that overexpression of pntAB is beneficial under anaerobic conditions. FIG. 8 provides data for the growth of the tested samples under anaerobic condition over the course of the fermentation. The first data point at 6 hours indicates the shift to anaerobic conditions.

Figure 9:
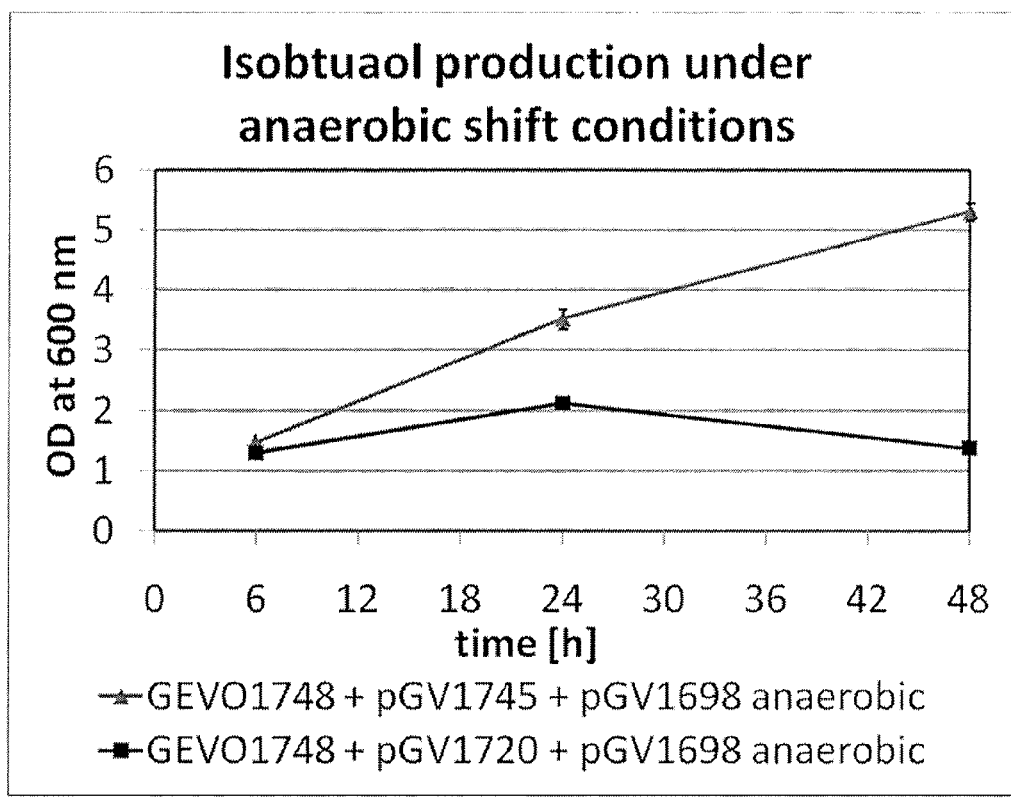
FIG. 9 illustrates biofuel production by exemplary biocatalysts under anaerobic conditions.

Furthermore, pntAB over-expression is beneficial for anaerobic isobutanol production. All samples featuring pntAB continued isobutanol production under anaerobic conditions until the fermentation was stopped at 48 hours whereas the samples lacking pntAB did not produce isobutanol between 24 and 48 hours (FIG. 8). FIG. 9 provides additional data for isobutanol production of the tested samples under anaerobic conditions over the course of the fermentation.

In the strain overexpressing pntAB volumetric productivity and titer are increased 2.4-fold, specific productivity by 85% and yield by 9% (Table 31).

Table 31 summarizes the results for volumetric productivity, specific productivity titer and yield reached in an anaerobic fermentation for the tested strains and plasmid systems:

Example 50

Chromosomal Integration of pntAB improves anaerobic isobutanol production: This example illustrates that overexpression of a transhydrogenase, exemplified by the *E. coli* pntAB operon product, from the chromosome improves isobutanol production under anaerobic conditions compared to the case in which pntAB is expressed from a low copy plasmid. Overnight cultures of GEVO1846, GEVO1859, GEVO1886 were started from glycerol stocks stored at −80° C. of previously transformed strains. These cultures were started in 3 mL M9 minimal medium (Sambrook, J., Russel, D. W. Molecular Cloning, A Laboratory Manual. 3 ed. 2001, Cold Spring Harbor, N.Y.: Cold Spring Harbor Laboratory Press), supplemented with 10 g/L yeast extract, 10 µM ferric citrate and trace metals, containing 8.5% glucose and the appropriate antibiotics in snap cap tubes about 14 h prior to the start of the fermentation. Isobutanol fermentations were then carried out in screw cap flasks containing 20 mL of the same medium that was inoculated with 0.2 mL of the overnight culture. The cells were incubated at 37° C./250 rpm until the strains had grown to an OD600 of 0.6-0.8 and were then induced with Isopropyl β-D-1-thiogalactopyranoside at 1 mM final concentration. Three hours after induction the cultures were either kept under the current conditions (microaerobic conditions) or shifted to anaerobic conditions by loosening the cap of the flasks and placing the flasks into to a Coy Laboratory Products Type B Vinyl anaerobic chamber (Coy Laboratory Products, Grass Lakes, Mich.) through an

| samples | Volumetric Productivity [g/L/h] | ± | Specific Productivity [g/L/h/OD] | ± | Titer [g/L] | ± | Yield [g/g] | ± |
|---|---|---|---|---|---|---|---|---|
| GEVO1748 + pGV1720 + pGV1698 (control) | 0.047 | | 0.022 | | 2.24 | | 0.279 | |
| GEVO1748 + pGV1745 + pGV1698 (pntAB) | 0.111 | 0.002 | 0.041 | 0.012 | 5.32 | 0.10 | 0.304 | 0.004 |

In the period from 6 to 48, i.e. under anaerobic conditions GEVO1748 transformed with plasmids pGV1698 and pGV1745 (carrying pntAB) demonstrated significantly higher productivity, titer, and yield of isobutanol compared to the control strain carrying pGV1720 (without pntAB) (Table 32).

Table 32 summarizes results for volumetric productivity, specific productivity titer and yield reached in the period from 6 to 48 h for the tested strains and plasmid systems:

airlock in which the flasks were cycled three times with nitrogen and vacuum, and then filled with the a hydrogen gas mix (95% Nitrogen, 5% Hydrogen). Once the flasks were inside the anaerobic chamber, the flasks were closed again and incubated without shaking at 30° C. The flasks in the anaerobic chamber were swirled twice a day. Samples (2 mL) were taken at the time of the shift and at 24 h and 48 h after inoculation, spun down at 22000 g for 1 min to separate the cell pellet from the supernatant and stored frozen at −20° C.

Figure 10:
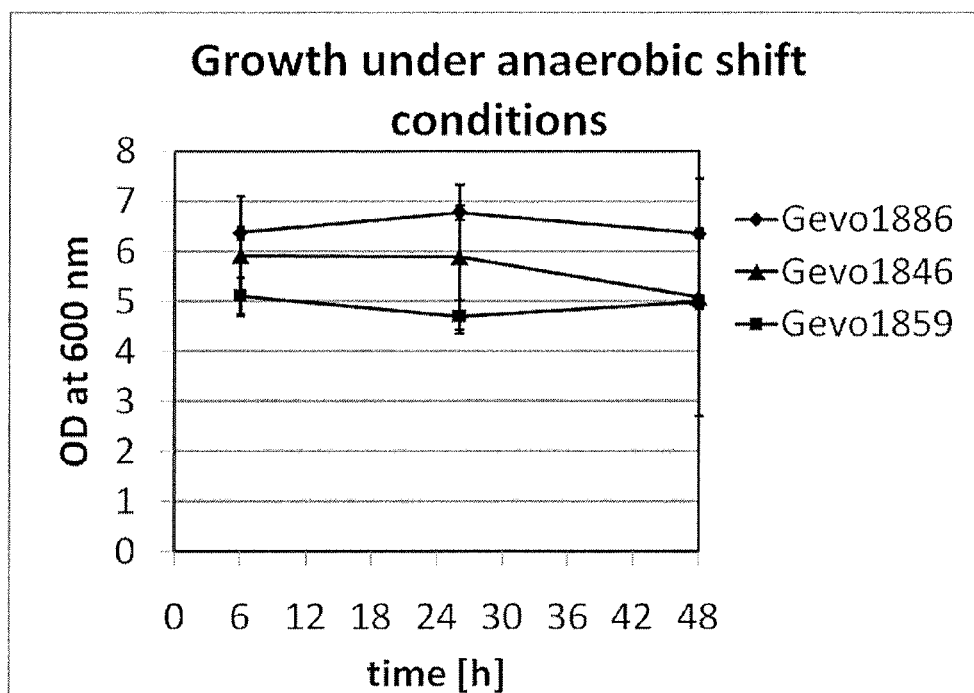
FIG. 10 illustrates the growth of an exemplary biocatalysts under anaerobic conditions.
Figure 11:
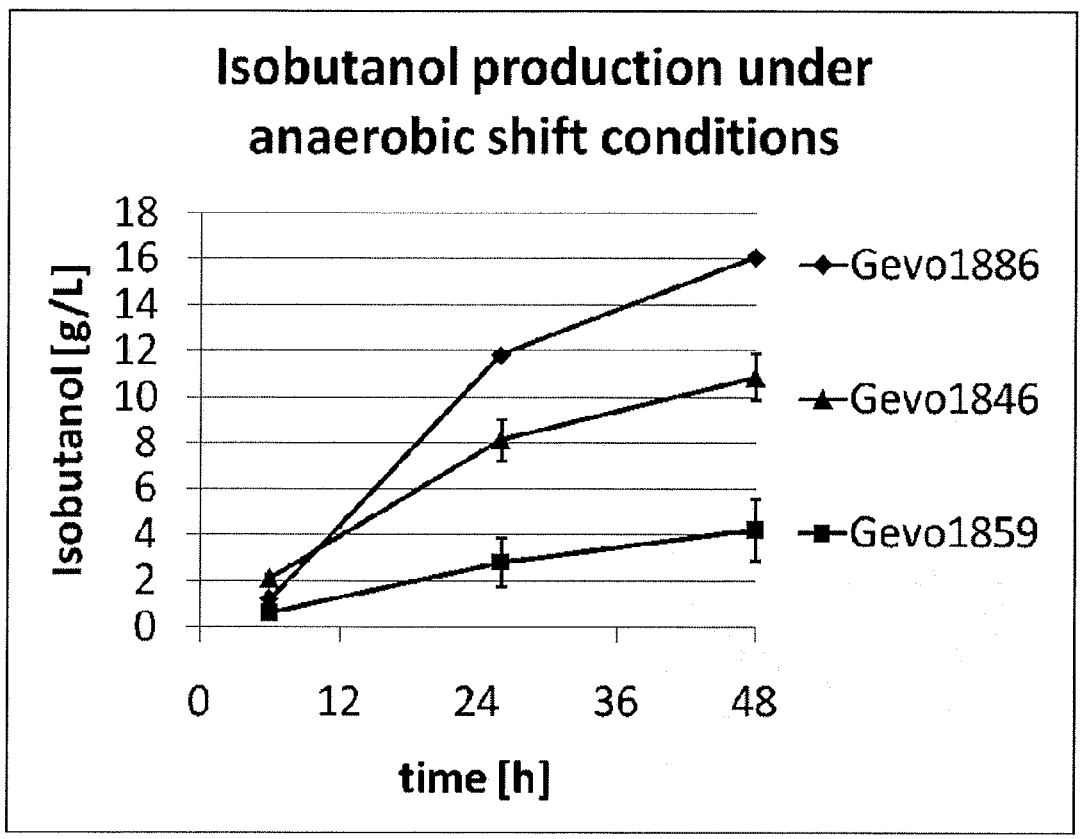
FIG. 11 illustrates biofuel production by exemplary biocatalysts under microaerobic conditions.
Figure 12:
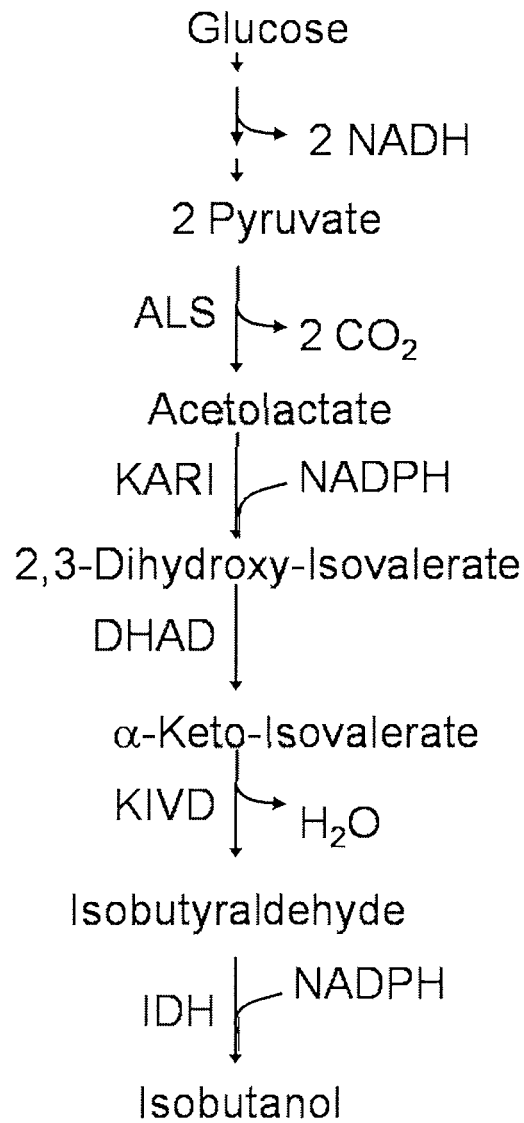
FIG. 12 illustrates an exemplary pathway for producing a biofuel.
Figure 13:
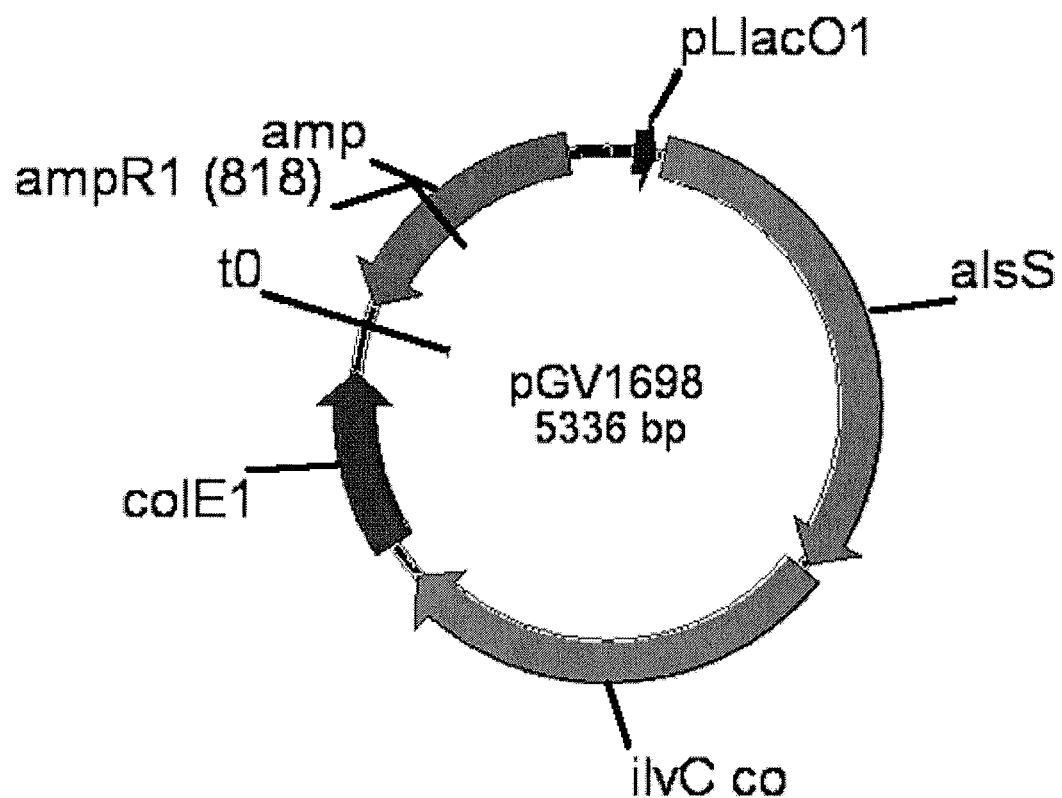
FIG. 13 illustrates a map of an exemplary plasmid useful for modifying a biocatalyst.
Figure 14:
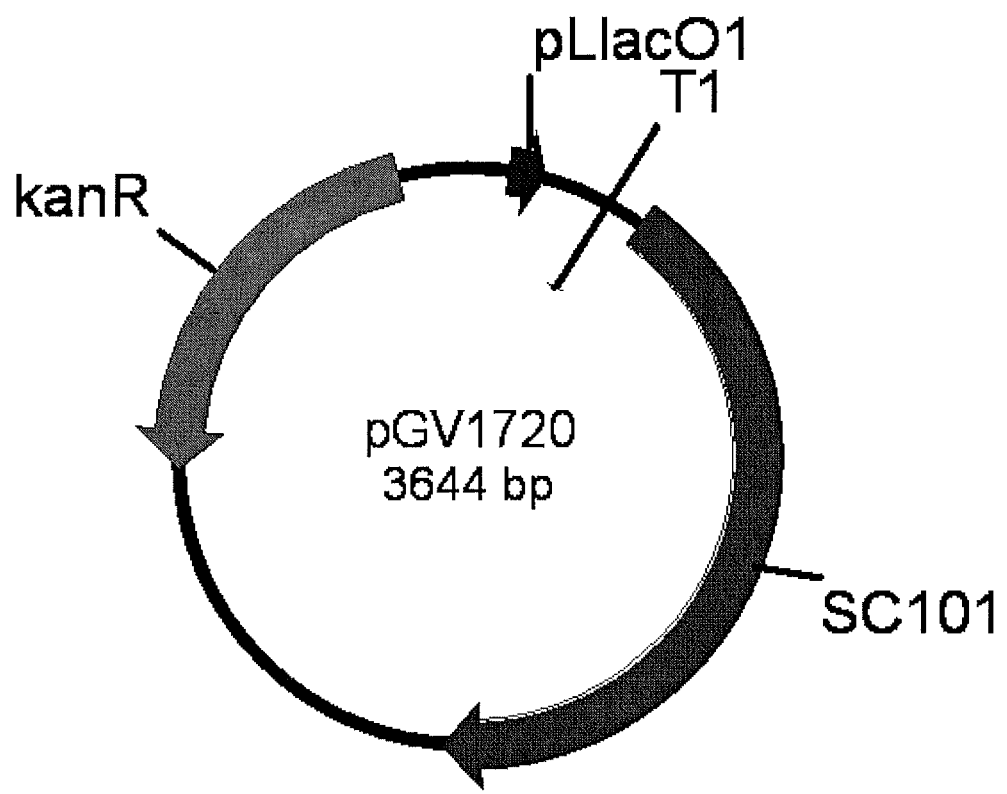
FIG. 14 illustrates a map of an exemplary plasmid useful for modifying a biocatalyst.
Figure 15:
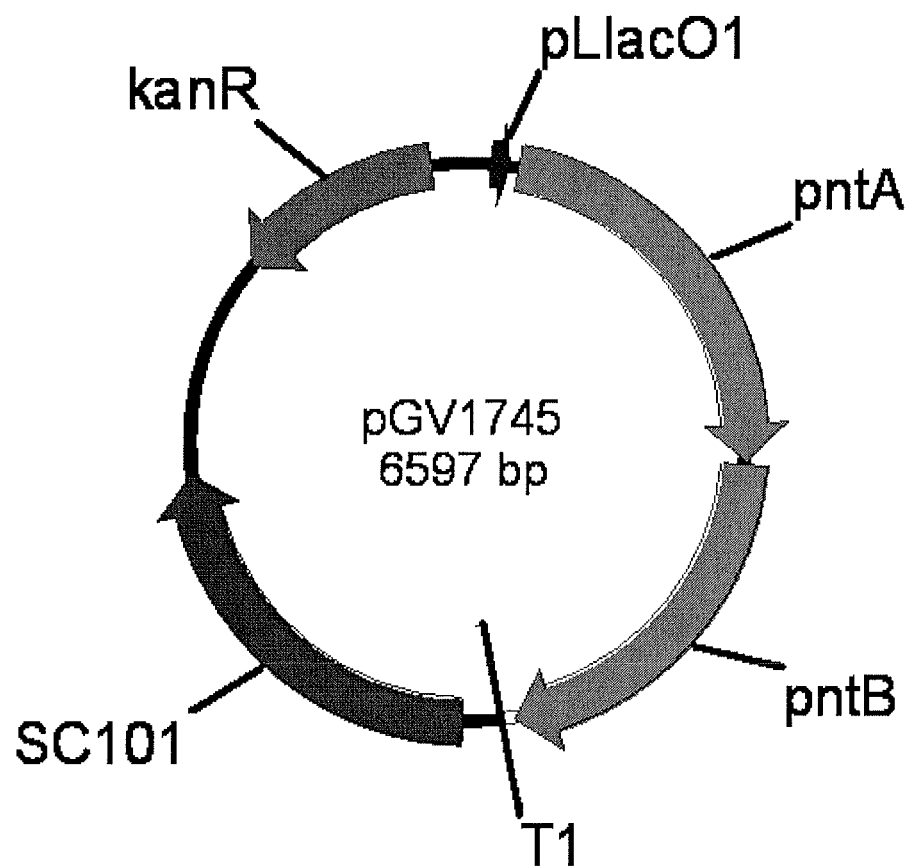
FIG. 15 illustrates a map of an exemplary plasmid useful for modifying a biocatalyst.
Figure 19:
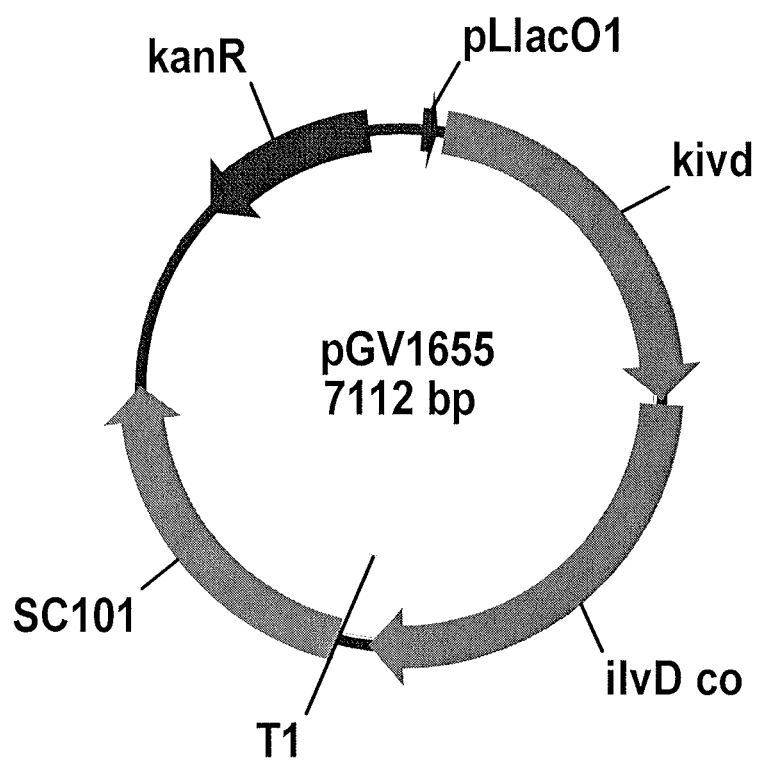
FIG. 19 illustrates a map of an exemplary plasmid useful for modifying a biocatalyst.
Figure 21:
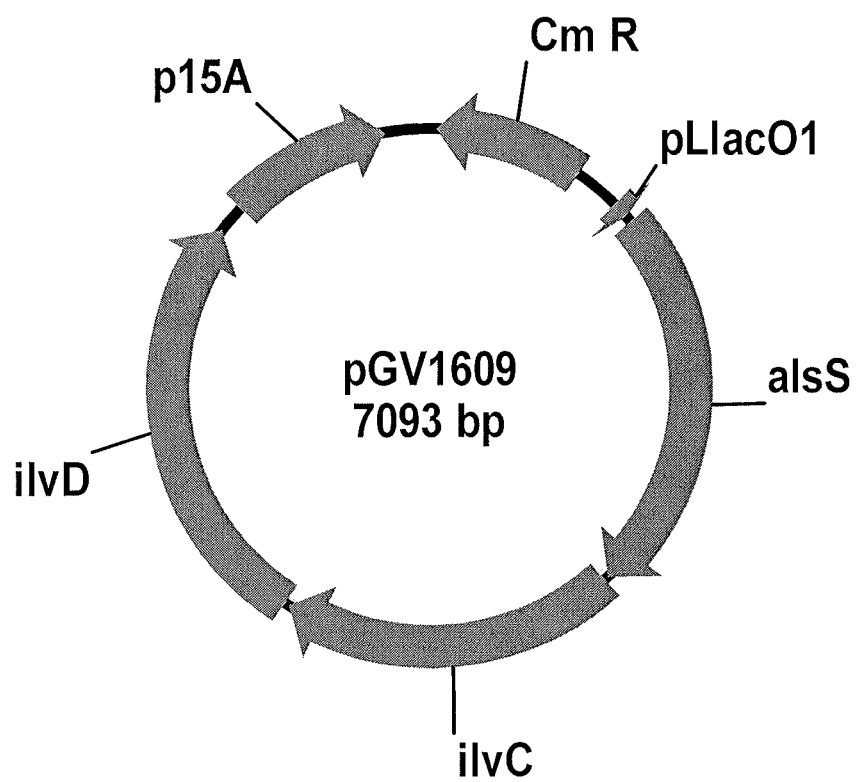
FIG. 21 illustrates a map of an exemplary plasmid useful for modifying a biocatalyst.
Figure 23:
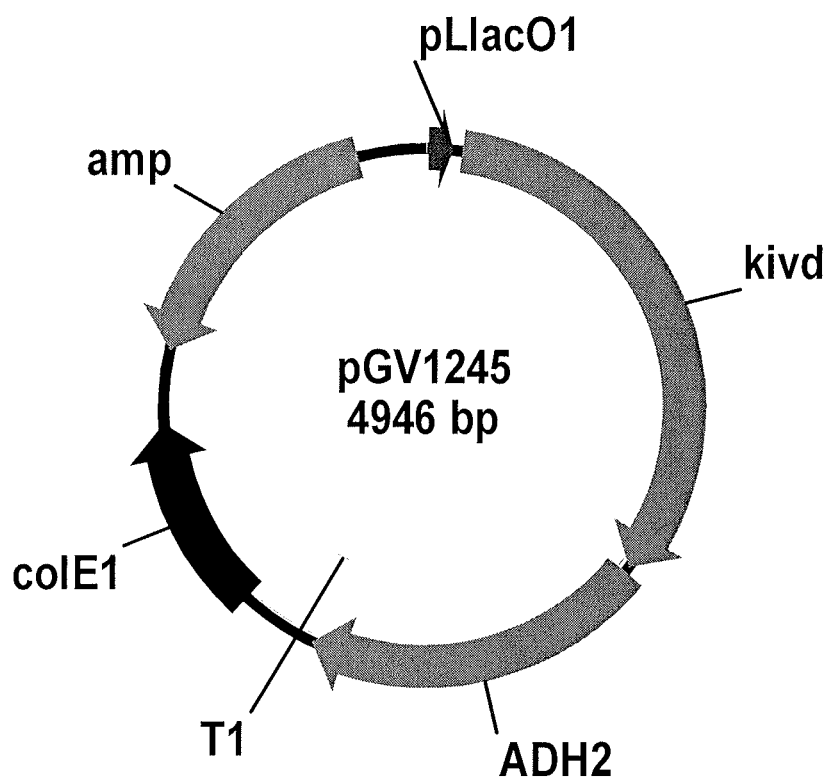
FIG. 23 illustrates a map of an exemplary plasmid useful for modifying a biocatalyst.
Figure 25:
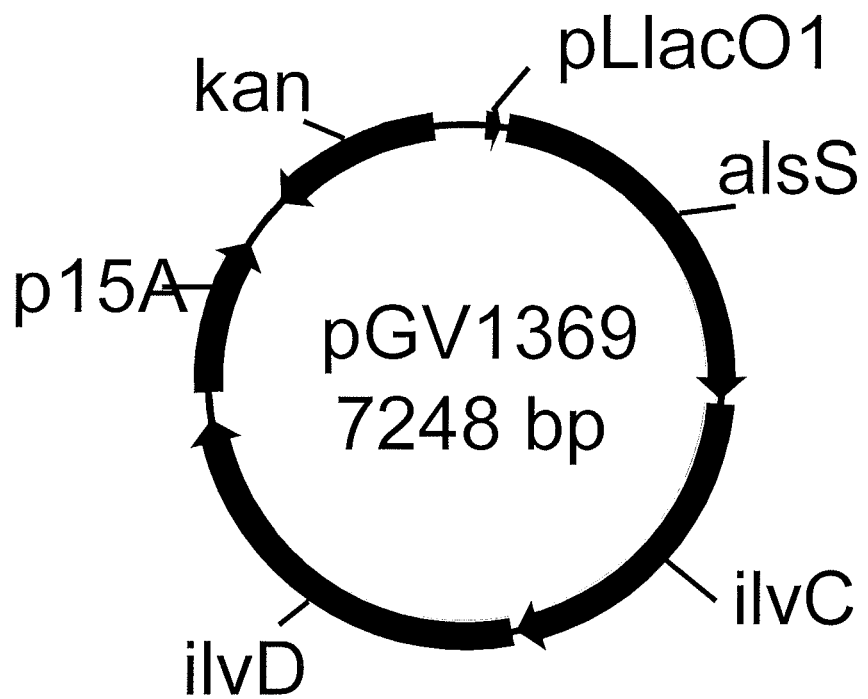
FIG. 25 illustrates a map of an exemplary plasmid useful for modifying a biocatalyst.

| samples | Volumetric Productivity [g/L/h] | ± | Specific Productivity [g/L/h/OD] | ± | Titer [g/L] | ± | Yield [g/g] | ± |
|---|---|---|---|---|---|---|---|---|
| GEVO1748 + pGV1720 + PGV1698 (control) | 0.029 | | 0.014 | | 1.21 | | 0.171 | |
| GEVO1748 + pGV1745 + pGV1698 (pntAB) | 0.096 | 0.003 | 0.035 | 0.015 | 4.01 | 0.15 | 0.246 | 0.002 | until analysis. The samples were analyzed using High performance liquid chromatography (HPLC) and gas chromatography GC. All experiments were performed in duplicate. GEVO1886, GEVO1859 and GEVO1846 were run in parallel. Each strain was run in triplicate. Stable OD values can be observed for all strains under anaerobic shift conditions over the course of the fermentation (FIG. 10). The over-expression of pntAB in the complete pathway integrant strain again showed improvement for isobutanol production over the course of the fermentation (FIG. 10). FIG. 10 illustrates growth under anaerobic shift conditions over the course of the fermentation. FIG. 11 illustrates isobutanol production under microaerobic conditions over the course of the fermentation.

Compared to the complete pathway integrant strain without pntAB knock-in (GEVO1859), volumetric productivity and titer are increased 3.8 fold, specific productivity is increased 2.8 fold and yield is 2.2 fold higher in GEVO1886 (Table 35). In addition, GEVO1886 shows superior performance compared to the plasmid system strain (GEVO1846) under anaerobic conditions. Volumetric productivity and titer are increased by 48%, specific productivity is increased by 18% and yield is 12% higher (Table 33). Comparing the performance of GEVO1886 aerobically and anaerobically volumetric.

Table 33 summarizes the results for volumetric productivity, specific productivity titer and yield reached in an anaerobic fermentation for the tested strains and plasmid systems:

| Samples | Volumetric Productivity [g/L/h] | ± | Specific Productivity [g/L/h/OD] | ± | Titer [g/L] | ± | Yield [g/g] | ± |
|---|---|---|---|---|---|---|---|---|
| GEVO1886 | 0.335 | 0.002 | 0.053 | 0.001 | 16.08 | 0.08 | 0.307 | 0.004 |
| GEVO1859 | 0.088 | 0.028 | 0.019 | 0.005 | 4.22 | 1.35 | 0.140 | 0.029 |
| GEVO1846 | 0.227 | 0.021 | 0.045 | 0.005 | 10.88 | 1.01 | 0.274 | 0.003 |

The performance numbers in the period from 6 to 48 demonstrate that most of isobutanol production occurred during under anaerobic conditions. Highest values for yield and specific productivity were reached by the strain featuring the complete pathway integration and the pntAB knock-in (GEVO1886) under anaerobic conditions. In addition this strain reached the highest values for volumetric productivity and titer under both conditions anaerobic and microaerobic (Table 34).

Table 34 summarizes results for volumetric productivity, specific productivity titer and yield reached in the period from 6 to 48 h for the tested strains and plasmid systems:

| Samples | Condition | Volumetric Productivity [g/L/h] | ± | Specific Productivity [g/L/h/OD] | ± | Titer [g/L] | ± | Yield [g/g] | ± |
|---|---|---|---|---|---|---|---|---|---|
| GEVO1886 | Micro-aerobic | 0.355 | 0.004 | 0.042 | 0.001 | 14.9 | 0.2 | 0.33 | 0.012 |
| GEVO1859 | Micro-aerobic | 0.266 | 0.010 | 0.040 | 0.004 | 11.2 | 0.4 | 0.33 | 0.016 |
| GEVO1846 | Micro-aerobic | 0.344 | 0.007 | 0.051 | 0.004 | 14.4 | 0.3 | 0.33 | 0.005 |
| GEVO1886 | Anaerobic | 0.355 | 0.008 | 0.056 | 0.001 | 14.9 | 0.1 | 0.35 | 0.004 |
| GEVO1859 | Anaerobic | 0.086 | 0.026 | 0.019 | 0.005 | 3.60 | 1.1 | 0.14 | 0.032 |
| GEVO1846 | Anaerobic | 0.209 | 0.019 | 0.041 | 0.004 | 8.79 | 0.8 | 0.27 | 0.006 |

The performance numbers in the period from 6 to 48 demonstrate that most of isobutanol production occurred during under anaerobic conditions. Highest values for yield and specific productivity were reached by the strain featuring the complete pathway integration and the pntAB knock-in (GEVO1886) under anaerobic conditions.

Example 51

Anaerobic batch fermentation of GEVO1886. This example illustrates that an engineered microorganism produces a biofuel in a batch fermentation at a productivity of about 0.4 g/L/h, a titer 21 g/L/h, and a yield of about 88% of theoretical.

An overnight culture was started in a 250 mL Erlenmeyer flask with GEVO1886 cells from a freshly streaked plate with a 40 mL volume of M9 medium (Miller, J. H. A Short Course in Bacterial Genetics: A laboratory manual and handbook for *Escherichia coli* and related bacteria. 1992. Cold Spring Harbor Laboratory Press, Cold Spring Harbor, N.Y.) containing 85 g/L glucose, 20 g/L yeast extract, 20 µM ferric citrate, trace metals, an additional 1 g/L NH$_4$Cl, an additional 1 mM MgSO$_4$ and an additional 1 mM CaCl$_2$ and at a culture OD$_{600}$ of about 0.05. The starter culture was grown for approximately 14 hours at 30° C. at 250 rpm.

Some of the starter culture was then transferred to a 400 mL DasGip fermenter vessel containing about 200 mL of M9 medium (Miller, J. H. A Short Course in Bacterial Genetics: A laboratory manual and handbook for *Escherichia coli* and related bacteria. 1992. Cold Spring Harbor Laboratory Press, Cold Spring Harbor, N.Y.) containing 85 g/L glucose, 20 g/L yeast extract, 20 µM ferric citrate, trace metals, an additional 1 g/L NH$_4$Cl, an additional 1 mM MgSO$_4$ and an additional 1 mM CaCl$_2$ to achieve a starting cell concentration by optical density at 600 nm of 0.1. The vessel was attached to a computer control system to monitor and control pH at 6.5 through addition of base, temperature at 30° C., dissolved oxygen, and agitation. The vessel was agitated, with a minimum agitation of 200 rpm and agitation was varied to maintain a dissolved oxygen content of about 50% using a 12 sL/h air sparge until the OD$_{600}$ was about 1.0. The vessel was then induced with 1 mM IPTG.

After continuing growth for 3 hours, the dissolved oxygen content was decreased to 0% with 200 rpm agitation and 2.5 sL/h sparge with nitrogen (N$_2$) gas. Measurement of the fermenter vessel off-gas for isobutanol and ethanol was performed throughout the experiment by passage of the off-gas stream through a mass spectrometer. Continuous measurement of off-gas concentrations of carbon dioxide and oxygen were also measured by a DasGip off-gas analyzer throughout the experiment. Samples were aseptically removed from the fermenter vessel throughout the experiment and used to measure $OD_{600}$, glucose concentration by HPLC, and isobutanol concentration in the broth by GC.

Isobutanol production reached a maximum titer of 21 g/L at a productivity of 0.4 g/L/h. Yield of the fermentation, calculated when the titer of isobutanol was between 1 g/L and 15 g/L, was approximately 88% of theoretical.

Example 52

(prophetical): Anaerobic batch fermentation of GEVO1886 with continuous product removal. This example illustrates that an engineered microorganism produces a biofuel at a yield of at greater than about 95% of theoretical.

An overnight culture is started in a 250 mL Erlenmeyer flask with GEVO1886 cells from a freezer stock with a 40 mL volume of modified M9 medium consisting of 85 g/L glucose, 20 g/L yeast extract, 20 µM ferric citrate, 5.72 mg/L $H_3BO_3$, 3.62 mg/L $MnCl_2.4H_2O$, 0.444 mg/L $ZnSO_4.7H_2O$, 0.78 mg/L $Na_2MnO_4.2H_2O$, 0.158 mg/L $CuSO_4.5H_2O$, 0.0988 mg/L $CoCl_2.6H_2O$, $NaHPO_4$ 6.0 g/L, $KH_2PO_4$ 3.0 g/L, NaCl 0.5 g/L, $NH_4Cl$ 2.0 g/L, $MgSO_4$ 0.0444 g/L and $CaCl_2$ 0.00481 g/L and at a culture $OD_{600}$ of about 0.05. The starter culture is grown for approximately 14 hrs in a 30° C. shaker at 250 rpm. Some of the starter culture is then transferred to a 2000 mL DasGip fermenter vessel containing about 1500 mL of modified M9 medium to achieve an initial culture $OD_{600}$ of about 0.1. The fermenter vessel is attached to a computer control system to monitor and control pH at 6.5 through addition of base, temperature at about 30° C., dissolved oxygen, and agitation. The vessel is agitated, with a minimum agitation of 400 rpm and agitation is varied to maintain a dissolved oxygen content of about 50% using a 25 sL/h air sparge until the $OD_{600}$ is about 1.0. The vessel is then induced with 0.1 mM IPTG. After continuing growth for about 3 hours, the dissolved oxygen content is decreased to 0% with 200 rpm agitation and 2.5 sL/h sparge with nitrogen ($N_2$) gas. Continuous measurement of the fermentor vessel off-gas by GC-MS analysis is performed for, isobutanol, ethanol, and carbon dioxide throughout the experiment. Samples are aseptically removed from the fermenter vessel throughout the experiment and used to measure $OD_{600}$, glucose concentration and isobutanol concentration in the broth. Throughout the experiment, supplements of pre-grown and pre-induced biocatalyst cells are added as a concentrate several times since the start of the experiment. These cells are the same strain and plasmids shown above and used in the fermenter. Supplemented cells are grown as 1 L cultures in 2.8 L Fernbach flasks and incubated at 30° C., 250 RPM in Modified M9 Medium with 85 g/L of glucose. Cultures are induced upon inoculation with 0.1 mM IPTG. When the cells reach an $OD_{600}$ of about 4.0-5.0, the culture is concentrated by centrifugation and then added to the fermenter. A sterile glucose feed of 500 g/L glucose in DI water is used intermittently during the production phase of the experiment at time points greater than 12 h to maintain glucose concentration in the fermenter of about 30 g/L or above.

The fermenter vessel is attached by tubing to a smaller 400 mL fermenter vessel that serves as a flash tank and is operated in a recirculation loop with the fermenter. The volume in the flash tank is approximately 100 mL and the hydraulic retention time is about 10 minutes. Heat and vacuum are applied to the flash tank. The vacuum level applied to the flash tank is initially set at about 45 mBar and the flash tank is set at about 36° C. These parameters are adjusted to maintain approximately 6-10 g/L isobutanol in the fermenter throughout the experiment. Generally, the vacuum ranges from about 30-100 mBar and the flash tank temperature ranges from 34° C. to 36° C. throughout the experiment. Vapor from the heated flash tank is condensed into a collection vessel as distillate. The fermentation broth is continuously returned from the flash tank to the fermentation vessel.

The distillate recovered in the experiment is strongly enriched for isobutanol. Isobutanol forms an azeotrope with water and usually leads to a two phase distillate: an isobutanol rich top phase and an isobutanol lean bottom phase. Distillate samples are analyzed by GC for isobutanol concentration. Isobutanol production reaches a maximum with a total titer of greater than 50 g/L. The percent theoretical yield is approximately 95%.

Example 53

Removal of the F' episome from GEVO1886 to generate a DNA marker-free isobutanol producing biocatalyst: The F' episomal plasmid present in biocatalyst strain GEVO1886 contains several genes, including a copy of the lacI repressor as well as the Tn10 operon, which contains a DNA marker for resistance to the antibiotic tetracycline and simultaneously confers sensitivity to fusaric acid. GEVO1886 contains no other DNA markers, neither on the chromosome nor on a plasmid. The sensitivity to fusaric acid will be exploited as a counter-selectable method to obtain a variant of GEVO1886 that is fusaric acid-resistant ($Fus^R$) and tetracycline-sensitive ($Tc^S$) and thus has lost the F' plasmid and has the tetracycline DNA marker removed. Loss of the plasmid is confirmed by PCR using F' plasmid-specific primer pairs.

Counter-selection against F' plasmid-containing cells on fusaric acid plate. Fusaric acid-containing plates are prepared by combining, in a first flask: 12 g Agar, 4 g Tryptone, 4 g Yeast Extract, 40 mg Chlortetracycline, and 400 mL water. In a second flask, 8 g of NaCl and 8 g of $NaH_2PO_4$ are dissolved in 400 mL water. The two flasks are autoclaved (20 minutes) and are allowed to cool to approximately 45° C. 9.6 mg of fusaric acid are dissolved in 0.5 mL dimethylformamide and added to the first flask. 4 mL of 20 mM $ZnCl_2$ are added to the second flask. The contents of the two flasks are mixed together well and poured into sterile plates (approximately 30 mL/plate). The plates are used within 36 hours of being poured.

GEVO1886 containing an F' plasmid carrying Tn10 [$Tc^R$] is grown overnight in LB liquid media containing tetracycline (at a final concentration of 5 µg/mL) or anhydrous tetracycline (aTc) at a final concentration of 0.1 µg/mL, to induce expression of the tetracycline-resistance cassette. Following overnight growth, 0.1 mL each of a $10^{-8}$, $10^{-7}$, $10^{-8}$, and $10^{-9}$ dilutions of the dense overnight culture are plated onto the fusaric acid plates and incubated at 42° C. until colonies appear, approximately 36 hours later. Colonies that arise are patched onto LB plates and grown at 37° C. until patches of cells are visible on the plates. The patches are then replica plated onto LB plates containing either tetracycline (15 µg/mL final concentration) or fusaric acid (as described, above) and grown at 37° C. until cells grow to confirm the, $Fus^R$ and $Tc^S$ phenotypes. Cells that are $Fus^R$, $Tc^S$ are likely to be F' plasmid cured and are the desired phenotype. Patches on tetracycline plates may not grow.

$Fus^R$ $Tc^S$ colonies, likely to be F' plasmid cured, are then screened by PCR for the presence of three distinct regions of the F plasmid. This technique will confirm the presence or loss of the F plasmid in each colony. The PCR primers used are listed below in Table 35.

Table 35 summarizes the sequences of PCR primers that may be used to confirm presence or absence of the F' plasmid:

| PRIMER # | Primer Name | Primer Sequence | Notes |
|---|---|---|---|
| 1278 | [1278]F' plasmid Ori2 CHECK FOR | Gtgaaaacgcaggttaagctggcttagc (SEQ ID NO: 22) | With 1279, OriV (Rep ORI 2) of F' plasmid. 530 bp product |
| 1279 | [1279]F' plasmid Ori2 CHECK REV | ATACTGTTATCTGGCTTTTAGTAAGCC (SEQ ID NO: 23) | |
| 1280 | [1280]F' plasmid ORI1 CHECK FOR | Gacataacataagctggagcaggtag (SEQ ID NO: 24) | With 1281, Rep ORI 1 of F' plasmid. 1165 bp product |
| 1281 | [1281]F' plasmid ORI1 CHECK REV | TACAACCTGTGGCGCTGATGCGTC (SEQ ID NO: 25) | |
| 1282 | [1282]F' plasmid ORI3 CHECK FOR | Caggagcctgtgtagcgtttatagg (SEQ ID NO: 26) | With 1283, Rep ORI 1 of F' plasmid. 790 bp product |
| 1283 | [1283]F' plasmid ORI3 CHECK REV | TCATGTTCCTGTAGGGTGCCATCAG (SEQ ID NO: 27) | |

For templates, a small amount of the cells from each colony are used in several typical colony PCR reactions. Only those colonies which fail to give any signal for all three primer sets in a reaction, where the same cocktail mix gave (1) positive, correct-sized product for the parental F' strain as template, and (2) give no product for no-template-added control samples, are deemed correct as F'-cured strains. An F' plasmid cured strain is selected, which is also tetracycline marker or DNA marker free, and named GEVO1948. GEVO1948 is contacted with an appropriate fermentation medium containing glucose, under the appropriate conditions, and isobutanol is produced.

Example 54

Comparison of Improved Biocatalysts Provided Herein to a Parental Strain SA237 for productivity, titer and yield: GEVO1530 and GEVO1780 are modified bacterial biocatalysts that contain genes on two plasmids which encode a pathway of enzymes that convert pyruvate into isobutanol. When the biocatalysts GEVO1530 and GEVO1780 were contacted with glucose in a medium suitable for growth of the biocatalyst, at about 30° C., the biocatalysts produced isobutanol from the glucose. Parental strain SA237 is a biocatalyst described previously (see e.g., WO 2008/098227, entitled "BIOFUEL PRODUCTION BY RECOMBINANT MICROORGANISMS" and incorporated herein by reference). Two 400 mL DasGip fermenter vessels containing 200 mL each of modified M9 medium comprising of 85 g/L glucose, 20 g/L yeast extract, 20 µM ferric citrate, 5.72 mg/L $H_3BO_3$, 3.62 mg/L $MnCl_2.4H_2O$, 0.444 mg/L $ZnSO_4.7H_2O$, 0.78 mg/L $Na_2MnO_4.2H_2O$, 0.158 mg/L $CuSO_4.5H_2O$, 0.0988 mg/L $CoCl_2.6H_2O$, $NaHPO_4$ 6.0 g/L, $KH_2PO_4$ 3.0 g/L, NaCl 0.5 g/L, $NH_4C$ 12.0 g/L, $MgSO_4$ 0.0444 g/L and $CaCl_2$ 0.00481 g/L were inoculated with GEVO1780, GEVO1530, or SA237 cells from frozen stocks. The vessels were attached to a computer control system to monitor and control pH at 6.5 through addition of base, temperature at about 30° C., dissolved oxygen, and agitation. The vessels were agitated, with a minimum agitation of 300 rpm and agitation was varied to maintain a dissolved oxygen content of about 50% using a 12 sL/h air sparge until the OD 600 was about 1.0. The vessels were then induced with 0.1 mM IPTG. The vessels were operated under these conditions for about 12 hours. At about 12 hours, the contents of the fermenter vessels were then poured into 500 ml sterile graduated plastic bottles and centrifuged for 20 minutes at 4500 rpm. The cells were resuspended in 50 ml total volume of modified M9 medium to create concentrated cells in medium. Duplicate 400 ml DasGip vessels containing 150 ml each of modified M9 medium were inoculated with 50 ml of the concentrated GEVO1530, GEVO1780, or SA237 cells in medium and then induced with 0.1 mM IPTG. The vessels were attached to a computer control system to monitor and control pH at 6.5 through addition of base, temperature at about 30° C., dissolved oxygen, and agitation. Constant dissolved oxygen content of about 5% was maintained using a 2.5 sL/h air sparge with variable agitation automatically controlled from 300 to 1200 rpm. Continuous measurement of each fermentor vessel off-gas by GC-MS analysis was performed for oxygen, isobutanol, ethanol, carbon dioxide, and nitrogen throughout the experiment. Samples were aseptically removed from the fermenter vessel throughout the experiment and used to measure OD600 and glucose concentration by HPLC, and isobutanol concentration in the broth by GC. Results reported are an average of duplicate fermentations. Volumetric productivity and yield were calculated when the titer of isobutanol was between 1 g/L and 15 g/L. For SA237, isobutanol production reached a maximum at around 21 hours with a titer of about 15.6 g/L and with a yield of approximately 67% maximum theoretical. Volumetric productivity of the SA237 fermentation, calculated when the titer of isobutanol was between 1 g/L and 15 g/L, was about 1.45 g/L/h. For GEVO1530, isobutanol production reached a maximum at around 24 hours with a titer of about 19.5 g/L and with a yield of approximately 73% maximum theoretical. Volumetric productivity of the GEVO1530 fermentation, calculated when the titer of isobutanol was between 1 g/L and 15 g/L, was about 1.51 g/L/h. For GEVO1780, isobutanol production reached a maximum at around 21.5 hours with a titer of about 21.3 g/L and with a yield of approximately 82% maximum theoretical. Volumetric productivity of the GEVO1780 fermentation, calculated when the titer of isobutanol was between 1 g/L and 15 g/L, was about 1.91 g/L/h.

Example 55

Comparison of Improved Biocatalysts Provided Herein to a Parental Strain SA237-Improved biocatalysts produce less acetate than SA237: GEVO1530 and GEVO1780 are modified bacterial biocatalysts that contain genes on two plasmids which encode a pathway of enzymes that convert pyruvate into isobutanol. When the biocatalysts GEVO1530 and GEVO1780 were contacted with glucose in a medium suitable for growth of the biocatalyst, at about 30° C., the biocatalysts produced isobutanol from the glucose. SA237 is a biocatalyst described previously ((WO 2008/098227) BIOFUEL PRODUCTION BY RECOMBINANT MICROORGANISMS). Overnight starter cultures of GEVO1530, GEVO1780, or SA237 were started in 250 mL Erlenmeyer flasks with cells from a fresh transformation plate or a frozen glycerol stock with a 40 mL volume of EZ Rich medium (Neidhardt, F. C., P. L. Bloch, and D. F. Smith. 1974. Culture medium for enterobacteria. J. Bacteriol. 119:736-47) containing 85 g/L glucose and 10 g/L yeast extract and at a culture OD600 of about 0.05. The starter cultures were grown for approximately 14 hrs in a 37° C. shaker at 250 rpm. Some of each starter culture was then transferred to respective 400 mL DasGip fermenter vessel containing about 200 mL of EZ Rich medium containing 85 g/L glucose and 10 g/L yeast extract to achieve a 1% v/v inoculum. The vessels were attached to a computer control system to monitor and control pH at 6.5 through addition of base, temperature at about 30° C., dissolved oxygen, and agitation. The vessels were agitated, with a minimum agitation of 300 rpm and agitation was varied to maintain a dissolved oxygen content of about 50% using a 12 sL/h air sparge until the OD600 was about 1.0. The vessels were then induced with 0.1 mM IPTG. After continuing growth for approximately 8-10 hrs, the dissolved oxygen content was decreased to about 5% with 300 rpm minimum agitation and 2.5 sl/h airflow. Measurement of each fermentor vessel off-gas by trapping in an octanol bubble trap then measurement by GC was performed for isobutanol and ethanol. Continuous measurement of off gas concentrations of carbon dioxide and oxygen were also measured by a DasGip off gas analyzer throughout the experiment. Samples were aseptically removed from the fermenter vessel throughout the experiment and used to measure OD600, glucose and acetate concentration by HPLC, and isobutanol concentration in the broth by GC. Table 36 summarizes the results for acetate and isobutanol production in each strain. The strains GEVO1530 and GEVO1780 produce about 50% less of the undesired byproduct acetate than SA237.

Table 36 summarizes the fermentation results of SA237 (parental), GEVO1530, and GEVO1780:

| | SA237 | | | | GEVO1530 | | | | GEVO1780 | | |
|---|---|---|---|---|---|---|---|---|---|---|---|
| Replicate # | EFT (h) | Acetate (g/L) | iBuOH (g/L) | Replicate # | EFT (h) | Acetate (g/L) | iBuOH (g/L) | Replicate # | EFT (h) | Acetate (g/L) | iBuOH (g/L) |
| 1 | 0.0 | 0.12 | 0.01 | 1 | 0.0 | 0.15 | 0.00 | 1 | 0.0 | 0.21 | 0.10 |
| 1 | 3.0 | 0.18 | 0.01 | 1 | 3.0 | 0.21 | 0.01 | 1 | 4.0 | 0.14 | 0.22 |
| 1 | 5.0 | 0.32 | 0.05 | 1 | 5.0 | 0.34 | 0.04 | 1 | 5.0 | ND | 0.00 |
| 1 | 7.0 | 0.44 | 0.47 | 1 | 7.0 | 0.43 | 0.45 | 1 | 10.0 | 0.30 | 3.48 |
| 1 | 9.0 | 0.50 | 1.66 | 1 | 9.0 | 0.61 | 1.73 | 1 | 20.0 | 0.61 | 14.30 |
| 1 | 21.0 | 1.17 | 12.38 | 1 | 21.0 | 0.61 | 13.04 | 1 | 24.0 | 0.73 | 16.86 |
| 1 | 24.5 | 1.19 | 15.37 | 1 | 24.5 | 0.48 | 14.77 | 1 | 28.0 | 0.78 | 19.39 |
| 1 | 27.5 | 1.52 | 16.16 | | | | | | | | |
| 2 | 0.0 | 0.14 | 0.01 | 2 | 0.0 | 0.15 | 0.01 | 2 | 0.0 | 0.22 | 0.15 |
| 2 | 3.0 | 0.19 | 0.01 | 2 | 3.0 | 0.19 | 0.01 | 2 | 4.0 | 0.16 | 0.17 |
| 2 | 5.0 | 0.34 | 0.05 | 2 | 5.0 | 0.35 | 0.04 | 2 | 5.0 | ND | 0.00 |
| 2 | 7.0 | 0.46 | 0.47 | 2 | 7.0 | 0.47 | 0.43 | 2 | 10.0 | 0.30 | 3.53 |
| 2 | 9.0 | 0.63 | 1.84 | 2 | 9.0 | 0.49 | 1.71 | 2 | 20.0 | 0.60 | 14.83 |
| 2 | 21.0 | 1.28 | 14.13 | 2 | 21.0 | 0.47 | 11.94 | 2 | 24.0 | 0.74 | 17.57 |
| 2 | 24.5 | 1.15 | 16.25 | 2 | 24.5 | 0.60 | 13.29 | 2 | 28.0 | 0.80 | 14.25 |
| 2 | 27.5 | 1.37 | 17.47 | 2 | 27.5 | 0.70 | 14.18 | 2 | 30.0 | 0.69 | 19.34 |
| 2 | 31.0 | 1.67 | 18.50 | 2 | 31.0 | 0.65 | 15.27 | 2 | 48.0 | 0.92 | 20.78 |
| 2 | 47.0 | 1.40 | 18.64 | 2 | 47.0 | 0.66 | 16.73 | | | | |

Abbreviations used in this table: ND, not determined; EFT, elapsed fermentation time in hours; iBuOH, isobutanol

Example 56

Tolerance of GEVO Biocatalyst to pH change during fermentation: Biocatalysts provided herein are operable under a wide range of pH units: GEVO1821 is a modified bacterial biocatalyst that contains genes on two plasmids which encode a pathway of enzymes that convert pyruvate into isobutanol. When the biocatalyst GEVO1821 was contacted with glucose in a medium suitable for growth of the biocatalyst, at about 30° C., the biocatalysts produced isobutanol from the glucose. The strain GEVO1821 was used in two different fermentations. Fermentation 1 was done in screw cap flasks without pH control. Fermentation 2 was done in a fermenter with pH control. For Fermentation 1 an overnight starter culture of GEVO1821 was inoculated from a fresh transformation plate in 14 mL culture tubes with a 3 mL volume of LB medium. The starter culture was grown for approximately 14 h at 37° C. and 250 rpm. The starter culture was then used to inoculate 250 mL screw cap flasks containing about 20 mL of M9 minimal medium according to Miller (Jeffrey H. Miller. A Short Course in Bacterial Genetics: A Laboratory Manual and Handbook for *Escherichia coli* and Related Bacteria. Published by CSHL Press, 1992, ISBN 0879693495), supplemented with 10 g/L yeast extract, 10 µM ferric citrate and 1× trace metals, containing 40 g/L of glucose and with a pH of 7. The flasks were inoculated to a starting OD600 of about 0.1. The cultures were incubated at 37° C. and 250 rpm until the $OD_{600}$ of the cultures reached between 0.6 and 0.8. At this time the cultures were induced with the addition of IPTG to a final concentration of 1 mM. The induced cultures were incubated at 30° C. and 250 rpm until 24 h past inoculation. At the 24 h timepoint samples were taken from the cultures and these samples were analyzed for $OD_{600}$, pH, glucose and metabolite concentrations by HPLC, and isobutanol concentration by GC.

For Fermentation 2, a 500 mL Erlenmeyer flask containing 40 mL of modified M9 medium containing twice the standard concentration of trace elements, $MgSO_4$, $CaCl_2$, ferric citrate and 20 g/L yeast extract at pH 6.5 (2×M9) (see Table 40 below) was inoculated with GEVO1821 from a frozen glycerol stock to a culture $OD_{600}$ of about 0.1. The starter culture was grown for approximately 16 h in a 30° C. shaker at 250 rpm. Some of the starter culture was then transferred to two 400 mL DasGip fermenter vessels containing about 200 mL each of 2×M9 medium to achieve an $OD_{600}$ of about 0.1.

The vessels were attached to a computer control system to monitor and control pH at 6.5 through addition of base, temperature at about 30° C., dissolved oxygen, and agitation. The vessels were agitated, with a minimum agitation of 200 rpm and agitation was varied to maintain a dissolved oxygen content of about 50% using a 12 sL/h air sparge until the $OD_{600}$ was about 0.8-1.0. The vessels were then induced with 0.1 mM IPTG. After continuing growth for approximately 6-8 h, the dissolved oxygen content was decreased to about 5% with 200 rpm minimum agitation and 2.5 sl/h airflow. Isobutanol and ethanol in the off-gas of each fermentor vessel were trapped in an octanol bubble trap and then measured by GC. Samples were aseptically removed from the fermenter vessel at 24 h after inoculation to measure $OD_{600}$, and isobutanol concentration in the broth by GC. Samples were also taken from the octanol bubble traps and these samples were analyzed for isobutanol by GC. The pH of the two cultures in Fermentation 1 dropped from pH 7 at the time of inoculation to pH 5.5 at 24 h after inoculation. The pH in the two fermenter vessels of Fermentation 2 was held constant at pH 6.5 throughout the fermentation. The strain GEVO1821 reached the same specific productivity in both Fermentation 1 and Fermentation 2. Specific productivities in the flasks of Fermentation 1 were 0.033 g/L/h/OD and 0.034 g/L/h/OD respectively. Specific productivities in the fermenter vessels of Fermentation 2 were 0.033 g/L/h/OD and 0.034 g/L/h/OD respectively. Strain GEVO1821 retained 100% of its productivity despite a drop in pH of 1.5 units. This shows that this biocatalyst is operable under a wide range of pH and tolerates changes in the pH during fermentation.

Table 37 summarizes the ingredients for modified M9 media termed "2×M9" that contains twice the normal amount of magnesium sulfate, calcium chloride, trace metals and ferric citrate. In addition to this, the yeast extract content has been doubled from the usual 10 g/L to 20 g/L.

Table 37 summarizes the ingredients for modified M9 media termed "2×M9":

| A. M9 salts (Miller) | (g/L) |
| --- | --- |
| $NaHPO_4$ | 6.0 |
| $KH_2PO_4$ | 3.0 |
| NaCl | 0.5 |
| $NH_4Cl$ | 2.0 |
| $MgSO_4$ | 0.0444 |
| $CaCl_2$ | 0.00481 |
| B. Trace Metals1 | (mg/L) |
| $H_3BO_3$ | 5.72 |
| $MnCl_2 \cdot 4H_2O$ | 3.62 |
| $ZnSO_4 \cdot 7H_2O$ | 0.444 |
| $Na_2MoO_4 \cdot 2H_2O$ | 0.78 |
| $CuSO_4 \cdot 5H_2O$ | 0.158 |
| $CoCl_2 \cdot 6H_2O$ | 0.0988 |
| C. Others | |
| Ferric Citrate | 20 µM |
| Yeast Extract | 20 g/L |
| Glucose | 85 g/L |

1Handbook of Media for Environmental Microbiology By Ronald M. Atlas. 1995. University of Chicago Press. p. 68.

Example 57

Anaerobic batch fermentation of GEVO1948 (Prophetic). This example illustrates that an engineered microorganism with no DNA markers and with DNA consisting of natural DNA produces a biofuel in a batch fermentation at a productivity of about 0.4 g/L/h, a titer of about 21 g/L/h, and a yield of about 88% of theoretical.

An overnight culture is started in a 250 mL Erlenmeyer flask with GEVO1948 cells from a freshly streaked plate with a 40 mL volume of M9 medium (Miller, J. H. A Short Course in Bacterial Genetics: A laboratory manual and handbook for *Escherichia coli* and related bacteria. 1992. Cold Spring Harbor Laboratory Press, Cold Spring Harbor, N.Y.) containing 85 g/L glucose, 20 g/L yeast extract, 20 µM ferric citrate, trace metals, an additional 1 g/L $NH_4Cl$, an additional 1 mM $MgSO_4$ and an additional 1 mM $CaCl_2$ and at a culture $OD_{600}$ of about 0.05. The starter culture is grown for approximately 14 hours at 30° C. at 250 rpm.

Some of the starter culture is then transferred to a 400 mL DasGip fermenter vessel containing about 200 mL of M9 medium (Miller, J. H. A Short Course in Bacterial Genetics: A laboratory manual and handbook for *Escherichia coli* and related bacteria. 1992. Cold Spring Harbor Laboratory Press, Cold Spring Harbor, N.Y.) containing 85 g/L glucose, 20 g/L yeast extract, 20 µM ferric citrate, trace metals, an additional 1 g/L $NH_4Cl$, an additional 1 mM $MgSO_4$ and an additional 1 mM $CaCl_2$ to achieve a starting cell concentration by optical density at 600 nm of about 0.1. The fermenter vessel is attached to a computer control system to monitor and control pH at 6.5 through addition of base, temperature at about 30° C., dissolved oxygen, and agitation. The vessel is agitated, with a minimum agitation of 200 rpm and agitation is varied to maintain a dissolved oxygen content of about 50% using a 12 sL/h air sparge until the $OD_{600}$ is about 1.0.

After continuing growth for 3 hours, the dissolved oxygen content is decreased to 0% with 200 rpm agitation and 2.5 sL/h sparge with nitrogen ($N_2$) gas. Measurement of the fermenter vessel off-gas for isobutanol and ethanol is performed throughout the experiment by passage of the off-gas stream through a mass spectrometer. Continuous measurement of off-gas concentrations of carbon dioxide and oxygen are also measured by a DasGip off-gas analyzer throughout the experiment. Samples are aseptically removed from the fermenter vessel throughout the experiment and used to measure $OD_{600}$, glucose concentration by HPLC, and isobutanol concentration in the broth by GC.

Isobutanol production reaches a maximum titer of greater than 10 g/L at a productivity of greater than 0.2 g/L/h. Yield of the fermentation is greater than 85% of theoretical. This example demonstrates that a biocatalyst that contains no DNA markers and a biocatalyst that contains DNA consisting of natural DNA produces isobutanol at titer, rate, and yield.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Singular forms "a", "an", and "the" include plural reference unless the context clearly dictates otherwise. The term "or" is not meant to be exclusive to one or the terms it designates. For example, as it is used in a phrase of the structure "A or B" may denote A alone, B alone, or both A and B.

Unless defined otherwise, all technical and scientific terms used herein have the same meanings as commonly understood by one of ordinary skill in the art to which this invention belongs. Abbreviations used herein and their meanings include: "s" means second(s), "min" means minute(s), "h" or "hr" or "hrs" means hour(s), "psi" means pounds per square inch, "nm" means nanometers, "d" means day(s), "µL" means microliter(s), "mL" means milliliter(s), "L" means liter(s), "sL/h" means standard liters per hour, a standard liter is a volume equal to a liter at standard temperature and pressure, "mm" millimeter(s), "nm" means nanometer(s), "mM" means millimolar, "µM" means micromolar, "g" means gram(s), "sL/h" means standard Liters per hour, "µg" means microgram(s), "OD" means optical density, "OD600" means optical density measured at a wavelength of 600 nm, "% w/v" means weight/volume percent, "rpm" or "RPM" means revolutions per minute, "% v/v" volume/volume percent, "IPTG" means isopropyl-b-D-thiogalactopyranoside, "HPLC" means high performance liquid chromatography and "GC" means gas chromatography.

Although any methods and systems similar or equivalent to those described herein can be used in the practice or testing of the present invention, the methods, systems, and materials are now described. All publications mentioned herein are incorporated herein by reference for the purpose of describing and disclosing the processes, compositions, and methodologies that are reported in the publications which might be used in connection with the invention. Nothing herein is to be construed as an admission that the invention is not entitled to antedate such disclosure by virtue of prior invention.

The foregoing detailed description has set forth various embodiments of the systems and/or methods via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware. It will further be understand that method steps may be presented in a particular order in flowcharts, and/or examples herein, but are not necessarily limited to being performed in the presented order. For example, steps may be performed simultaneously, or in a different order than presented herein, and such variations will be apparent to one of skill in the art in light of this disclosure.

In a general sense, those skilled in the art will recognize that the various embodiments described herein can be implemented, individually and/or collectively, by various types of systems having a wide range of components.

One skilled in the art will recognize that the herein described components (e.g., steps), devices, and objects and the discussion accompanying them are used as examples for the sake of conceptual clarity and that various configuration modifications are within the skill of those in the art. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for producing distillers dried grains obtained from a fermentation process for the production of isobutanol, said method comprising:
   (a) cultivating a yeast biocatalyst in a fermentation vessel containing a culture medium comprising at least one carbon source to produce isobutanol, wherein said yeast biocatalyst is engineered to express exogenous genes encoding an acetolactate synthase, a ketol-acid reductoisomerase, a dihydroxy acid dehydratase, a ketoisovalerate decarboxylase, and an isobutyraldehyde dehydrogenase;
   (b) removing at least a portion of an insoluble material from the fermentation vessel after isobutanol is produced, wherein said insoluble material comprises said yeast biocatalyst; and
   (c) drying said insoluble material comprising said yeast biocatalyst to produce the distillers dried grains.

2. The method of claim 1, wherein said method further comprises step (d) of adding soluble residual material from the fermentation process to said distillers dried grains to produce distillers dried grains and solubles.

3. The method of claim 1, wherein said distillers dried grains comprise at least one additional product selected from the group consisting of unconsumed feedstock solids, nutrients, proteins, fibers, and oils.

4. The method of claim 1, wherein said acetolactate synthase catalyzes the conversion of pyruvate to acetolactate.

5. The method of claim 1, wherein said ketol-acid reductoisomerase catalyzes the conversion of acetolactate to 2,3-dihydroxyisovalerate.

6. The method of claim 1, wherein said dihydroxy acid dehydratase catalyzes the conversion of 2,3-dihydroxyisovalerate to α-ketoisovalerate.

7. The method of claim 1, wherein said ketoisovalerate decarboxylase catalyzes the conversion of α-ketoisovalerate to isobutyraldehyde.

8. The method of claim 1, wherein said isobutyraldehyde dehydrogenase catalyzes the conversion of isobutyraldehyde to isobutanol.

9. The method of claim 1, wherein said yeast biocatalyst does not contain DNA markers.

10. The method of claim 1, wherein said carbon source is a six-carbon sugar.

11. The method of claim 10, wherein said six-carbon sugar is selected from the group consisting of glucose, galactose, and mannose.

12. The method of claim 1, wherein said carbon source is a five-carbon sugar.

13. The method of claim 12, wherein said five-carbon sugar is selected from the group consisting of arabinose and xylose.

14. The method of claim 1, wherein said carbon source is obtained from dry corn.

15. The method of claim 14, wherein said dry corn is milled to produce dry milled corn.

16. The method of claim 15, wherein said dry milled corn is slurried and contacted with alpha-amylase to produce a corn liquefact.

17. The method of claim 16, wherein said corn liquefact is contacted with gluco-amylase to produce a corn slurry.

18. The method of claim 17, wherein said corn slurry is added to the culture medium prior to the production of isobutanol.

\* \* \* \* \*